US010227662B2

(12) United States Patent
Rey et al.

(10) Patent No.: US 10,227,662 B2
(45) Date of Patent: *Mar. 12, 2019

(54) NON-REPLICATIVE TRANSDUCTION PARTICLES AND TRANSDUCTION PARTICLE-BASED REPORTER SYSTEMS

(71) Applicant: GeneWeave Biosciences, Inc., Los Gatos, CA (US)

(72) Inventors: Diego Ariel Rey, Palo Alto, CA (US); Nikol de Forest, Scotts Valley, CA (US); Heather Cox, Los Gatos, CA (US); Soni Shukla, Santa Clara, CA (US)

(73) Assignee: GeneWeave Biosciences, Inc., Los Gatos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/649,181

(22) Filed: Jul. 13, 2017

(65) Prior Publication Data

US 2017/0321289 A1 Nov. 9, 2017

Related U.S. Application Data

(63) Continuation of application No. 15/183,303, filed on Jun. 15, 2016, now Pat. No. 9,752,200, which is a continuation of application No. 14/550,335, filed on Nov. 21, 2014, now Pat. No. 9,388,453, which is a continuation-in-part of application No. PCT/US2014/026536, filed on Mar. 13, 2014.

(60) Provisional application No. 61/939,126, filed on Feb. 12, 2014, provisional application No. 61/897,040, filed on Oct. 29, 2013, provisional application No. 61/779,177, filed on Mar. 13, 2013.

(51) Int. Cl.

| *C12Q 1/68* | (2018.01) |
| *C12Q 1/6897* | (2018.01) |
| *C12N 1/20* | (2006.01) |
| *C12N 7/00* | (2006.01) |
| *C12N 15/74* | (2006.01) |
| *C12Q 1/66* | (2006.01) |
| *C12Q 1/14* | (2006.01) |
| *C12Q 1/18* | (2006.01) |
| *C12N 15/70* | (2006.01) |

(52) U.S. Cl.
CPC ............ *C12Q 1/6897* (2013.01); *C12N 1/20* (2013.01); *C12N 7/00* (2013.01); *C12N 15/70* (2013.01); *C12N 15/74* (2013.01); *C12Q 1/14* (2013.01); *C12Q 1/18* (2013.01); *C12Q 1/66* (2013.01); *C12Y 113/12007* (2013.01); *C12N 2795/10143* (2013.01); *C12N 2795/10152* (2013.01); *C12N 2795/10343* (2013.01); *C12N 2795/10352* (2013.01); *G01N 2333/31* (2013.01); *G01N 2333/90241* (2013.01)

(58) Field of Classification Search
None
See application file for complete search history.

(56) References Cited

U.S. PATENT DOCUMENTS

| 3,122,420 A | 2/1964 | Rebar et al. |
| 3,826,574 A | 7/1974 | Brown, Jr. |
| 4,057,148 A | 11/1977 | Meyer et al. |
| 4,730,933 A | 3/1988 | Lohr |
| 4,861,709 A | 8/1989 | Ulitzur et al. |
| 5,086,233 A | 2/1992 | Stafford et al. |
| 5,139,745 A | 8/1992 | Barr et al. |
| 5,139,941 A | 8/1992 | Muzyczka et al. |
| 5,188,455 A | 2/1993 | Hammerstedt |
| 5,221,623 A | 6/1993 | Legocki et al. |
| 5,242,660 A | 9/1993 | Hsei |
| 5,252,479 A | 10/1993 | Srivastava |
| 5,447,687 A | 9/1995 | Lewis et al. |
| 5,494,646 A | 2/1996 | Seymour |
| 5,498,525 A | 3/1996 | Rees et al. |
| 5,582,969 A | 12/1996 | Pearson et al. |
| 5,645,801 A | 7/1997 | Bouma et al. |
| 5,656,424 A | 8/1997 | Jurgensen et al. |
| 5,677,124 A | 10/1997 | DuBois et al. |
| 5,736,388 A | 4/1998 | Chada et al. |
| 5,814,022 A | 9/1998 | Antanavich et al. |
| 5,824,468 A | 10/1998 | Scherer et al. |
| 5,858,693 A | 1/1999 | Cottingham |

(Continued)

FOREIGN PATENT DOCUMENTS

| EP | 0274527 A1 | 7/1987 |
| EP | 0168933 A2 | 4/1993 |

(Continued)

OTHER PUBLICATIONS

International Search Report and Written Opinion for International Application No. PCT/US2014/023422, dated Sep. 8, 2014.
Office Action for U.S. Appl. No. 14/048,974, dated Jan. 28, 2014.
Office Action for U.S. Appl. No. 14/048,974, dated May 30, 2014.
Dual-Glo Luciferase Assay System, Instructions for Use of Products E2920, E2940 and E2980, Technical Manual, Promega, 2011, 27 pages.
Hakamata, T. et al. (eds.), Chapter 14—Applications in Photomultiplier Tubes, Basics and Applications, Third Edition (Edition 3a), Hamamatsu Photonics K. K., 2007, 48 pages.
KeyPath MRSA/MSSA Blood Culture Test—BT, 510(k) Summary, MicroPhage, Inc., Apr. 29, 2011, 15 pages.

(Continued)

*Primary Examiner* — Mindy G Brown
(74) *Attorney, Agent, or Firm* — David J. Chang

(57) ABSTRACT

Methods and systems are provided for packaging reporter nucleic acid molecules into non-replicative transduction particles for use as reporter molecules. The non-replicative transduction particles can be constructed from viruses and use viral transduction and replication systems. The reporter nucleic acid molecules include a reporter gene, such as a reporter molecule or selectable marker, for detecting target genes or cells. Methods and systems are provided for detection of cells and target nucleic acid molecules using the non-replicative transduction particles as reporter molecules.

17 Claims, 35 Drawing Sheets

Specification includes a Sequence Listing.

(56) References Cited

U.S. PATENT DOCUMENTS

| | | |
|---|---|---|
| 5,912,119 A | 6/1999 | Radman et al. |
| 5,919,625 A | 7/1999 | DuBois et al. |
| 5,939,262 A | 8/1999 | Pasloske et al. |
| 5,965,415 A | 10/1999 | Radman et al. |
| 5,989,499 A | 11/1999 | Catanzariti et al. |
| 6,144,448 A | 11/2000 | Mitoma |
| 6,189,580 B1 | 2/2001 | Thibault et al. |
| 6,218,176 B1 | 4/2001 | Berthold et al. |
| 6,271,034 B1 | 8/2001 | Bardarov et al. |
| 6,300,061 B1 | 10/2001 | Jacobs, Jr. et al. |
| 6,326,208 B1 | 12/2001 | Denney |
| 6,451,258 B1 | 9/2002 | Malmqvist |
| 6,544,729 B2 | 4/2003 | Sayler et al. |
| 6,555,312 B1 | 4/2003 | Nakayama |
| 6,818,185 B1 | 11/2004 | Petersen et al. |
| 7,001,719 B2 | 2/2006 | Wicks et al. |
| 7,087,226 B2 | 8/2006 | Ramachandran et al. |
| 7,125,727 B2 | 10/2006 | Massaro |
| 7,160,511 B2 | 1/2007 | Takahashi et al. |
| 7,166,425 B2 | 1/2007 | Madonna et al. |
| 7,244,612 B2 | 7/2007 | Goodridge |
| 7,284,900 B2 | 10/2007 | Mayer |
| 7,364,843 B2 | 4/2008 | Peak |
| 7,695,682 B2 | 4/2010 | Chojnacki et al. |
| 7,972,773 B2 | 7/2011 | Madonna et al. |
| 8,021,343 B2 | 9/2011 | Nalesso et al. |
| 8,057,756 B2 | 11/2011 | Londo et al. |
| 8,092,990 B2 | 1/2012 | Voorhees |
| 8,124,024 B2 | 2/2012 | Ching et al. |
| 8,153,119 B2 | 4/2012 | Collins et al. |
| 8,182,804 B1 | 5/2012 | Collins et al. |
| 8,216,780 B2 | 7/2012 | Smith et al. |
| 8,329,889 B2 | 12/2012 | Collins et al. |
| 8,377,398 B2 | 2/2013 | McDevitt et al. |
| 8,455,186 B2 | 6/2013 | Smith et al. |
| 8,530,178 B2 | 9/2013 | Sobek et al. |
| 8,619,257 B2 | 12/2013 | Plowman et al. |
| 8,829,473 B1 | 9/2014 | Griswold et al. |
| 9,388,453 B2 | 7/2016 | Rey |
| 9,771,622 B2 | 9/2017 | Rey et al. |
| 2004/0126783 A1 | 7/2004 | Bortolin et al. |
| 2004/0191863 A1 | 9/2004 | Cheng et al. |
| 2005/0003346 A1 | 1/2005 | Voorhees et al. |
| 2005/0118719 A1 | 6/2005 | Schmidt et al. |
| 2005/0155438 A1 | 7/2005 | Belgardt |
| 2005/0206895 A1 | 9/2005 | Salmelainen |
| 2005/0273869 A1 | 12/2005 | Court et al. |
| 2006/0099115 A1 | 5/2006 | Sandberg |
| 2006/0205085 A1 | 9/2006 | Handique et al. |
| 2006/0210968 A1 | 9/2006 | Goodridge |
| 2006/0257991 A1 | 11/2006 | McDevitt et al. |
| 2007/0003950 A1 | 1/2007 | Shen et al. |
| 2007/0072174 A1 | 3/2007 | Sayler et al. |
| 2007/0136827 A1 | 6/2007 | Collins et al. |
| 2007/0178450 A1 | 8/2007 | Wheeler et al. |
| 2007/0292397 A1 | 12/2007 | McNulty et al. |
| 2008/0003564 A1 | 1/2008 | Chen et al. |
| 2008/0153096 A1 | 6/2008 | Witty et al. |
| 2008/0193946 A1 | 8/2008 | McMillan |
| 2008/0241819 A1 | 10/2008 | Smith |
| 2008/0272283 A1 | 11/2008 | Feldsine et al. |
| 2008/0286757 A1 | 11/2008 | Gaisford et al. |
| 2009/0123977 A1 | 5/2009 | Mendez et al. |
| 2009/0155768 A1 | 6/2009 | Scholl et al. |
| 2009/0155838 A1 | 6/2009 | Hale |
| 2010/0055669 A1 | 3/2010 | Luque et al. |
| 2010/0112549 A1 | 5/2010 | Rey et al. |
| 2010/0133200 A1 | 6/2010 | Gin et al. |
| 2010/0196877 A1 | 8/2010 | Smith et al. |
| 2010/0225920 A1 | 9/2010 | Xia et al. |
| 2011/0033847 A1 | 2/2011 | Walsh et al. |
| 2011/0076672 A1 | 3/2011 | Schofield |
| 2011/0097702 A1 | 4/2011 | Voorhees |
| 2011/0117025 A1 | 5/2011 | Dacosta et al. |
| 2011/0183314 A1 | 7/2011 | Smith |
| 2012/0003630 A1 | 1/2012 | Collins et al. |
| 2012/0071342 A1 | 3/2012 | Lochhead et al. |
| 2012/0134975 A1 | 5/2012 | Hyde et al. |
| 2012/0143024 A1 | 6/2012 | Phillips et al. |
| 2012/0225423 A1 | 9/2012 | Schwoebel et al. |
| 2012/0252699 A1 | 10/2012 | Jaffrey et al. |
| 2012/0288897 A1 | 11/2012 | Ching et al. |
| 2012/0328576 A1 | 12/2012 | Jayasheela et al. |
| 2013/0122549 A1 | 5/2013 | Lu et al. |
| 2014/0134656 A1 | 5/2014 | Dortet et al. |
| 2014/0272928 A1 | 9/2014 | Rey et al. |

FOREIGN PATENT DOCUMENTS

| | | |
|---|---|---|
| WO | WO 1987/006706 A1 | 11/1987 |
| WO | 2009004041 A1 | 4/1990 |
| WO | WO 93/24641 A2 | 12/1993 |
| WO | WO 94/13788 A1 | 6/1994 |
| WO | WO 1994/025572 A1 | 11/1994 |
| WO | WO 1996/021007 A2 | 7/1996 |
| WO | WO 00/61804 A1 | 10/2000 |
| WO | WO 2002/081679 A2 | 10/2002 |
| WO | WO 2003/060066 A2 | 7/2003 |
| WO | WO 2005/085855 A2 | 9/2005 |
| WO | WO 2006/075996 A2 | 7/2006 |
| WO | WO 2007/115378 A1 | 10/2007 |
| WO | WO 2008/049036 A2 | 4/2008 |
| WO | 2008131230 A1 | 10/2008 |
| WO | 2008131239 A1 | 10/2008 |
| WO | WO 2008/131230 A1 | 10/2008 |
| WO | WO 2010/096584 A1 | 8/2010 |
| WO | WO 2013/049121 A2 | 4/2013 |
| WO | WO 2014/160418 A2 | 10/2014 |
| WO | WO 2014/164768 A1 | 10/2014 |

OTHER PUBLICATIONS

Lampinen, J. et al., Comparison of flash and glow ATP assays with thermo scientific varioskan flash luminometry,: Application Note: AP-MIB-VARIO12-0108, Thermo Scientific, 2008, 6 pages.

Luciferase Measurements using the Clarity Luminescence Microplate Reader. Luminescence made easy. Application Note, BioTek Instruments, Inc., 2006, 5 pages.

NucliSENS EasyQ MRSA Assay, 510(k) Summary, bioMerieux, Inc., Sep. 20, 2010, 23 pages.

Ulitzur, S. et al., "Introduction of Lux Genes into Bacteria: A New Approach for Specific Determination of Bacteria and Their Antibiotic Susceptibility," Schlómerich J. et al. (eds.), Bioluminescence and Chemiluminescence New Perspectives, Chichester: John Wiley and Sons, 1987, pp. 463-472.

Vandercam, B. et al., "Amplification-based DNA analysis in the diagnosis of prosthetic joint infection," Journal of Molecular Diagnostics, 10(6):537-543 (2008).

Watanabe, T. et al., "Studies on Luciferase from Photobacterium phosphoreum," Journal of Biochemistry, 1972, pp. 647-653, vol. 72, No. 3.

Carriere, C. et al., "Conditionally Replicating Luciferase Reporter Phages: Improved Sensitivity for Rapid Detection and Assessment of Drug Susceptibility of Mycobacterium tuberculosis," Journal of Clinical Microbiology, Dec. 1997, pp. 3232-3239, vol. 35, No. 12.

Cronan, JE, "Cosmid-Based System for Transient Expression and Absolute Off-to-On Transcriptional Control of *Escherichia coli* Genes", Journal of Bacteriology, 2003, 185 (22): p. 6522-6529.

Cronan, JE, "Improved Plasmid-Based System for Fully Regulated Off-To-On Gene Expression in *Escherichia coli*: Application to Production of Toxic Proteins", Plasmid, 2013, 69(1): p. 81-69.

Anderson W. F., "Human Gene Therapy," Nature, Apr. 30,1998, pp. 25-30, vol. 392, No. 6679.

Arnaud, M. et al., "New Vector for Efficient Allelic Replacement in Naturally Nontransformable, Low-GC-Content, Gram-Positive Bacteria," Applied and Environmental Microbiology, Nov. 2004, pp. 6887-6891, vol. 70, Issue 11.

Arthur, M., et al., "The VanS Sensor Negatively Controls VanR-Mediated Transcriptional Activation of Glycopeptide Resistance

(56) References Cited

OTHER PUBLICATIONS

Genes of Tn1546 and Related Elements in the Absence of Induction," Journal of Bacteriology, 1997, pp. 97-106, vol. 179, No. 1.
Brantl, S. "Antisense—RNA Regulation and RNA Interference," Biochimica et Biophysica Acta (BBA)—Gene Structure and Expression, 2002, pp. 15-25, vol. 1575, No. 1-3.
Brantl, S., "Regulatory Mechanisms Employed by cis-Encoded Antisense RNAs," Current Opinion in Microbiology, 2007, pp. 102-109, vol. 10.
Carriere, C. et al., "Conditionally Replicating Luciferase Reporter Phages: Improved Sensitivity for Rapid Detection and Assessment of Drug Susceptibility of Mycobacterium Tuberculosis," Journal of Clinical Microbiology, 1997, pp. 3232-3239, vol. 35, No. 12.
Charpentier, E. et al., "Novel Cassette-Based Shuttle Vector System for Gram-Positive Bacteria," Applied and Environmental Microbiology, Oct. 2004, pp. 6076-6085, vol. 70, No. 10.
Chen, H.J. et al., "New Structure of Phage-Related Islands Carrying fusB and A Virulence Gene in Fusidic Acid-Resistant *Staphylococcus epidermis*," GenBank Accession No. AB82059.1: *Staphylococcus epidermis* DNA, Pathogenicity Island Region, Strain: NTUH-3692, Anbimicrob. Agents Chemother., 2013, pp. 5737-5739, vol. 57, No. 11.
Christie, G.E. et al., "The Complete Genomes of *Staphylococcus aureus* Bacteriophages 80 and 80alpha—Implications for the Specificity of SaPI Mobilization," Virology, Nov. 25, 2010, pp. 381-390, vol. 407, No. 2.
Desamparados Ferrer, M. et al., "RinA Controls Phage-Mediated Packaging and Transfer of Virulence Genes in Gram-Positive Bacteria," Nucleic Acids Research, 2011, pp. 5866-5878, vol. 39, No. 14.
Dornburg, R., "Reticuloendotheliosis Viruses and Derived Vectors," Gene Therapapy, 1995, pp. 301-310, vol. 2.
Eglitis, M. A. et al., "Retroviral Vectors for Introduction of Genes into Mammalian Cells," Biotechniques, Jul./Aug. 1988, pp. 608-614, vol. 6, No. 7.
Fisher, K. J. et al., "Transduction with Recombinant Adeno-Associated Virus for Gene Therapy is Limited by Leading-Strand Synthesis," Journal of Virology, 1996, pp. 520-532, vol. 70, No. 1.
Frees, D., et al., "Clp ATPases are Required for Stress Tolerance, Intracellular Replication and Biofilm Formation in *Staphylococcus aureus*," Molecular Microbiology, 2004, pp. 1445-1462, vol. 54, No. 5.
Good, L., "Translation Repression by Antisense Sequences," Cellular and Molecular Life Sciences, 2003, pp. 854-861, vol. 60, No. 5.
Isaacs, F.J. et al., "Engineered Riboregulators Enable Post-Transcriptional Control of Gene Expression," Nature Biotechnology, Jul. 2004, pp. 841-847, vol. 22, No. 7.
Karlsson, S., et al., "Expression of Clostridium difficile Toxins A and B and Their Sigma Factor TcdD is Controlled by Temperature," Infection and Immunity, Apr. 2003, pp. 1784-1793, vol. 71, No. 4.
Kreiswirth, B.N. et al., "The Toxic Shock Syndrome Exotoxin Structural Gene is Not Detectably Transmitted by a Prophage," Nature, Oct. 20-26, 1983, pp. 709-712, vol. 305, No. 5936.
Lobocka, M.B. et al., "Genome of Bacteriophage P1," Journal of Bacteriology, Nov. 2004, pp. 7032-7068, vol. 186, No. 21.
Lofdahl, S. et al., "Cloning of Restriction Fragments of DNA From *Staphylococcal Bacteriophage* ɸ11," Journal of Virology, 1981, pp. 795-801, vol. 37, No. 2.
Maiques, E. et al., "Role of Staphylococcal Phage and SaPI Integrase in Intra- and Interspecies SaPI Transfer," Journal of Bacteriology, Aug. 2007, pp. 5608-5616, vol. 189, No. 15.
Miller, A. D., "Retrovirus Packaging Cells," Human Gene Therapapy, 1990, pp. 5-14, vol. 1.
Novick, R.P. et al., "Small *Staphylococcus-auerus* Plasmids are Transduced as Linear Multimers That are Formed and Resolved by Replicative Processes," Journal of Molecular Biology, 1986, pp. 209-220, vol. 192, No. 2.

Opdyke, J.A. et al., "GadY, a Small-RNA Regulator of Acid Response Genes in *Escherichia coli*," Journal of Bacteriology, 2004, pp. 6698-6705, vol. 186, No. 20.
Otsuji, N. et al., "Induction of Phage Formation in the Lysogenic *Escherichia coli* K12 by Mitomycin C," Nature, 1959, pp. 1079-1080, vol. 184, No. 4692.
PCT International Search Report and Written Opinion, PCT Application No. PCT/US14/26536, dated Jan. 14, 2015, 57 pages.
PCT Invitation to Pay Additional Fees, PCT Application No. PCT/US14/26536, dated Oct. 24, 2014, 6 pages.
Pfeiffer, V. et al., "Coding Sequence Targeting by MicC RNA Reveals Bacterial mRNA Silencing Downstream of Translational Initiation," Nature Structural Molecular Biology, 2009, pp. 840-846, vol. 16.
Primrose, S.B. et al., "Principles of Gene Manipulation and Genomics," Blackwell Publishing, 2006, Seventh Edition, pp. 55-95.
Rubinson, D. A .et al., "A Lentivirus-Based System to Functionally Silence Genes in Primary Mammalian Cells, Stem Cells and Transgenic Mice by RNA Interference," Nature Genetics, Mar. 2003, pp. 401-406, vol. 33.
Samulski, R.J. et al., "A Recombinant Plasmid from Which an Infectious Adeno-Associated Virus Genome Can Be Excised In Vitro and Its Use to Study Viral Replication," Journal of Virology, Oct. 1987, pp. 3096-3101, vol. 61, No. 10.
Samulski, R.J. et al. "Helper-Free Stocks of Recombinant Adeno-Associated Viruses: Normal Integration Does Not Require Viral Gene Expression," Journal of Virology, Sep. 1989, pp. 3822-3826, vol. 63, No. 9.
Tormo, M.A. et al., "*Staphylococcus aureus* Pathogenicity Island DNA is Packaged in Particles Composed of Phage Proteins," Journal of Bacteriology, Apr. 2008, pp. 2434-2440, vol. 190, No. 7.
Ubeda, C. et al., "Specificity of Staphylococcal Phage and SaPI DNA Packaging as Revealed by Integrase and Terminase Mutations," Molecular Microbiology, Apr. 2009, pp. 98-108, vol. 72, No. 1.
Viral Vectors for Gene Therapy : Methods and Protocols. Methods in Molecular Biology, Merten, O.-W. et al. (eds.), 466 pages, vol. 737. 2011.
Westwater, C., et al., "Development of a P1 Phagemid System for the Delivery of DNA into Gram-Negative Bacteria," Microbiology, 2002, pp. 943-950, vol. 148, No. 4.
Xia, H. et al., "siRNA-Mediated Gene Silencing in vitro and in vivo," Nature Biotechnology, Oct. 2002, pp. 1006-1010, vol. 20, No. 10.
Ye, Z-H. et al., "Cloning, Sequencing, and Genetic Characterization of Regulatory Genes, rinA and rinB, Required for the Activiation of Staphylococcal Phage ɸ11 int Expression," Journal of Bacteriology, Feb. 1993, pp. 1095-1102, vol. 175, No. 4.
Billard, P., et al., Bioluminescence-Based Assays for Detection and Characterization of Bacteria and Chemicals in Clinical Laboratories, Clinical Biochemistry, Feb. 1, 1998, pp. 1-14, vol. 31, No. 1, Elsevier.
Extended European Search Report dated Jan. 4, 2017 in Application No. 14775849.4, 8 pages.
Juhas et al, Genomic islands: tools of bacterial horizontal gene transfer and evolution, FEMS Microbiology Review, 2009, pp. 376-393, vol. 33.
Khan, S.A., et al., Functional origin of replication of pT181 plasmid DNA is contained within a 168-base-pair segment, Proceedings of the National Academy of Sciences, Aug. 1982, pp. 4580-4584, vol. 79, No. 15.
Lin, H., et al., DNA Requirements in Vivo for Phage T4 Packaging, Virology, Mar. 1998, pp. 118-127, vol. 242, No. 1, Academic Press.
Ram, G., et al., Staphylococcal pathogenicity island interference with helper phage reproduction is a paradigm of molecular parasitism, Proceedings of the National Academy of Sciences, Oct. 2, 2012, pp. 16300-16305, vol. 109, No. 40, National Institutes of Health, National Cancer Institute.
Russell et al, Characterization of the B-lactamase promoter of pBR322, Nucleic Acids Research, 1981, pp. 2517-2533, vol. 9, No. 11.
Search Report and Written Opinion dated Feb. 8, 2017 in Singapore Application No. 11201507463W, 12 pages.

(56) References Cited

OTHER PUBLICATIONS

Ubeda, C., et al., SaPI operon I is required for SaPI packaging and is controlled by LexA, Molecular Microbiology, Jul. 2007, pp. 41-50, vol. 65, No. 1, Blackwell Publishing Ltd.

Schematic of pGWP10001

Schematic of a pac-site deletion/complementation packaging system (300)

Schematic of pGW80A0001

*Schematic of a natural genomic-island packaging system (500)*

Schematic of a genomic island (GI)-based packaging system.

*Schematic of a genomic-island packaging system that does not integrate into host genome (700)*

*Schematic of a SaPIbov2 packaging system that does not integrate into host genome (800)*

Photograph of transduced MRSA clinical isolates

Luminescence in S. aureus and distinguishing MRSA vs. MSSA

*Luminescence obtained from MRSA and MSSA at various concentrations of cefoxitin* mecA
(SEQ ID NO: 19)

mecA T23 (SEQ ID NO:23)

FIGURE 30

RBS 3001, Coding Sequence 3002

(SEQ ID NO: 16)

(SEQ ID NO: 18)

NON-REPLICATIVE TRANSDUCTION PARTICLES AND TRANSDUCTION PARTICLE-BASED REPORTER SYSTEMS

CROSS REFERENCE TO RELATED APPLICATIONS

This application is a continuation of U.S. patent application Ser. No. 15/183,303, filed on Jun. 15, 2016 which is a continuation of U.S. patent application Ser. No. 14/550,335, filed on Nov. 21, 2014, now U.S. Pat. No. 9,388,453, which claims the benefit of priority to International Application No. PCT/US2014/026536, filed on Mar. 13, 2014, U.S. Provisional Application No. 61/779,177, filed on Mar. 13, 2013, U.S. Provisional Application No. 61/897,040, filed on Oct. 29, 2013, and U.S. Provisional Application No. 61/939,126, filed on Feb. 12, 2014, each of which is hereby incorporated in its entirety by reference.

REFERENCE TO SEQUENCE LISTING

This application contains a Sequence Listing submitted as an electronic text file named "33165—US5.txt", having a size in bytes of 65 kb, and created on Jan. 5, 2017. The information contained in this electronic file is hereby incorporated by reference in its entirety pursuant to 37 CFR § 1.52(e)(5).

BACKGROUND OF THE INVENTION

Field of the Invention

The invention relates to methods and compositions for packaging and delivery of non-replicative transduction reporter molecules into cells for detecting target genes in cells.

Description of the Related Art

A transduction particle refers to a virus capable of delivering a non-viral nucleic acid into a cell. Viral-based reporter systems have been used to detect the presence of cells and rely on the lysogenic phase of the virus to allow expression of a reporter molecule from the cell. These viral-based reporter systems use replication-competent transduction particles that express reporter molecules and cause a target cell to emit a detectable signal.

However, the lytic cycle of the virus has been shown to be deleterious to viral-based reporter assays. Carriere, C. et al., *Conditionally replicating luciferase reporter phages: Improved sensitivity for rapid detection and assessment of drug susceptibility of Mycobacterium tuberculosis*. Journal of Clinical Microbiology, 1997. 35(12): p. 3232-3239. Carrière et al. developed *M. tuberculosis/bacillus* Calmette-Guèrin (BCG) luciferase reporter phages that have their lytic cycles suppressed at 30° C., but active at 37° C. Using this system, Carrière et al. have demonstrated the detection of BCG using phage reporters with a suppressed lytic cycle.

There are disadvantages, however, associated with suppressing but not eliminating the replication functions of the bacteriophage in bacteriophage-based reporter assays. First, controlling replication functions of the bacteriophage imposes limiting assay conditions. For example, the lytic cycle of the reporter phage phAE40 used by Carrière et al. was repressed when the phage was used to infect cells at the non-permissive temperature of 30° C. This temperature requirement imposed limiting conditions on the reporter assay in that the optimum temperature for the target bacteria was 37° C. These limiting conditions hinder optimum assay performance.

Moreover, the replication functions of the virus are difficult to control. The replication of the virus should be suppressed during the use of the transduction particles as a reporter system. For example, the lytic activity of the reporter phage phAE40 reported by Carrière et al. was reduced but was not eliminated, resulting in a drop in luciferase signal in the assay. Carrière et al. highlighted possible causes for the resulting drop in reporter signal, such as intact phage-expressed genes and temperature limitations of the assay, all stemming from the fact that the lytic cycle of the phage reporter was not eliminated.

Reporter assays relying on the natural lysogenic cycle of phages can be expected to exhibit lytic activity sporadically. In addition, assays that rely on the lysogenic cycle of the phage can be prone to superinfection immunity from target cells already lysogenized with a similar phage, as well as naturally occurring host restriction systems that target incoming virus nucleic acid, thus limiting the host range of these reporter phages.

In other examples, transduction particle production systems are designed to package exogenous nucleic acid molecules, but the transduction particle often contains a combination of exogenous nucleic acid molecules and native progeny virus nucleic acid molecules. The native virus can exhibit lytic activity that is a hindrance to assay performance, and the lytic activity of the virus must be eliminated in order to purify transduction particles. However, this purification is generally not possible. In U.S. 2009/0155768 A, entitled *Reporter Plasmid Packaging System for Detection of Bacteria*, Scholl et al. describes the development of such a transduction particle system. The product of the system is a combination of reporter transduction particles and native bacteriophage (FIG. 8 in the reference). Although the authors indicate that the transduction particle and native bacteriophage can be separated by ultracentrifugation, this separation is only possible in a system where the transduction particle and the native virus exhibit different densities that would allow separation by ultracentrifugation. While this characteristic is exhibited by the bacteriophage T7-based packaging system described in the reference, this is not a characteristic that is generally applicable for other virus systems. It is common for viral packaging machinery to exhibit headful packaging that would result in native virus and transduction particles to exhibit indistinguishable densities that cannot be separated by ultracentrifugation. Virus packaging systems also rely on a minimum amount of packaging as a requirement for proper virus structural assembly that results in native virus and transduction particles with indistinguishable densities.

Thus, there is a need for non-replicative transduction particles that do not suffer from the deleterious effects from lytic functions of the virus and the possibility of being limited by superinfection immunity and host restriction mechanisms that target virus nucleic acid molecules and viral functions, all of which can limit the performance of the reporter assay by increasing limits of detection and resulting in false negative results.

Even where transduction particles have been engineered, methods for using the transduction particles to detect and report the presence of target nucleic acid molecules in cells have limitations. Some methods require disruption of the cell and cumbersome techniques to isolate and detect transcripts in the lysate. Detection methods include using labeled probes such as antibodies, aptamers, or nucleic acid probes. Labeled probes directed to a target gene can result in non-specific binding to unintended targets or generate signals that have a high signal-to-noise ratio. Therefore, there is a need for specific, effective and accurate methods for detection and reporting of endogenous nucleic acid molecules in cells.

Accordingly, methods and systems are needed for generating non-replicative transduction particles that allow packaging and expression of reporter molecules in cells, while eliminating replication-competent progeny virus. Effective and accurate methods for detecting molecules in cells using the expressed reporter molecules are also needed.

SUMMARY OF THE INVENTION

Disclosed herein is a bacterial cell packaging system for packaging a reporter nucleic acid molecule into a non-replicative transduction particle, said bacterial cell comprising a lysogenized bacteriophage genome lacking a bacteriophage gene encoding a packaging initiation site sequence, wherein deletion of said bacteriophage gene prevents packaging of a bacteriophage nucleic acid molecule into said non-replicative transduction particle; and a reporter nucleic acid molecule comprising a second bacteriophage gene, wherein said second bacteriophage gene encodes a packaging initiation site sequence and facilitates the packaging a replica of said reporter nucleic acid molecule into said non-replicative transduction particle, wherein said second bacteriophage gene is capable of expressing a protein that is encoded by said gene, wherein said replica of said reporter nucleic acid molecule forms a replicon amenable to packaging into said non-replicative transduction particle.

In some embodiments, the reporter nucleic acid molecule is operatively linked to a promoter. In another embodiment, the promoter is selected for contributing to reactivity of a reporter molecule expressed from said reporter nucleic acid molecule in said bacterial cell. In one embodiment, the reporter nucleic acid molecule comprises an origin of replication. In yet another embodiment, the replicon comprises a concatamer amenable to packaging into said non-replicative transduction particle.

In an embodiment, the first and said second bacteriophage genes each comprises a pacA gene of the Enterobacteriaceae bacteriophage P1 and comprises said packaging initiation site sequence. In one embodiment, the second bacteriophage gene comprises the sequence of SEQ ID NO:9. In another embodiment, the replicon is the Enterobacteriaceae bacteriophage P1 lytic replicon. In certain embodiments, the replicon comprises a C1 repressor-controlled P53 promoter, a promoter P53 antisense, a repL gene, and an in-frame deletion of a kilA gene. In one embodiment, the replicon comprises of the sequence of SEQ ID NO:3.

In yet another embodiment, the first and said second bacteriophage genes each comprises a small terminase (terS) gene comprising said packaging initiation site sequence. In one embodiment, the terS gene is a S. aureus bacteriophage φ11 or φ80α terS gene.

In another embodiment, the replicon is derived from a S. aureus pT181 plasmid origin of replication. In yet another embodiment, the replicon comprises the sequence of SEQ ID NO:5. In some embodiments, the packaging initiation site sequence of said second bacteriophage gene comprises a pac-site. In other embodiments, the pac-site of said second bacteriophage gene comprises the sequence of SEQ ID NO:7. In one aspect, the packaging initiation site sequence of said second bacteriophage gene comprises a cos-site. In another aspect, the packaging initiation site sequence of said second bacteriophage gene comprises a concatamer junction.

In another aspect, a plasmid comprises said reporter nucleic acid molecule. In one aspect, the second bacteriophage gene is operatively linked to a promoter. In another embodiment, the promoter is an inducible promoter or a constitutive promoter. In one embodiment, the bacteriophage comprises the Enterobacteriaceae bacteriophage P1. In yet another embodiment, the bacteriophage comprises a S. aureus bacteriophage φ80α or a bacteriophage φ11. In one aspect, the bacterial cell comprises an E. coli cell. In another aspect, the bacterial cell comprises an S. aureus cell. In yet another embodiment, the bacterial cell comprises a Gram-negative cell. In other embodiments, the bacterial cell comprises a Gram-positive cell.

In another aspect, the reporter nucleic acid molecule comprises a reporter gene. In one aspect, the reporter gene encodes a detectable and/or a selectable marker. In certain aspects, the reporter gene is selected from the group consisting of enzymes mediating luminescence reactions (luxA, luxB, luxAB, luc, mc, nluc), enzymes mediating colorimetric reactions (lacZ, HRP), fluorescent proteins (GFP, eGFP, YFP, RFP, CFP, BFP, mCherry, near-infrared fluorescent proteins), affinity peptides (His-tag, 3X-FLAG), and selectable markers (ampC, tet(M), CAT, erm). In another aspect, the reporter nucleic acid molecule comprises an aptamer. In yet another aspect, the reporter nucleic acid molecule comprises a nucleic acid transcript sequence that is complementary to a second sequence in said reporter nucleic acid molecule.

In one embodiment, the nucleic acid transcript sequence is complementary to a cellular transcript. In another embodiment, the nucleic acid transcript sequence comprises a cis-repressing sequence. In yet another embodiment, the replica of said reporter nucleic acid molecule comprises a nucleic acid transcript sequence that is complementary to a second sequence in said replica of said reporter nucleic acid molecule, wherein the nucleic acid transcript sequence is complementary to a cellular transcript and wherein said nucleic acid transcript sequence comprises a cis-repressing sequence.

In some embodiments, the method for packaging a reporter nucleic acid molecule into a non-replicative transduction particle, comprising providing conditions to said bacterial cell described herein that induce a lytic phase of said bacteriophage to produce non-replicative transduction particles packaged with said reporter nucleic acid molecule; and isolating said non-replicative transduction particle comprising said reporter nucleic acid molecule. In one embodiment, the non-replicative transduction particle does not contain a replicated bacteriophage genome. In another embodiment, induction of said lytic phase triggers excision of said genomic island nucleic acid molecule from said genome of said bacterial cell.

In another embodiment, the composition comprising said non-replicative transduction particle comprising a replica of said reporter nucleic acid molecule produced from the method described herein.

The invention comprises a bacterial cell packaging system for packaging a reporter nucleic acid molecule into a non-replicative transduction particle, said bacterial cell comprising a lysogenized bacteriophage genome comprising a first bacteriophage packaging initiation site sequence, wherein said first bacteriophage packaging initiation site sequence comprises a mutation that prevents packaging of a bacteriophage nucleic acid molecule into said non-replicative transduction particle; and a reporter nucleic acid molecule comprising a second bacteriophage packaging initiation site sequence, wherein said second bacteriophage packaging initiation site sequence lacks said mutation and facilitates the packaging of a replica of said reporter nucleic acid molecule into said non-replicative transduction particle, wherein said replica of said reporter nucleic acid molecule forms a replicon for packaging into said non-replicative transduction particle.

In one embodiment, the reporter nucleic acid molecule is operatively linked to a promoter. In another embodiment, the promoter is selected for contributing to reactivity of a reporter molecule expressed from said reporter nucleic acid molecule in said bacterial cell. In yet another embodiment, the reporter nucleic acid molecule comprises an origin of replication. In one embodiment, the replicon comprises a concatamer amenable to packaging into said non-replicative transduction particle. In another aspect, the first and said second bacteriophage packaging initiation site sequences each comprise a packaging initiation site sequence from a small terminase gene. In one aspect, the first and said second bacteriophage packaging initiation site sequences each comprise a pac-site sequence from a pacA gene of the Enterobacteriaceae bacteriophage P1. In another aspect, the first bacteriophage packaging initiation site sequence comprises SEQ ID NO:2. In yet another aspect, the second bacteriophage packaging initiation site sequence comprises SEQ ID NO:1. In one embodiment, the replicon comprises an Enterobacteriaceae bacteriophage P1 lytic replicon. In another embodiment, the replicon comprises a C1 repressor-controlled P53 promoter, a promoter P53 antisense, a repL gene, and an in-frame deletion of a kilA gene. In another aspect, the replicon comprises the sequence of SEQ ID NO:3. In certain aspects, the first and said second bacteriophage packaging initiation site sequences each comprise a pac-site sequence from a small terminase (terS) gene of an S. aureus bacteriophage φ11 or φ80α. In another aspect, the replicon is derived from a S. aureus pT181 plasmid origin of replication. In yet another aspect, the replicon comprises the sequence of SEQ ID NO:5. In one aspect, the first bacteriophage packaging initiation site sequence comprises the sequence of SEQ ID NO:2. In some embodiments, the second bacteriophage packaging initiation site sequence comprises the sequence of SEQ ID NO:1. In other embodiments, the packaging initiation site sequence comprises a pac-site. In another embodiment, the packaging initiation site sequence comprises a cos-site. In yet another embodiment, the packaging initiation site sequence comprises a concatamer junction. In some embodiments, the mutation in said first bacteriophage packaging initiation site sequence comprises a silent mutation. In another embodiment, the mutation in said first bacteriophage packaging initiation site sequence prevents cleavage of said packaging initiation sequence. In another embodiment, a plasmid comprises said reporter nucleic acid molecule. In one embodiment, the bacteriophage comprises Enterobacteriaceae bacteriophage P1.

In another embodiment, the bacteriophage comprises the S. aureus bacteriophage φ11 or φ80α. In one embodiment, the bacterial cell comprises an E. coli cell. In another embodiment, the bacterial cell comprises an S. aureus cell. In some embodiments, the bacterial cell comprises a Gram-negative bacterial cell. In one aspect, the bacterial cell comprises a Gram-positive bacterial cell. In another aspect, the reporter nucleic acid molecule comprises a reporter gene. In yet another aspect, the reporter gene encodes a detectable marker and/or a selectable marker.

In other aspects, the reporter gene is selected from the group consisting of: genes encoding enzymes mediating luminescence reactions (luxA, luxB, luxAB, luc, mc, nluc), genes encoding enzymes mediating colorimetric reactions (lacZ, HRP), genes encoding fluorescent proteins (GFP, eGFP, YFP, RFP, CFP, BFP, mCherry, near-infrared fluorescent proteins), nucleic acid molecules encoding affinity peptides (His-tag, 3X-FLAG), and genes encoding selectable markers (ampC, tet(M), CAT, erm). In another aspect, the reporter nucleic acid molecule comprises an aptamer. In other aspects, the replicon is packaged into said non-replicative transduction particle by bacteriophage packaging machinery. In some embodiments, the reporter nucleic acid molecule comprises a nucleic acid transcript sequence that is complementary to a second sequence in said reporter nucleic acid molecule. In another embodiment, the nucleic acid transcript sequence is complementary to a cellular transcript.

In one aspect, the nucleic acid transcript sequence comprises a cis-repressing sequence. In another aspect, the replica of said reporter nucleic acid molecule comprises a nucleic acid transcript sequence that is complementary to a second sequence in said replica of said reporter nucleic acid molecule, wherein said nucleic acid transcript sequence is complementary to a cellular transcript, and wherein said nucleic acid transcript sequence comprises a cis-repressing sequence.

In certain aspects, the method for packaging a reporter nucleic acid molecule into a non-replicative transduction particle, comprising: providing conditions to said bacterial cell described herein that induce a lytic phase of said bacteriophage to produce non-replicative transduction particles packaged with said reporter nucleic acid molecule; and isolating said non-replicative transduction particle comprising said reporter nucleic acid molecule.

In other aspects, the non-replicative transduction particle does not contain a replicated bacteriophage genome. In one aspect, the induction of said lytic phase triggers excision of said genomic island nucleic acid molecule from said genome of said bacterial cell.

In another aspect, the invention comprises a composition comprising said non-replicative transduction particle comprising a replica of said reporter nucleic acid molecule produced from said method described herein.

In one aspect, the invention includes a bacterial cell packaging system for packaging a reporter nucleic acid molecule into a non-replicative transduction particle, said bacterial cell comprising: a lysogenized bacteriophage genome comprising a first bacteriophage gene comprising a deletion of a packaging initiation site sequence of said first bacteriophage gene that prevents packaging of a bacteriophage nucleic acid molecule into said non-replicative transduction particle; and a reporter nucleic acid molecule comprising a second bacteriophage gene comprising a second packaging initiation site sequence that facilitates the packaging a replica of said reporter nucleic acid molecule into said non-replicative transduction particle, wherein said second bacteriophage gene encodes a protein, wherein said replica of said reporter nucleic acid molecule forms a replicon for packaging into said non-replicative transduction particle.

In another aspect, the reporter nucleic acid molecule is operatively linked to a promoter. In one aspect, the promoter is selected for contributing to reactivity of a reporter molecule expressed from said reporter nucleic acid molecule in said bacterial cell. In certain aspects, the reporter nucleic acid comprises an origin of replication. In another aspect, the replicon comprises a concatamer amenable to packaging into said non-replicative transduction particle. In one aspect, the first and said second bacteriophage genes each comprises a pacA gene of the Enterobacteriaceae bacteriophage P1 and comprise said packaging initiation site sequence. In another aspect, the first bacteriophage gene comprises the sequence of SEQ ID NO:6. In certain aspects, the second bacteriophage gene comprises the sequence SEQ ID NO:7. In one aspect, the replicon comprises an Enterobacteriaceae bacteriophage P1 lytic replicon. In yet another aspect, the replicon comprises a C1 repressor-controlled P53 promoter, a promoter P53 antisense, a repL gene, and an in-frame deletion of a kilA gene. In another aspect, the replicon comprises the sequence of SEQ ID NO:3. In other aspects, the first and said second bacteriophage genes each comprises a small terminase (terS) gene comprising said packaging initiation site sequence. In one aspect, the terS gene is a S. aureus bacteriophage φ11 or φ80α terS gene. In another aspect, the first bacteriophage gene comprises the sequence of SEQ ID NO:8. In yet another aspect, the second bacteriophage gene comprises the sequence of SEQ ID NO:9. In one aspect, the replicon is derived from a S. aureus pT181 plasmid origin of replication. In one embodiment, the replicon comprises the sequence of SEQ ID NO:5, In another embodiment, the packaging initiation site sequence of said second bacteriophage gene comprises a pac-site. In yet another embodiment, the packaging initiation site sequence of said second bacteriophage gene comprises a cos-site.

In certain embodiments, the packaging initiation site sequence of said second bacteriophage gene comprises a concatamer junction. In one embodiment, a plasmid comprises said reporter nucleic acid molecule. In another embodiment, the second bacteriophage gene is operatively linked to a promoter. In yet another embodiment, the promoter is an inducible promoter or a constitutive promoter. In certain embodiments, the bacteriophage comprises the Enterobacteriaceae bacteriophage P1. In one embodiment, the bacteriophage comprises the S. aureus bacteriophage φ80α or bacteriophage φ11. In other embodiments, the bacterial cell comprises an E. coli cell. In another embodiment, the bacterial cell comprises an S. aureus cell. In one embodiment, the bacterial cell comprises a Gram-negative cell. In another embodiment, the bacterial cell comprises a Gram-positive cell.

In another aspect, the reporter nucleic acid molecule comprises a reporter gene. In one aspect, the reporter gene encodes a detectable and/or a selectable marker. In another aspect, the reporter gene is selected from the group consisting of genes encoding enzymes mediating luminescence reactions (luxA, luxB, luxAB, luc, ruc, nluc), genes encoding enzymes mediating colorimetric reactions (lacZ, HRP), genes encoding fluorescent proteins (GFP, eGFP, YFP, RFP, CFP, BFP, mCherry, near-infrared fluorescent proteins), nucleic acid molecules encoding affinity peptides (His-tag, 3X-FLAG), and genes encoding selectable markers (ampC, tet(M), CAT, erm). In one embodiment, the reporter nucleic acid molecule comprises an aptamer. In another embodiment, the replicon is packaged into said non-replicative transduction particle by bacteriophage packaging machinery. In yet another embodiment, the reporter nucleic acid molecule comprises a nucleic acid transcript sequence that is complementary to a second sequence in said reporter nucleic acid molecule. In one embodiment, the nucleic acid transcript sequence is complementary to a cellular transcript. In another embodiment, the nucleic acid transcript sequence comprises a cis-repressing sequence. In certain embodiments, the replica of said reporter nucleic acid molecule comprises a nucleic acid transcript sequence that is complementary to a second sequence in said replica of said reporter nucleic acid molecule, wherein said nucleic acid transcript sequence is complementary to a cellular transcript and wherein said nucleic acid transcript sequence comprises a cis-repressing sequence.

The invention includes a method for packaging a reporter nucleic acid molecule into a non-replicative transduction particle, comprising: providing conditions to said bacterial cell that induce a lytic phase of said bacteriophage to produce non-replicative transduction particles packaged with said reporter nucleic acid molecule; and isolating said non-replicative transduction particle comprising said reporter nucleic acid molecule. In one embodiment, the non-replicative transduction particle does not contain a replicated bacteriophage genome. In another embodiment, the induction of said lytic phase triggers excision of said genomic island nucleic acid molecule from said genome of said bacterial cell.

In some aspects, the invention includes a composition comprising said non-replicative transduction particle comprising a replica of said reporter nucleic acid molecule produced from said method described herein.

In another aspect, the invention includes a bacterial cell packaging system for packaging a reporter nucleic acid molecule into a non-replicative transduction particle, said bacterial cell comprising: a lysogenized bacteriophage genome lacking a packaging gene and comprising genes that encode proteins that form said non-replicative transduction particle; and a genomic island nucleic acid molecule comprising a reporter nucleic acid molecule and a packaging gene. In one aspect, the packaging gene comprises a small terminase (terS) gene. terS gene comprises a S. aureus bacteriophage φ80α terS gene or a bacteriophage φ11 terS gene.

In one aspect, the terS gene comprises the sequence of SEQ ID NO:9. In another aspect, the genomic island nucleic acid molecule comprises a SaPIbov2 genomic island nucleic acid molecule. In yet another aspect, the genomic island nucleic acid molecule is selected from the group consisting of a SaPI, a SaPI1, a SaPI2, a SaPIbov1 and a SaPibov2 genomic island nucleic acid molecule. In another embodiment, the reporter nucleic acid molecule is operatively linked to a promoter. In yet another embodiment, the reporter nucleic acid molecule comprises an origin of replication. In some embodiments, the bacteriophage comprises a S. aureus bacteriophage φ80α or bacteriophage φ11. In other embodiments, the bacterial cell comprises an S. aureus cell. In one embodiment, the genomic island nucleic acid molecule comprises an integrase gene and wherein said integrase gene encodes an integrase protein for excising and integrating said genomic island nucleic acid molecule out of and into a bacterial genome of said bacterial cell. In another embodiment, the integrase gene comprises the sequence of SEQ ID NO:10. In yet another embodiment, the genomic island nucleic acid molecule is integrated into a bacterial genome of said bacterial cell.

In certain aspects, the genomic island nucleic acid molecule can be replicated and forms molecule replicon that is amenable to packaging by the bacteriophage packaging machinery in said bacterial cell. In another aspect, the nucleic acid molecule forms a concatamer. In yet another aspect, the replicated genomic island nucleic acid molecule is capable of being packaged into said non-replicative transduction particle. In certain aspects, the packaging gene comprises a pac site sequence. In another aspect, the packaging gene comprises a cos-site sequence. In yet another embodiment, the packaging gene comprises a concatamer junction.

In other embodiments, the reporter nucleic acid molecule comprises a reporter gene. In some embodiments, the reporter gene encodes a selectable marker and/or a selectable marker. In another embodiment, the reporter gene is selected from the group consisting of enzymes mediating luminescence reactions (luxA, luxB, luxAB, luc, ruc, nluc), enzymes mediating colorimetric reactions (lacZ, HRP), fluorescent proteins (GFP, eGFP, YFP, RFP, CFP, BFP, mCherry, near-infrared fluorescent proteins), affinity peptides (His-tag, 3X-FLAG), and selectable markers (ampC, tet(M), CAT, erm). In certain embodiments, the reporter nucleic acid molecule comprises an aptamer. In other embodiments, the genomic island nucleic acid molecule lacks an integrase gene. In another embodiment, the invention includes a bacterial gene comprising an integrase gene operatively linked to a promoter and wherein said integrase gene encodes an integrase protein for excising and integrating said genomic island nucleic acid molecule out of and into a bacterial genome of said bacterial cell. In one embodiment, the reporter nucleic acid molecule comprises a nucleic acid transcript sequence that is complementary to a second sequence in said reporter nucleic acid molecule. In other embodiments, the nucleic acid transcript sequence is complementary to a cellular transcript. In yet other embodiments, the nucleic acid transcript sequence comprises a cis-repressing sequence. In another embodiment, the replica of said reporter nucleic acid molecule comprises a nucleic acid transcript sequence that is complementary to a second sequence in said replica of said reporter nucleic acid molecule. In other embodiments, the nucleic acid transcript sequence is complementary to a cellular transcript. In other embodiments, the nucleic acid transcript sequence comprises a cis-repressing sequence.

The invention includes a method for packaging a reporter nucleic acid molecule into a non-replicative transduction particle, comprising: providing conditions to said bacterial cell that induce a lytic phase of said bacteriophage to produce non-replicative transduction particles packaged with said reporter nucleic acid molecule; and isolating said non-replicative transduction particle comprising said reporter nucleic acid molecule. In some embodiments, the non-replicative transduction particle does not contain a replicated bacteriophage genome. In one embodiment, the induction of said lytic phase triggers excision of said genomic island nucleic acid molecule from said genome of said bacterial cell.

In another embodiment, the invention includes a composition comprising said non-replicative transduction particle comprising a replica of said reporter nucleic acid molecule produced from said method described herein.

The invention also includes a method for detecting a presence or an absence of a bacterial cell in a sample, comprising: introducing into a sample a non-replicative transduction particle comprising a reporter gene encoding a reporter molecule and lacking a bacteriophage genome under conditions such that said non-replicative transduction particle can transduce said bacterial cell and wherein said reporter gene can be expressed in said bacterial cell; providing conditions for activation of said reporter molecule; and detecting for a presence or an absence of a reporter signal transmitted from said expressed reporter molecule, wherein a presence of said reporter signal correctly indicates said presence of said bacterial cell.

In one embodiment, the method achieves at least 80% specificity of detection with reference to a standard, at least 90% specificity of detection with reference to a standard, or at least 95% specificity of detection with reference to a standard. In another embodiment, the method achieves at least 80% sensitivity of detection with reference to a standard, at least 85% sensitivity of detection with reference to a standard, or at least 90% sensitivity of detection with reference to a standard, or at least 95% sensitivity of detection with reference to a standard. In yet another embodiment, the method achieves at least 95% specificity of detection and at least 90% sensitivity of detection with reference to a standard. In another embodiment, the standard is a Gold standard. In yet another embodiment, the bacterial cell comprises a Methicillin Resistant *Staphylococcus aureus* (MRSA) cell. In other embodiments, the bacterial cell comprises a Methicillin Sensitive *Staphylococcus aureus* (MSSA) cell.

In another embodiment, the reporter gene encodes a detectable or selectable marker. In one embodiment, the reporter gene is selected from the group consisting of genes encoding enzymes mediating luminescence reactions (luxA, luxB, luxAB, luc, ruc, nluc), genes encoding enzymes mediating colorimetric reactions (lacZ, HRP), genes encoding fluorescent proteins (GFP, eGFP, YFP, RFP, CFP, BFP, mCherry, near-infrared fluorescent proteins), nucleic acid molecules encoding affinity peptides (His-tag, 3X-FLAG), and genes encoding selectable markers (ampC, tet(M), CAT, erm). In one embodiment, the reporter gene is operatively linked to a constitutive promoter.

In another aspect, the reporter signal can be detected from a sample at a limit of detection (LoD) of less than 1,000 colony forming units (CFU). In other aspects, the reporter signal can be detected from a sample at a limit of detection (LoD) of less than 100 colony forming units (CFU). In one aspect, the reporter signal can be detected from a sample at a limit of detection (LoD) of less than 10 colony forming units (CFU). In other aspects, the reporter signal can be detected from a sample at a LoD less than five CFU. In another aspect, the reporter signal can be detected from a sample at a LoD of three or less CFU.

In one embodiment, the method includes providing an antibiotic to said sample at a pre-determined concentration and detecting a presence or absence of said reporter signal to determine whether said bacterial cell is resistant or sensitive to said antibiotic. In another embodiment, the method includes providing varying pre-determined concentrations antibiotic to said sample and detecting the amount of said reporter signal to determine the minimum inhibitory concentration of said bacterial cell to said antibiotic.

In one aspect, the invention includes a composition comprising a nucleic acid construct that encodes a nucleic acid reporter transcript that is capable of forming at least two conformations comprising a first conformation that prevents reporter expression comprising an intramolecular double stranded region comprising a first subsequence and a second subsequence, and a second conformation that lacks said intramolecular double-stranded region and allows reporter gene expression, wherein conversion between said first and second conformations is mediated by competitive binding of a cellular transcript to said first and/or said second subsequence.

In another aspect, the invention includes a non-replicative transduction particle comprising said nucleic acid construct. In yet another aspect, the competitive binding of said cellular transcript to said first and/or said second subsequence results in said second conformation of said nucleic acid reporter construct. In one aspect, the first subsequence or said second subsequence comprises a cis-repressing sequence. In another aspect, the cis-repressing sequence comprises a sequence that is complementary or substantially complementary to a portion of said cellular transcript. In other aspects, the first subsequence or said second subsequence comprises a reporter gene sequence. In yet another aspect, the reporter gene sequence comprises a ribosome binding site. In other aspects, the reporter gene sequence encodes a detectable molecule. In another aspect, the detectable marker comprises a fluorescent molecule or an enzyme capable of mediating a luminescence or colorimetric reaction. In one embodiment, the reporter gene sequence encodes a selectable marker. In another embodiment, the selectable marker comprises an antibiotic resistance gene.

In other embodiments, the first subsequence and said second subsequence are located cis to each other on said nucleic acid construct to form said intramolecular double stranded region. In certain embodiments, the first subsequence and said second subsequence are complementary or substantially complementary to each other to form said intramolecular double stranded region. In one embodiment, the first subsequence or said second subsequence of said first conformation comprises a transcriptional enhancer sequence, and wherein said transcriptional enhancer sequence is upstream from a coding region of said reporter gene sequence. In another embodiment, the first conformation of said nucleic acid reporter transcript is capable of binding to a cleaving enzyme. In other embodiments, the first conformation of said nucleic acid reporter transcript is a target for degradation by a cellular enzyme. In other aspects, the first conformation comprises a non-binding intramolecular region. In another aspect, the non-binding intramolecular region is located 3' of said first subsequence and 5' of said second subsequence. In other aspects, the non-binding intramolecular region comprises a sequence YUNR, wherein Y is a pyrimidine, U is a Uracil, N is any nucleotide, and R is a purine.

In one embodiment, the first subsequence or said second subsequence comprises a modified sequence of said cellular transcript. In another embodiment, the modified sequence comprises a nucleotide substitution. In yet another embodiment, the modified sequence comprises a sequence insertion, a deletion or an inversion of said cellular transcript.

The method includes a composition comprising a nucleic acid construct that encodes a nucleic acid reporter transcript comprising a gene reporter sequence and that is capable of forming at least two conformations of said nucleic acid reporter transcript, a first unstable conformation that prevents translation of said reporter gene sequence in said nucleic acid reporter transcript, and a second stable conformation resulting from binding of said first unstable conformation with a cellular transcript, said second stable secondary conformation allowing translation of said reporter gene sequence of said nucleic acid reporter transcript.

In one embodiment, the composition comprises a non-replicative transduction particle comprising said nucleic acid construct. In another embodiment, the cellular transcript binds at a 3'UTR sequence of said nucleic acid reporter transcript. In one embodiment, the second stable secondary conformation is formed by cleavage of a portion of a sequence of said first unstable secondary conformation. In another embodiment, the reporter gene sequence encodes a detectable molecule. In some embodiments, the detectable marker comprises a fluorescent molecule or an enzyme capable of mediating a luminescence or colorimetric reaction. In other embodiments, the reporter gene sequence encodes a selectable marker. In another embodiment, the selectable marker comprises an antibiotic resistance gene.

The invention also includes a composition comprising a nucleic acid construct that encodes a nucleic acid reporter transcript comprising a reporter gene sequence and that is capable of forming at least two conformations of said nucleic acid reporter transcript, comprising a first conformation that prevents further transcription of said nucleic acid construct, and a second conformation formed upon binding of said first conformation with a cellular transcript, wherein said second conformation allows transcription of said nucleic acid construct. In some embodiments, the composition comprises a non-replicative transduction particle comprising said nucleic acid construct. In another embodiment, the nucleic acid reporter transcript comprises a cis-repressing sequence.

In one embodiment, the nucleic acid reporter transcript comprises a reporter gene sequence. In another embodiment, the first conformation forms from a binding of said cis-repressing sequence to said reporter gene sequence. In some embodiments, the first conformation is a substrate for a cleaving enzyme. In one embodiment, the first conformation of said nucleic acid reporter transcript comprises a sequence that forms a transcription termination structure. In other embodiments, the binding of said cellular transcript to said sequence that forms a transcription termination structure results in cleavage of a portion of said nucleic acid reporter transcript and formation of said second conformation.

The invention comprises a vector comprising a regulatory sequence operably linked to a nucleic acid sequence that encodes said nucleic acid reporter transcript described herein.

The invention includes a method for detecting a target transcript in a cell, comprising: introducing into said cell said nucleic acid reporter construct described herein; and detecting the presence or absence of an output signal from said cell, wherein said presence of said output signal indicates the presence of the target transcript in said cell. The method includes detecting a presence of a bacterial cell based on detecting said presence of said target transcript.

In one embodiment, the method for detecting a presence of a bacterial cell in a sample comprising introducing into said sample said nucleic acid reporter construct described herein; and detecting the presence or absence of an output signal from said sample, wherein said presence of said output signal indicates the presence of the bacterial cell in said sample.

The invention comprises a kit, comprising a compartment for holding a sample comprising a cell and said nucleic acid reporter construct described herein; and instructions for detecting the presence or absence of an output signal from said sample, wherein the presence of the output signal indicates the presence of a target transcript in said cell The invention comprises a composition, comprising a non-replicative transduction particle comprising a nucleic acid reporter construct, the nucleic acid reporter construct comprising a first promoter operatively linked a reporter gene, wherein said first promoter is capable of being induced by an inducer protein endogenous in a bacterial cell.

The invention includes a method for detecting a presence of a bacterial cell in a sample comprising contacting said sample with a non-replicative transduction particle comprising nucleic acid reporter construct comprising a first promoter operatively linked to a reporter gene, wherein said first promoter is capable of being induced by an inducer protein endogenous to said bacterial cell; and detecting the presence or absence of an output signal from said reporter gene, wherein said presence of said output signal indicates the presence of said bacterial cell in said sample.

In one embodiment, the first promoter is the same as an inducible promoter operatively linked to a target nucleic acid molecule in said bacterial cell.

The invention comprises a composition, comprising a non-replicative transduction particle comprising a nucleic acid reporter construct, the nucleic acid reporter construct comprising a reporter gene that encodes a reporter molecule, the non-replicative transduction particle capable of entering a bacterial cell; and a caged substrate that exogenous to said bacterial cell that once un-caged is capable of reacting to said reporter molecule in said cell.

The invention comprises a method for detecting a presence of a bacterial cell in a sample comprising contacting said sample with a caged substrate and a non-replicative transduction particle comprising a nucleic acid reporter construct, the nucleic acid reporter construct comprising a reporter gene that encodes a reporter molecule, the caged substrate exogenous to said cell that once un-caged is capable of binding to said reporter molecule in said bacterial cell; and detecting the presence or absence of an output signal from said reporter molecule, wherein said presence of said output signal indicates the presence of said bacterial cell in said sample.

In one embodiment, a target enzyme in said cell binds said caged substrate to produce an un-caged substrate. In some embodiments, the un-caged substrate reacts with said reporter molecule to produce said output signal.

The invention also includes a composition, comprising a non-replicative transduction particle comprising a nucleic acid reporter construct, the nucleic acid reporter construct encoding a switchable molecule capable of binding to a target molecule in a bacterial cell to form a complex; and a substrate capable of penetrating said cell and binding said complex to produce a detectable signal from said cell.

The invention includes a method for detecting a presence of a bacterial cell in a sample comprising contacting said sample with a substrate and a non-replicative transduction particle comprising a nucleic acid reporter construct encoding a switchable molecule, the switchable molecule capable of binding a target molecule in said cell to form a complex, the substrate capable of binding said complex to form a substrate-bound complex; and detecting the presence or absence of an output signal from said substrate-bound complex, wherein said presence of said output signal indicates the presence of said bacterial cell in said sample. In one embodiment, the binding of said switchable molecule to said target molecule produces a conformational change in said switchable molecule. In another embodiment, the conformational change in said switchable molecule allows said substrate to bind to said complex.

BRIEF DESCRIPTION OF THE SEVERAL VIEWS OF THE DRAWINGS

These and other features, aspects, and advantages of the present invention will become better understood with regard to the following description, and accompanying drawings, where:

Figure 30:
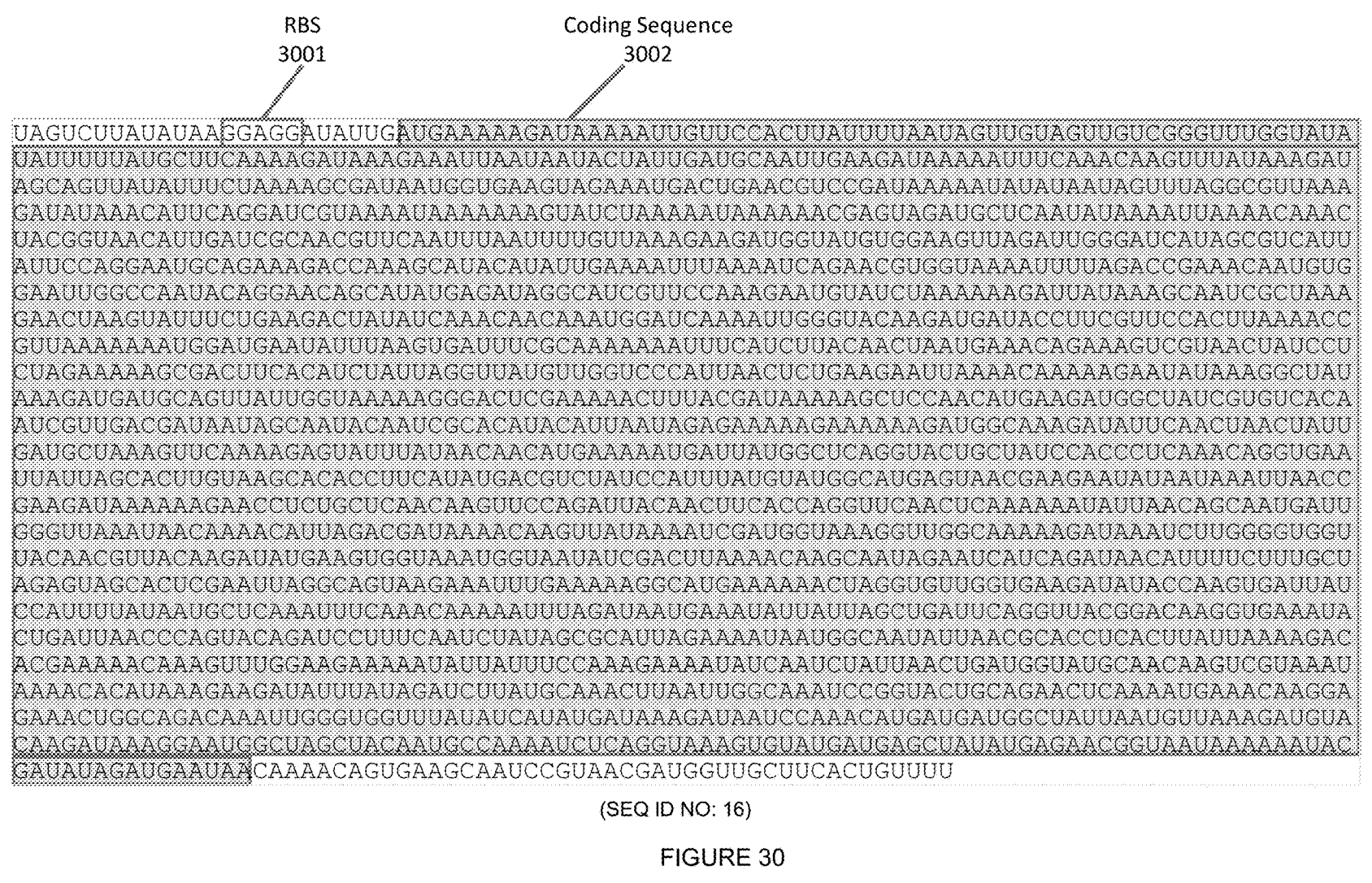

FIG. 30 shows an exemplary mecA transcript sequence that can be used for designing a reporter transcript (SEQ ID NO:16), according to an embodiment of the invention.

DETAILED DESCRIPTION OF THE INVENTION

I. Definitions

Figure 1:
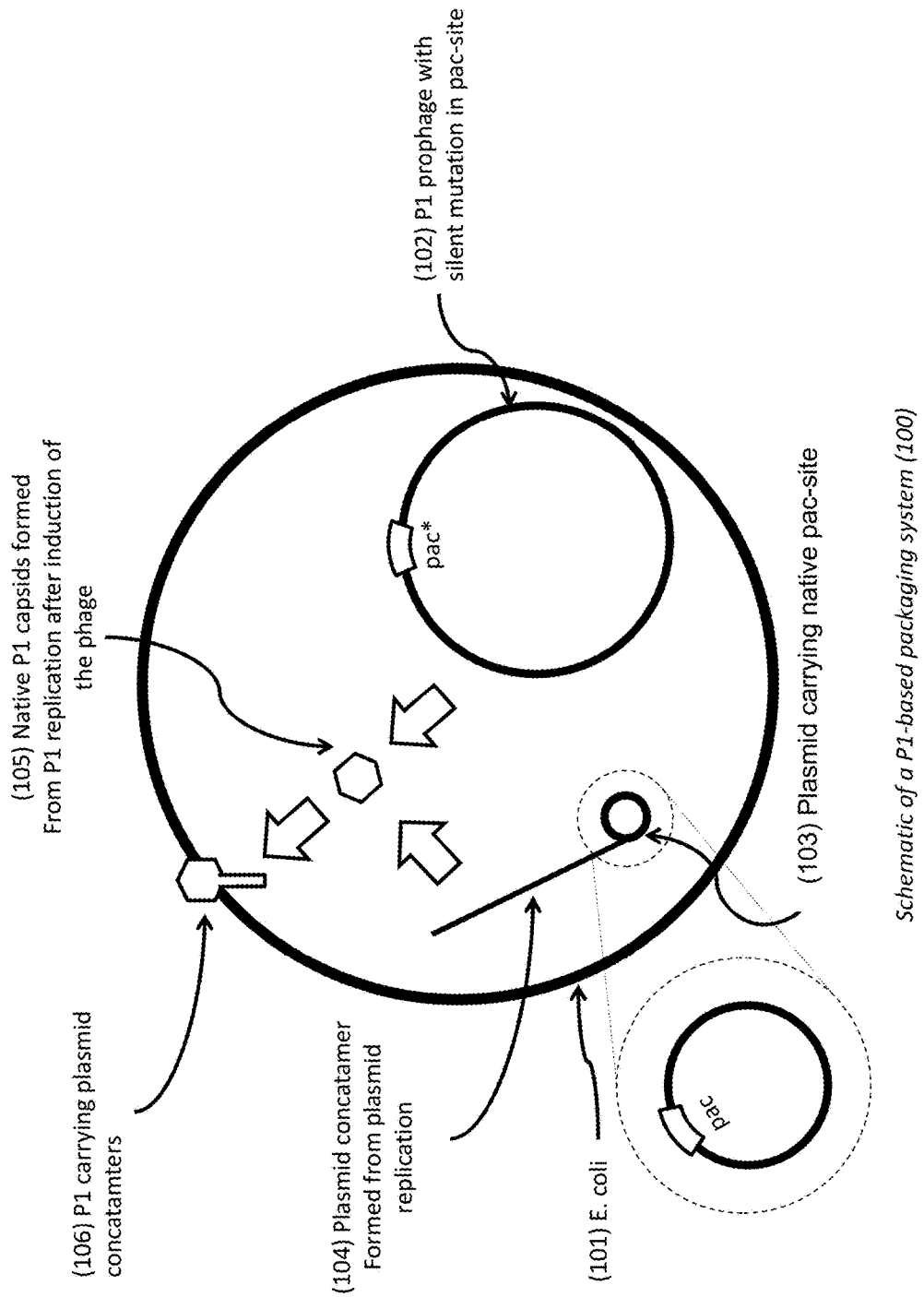
FIG. 1 illustrates an example of the design and function of the silent mutation/complementation-based P1 plasmid packaging system, according to an embodiment of the invention.

Terms used in the claims and specification are defined as set forth below unless otherwise specified.

As used herein, "reporter nucleic acid molecule" refers to a nucleotide sequence comprising a DNA or RNA molecule. The reporter nucleic acid molecule can be naturally occurring or an artificial or synthetic molecule. In some embodiments, the reporter nucleic acid molecule is exogenous to a host cell and can be introduced into a host cell as part of an exogenous nucleic acid molecule, such as a plasmid or vector. In certain embodiments, the reporter nucleic acid molecule can be complementary to a target gene in a cell. In other embodiments, the reporter nucleic acid molecule comprises a reporter gene encoding a reporter molecule (e.g., reporter enzyme, protein). In some embodiments, the reporter nucleic acid molecule is referred to as a "reporter construct" or "nucleic acid reporter construct."

A "reporter molecule" or "reporter" refers to a molecule (e.g., nucleic acid or protein) that confers onto an organism a detectable or selectable phenotype. The detectable phenotype can be colorimetric, fluorescent or luminescent, for example. Reporter molecules can be expressed from reporter genes encoding enzymes mediating luminescence reactions (luxA, luxB, luxAB, luc, mc, nluc), genes encoding enzymes mediating colorimetric reactions (lacZ, HRP), genes encoding fluorescent proteins (GFP, eGFP, YFP, RFP, CFP, BFP, mCherry, near-infrared fluorescent proteins), nucleic acid molecules encoding affinity peptides (His-tag, 3X-FLAG), and genes encoding selectable markers (ampC, tet(M), CAT, erm). The reporter molecule can be used as a marker for successful uptake of a nucleic acid molecule or exogenous sequence (plasmid) into a cell. The reporter molecule can also be used to indicate the presence of a target gene, target nucleic acid molecule, target intracellular molecule, or a cell, as described herein. Alternatively, the reporter molecule can be a nucleic acid, such as an aptamer or ribozyme.

In some aspects of the invention, the reporter nucleic acid molecule is operatively linked to a promoter. In other aspects of the invention, the promoter can be chosen or designed to contribute to the reactivity and cross-reactivity of the reporter system based on the activity of the promoter in specific cells (e.g., specific species) and not in others. In certain aspects, the reporter nucleic acid molecule comprises an origin of replication. In other aspects, the choice of origin of replication can similarly contribute to reactivity and cross-reactivity of the reporter system, when replication of the reporter nucleic acid molecule within the target cell contributes to or is required for reporter signal production based on the activity of the origin of replication in specific cells (e.g., specific species) and not in others. In some embodiments, the reporter nucleic acid molecule forms a replicon capable of being packaged as concatameric DNA into a progeny virus during virus replication.

As used herein, a "target transcript" refers to a portion of a nucleotide sequence of a DNA sequence or an mRNA molecule that is naturally formed by a target cell including that formed during the transcription of a target gene and mRNA that is a product of RNA processing of a primary transcription product. The target transcript can also be referred to as a cellular transcript or naturally occurring transcript.

As used herein, the term "transcript" refers to a length of nucleotide sequence (DNA or RNA) transcribed from a DNA or RNA template sequence or gene. The transcript can be a cDNA sequence transcribed from an RNA template or an mRNA sequence transcribed from a DNA template. The transcript can be protein coding or non-coding. The transcript can also be transcribed from an engineered nucleic acid construct.

A transcript derived from a reporter nucleic acid molecule can be referred to as a "reporter transcript." The reporter transcript can include a reporter sequence and a cis-repressing sequence. The reporter transcript can have sequences that form regions of complementarity, such that the transcript includes two regions that form a duplex (e.g., an intermolecular duplex region). One region can be referred to as a "cis-repressing sequence" and has complementarity to a portion or all of a target transcript and/or a reporter sequence. A second region of the transcript is called a "reporter sequence" and can have complementarity to the cis-repressing sequence. Complementarity can be full complementarity or substantial complementarity. The presence and/or binding of the cis-repressing sequence with the reporter sequence can form a conformation in the reporter transcript, which can block further expression of the reporter molecule. The reporter transcript can form secondary structures, such as a hairpin structure, such that regions within the reporter transcript that are complementary to each other can hybridize to each other.

"Introducing into a cell," when referring to a nucleic acid molecule or exogenous sequence (e.g., plasmid, vector, construct), means facilitating uptake or absorption into the cell, as is understood by those skilled in the art. Absorption or uptake of nucleic acid constructs or transcripts can occur through unaided diffusive or active cellular processes, or by auxiliary agents or devices including via the use of bacteriophage, virus, and transduction particles. The meaning of this term is not limited to cells in vitro; a nucleic acid molecule may also be "introduced into a cell," wherein the cell is part of a living organism. In such instance, introduction into the cell will include the delivery to the organism. For example, for in vivo delivery, nucleic acid molecules, constructs or vectors of the invention can be injected into a tissue site or administered systemically. In vitro introduction into a cell includes methods known in the art, such as electroporation and lipofection. Further approaches are described herein or known in the art.

A "transduction particle" refers to a virus capable of delivering a non-viral nucleic acid molecule into a cell. The virus can be a bacteriophage, adenovirus, etc.

A "non-replicative transduction particle" refers to a virus capable of delivering a non-viral nucleic acid molecule into a cell, but does not package its own replicated viral genome into the transduction particle. The virus can be a bacteriophage, adenovirus, etc.

A "plasmid" is a small DNA molecule that is physically separate from, and can replicate independently of, chromosomal DNA within a cell. Most commonly found as small circular, double-stranded DNA molecules in bacteria, plasmids are sometimes present in archaea and eukaryotic organisms. Plasmids are considered replicons, capable of replicating autonomously within a suitable host.

A "vector" is a nucleic acid molecule used as a vehicle to artificially carry foreign genetic material into another cell, where it can be replicated and/or expressed.

A "virus" is a small infectious agent that replicates only inside the living cells of other organisms. Virus particles (known as virions) include two or three parts: i) the genetic material made from either DNA or RNA molecules that carry genetic information; ii) a protein coat that protects these genes; and in some cases, iii) an envelope of lipids that surrounds the protein coat.

"MRSA" refers to Methicillin-resistant *Staphylococcus aureus.*

"MSSA" refers to Methicillin-sensitive *Staphylococcus aureus.*

The term "ameliorating" refers to any therapeutically beneficial result in the treatment of a disease state, e.g., a disease state, including prophylaxis, lessening in the severity or progression, remission, or cure thereof.

The term "in situ" refers to processes that occur in a living cell growing separate from a living organism, e.g., growing in tissue culture.

The term "in vivo" refers to processes that occur in a living organism.

The term "mammal" as used herein includes both humans and non-humans and include but is not limited to humans, non-human primates, canines, felines, murines, bovines, equines, and porcines.

"G," "C," "A" and "U" each generally stand for a nucleotide that contains guanine, cytosine, adenine, and uracil as a base, respectively. "T" and "dT" are used interchangeably herein and refer to a deoxyribonucleotide wherein the nucleobase is thymine, e.g., deoxyribothymine. However, it will be understood that the term "ribonucleotide" or "nucleotide" or "deoxyribonucleotide" can also refer to a modified nucleotide, as further detailed below, or a surrogate replacement moiety. The skilled person is well aware that guanine, cytosine, adenine, and uracil may be replaced by other moieties without substantially altering the base pairing properties of an oligonucleotide comprising a nucleotide bearing such replacement moiety. For example, without limitation, a nucleotide comprising inosine as its base may base pair with nucleotides containing adenine, cytosine, or uracil. Hence, nucleotides containing uracil, guanine, or adenine may be replaced in the nucleotide sequences of the invention by a nucleotide containing, for example, inosine. Sequences comprising such replacement moieties are embodiments of the invention.

As used herein, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Complementary sequences are also described as binding to each other and characterized by binding affinities.

For example, a first nucleotide sequence can be described as complementary to a second nucleotide sequence when the two sequences hybridize (e.g., anneal) under stringent hybridization conditions. Hybridization conditions include temperature, ionic strength, pH, and organic solvent concentration for the annealing and/or washing steps. The term stringent hybridization conditions refers to conditions under which a first nucleotide sequence will hybridize preferentially to its target sequence, e.g., a second nucleotide sequence, and to a lesser extent to, or not at all to, other sequences. Stringent hybridization conditions are sequence dependent, and are different under different environmental parameters. Generally, stringent hybridization conditions are selected to be about 5° C. lower than the thermal melting point ($T_m$) for the nucleotide sequence at a defined ionic strength and pH. The $T_m$ is the temperature (under defined ionic strength and pH) at which 50% of the first nucleotide sequences hybridize to a perfectly matched target sequence. An extensive guide to the hybridization of nucleic acids is found in, e.g., Tijssen (1993) Laboratory Techniques in Biochemistry and Molecular Biology—Hybridization with Nucleic Acid Probes part I, chap. 2, "Overview of principles of hybridization and the strategy of nucleic acid probe assays," Elsevier, N.Y. ("Tijssen"). Other conditions, such as physiologically relevant conditions as may be encountered inside an organism, can apply. The skilled person will be able to determine the set of conditions most appropriate for a test of complementarity of two sequences in accordance with the ultimate application of the hybridized nucleotides.

This includes base-pairing of the oligonucleotide or polynucleotide comprising the first nucleotide sequence to the oligonucleotide or polynucleotide comprising the second nucleotide sequence over the entire length of the first and second nucleotide sequence. Such sequences can be referred to as "fully complementary" with respect to each other herein. However, where a first sequence is referred to as "substantially complementary" with respect to a second sequence herein, the two sequences can be fully complementary, or they may form one or more, but generally not more than 4, 3 or 2 mismatched base pairs upon hybridization, while retaining the ability to hybridize under the conditions most relevant to their ultimate application. However, where two oligonucleotides are designed to form, upon hybridization, one or more single stranded overhangs, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, may yet be referred to as "fully complementary" for the purposes described herein.

"Complementary" sequences, as used herein, may also include, or be formed entirely from, non-Watson-Crick base pairs and/or base pairs formed from non-natural and modified nucleotides, in as far as the above requirements with respect to their ability to hybridize are fulfilled. Such non-Watson-Crick base pairs includes, but not limited to, G:U Wobble or Hoogstein base pairing.

The terms "complementary," "fully complementary" and "substantially complementary" herein may be used with respect to the base matching between two strands of a dsRNA, or between the antisense strand of a dsRNA and a target sequence, between complementary strands of a single stranded RNA sequence or a single stranded DNA sequence, as will be understood from the context of their use.

As used herein, a "duplex structure" comprises two antiparallel and substantially complementary nucleic acid sequences. Complementary sequences in a nucleic acid construct, between two transcripts, between two regions within a transcript, or between a transcript and a target sequence can form a "duplex structure." In general, the majority of nucleotides of each strand are ribonucleotides, but as described in detail herein, each or both strands can also include at least one non-ribonucleotide, e.g., a deoxyribonucleotide and/or a modified nucleotide. The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5'-end of the respective other strand forming the duplex structure, the connecting RNA chain is referred to as a "hairpin loop." Where the two strands are connected covalently by means other than an uninterrupted chain of nucleotides between the 3'-end of one strand and the 5'-end of the respective other strand forming the duplex structure, the connecting structure is referred to as a "linker." The RNA strands may have the same or a different number of nucleotides. The maximum number of base pairs is the number of nucleotides in the shortest strand of the duplex minus any overhangs that are present in the duplex. Generally, the duplex structure is between 15 and 30 or between 25 and 30, or between 18 and 25, or between 19 and 24, or between 19 and 21, or 19, 20, or 21 base pairs in length. In one embodiment the duplex is 19 base pairs in length. In another embodiment the duplex is 21 base pairs in length. When two different siRNAs are used in combination, the duplex lengths can be identical or can differ.

As used herein, the term "region of complementarity" refers to the region on the antisense strand that is substantially complementary to a sequence, for example a target sequence, as defined herein. Where the region of complementarity is not fully complementary to the target sequence, the mismatches are most tolerated in the terminal regions and, if present, are generally in a terminal region or regions, e.g., within 6, 5, 4, 3, or 2 nucleotides of the 5' and/or 3' terminus.

The term percent "identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information.

The term "sufficient amount" means an amount sufficient to produce a desired effect, e.g., an amount sufficient to produce a detectable signal from a cell.

The term "therapeutically effective amount" is an amount that is effective to ameliorate a symptom of a disease. A therapeutically effective amount can be a "prophylactically effective amount" as prophylaxis can be considered therapy.

It must be noted that, as used in the specification and the appended claims, the singular forms "a," "an" and "the" include plural referents unless the context clearly dictates otherwise.

II. Lysogenic and Lytic Cycle of Viruses

Viruses undergo lysogenic and lytic cycles in a host cell. If the lysogenic cycle is adopted, the phage chromosome can be integrated into the bacterial chromosome, or it can establish itself as a stable plasmid in the host, where it can remain dormant for long periods of time. If the lysogen is induced, the phage genome is excised from the bacterial chromosome and initiates the lytic cycle, which culminates in lysis of the cell and the release of phage particles. The lytic cycle leads to the production of new phage particles which are released by lysis of the host.

Certain temperate phage can exhibit lytic activity, and the propensity for this may vary with varying host bacteria. To illustrate this phenomenon, the lytic activity of two temperate S. aureus phages on ten MRSA clinical isolates was examined via plaque assay (Table 1). The phage φ11 exhibited lytic activity on 10 out of 10 clinical MRSA isolates and φ80α exhibited lytic activity on six of the 10 clinical MRSA isolates. Thus, reporter assays relying on the natural lysogenic cycle of phages can be expected to exhibit lytic activity sporadically.

TABLE 1

Lytic activity (denoted by the letter "x") of the S. aureus temperate phages φ11 and φ80α on ten clinical MRSA isolates

| MRSA isolate | φ11 | φ80α |
| --- | --- | --- |
| 1 | x | |
| 2 | x | |
| 3 | x | x |
| 4 | x | x |
| 5 | x | x |
| 6 | x | |
| 7 | x | x |
| 8 | x | |
| 9 | x | x |
| 10 | x | x |

In addition, virus-based reporter assays, such as phage-based reporters, can suffer from limited reactivity (i.e., analytical inclusivity) due to limits in the phage host range caused by host-based and prophage-derived phage resistance mechanisms. These resistance mechanisms target native phage nucleic acid that can result in the degradation or otherwise inhibition of the phage DNA and functions. Such resistance mechanisms include restriction systems that cleave phage DNA and CRISPR systems that inhibit phage-derived transcripts.

Both lytic activity and phage resistance can be inhibitory to assays based on reporter phages. Lytic activity can inhibit signal by destroying or otherwise inhibiting the cell in its ability to generate a detectable signal and thus affecting limits of detection by reducing the amount of detectable signal or preventing the generation of a detectable signal. Phage resistance mechanisms can limit the host range of the phage and limit the inclusivity of the phage-based reporter, similarly affecting limits of detection by reducing the amount of detectable signal or preventing the generation of a detectable signal. Both lytic activity and phage resistance caused by the incorporation of phage DNA in a reporter phage can lead to false-negative results in assays that incorporate these phage reporters.

III. Methods for Producing Non-Replicative Transduction Particles (NRTP)

A. Disruption/Complementation-Based Methods for Producing Non-Replicative Transduction Particles 1) Silent Mutation/Complementation Packaging System The invention includes methods for producing NRTPs using a silent mutation/complementation-based method.

This non-replicative transduction particle packaging system is based on introducing a silent mutation into a component of the genome of a virus that is recognized by the viral packaging machinery as the element from which genomic packaging is initiated during viral production. Examples of such an element include the pac-site sequence of pac-type bacteriophages and the cos-site sequence of cos-type bacteriophages.

Because these packaging initiation sites are often found within coding regions of genes that are essential to virus production, the silent mutation is introduced such that the pac-site is no longer recognized as a site of packaging initiation by the viral packaging machinery. At the same time, the mutation does not disrupt the gene in which the site is encoded. By disrupting the packaging site sequence, the mutated virus is able to undergo a lytic cycle, but is unable to package its genomic DNA into its packaging unit.

An exogenous reporter nucleic acid molecule, such as plasmid DNA, can be introduced into a host cell that has been lysogenized with a viral genome with a mutated packaging initiation site sequence. The exogenous reporter nucleic acid molecule can include a native packaging initiation site sequence. The exogenous reporter nucleic acid molecule can be introduced into the cell and replicated in the cell. When the mutated virus is undergoing a lytic cycle, the expressed viral packaging machinery packages the exogenous reporter nucleic acid molecule with the native packaging initiation site sequence into the viral packaging unit. The viral genome is not packaged into the packaging unit because its packaging initiation site sequence has been mutated. In certain embodiments, the mutation in the packaging initiation site sequence comprises a silent mutation that prevents cleavage of the packaging initiation sequence, but does not disrupt the expression of the gene product that encompasses the packaging initiation site sequence. This produces non-replicative transduction particles, e.g., viral structural components carrying the replicated exogenous nucleic acid molecule.

An example of such a system is based on the bacteriophage P1, a pac-type phage. In an embodiment, a plasmid including a native P1 pac site is transformed into a cell. The cell is lysogenized with a P1 prophage genome. The P1 prophage genome includes a silent mutation in the pac-site sequence encoded within the pacA gene of P1. When the lytic cycle of the prophage is induced, the system results in the production of P1-based transduction particles carrying the plasmid DNA. An example of a silent mutation that is suitable for this system is described in U.S. Pub. No. 2005/0118719, filed on Nov. 7, 2002, which is incorporated by reference in its entirety. An example is also found in SEQ ID NO: 2, listed below (P1 pac-site with silent mutations, lower case letters signify mutated bases).

FIG. 1 illustrates an example of the design and function of the silent mutation/complementation-based P1 plasmid packaging system 100, according to an embodiment of the invention. In this system, an E. coli cell 101 is lysogenized with a P1 prophage 102 that includes a silent mutation in its packaging initiation site sequence (e.g., pac-site). The cell is transformed with a plasmid containing the native pac-site 103, and the plasmid is replicated in the cell to form plasmid concatamers 104. The plasmid can also include a reporter gene that encodes a reporter molecule. When the lytic cycle of the P1 prophage is induced, the P1 prophage is excised from the bacterial genome and the P1 structural components, such as capsid proteins, 105 are expressed. The P1 structural components only package DNA that contains a native pac-site (e.g., plasmid DNA), thus producing non-replicative transduction particles carrying plasmid DNA 106 (e.g., a reporter gene).

Figure 2:
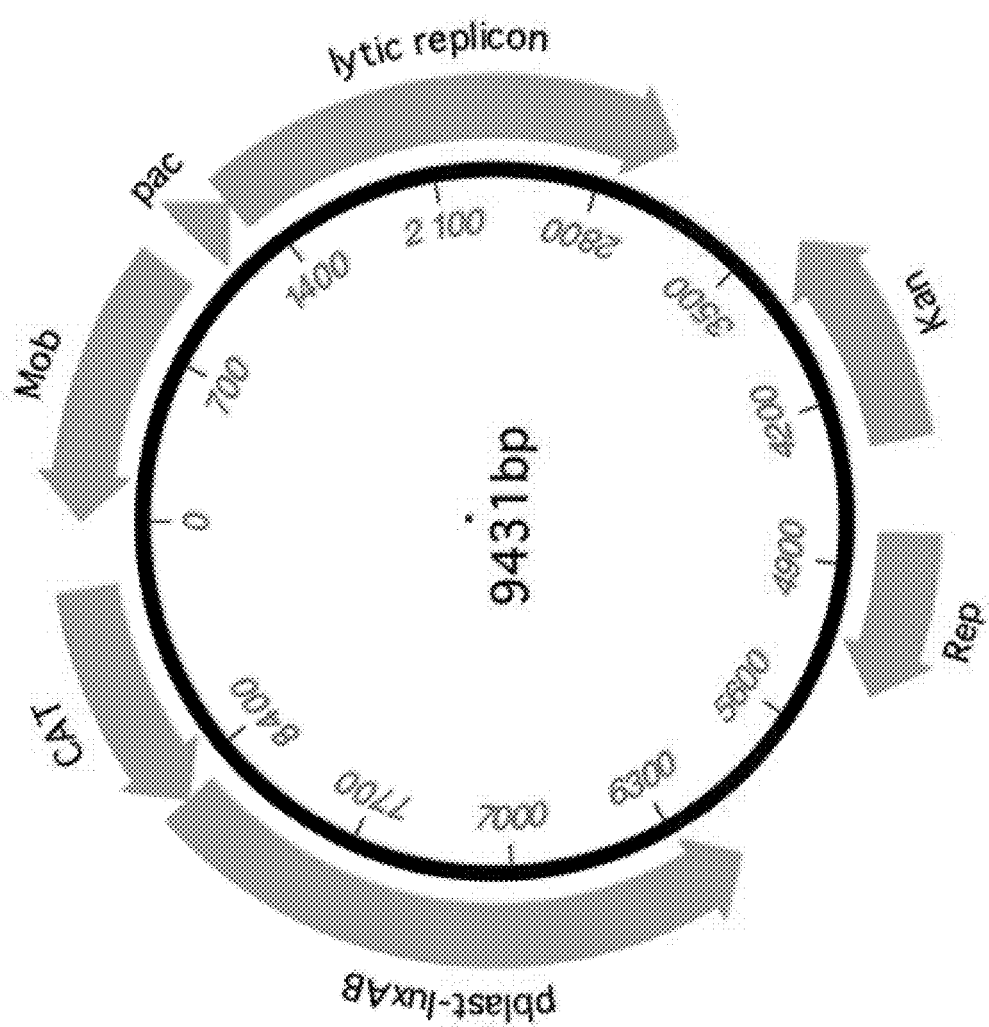
FIG. 2 illustrates a schematic of the pGWP10001 vector, according to an embodiment of the invention.

An example vector for use in the silent mutation/complementation-based P1 plasmid packaging system is shown in FIG. 2. Details about how to construct the strains and vectors of the silent mutation/complementation-based P1 plasmid packaging system are described in detail in Example 1 below.

2) Deletion/Complementation-Based Packaging System

The invention includes methods for producing NRTPs using a deletion/complementation-based method.

This non-replicative transduction particle packaging system is based on deletion of a component of the genome of a virus that is recognized by the viral packaging machinery as the element from which genomic packaging is initiated during viral production. Examples of such an element include the pac-site sequence of pac-type bacteriophages and the cos-site sequence of cos-type bacteriophages. These packaging initiation sites are often found within coding regions of genes that are essential to virus production. In some embodiments, the packaging initiation site alone is deleted, which allows the mutated virus to undergo a lytic cycle but does not allow the virus to package its genomic DNA. For example, SEQ ID NO: 6 is an example of a P1 pacA gene with a deleted pac-site sequence (lower case letters indicate the deleted pac-site sequence). In other embodiments, the entire gene comprising the packaging initiation site is deleted. For example, SEQ ID NO: 8 shows the deletion of the terS gene (lower case characters show the deleted sequence).

In one example, a cell's genome is lysogenized with a viral genome where the packaging initiation site has been deleted. A complementing plasmid is introduced into the cell, and the plasmid DNA includes a gene with a packaging initiation site sequence that complements the deleted packaging initiation site sequence in the viral genome. When the mutated virus is undergoing a lytic cycle, the viral packaging proteins package a replicon of the plasmid DNA into the packaging unit because of its packaging initiation site, and non-replicative transduction particles are produced carrying the replicated plasmid DNA.

In some embodiments, it is preferable that the deletion/complementation is designed such that there is no homology between the mutated virus DNA and the complementing exogenous DNA. This is because lack of homology between the mutated virus DNA and the complementing exogenous DNA avoids the possibility of homologous recombination between the two DNA molecules that can result in re-introduction of a packaging sequence into the virus genome. To accomplish a lack of homology, one strategy is to delete the entire gene that contains the packaging initiation site sequence from the virus genome and then complement this gene with an exogenous DNA molecule that contains no more than exactly the DNA sequence that was deleted from virus. In this strategy, the complementing DNA molecule is designed to express the gene that was deleted from the virus.

Another example of such a system is provided using the bacteriophage φ80α, a pac-type phage. The phage genome is lysogenized in a host bacterial cell, and the phage genome includes a small terminase gene where the pac-site of a pac-type prophage φ80α has been deleted. A plasmid including a complementary small terminase gene with a native pac-site is transformed into the cell. When the lytic cycle of the lysogenized prophage is induced, the bacteriophage packaging system packages plasmid DNA into progeny bacteriophage structural components, rather than packaging the native bacteriophage DNA. The packaging system thus produces non-replicative transduction particles carrying plasmid DNA.

Figure 3:
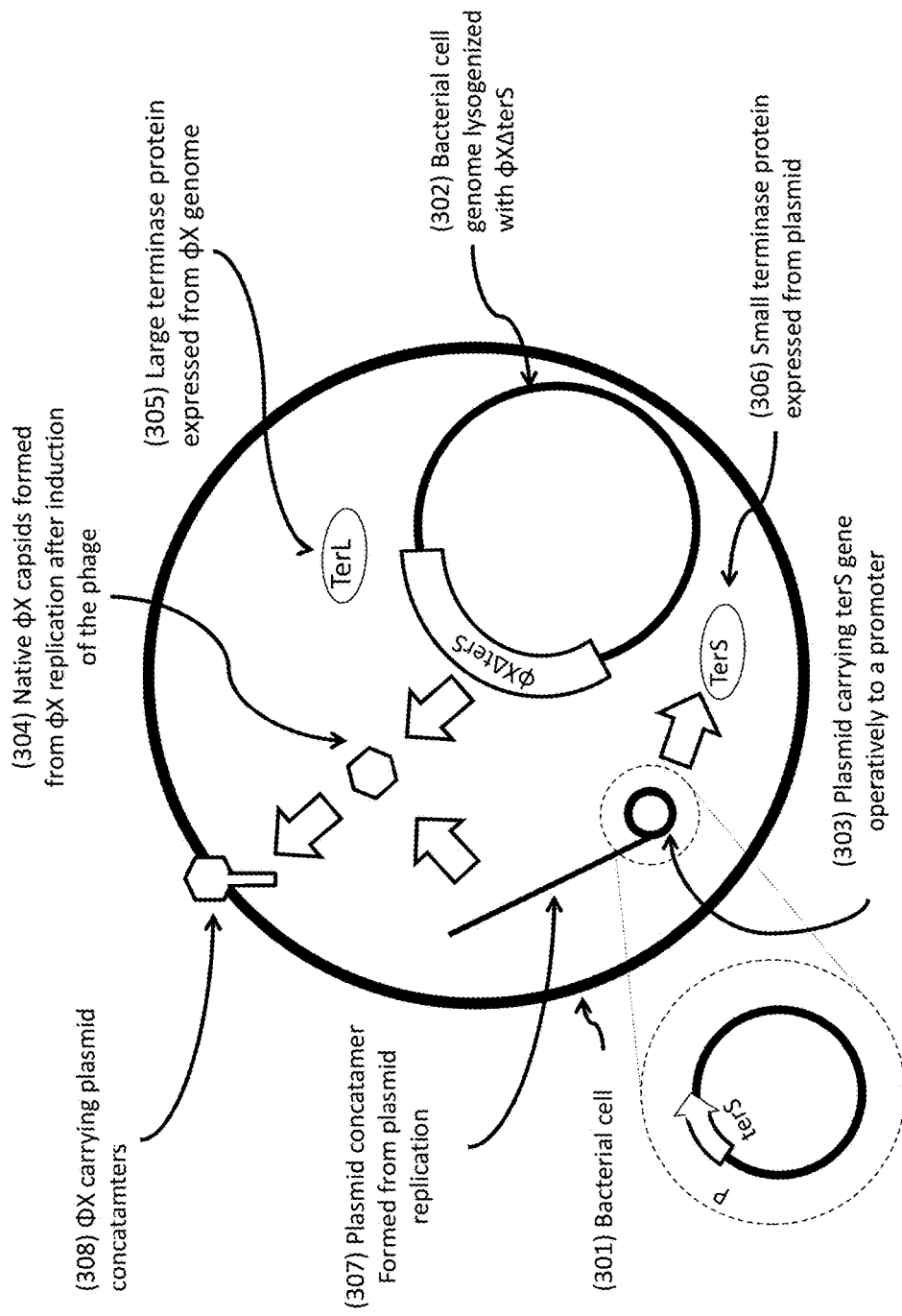
FIG. 3 illustrates an example of the design and function of a pac-site deletion/complementation plasmid packaging system, according to an embodiment of the invention.

FIG. 3 illustrates an example of the design and function of a pac-site deletion/complementation plasmid packaging system 300, according to an embodiment of the invention. A bacterial cell 301 is lysogenized with a pac-type phage 302 that has its small terminase (terS) gene deleted. The cell is transformed with a rolling circle replication plasmid 303 that includes a small terminase gene that complements the terS gene deletion in the phage. The small terminase gene contains the packaging initiation site sequence, e.g., a pac-site. The plasmid 303 can also include a reporter gene that encodes a reporter molecule.

Figure 4:
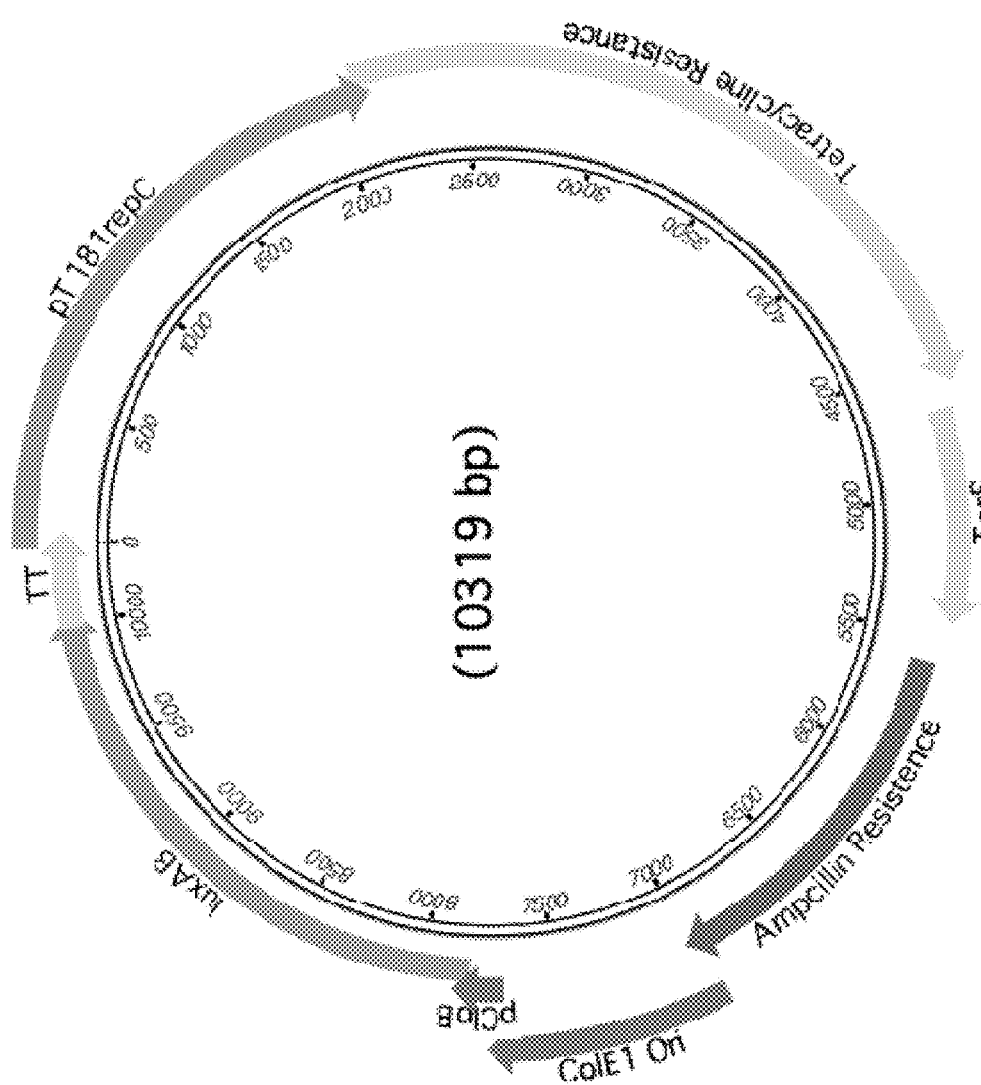
FIG. 4 illustrates a schematic of the pGW80A0001 vector, according to an embodiment of the invention.

A protein complex comprising the small terminase and large terminase proteins is able to recognize and cleave a double-stranded DNA molecule at or near the pac-site, and this allows the plasmid DNA molecule to be packaged into a phage capsid. When the prophage in the cell is induced, the lytic cycle of the phage produces the phage's structural proteins 304 and the phage's large terminase protein 305. The complementing plasmid is replicated, and the small terminase protein 306 is expressed. The replicated plasmid DNA 307 containing the terS gene (and the reporter gene) are packaged into phage capsids, resulting in non-replicative transduction particles carrying only plasmid DNA 308. FIG. 4 shows an example of a resulting vector used in the pac-site deletion/complementation plasmid packaging system. Further details about the components and construction of pac-site deletion/complementation plasmid packaging system are in Example 2 below.

B. Pathogenicity Island-Based Packaging System

Pathogenicity islands (PTIs) are a subset of horizontally transferred genetic elements known as genomic islands. There exists a particular family of highly mobile PTIs in Staphylococcus aureus that are induced to excise and replicate by certain resident prophages. These PTIs are packaged into small headed phage-like particles and are transferred at frequencies commensurate with the plaque-forming titer of the phage. This process is referred to as the SaPI excision replication-packaging (ERP) cycle, and the high-frequency SaPI transfer is referred to as SaPI-specific transfer (SPST) to distinguish it from classical generalized transduction (CGT). The SaPIs have a highly conserved genetic organization that parallels that of bacteriophages and clearly distinguishes them from all other horizontally acquired genomic islands. The SaPI1-encoded and SaPIbov2-encoded integrases are required for both excision and integration of the corresponding elements, and it is assumed that the same is true for the other SaPIs. Phage 80α can induce several different SaPIs, including SaPI1, SaPI2, and SaPIbov1, whereas φ11 can induce SaPIbov1 but neither of the other two SaPIs.

Figure 5:
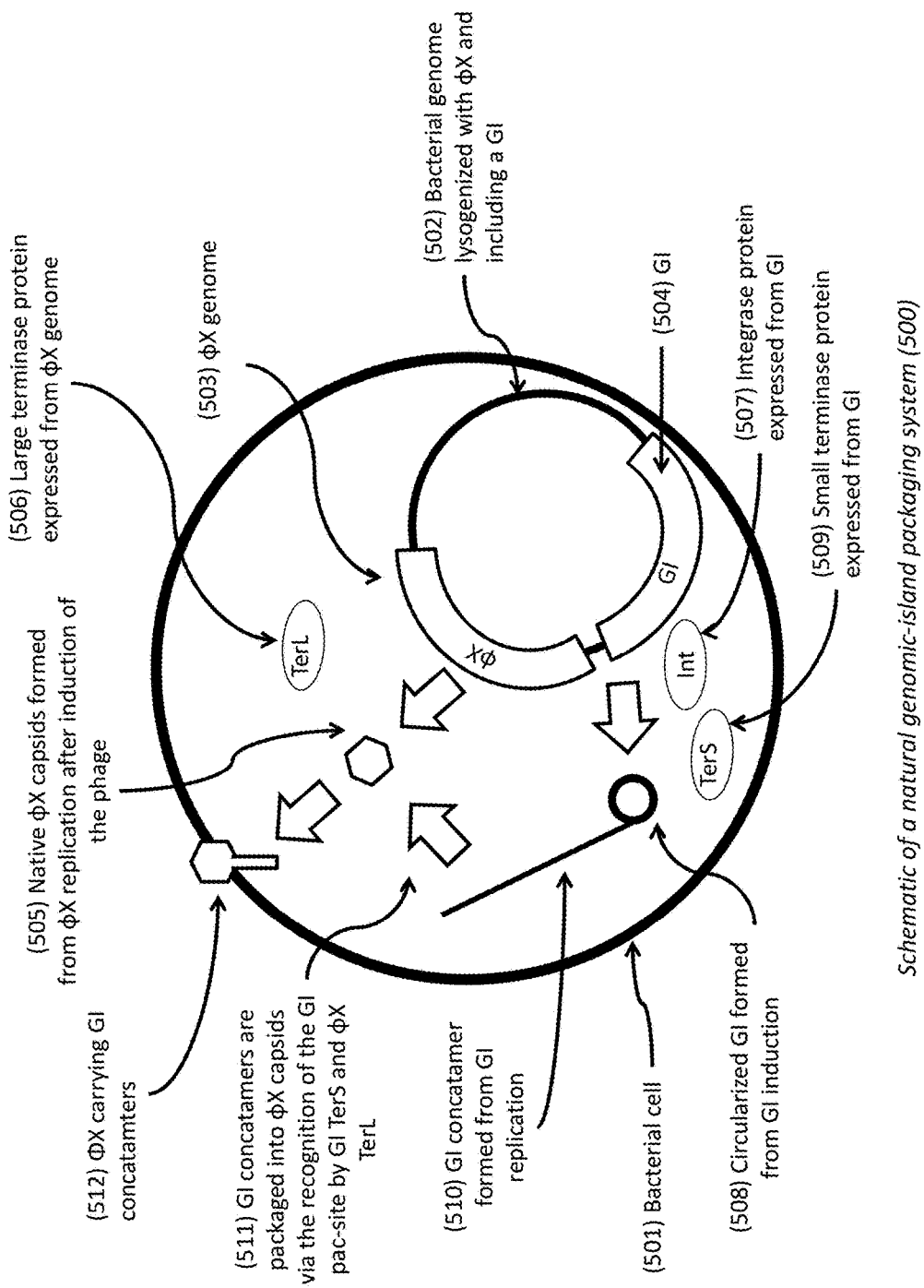
FIG. 5 depicts the process for genomic island (GI) packaging by a bacteriophage, according to an embodiment of the invention.

FIG. 5 depicts the natural process for genomic island (GI) packaging 500 by a bacteriophage. In nature, a bacterial cell 501 lysogenized with a suitable prophage 503 and carrying a GI 504 can produce phage particles carrying GI concatamers 512. In this process, when the phage is induced into its lytic cycle, the phage genome is excised (not shown) from the bacterial genome 502, which then expresses bacteriophage proteins including capsid constituents 505 and the large terminase protein (TerL) 506. Prophage induction also triggers GI excision via the expression of the GI integrase protein (int) 507. In a similar manner to the excised phage genome (not shown), the GI circularizes 508, expresses its own small terminase protein (TerS) 509, and begins to replicate forming a GI concatamer 510. The phage TerL gene and GI TerS gene can then combine bind and cleave the GI concatamer via a pac-site sequence in the GI genome, and the GI concatamer can then be packaged into phage capsids 511 resulting in phage particles carrying GI concatamers 512.

In natural systems, as depicted in FIG. 5, the resulting lysate produced from phage production includes both native phage particles, as well as GI-containing phage particles. The native phage particles are a result of packaging of the native phage genome due to recognition of the pac-site within phage genome concatamers.

1) Genomic Island (GI) Packaging System Design and Function

Methods of the invention for producing NRTPs include a GI based-packaging system.

Compared to a plasmid packaging system, the natural GI-packaging system benefits from the fact that the DNA that is packaged is derived from a genomic region within the bacterial genome and thus does not require the maintenance of a plasmid by the bacterial host.

In some embodiments, the invention includes a bacterial cell packaging system for packaging a reporter nucleic acid molecule into a non-replicative transduction particle, wherein the bacterial cell comprises a lysogenized bacteriophage genome lacking a packaging gene, and a genomic island, cryptic phage, or other nucleic acid molecule requiring a bacteriophage (e.g., a heper phage) for mobilization of the nucleic acid molecule and comprising a reporter nucleic acid molecule and a packaging gene. Genomic island-based systems can be based on *S. aureus* Pathogenicity Islands (SaPIs), the *E. coli* criptic phage P4 and helper phage P2, and the *Enterococci* criptic phage P7 and helper phage P1, for example.

GI-packaging systems can be exploited such that exogenous nucleic acid sequences are packaged by the bacteriophage. This can be accomplished by incorporating such exogenous nucleic acids sequences into the GI.

In order to eliminate the native phage from this process, the small terminase gene of the prophage can be deleted. The small terminase gene sequence contains the pac-site sequence of the native phage, and this deletion has the effect of preventing the packaging of native phage DNA. In other embodiments, only the pac site of the small terminase gene can be deleted. The GI that will be packaged includes its own pac-site and a small terminase gene that expresses a suitable small terminase protein, and only GI DNA will be amenable for packaging in this system.

Figure 6:
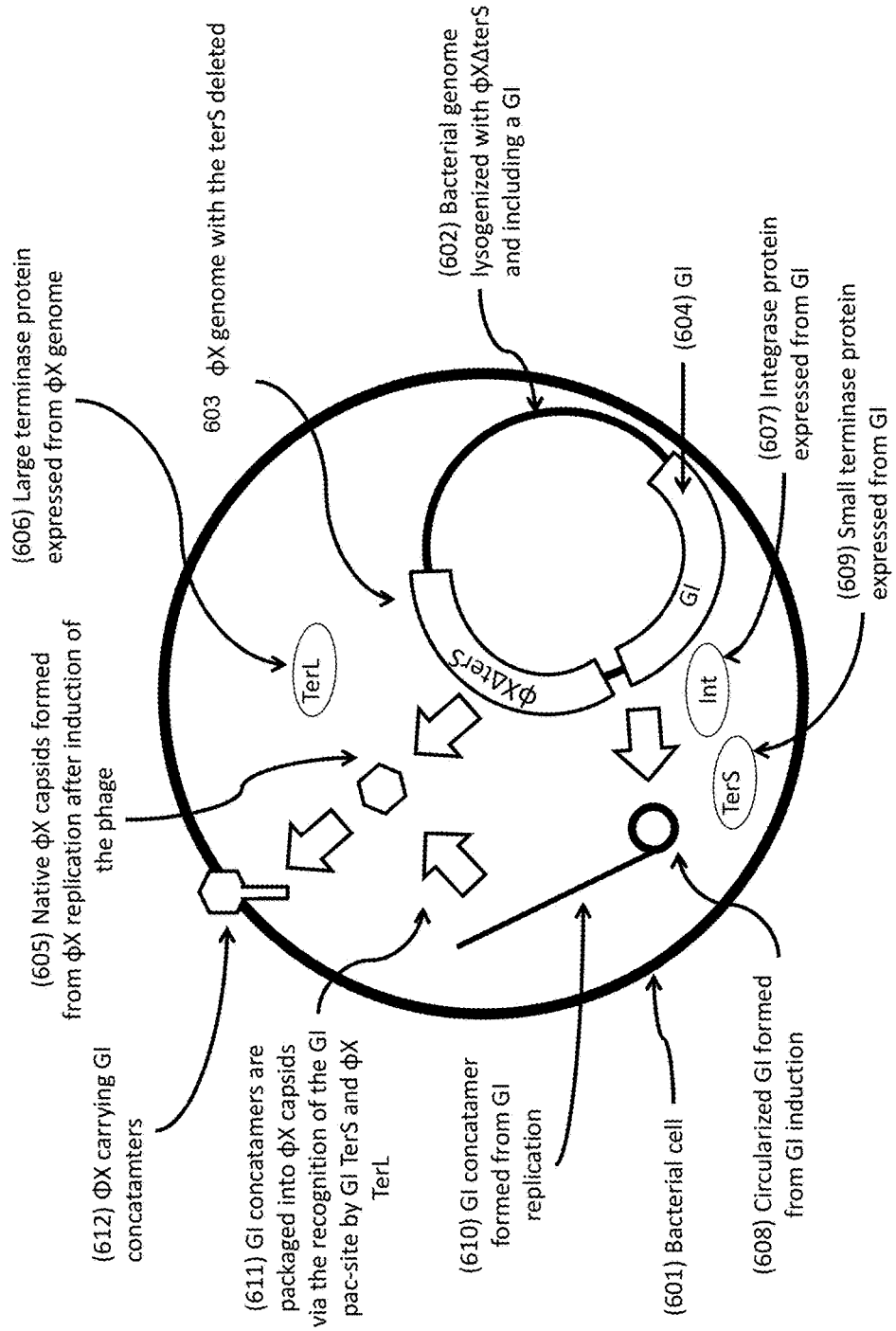
FIG. 6 depicts an example of the design and function of a GI-based packaging system, according to an embodiment of the invention.

FIG. 6 depicts an example of the design and function of a GI-based packaging system 600, according to an embodiment of the invention. In this system, a bacterial cell 601 has its genome lysogenized with a suitable prophage 603 that has its small terminase gene deleted, and the cell's genome 602 carries a GI 604. When the phage is induced into its lytic cycle, the phage genome is excised (not shown) from the bacterial genome 602. The phage genome expresses bacteriophage proteins, including capsid constituents 605 and the large terminase protein (TerL) 606. Prophage induction also triggers GI excision via the expression of the GI integrase protein (int) 607. In a similar manner to the excised phage genome (not shown), the GI circularizes 608 and expresses its own small terminase protein (TerS) 609 and is replicated forming a GI concatamer 610. The phage TerL gene and GI TerS gene can then combine, bind and cleave the GI concatamer via a pac-site sequence in the GI DNA. The GI concatamer can then be packaged into phage capsids 611 resulting in phage particles carrying GI concatamers 612. In this system, phage DNA will not be packaged into phage particles, since it lacks the terS gene that contains the phage's pac-site sequence, and thus cannot be recognized by the expressed GI TerS and phage TerL proteins.

When phage particles containing packaged GI DNA are administered to a recipient cell, the phage will bind to the recipient cell's surface and then introduce the packaged GI DNA concatamer into the cell. Once inside the cell, the GI can again express its integrase protein, and the GI can then integrate into its specific site in the recipient cell's genome. If exogenous DNA sequences are included in the GI prior to packaging, the packaging system thus allows for delivering exogenous DNA sequences to a recipient cell and integrating these exogenous DNA sequences into the recipient cell's genome.

2) GI-Based Packaging System Lacking Integrase

In another embodiment, the packaging system described above is designed such that packaged GI DNA cannot integrate into a recipient cell's genome. This can be accomplished by deleting the integrase gene in the GI and complementing the deletion by causing the expression of the integrase gene in trans from the GI. In this manner, the integrase protein is available for excision of the GI in the packaging host cell, and the GI DNA that has been packaged in a bacteriophage does not contain the integrase gene and cannot express the integrase protein, thus preventing integration of the delivered GI.

Figure 7:
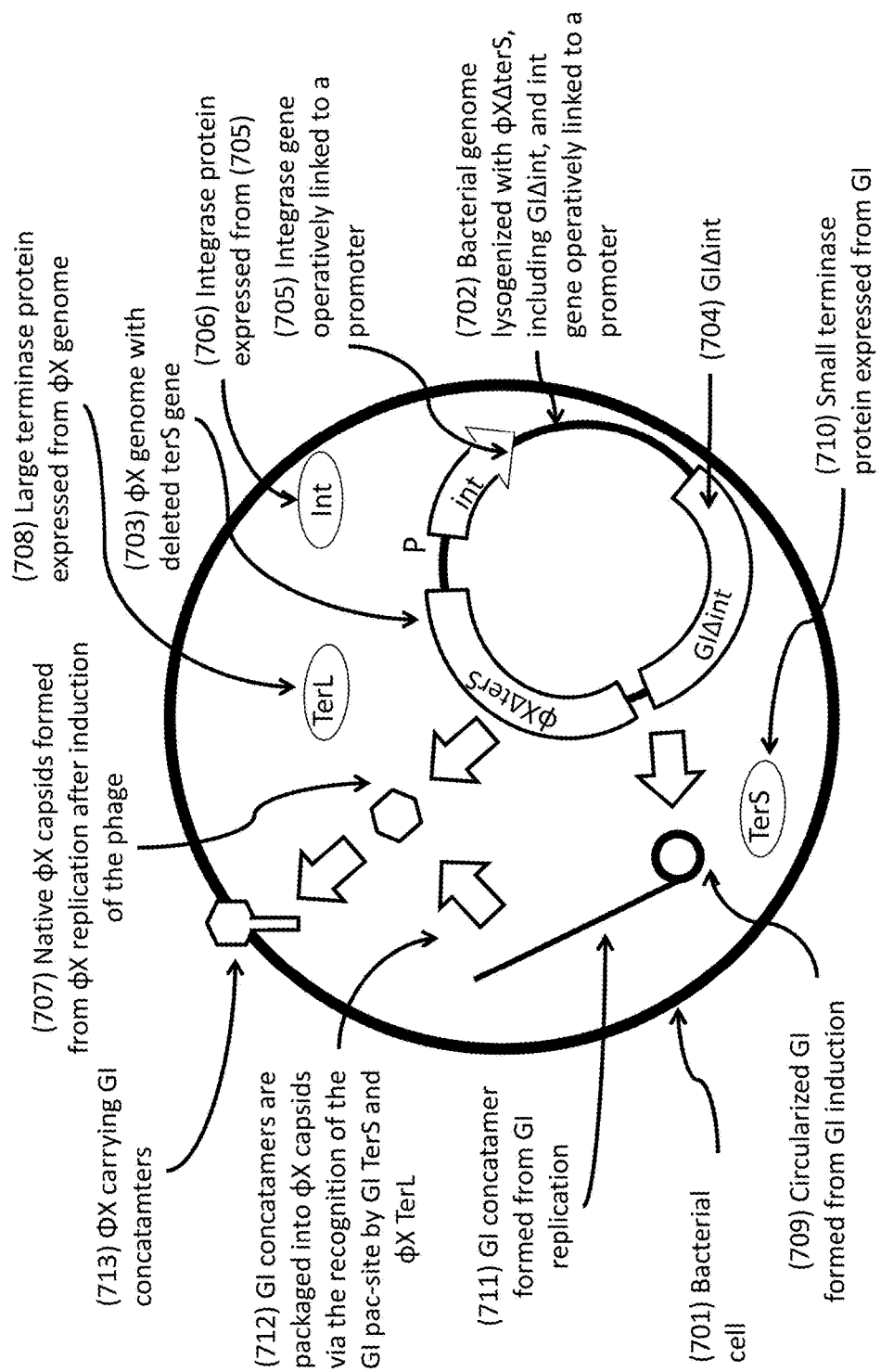
FIG. 7 depicts the design and function of a GI-based packaging system that lacks the integrase gene, according to an embodiment of the invention.

FIG. 7 depicts the design and function of a GI-based packaging system that lacks the int gene 700, according to an embodiment of the invention. In this system, a bacterial cell 701 is lysogenized with a suitable prophage that has had its small terminase gene deleted 703. The cell's genome 702 carries a GI that has its integrase (int) gene deleted 704 and also carries the deleted int gene operatively linked to a suitable promoter 705. The int gene can thus express the integrase protein (Int) in trans from the GI 706. When the phage is induced into its lytic cycle, the phage genome is excised (not shown) from the bacterial genome 702, which then expresses bacteriophage proteins including capsid constituents 707 and the large terminase protein (TerL) 708. Prophage induction also triggers GI excision via the expression of the integrase protein 707. In a similar manner to the excised phage genome (not shown), the excised GI circularizes 709, expresses its own small terminase protein (TerS) 710, and begins to replicate forming a GI concatamer 711. The phage TerL gene and GI TerS gene can then combine, bind and cleave the GI concatamer via a pac-site sequence in the GI DNA, and the GI concatamer can then be packaged into phage capsids 712 resulting in phage particles carrying GI concatamers 713. In this system, phage DNA will not be packaged since it lacks the terS gene that contains the phage's pac-site sequence and thus cannot be recognized by the expressed GI TerS and phage TerL proteins.

When phage particles containing packaged GI DNA lacking the int gene are administered to a recipient cell, the phage will bind to the recipient cell's surface and then introduce the packaged GI DNA concatamer into the cell. Once inside the cell, the GI cannot express its integrase protein due to the lack of the integrase gene and the GI cannot then integrate into its specific site in the recipient cell's genome. If exogenous DNA sequences are included in the GI prior to packaging, the packaging system thus allows for delivering exogenous DNA sequences to a recipient cell and the delivered DNA sequences do not integrate into the recipient cell's genome at the specific site for GI integration.

3) Design and Function of SaPIbov2-Based Packaging Lacking Integrase

In some embodiments, the method of producing NRTPs employ a GI SaPIbov2 and a bacteriophage φ11 in a GI-based packaging system. Alternative embodiments can employ other SaPI GI's and other suitable bacteriophages, including the SaPI's SaPI1, SaPI2, SaPIbov1, and SaPIbov2 along with the bacteriophage 80α, and the SaPI's SaPIbov1 and SaPIbov2 along with the bacteriophage φ11. Based on the description below, one of skill in the art would know how to develop a GI-based packaging system that does not lack the int gene, as described in Section II A.

Figure 8:
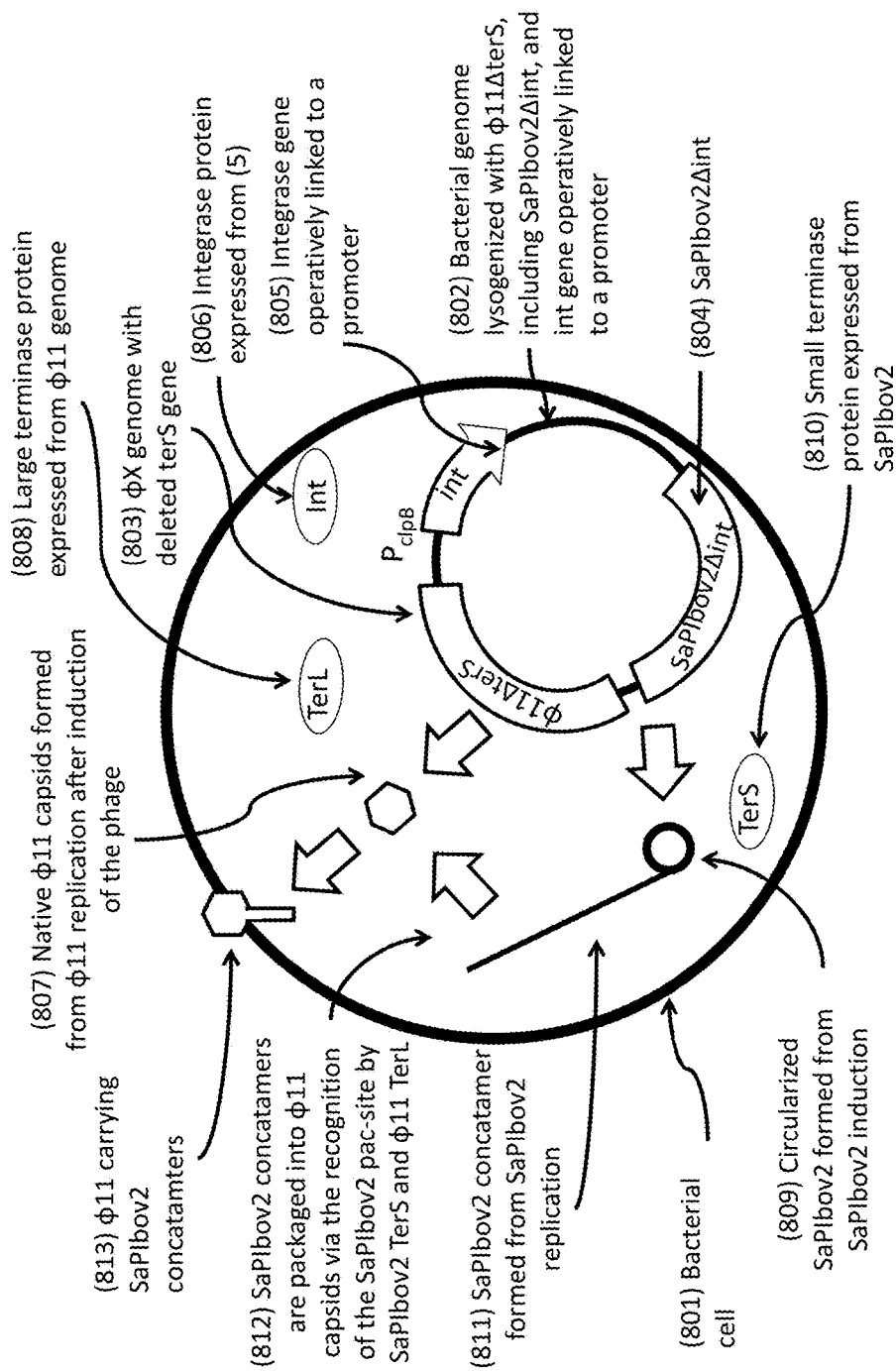
FIG. 8 depicts the design and function of a SaPIbov2-based packaging system that lacks the integrase gene, according to an embodiment of the invention.

FIG. 8 depicts the design and function of a SaPIbov2-based packaging system 800 that lacks the int gene, according to an embodiment of the invention. In this system, a *S. aureus* cell 801 is lysogenized with φ11 that has its small terminase gene deleted 803. The cell's genome 802 carries SaPIbov2 that has its integrase (int) gene deleted 804 and also carries the deleted int gene operatively linked the constitutively expressed PclpB gene promoter 805. The int gene can express the integrase protein (Int) in trans from SaPIbov2 806. When the phage is induced into its lytic cycle, the phage genome is excised (not shown) from the bacterial genome 802, which then expresses bacteriophage proteins including capsid constituents 807 and the large terminase protein (TerL) 808. Prophage induction also triggers SaPIbov2 excision via the expression of the integrase protein 806. In a similar manner to the excised phage genome (not shown), the excised SaPIbov2 circularizes 809, expresses its own small terminase protein (TerS) 810 and begins to replicate forming a SaPIbov2 concatamer 811. The phage TerL gene and SaPIbov2 TerS gene can then combine bind and cleave the SaPIbov2 concatamer via a pac-site sequence in the SaPIbov2 DNA and the SaPIbov2 concatamer can then be packaged into phage capsids 812 resulting in phage particles carrying SaPIbov2 concatamers 813. In this system, phage DNA will not be packaged since it lacks the terS gene that contains the phage's pac-site sequence and thus cannot be recognized by the expressed SaPIbov2 TerS and phage TerL proteins.

IV. Reporters

In some embodiments, the NRTPs and constructs of the invention comprise a reporter nucleic acid molecule including a reporter gene. The reporter gene can encode a reporter molecule, and the reporter molecule can be a detectable or selectable marker. In certain embodiments, the reporter gene encodes a reporter molecule that produces a detectable signal when expressed in a cell.

In certain embodiments, the reporter molecule can be a fluorescent reporter molecule, such as, but not limited to, a green fluorescent protein (GFP), enhanced GFP, yellow fluorescent protein (YFP), cyan fluorescent protein (CFP), blue fluorescent protein (BFP), red fluorescent protein (RFP) or mCherry, as well as near-infrared fluorescent proteins.

In other embodiments, the reporter molecule can be an enzyme mediating luminescence reactions (luxA, luxB, luxAB, luc, ruc, nluc, etc.). Reporter molecules can include a bacterial luciferase, a eukaryotic luciferase, an enzyme suitable for colorimetric detection (lacZ, HRP), a protein suitable for immunodetection, such as affinity peptides (His-tag, 3X-FLAG), a nucleic acid that function as an aptamer or that exhibits enzymatic activity (ribozyme), or a selectable marker, such as an antibiotic resistance gene (ampC, tet(M), CAT, erm). Other reporter molecules known in the art can be used for producing signals to detect target nucleic acids or cells.

In other aspects, the reporter molecule comprises a nucleic acid molecule. In some aspects, the reporter molecule is an aptamer with specific binding activity or that exhibits enzymatic activity (e.g., aptazyme, DNAzyme, ribozyme).

Reporters and reporter assays are described further in Section V herein.

V. NRTPs and Reporter Assays

A. Inducer Reporter Assay

The invention comprises methods for the use of NRTPs as reporter molecules for use with endogenous or native inducers that target gene promoters within viable cells. The NRTPs of the invention can be engineered using the methods described in Section III and below in Examples 1-6.

In some embodiments, the method comprises employing a NRTP as a reporter, wherein the NRTP comprises a reporter gene that is operably linked to an inducible promoter that controls the expression of a target gene within a target cell. When the NRTP that includes the reporter gene is introduced into the target cell, expression of the reporter gene is possible via induction of the target gene promoter in the reporter nucleic acid molecule.

Figure 9:
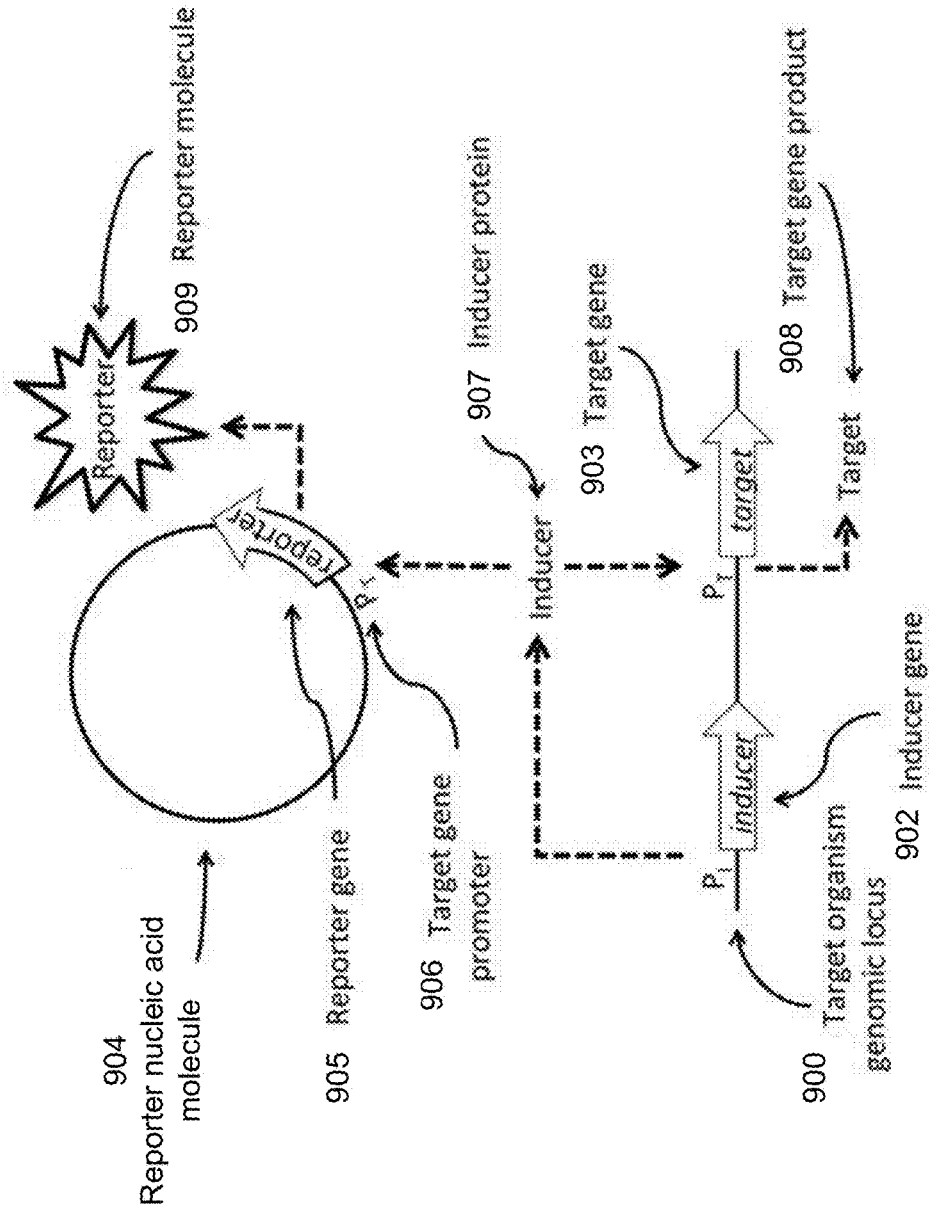
FIG. 9 depicts a system for the use of NRTPs for the detection of inducers to target gene promoters within viable cells, according to an embodiment of the invention.

FIG. 9 depicts a genomic locus of a target cell 900 with two genes, a gene encoding an inducer 902 and a target gene 903. Also depicted is a reporter nucleic acid molecule 904 that includes a reporter gene 905 that is operatively linked to the promoter 906 of the target gene of the target cell. The reporter nucleic acid molecule 904 can be introduced into the cell via a NRTP. In the native cell, when the inducer gene 902 is expressed and produces the inducer protein 907, the inducer protein 907 is able to induce the target gene promoter 906 that is operatively linked to the target gene, thus causing the expression of the target gene and the production of the target gene product 908.

When the reporter nucleic acid molecule 904 is present within the target organism, the inducer 907 is also able to induce the target gene promoter 906 present within the reporter nucleic acid molecule 904, thus causing the expression of the reporter gene 905 resulting in the production of a reporter molecule 909 capable of generating a detectable signal.

Thus, the production of a detectable signal from the reporter molecule 909 is indicative of the presence of the cell, based on the presence of the inducer protein 907 within a target cell.

1) VanR Reporter System

In one embodiment, the reporter system includes NRTP comprising a reporter nucleic acid molecule (e.g., plasmid). The reporter nucleic acid molecule can be constructed for detecting VanR, the inducer of the promoter of the vancomycin resistance (vanA) gene in *Enterococcus faecium* (or *E. faecalis*). The reporter plasmid carries a reporter gene that is operatively linked to the vanA gene promoter.

Figure 10:
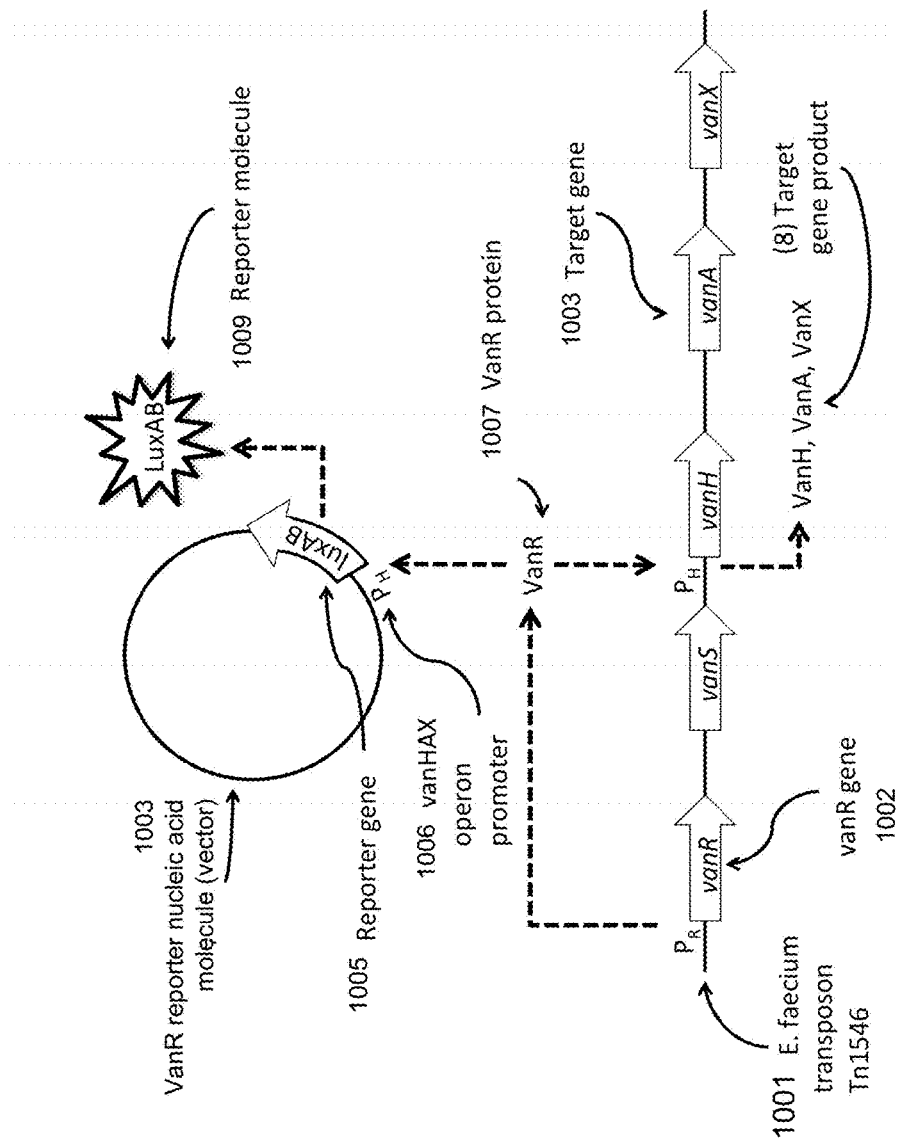
FIG. 10 depicts a reporter system that includes a reporter nucleic acid molecule (e.g., plasmid) that is constructed for detecting VanR, the inducer of the promoter of the vancomycin resistance (vanA) gene in *Enterococcus faecium* (or *E. faecalis*), according to an embodiment of the invention. The reporter plasmid carries a reporter gene that is operatively linked to the vanA gene promoter.
Figure 11:
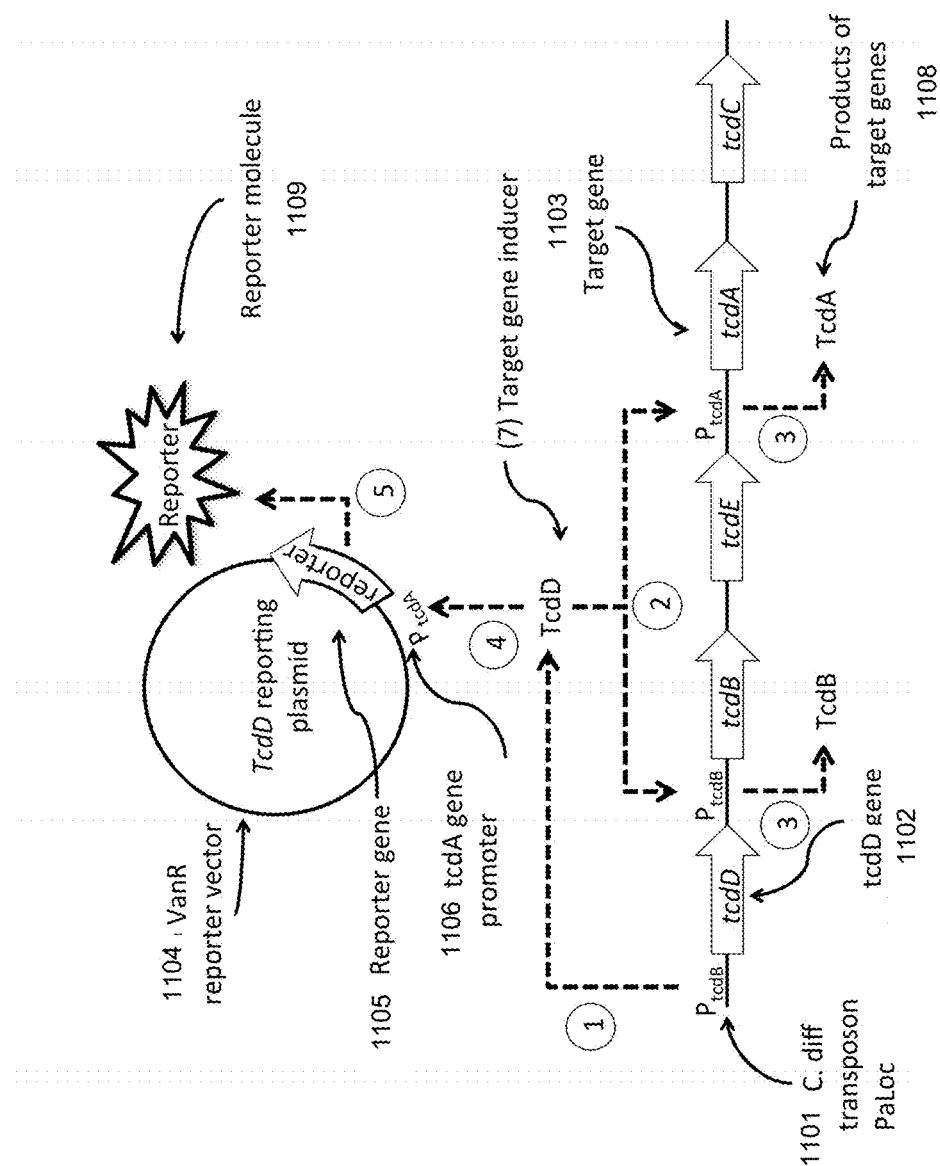
FIG. 11 depicts a reporter system that includes a reporter nucleic acid molecule constructed for detecting TcdD, the inducer of the promoters of the toxins A and B genes (tcdA and tcdB, respectively) of *C. difficile*, according to an embodiment of the invention. The reporter nucleic acid molecule includes a reporter gene that is operatively linked to the tcdA gene promoter.
Figure 12:
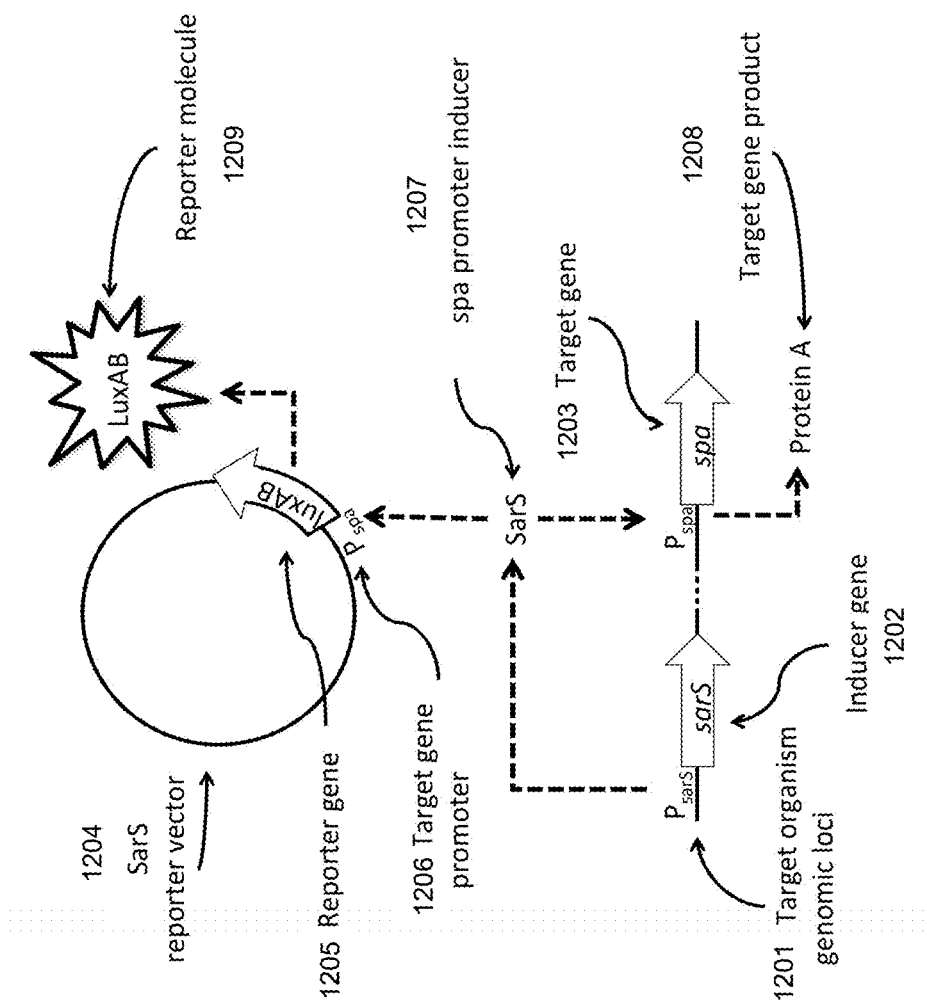
FIG. 12 depicts a reporter system that includes a reporter nucleic acid molecule is constructed for detecting SarS, the inducer of the promoter of the Protein A gene (spa) in *S. aureus*, according to an embodiment of the invention. The reporter nucleic acid molecule includes the bacterial luciferase genes luxA and luxB operatively linked to the spa gene promoter ($P_{spa}$).
Figure 13:
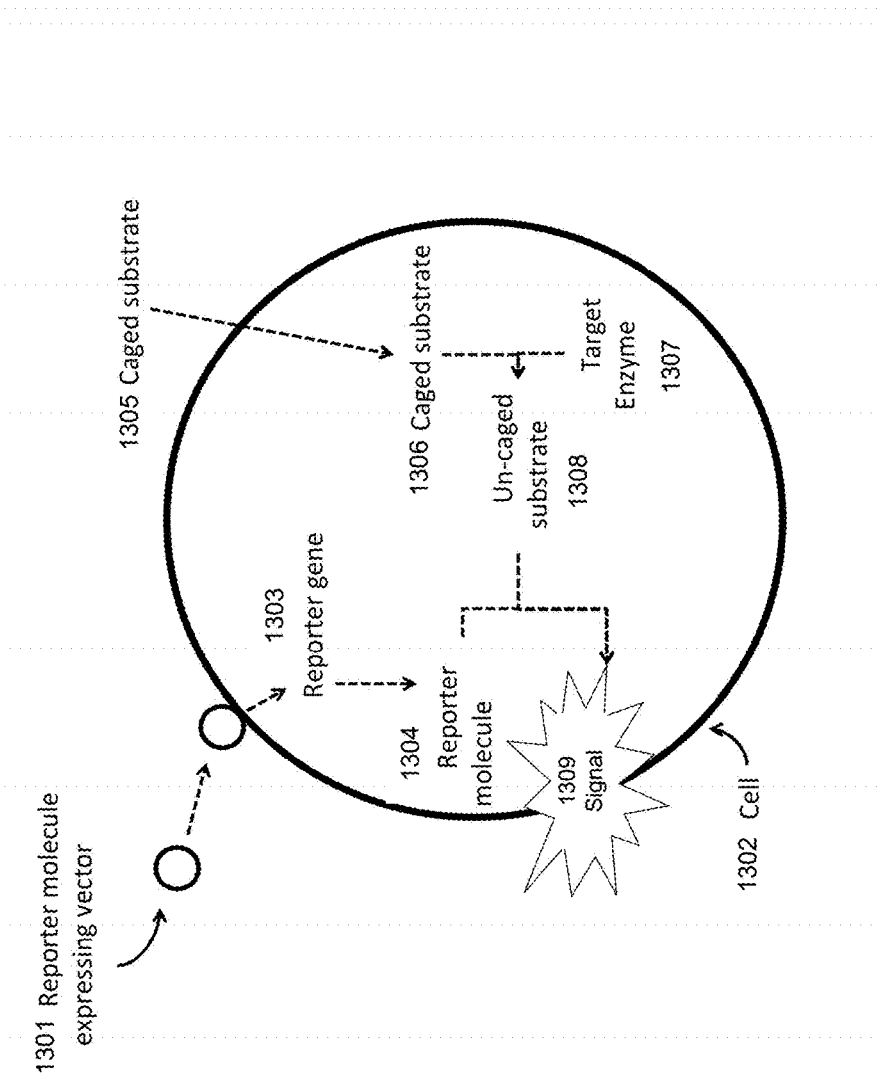
FIG. 13 shows a reporter system that comprises a system for the detection of intracellular enzymes within viable cells that employs caged substrate molecules that can be un-caged by a target intracellular enzyme, according to an embodiment of the invention.

FIG. 10 outlines the design and function of a VanR reporter system. FIG. 10 depicts a region of the transposon Tn1546 1001 that may be present in *E. faecium*. The Tn1546 transposon can include the vanR inducer gene 1002 and the vanA target gene 1003. Also depicted in the figure is a reporter nucleic acid molecule 1004 that can be packaged in a NRTP and introduced into the cell. The reporter nucleic acid molecule 1004 includes a reporter gene 1005 that is operatively linked to a promoter $P_H$ 1006 that controls the expression of the vanHAX operon that includes the vanA gene. In the native cell, when the vanR gene 1002 is expressed and produces the VanR protein 1007, VanR is able to induce $P_H$ 1006 in the Tn1546 transposon, thus causing the expression of the vanA gene and thus producing the VanA protein 1008. When the reporter nucleic acid molecule 1003 (vector) is present within the target organism, VanR is also able to induce $P_H$ 1006 within the reporter nucleic acid molecule 1003, thus causing the expression of a reporter molecule 1009. Thus, the production of a reporter molecule is indicative of the presence of VanR within a target cell.

Examples of promoters that are suitable for the development of a VRE assay include: the vanA gene promoter and a vanB gene promoter. Arthur, M., et al., *The VanS sensor negatively controls VanR-mediated transcriptional activation of glycopeptide resistance genes of Tn1546 and related elements in the absence of induction*. J. Bacteriol., 1997. 179(1): p. 97-106.

2) TcdD reporter system

In another embodiment of this system, a reporter nucleic acid molecule is introduced into a cell using a NRTP. The reporter nucleic acid molecule can be constructed for detecting TcdD, the inducer of the promoters of the toxins A and B genes (tcdA and tcdB, respectively) of *C. difficile*. The reporter nucleic acid molecule includes a reporter gene that is operatively linked to the tcdA gene promoter.

FIG. 11 outlines the design and function of a TcdD reporter system, according to an embodiment of the invention. FIG. 11 depicts a region of the transposon PaLoc 1101 that may be present in *C. difficile*. The PaLoc transposon may contain the tcdD gene 1102 and the tcdA target gene 1103. Also depicted in the figure is a reporter nucleic acid molecule 1104 (e.g., vector) that is introduced into the cell using a NRTP. The reporter nucleic acid molecule 1104 includes the reporter gene 1105 that operatively linked to the tcdA gene promoter ($P_{tcdA}$) 1106.

In the native cell, when the tcdD gene is expressed and produces the TcdD protein 1107, TcdD is able to induce $P_{tcdA}$ 1106 in the PaLoc transposon 1101, thus causing the expression of the tcdA gene 1103 and thus producing the toxin A protein 1108.

When the reporter nucleic acid molecule 1104 is present within the target organism, TcdD is also able to induce $P_{tcdA}$ 1106 within the reporter vector, thus causing the expression of a reporter molecule 1109. Thus, the production of a reporter molecule 1109 is indicative of the presence of TcdD within a target cell.

Examples of promoters suitable for the development of a *C. difficile* assay include: the tcdA gene promoter and the tcdB gene promoter. Karlsson, S., et al., *Expression of Clostridium difficile Toxins A and B and Their Sigma Factor TcdD Is Controlled by Temperature*. Infect. Immun., 2003. 71(4): p. 1784-1793.

Target Cells and Inducers:

Target cells can include eukaryotic and prokaryotic cell targets and associated inducers.

Vector Delivery Systems:

The delivery of the vector containing the recombinant DNA can by performed by abiologic or biologic systems. Including but not limited to liposomes, virus-like particles, transduction particles derived from phage or viruses, and conjugation.

3) Bacteriophage-Based SarS Reporter System

In another embodiment of the invention, a reporter nucleic acid molecule is constructed for detecting SarS, the inducer of the promoter of the Protein A gene (spa) in *S. aureus*. The reporter nucleic acid molecule can be introduced into the cell in a NRTP and includes the bacterial luciferase genes luxA and luxB operatively linked to the spa gene promoter ($P_{spa}$). The reporter nucleic acid molecule is delivered to *S. aureus* via a NRTP, for example. If SarS is present in the cell, it will induce the expression of the luxAB genes, thus producing luciferase enzyme that is capable of generating a luminescent signal.

FIG. 12 outlines the design and function of a SarS reporter system, according to one embodiment of the invention. FIG. 12 depicts a region of the *S. aureus* genome 1201 that contain the sarS gene 1202 and spa gene 1203. Also depicted in the figure is a reporter nucleic acid molecule (e.g., vector) 1204 delivered by NRTP to the cell and that includes the luxAB reporter genes 1205 that operatively linked to the promoter $P_{spa}$ 1206 that controls the expression of the spa gene 1203.

In the native cell, when the sarS gene 1202 is expressed, producing SarS protein 1207, the protein is able to induce $P_{spa}$ 1206 in the *S. aureus* genome transposon, thus causing the expression of the spa gene 1203 and producing the Protein A 1208.

When the reporter nucleic acid molecule 1204 is present within the target organism, SarS 1207 is also able to induce $P_{spa}$ 1206 within the reporter nucleic acid molecule 1204, thus causing the expression of luxAB resulting in the production of the luciferase enzyme 1209 that can generate a luminescent signal. Thus, the production of luciferase is indicative of the presence of SarS within a target cell.

B. Enzyme Reporter Assay

The invention comprises a system for the detection of intracellular enzymes within viable cells that employs caged substrate molecules that can be un-caged by a target intracellular enzyme, according to an embodiment of the invention.

FIG. 13 depicts the design and function of an intracellular enzyme detection system. A reporter molecule-expressing vector 1301 is delivered to a target cell 1302 with a NRTP (not shown). The reporter molecule-expressing vector 1301 is able to penetrate the target cell 1302 via the NRTP and deliver a reporter molecule gene 1303 into the target cell 1302, and a reporter molecule 1304 can then be expressed from the reporter molecule gene 1303. A caged substrate 1305 is also added to the target cell 1302 and is able to penetrate into the target cell 1302. If a target intracellular enzyme 1307 is present in the target cell 1306, the enzyme 1307 is able to remove the caging component of the caged substrate 1305, thus producing an un-caged substrate 1308. The un-caged substrate 1308 can then react with the reporter molecule 1304 inside of the cell 1302, and the product of this reaction results in a detectable signal 1309.

Target Cells and Enzymes:

Target cells can include eukaryotic and prokaryotic cell targets and associated enzymes, including, for example, β-lactamases in *S. aureus*.

Vector Delivery Systems:

The delivery of the vector containing the recombinant DNA can by performed by abiologic or biologic systems. Including but not limited to liposomes, virus-like particles, transduction particles derived from phage or viruses, and conjugation.

Reporter Molecules and Caged Substrates:

Various reporter molecules and caged substrates can be employed as those described in Daniel Sobek, J. R., Enzyme detection system with caged substrates, 2007, Zymera, Inc.

1) Bacteriophage-Based β-Lactamase Reporter

In one embodiment, a reporter molecule-expressing vector can be carried by a NRTP, such that the vector can be delivered into a bacterial cell. The reporter molecule to be expressed can be Renilla luciferase, and the caged substrate can be Renilla luciferin that is caged, such that a β-lactamase enzyme that is endogenous to the target cell is able to cleave the caging compound from the caged luciferin and release un-caged luciferin.

Figure 14:
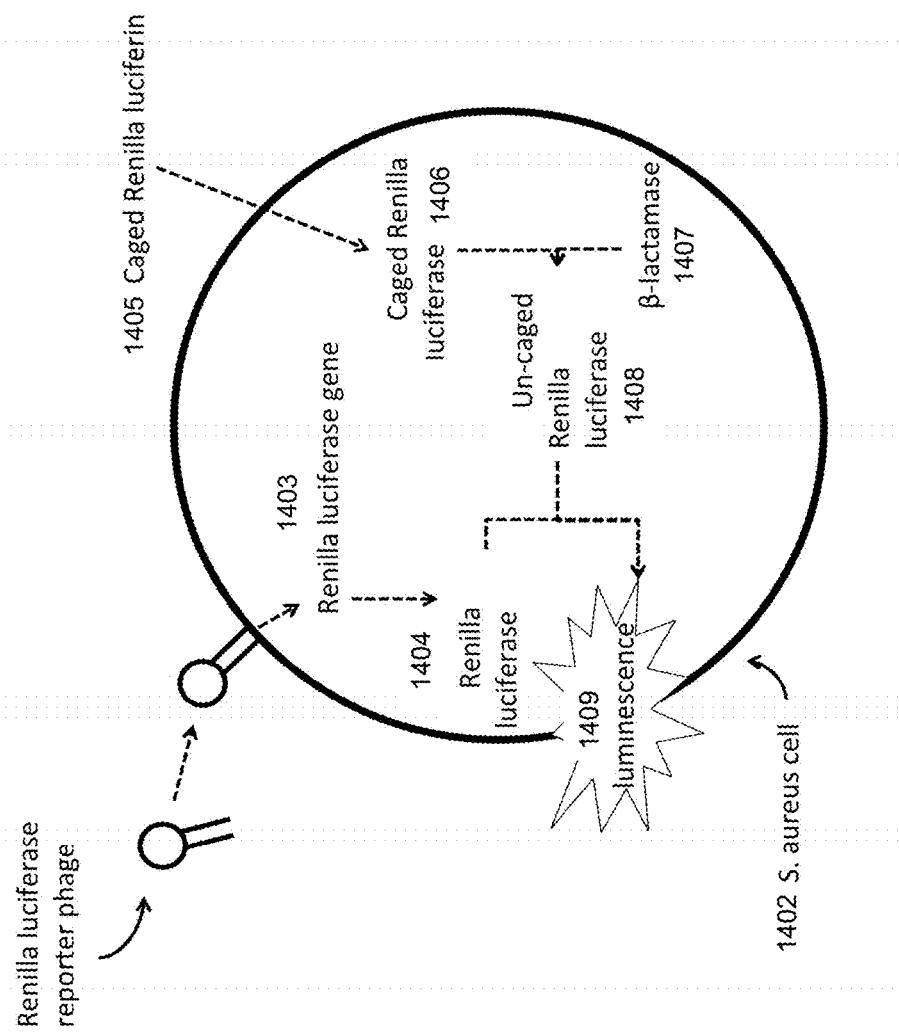
FIG. 14 depicts the design and function of a β-lactamase enzyme detection system, according to an embodiment of the invention.

FIG. 14 depicts the design and function of a β-lactamase enzyme detection system, according to an embodiment of the invention. A Renilla luciferase-expressing vector carried by a bacteriophage-based NRTP 1401 is added to a target S. aureus cell 1402. The Renilla luciferase-expressing vector is able to penetrate the target cell 1402 using a NRTP comprising the vector. The NRTP delivers the Renilla luciferase gene 1403 into the target cell 1402, and Renilla luciferase 1404 can then be expressed from its gene. Caged Renilla luciferin 1405 is also added to the target cell 1402 and is able to penetrate into the target cell 1402. If an intracellular α-lactamase 1407 is present in the target cell 1402, the enzyme is able to remove the caging component of the caged luciferin 1406, thus producing an un-caged luciferin 1408. The un-caged luciferin 1408 can then react with the Renilla luciferase 1404 inside of the cell 1402, and the product of this reaction results in luminescence 1409.

In this manner, when a target cell that contains the β-lactamase is exposed to the NRTP and caged luciferin, the cell will exhibit a luminescent signal that is indicative of the presence of the β-lactamase present in the cell.

C. Intracellular Molecule Reporter

The invention includes a system for the detection of intracellular molecules within viable cells that employs switchable molecules capable of generating a detectable signal upon their binding to a target molecule.

Figure 15:
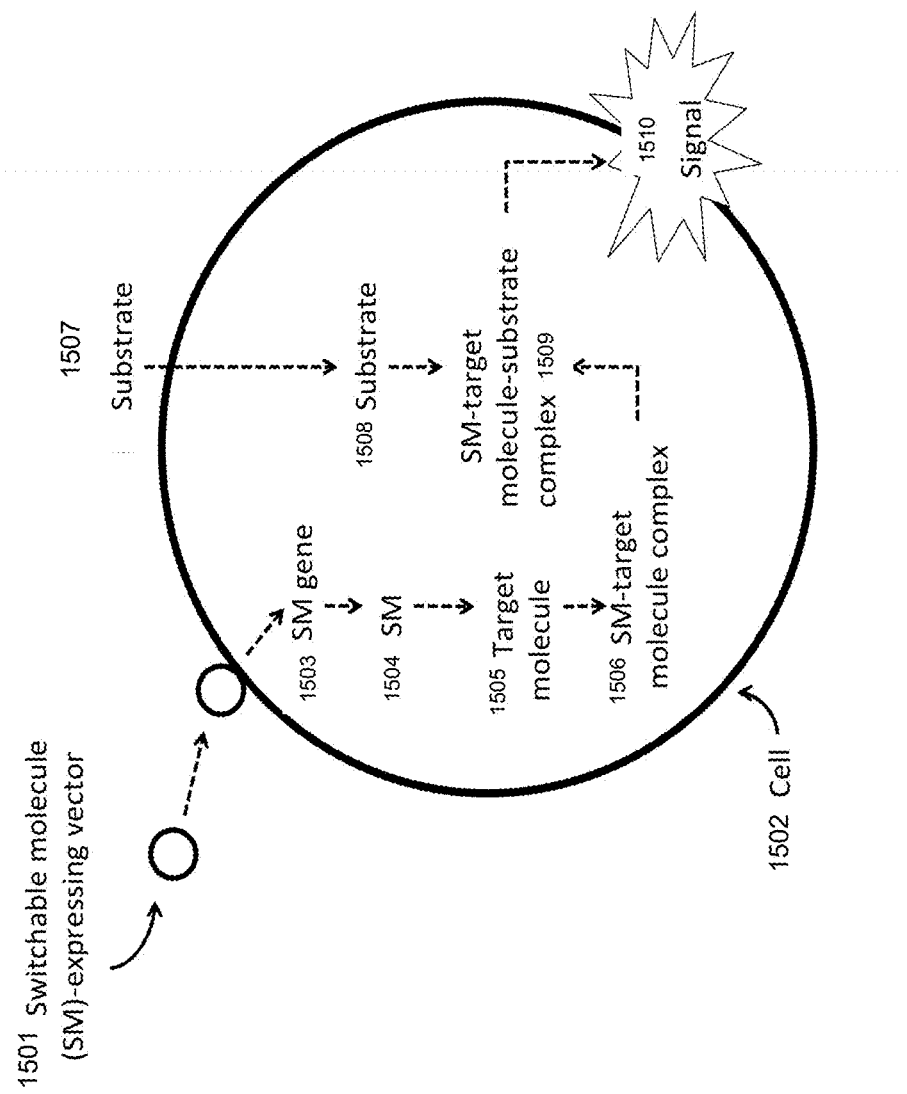
FIG. 15 shows a reporter system for the detection of intracellular molecules within viable cells that employs switchable molecules capable of generating a detectable signal upon their binding to a target molecule, according to an embodiment of the invention.

FIG. 15 depicts the design and function of a switchable molecule (SM)-based intracellular molecule detection system. A SM-expressing vector 1501 is delivered to a target cell 1502 in a NRTP. The SM-expressing vector 1501 is able to penetrate the target cell 1502 and deliver a SM gene 1503 into the target cell 1502. A SM protein 1504 can then be expressed from the SM gene 1503. The SM protein 1504 can then bind to a target molecule 1505 inside of the cell and thus forms an SM-target molecule complex 1506. The binding of the SM 1504 to the target molecule 1505 results in a conformational change in the SM 1504 that makes the bound SM amenable to binding of a substrate. A substrate 1508 is added to the cell 1507 and is able to penetrate into the cell 1502. Bound SM inside of the cell 1502 is able to also bind the substrate, thus forming a SM-target molecule-substrate complex 1509. Finally, the binding of the substrate 1508 by the target molecule-bound SM has the effect of producing a detectable signal 1510. Thus a detectable signal generated by the system is indicative of the presence of a target molecule inside of a cell.

Target Cells and Molecules:

Various eukaryotic and prokaryotic cell targets can be employed and switchable aptamer-based SM's can be designed to target various nucleic acid and amino acid-based intracellular molecular targets as described in Samie Jaffrey, J. P., *Coupled recognition/detection system for in vivo and in vitro use*, 2010, Cornell University.

Vector Delivery Systems:

The delivery of the vector containing the recombinant DNA can by performed by abiologic or biologic systems. Including but not limited to liposomes, virus-like particles, transduction particles derived from phage or viruses, and conjugation.

1) Non-Replicative Transduction Particle/Switchable Aptamer-Based Intracellular Molecule Reporter System In one example of this method, a switchable molecule-expressing vector can be carried by a bacteriophage-based transduction particle such that the vector can be delivered into a bacterial cell. The switchable molecule to be expressed can be a switchable aptamer that is designed to undergo a conformational change upon its binding to an intracellular target molecule. The conformational change allows the aptamer to then bind a fluorophore that exhibits enhanced fluorescence when bound by the aptamer.

Figure 16:
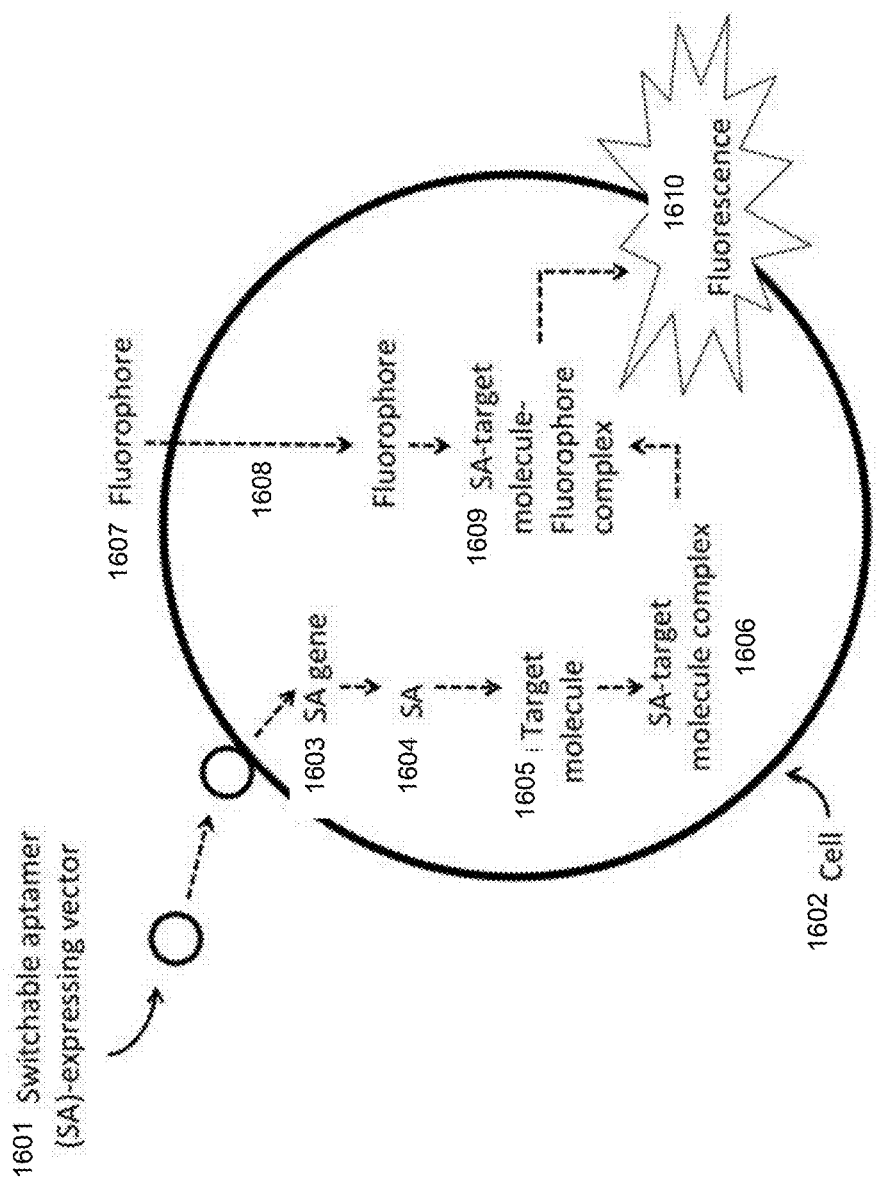
FIG. 16 depicts the design and function of a bacteriophage/switchable-aptamer (SA)-based intracellular molecule reporter system, according to an embodiment of the invention.

FIG. 16 depicts the design and function of a bacteriophage/switchable-aptamer (SA)-based intracellular molecule reporter system. A SA-expressing vector carried by a NRTP 1601 is added to a target cell 1602. The NRTP 1601 is able to deliver the SA-expressing vector and the SA-expressing gene 1603 into the target cell 1602. An SA protein 1604 can then be expressed from the SA gene 1603. The SA protein 1604 can then bind to a target molecule 1605 inside of the cell and thus form an SA-target molecule complex 1606. The binding of the SA 1604 to the target molecule 1605 results in a conformational change in the SA that makes the bound SA amenable to binding of a fluorophore 1608. A fluorophore 1607 is added to the cell and is able to penetrate into the cell 1608. Bound SA inside of the cell is able to also bind the fluorophore thus forming an SA-target molecule-fluorophore complex 1609. Finally, the binding of the fluorophore by the target molecule-bound SA has the effect of enhancing the fluorescence of the fluorophore 1610. Thus, a detectable fluorescent signal generated by the system is indicative of the presence of a target molecule inside of a cell.

D. Transcript Reporter Assay

The invention comprises a reporter assay comprising an antisense RNA-based method for detecting target transcripts within viable cells by causing the expression of a reporter molecule if a target transcript is present within a cell.

Certain intracellular methods in the art for inhibiting gene expression employ small interfering RNA, such as double-stranded RNA (dsRNA), to target transcribed genes in cells. The dsRNA comprise antisense and sense strands that are delivered into or expressed in cells, and the strands of the dsRNA act via a trans-acting inhibition mechanism, where one strand (typically the antisense strand) binds to a target gene sequence (RNA transcript) and prevents expression of the target gene sequence. Double-stranded RNA molecules have been shown to block (knock down) gene expression in a highly conserved regulatory mechanism known as RNA interference (RNAi). WO 99/32619 (Fire et al.) discloses the use of a dsRNA of at least 25 nucleotides in length to inhibit the expression of genes in *C. elegans*. dsRNA has also been shown to degrade target RNA in other organisms, including plants (see, e.g., WO 99/53050, Waterhouse et al.; and WO 99/61631, Heifetz et al.), *Drosophila* (see, e.g., Yang, D., et al., Curr. Biol. (2000) 10:1191-1200), and mammals (see WO 00/44895, Limmer; and DE 101 00 586.5, Kreutzer et al.). However, binding of a strand of the dsRNA to the target gene can be non-specific. If a similar mechanism were to be applied to a detection system, this non-specific binding can result in high false positive rates, which make it unsuitable for the development of clinically useful detection systems.

Previous trans-acting inhibition mechanisms have been shown to be unsuitable for development of clinically useful detection systems. For example, some methods result in high levels of non-specific signals and up to 90% false positive rate, when achieving a 90% sensitivity of the assay. See U.S. Pat. No. 8,329,889. Certain methods for post-transcriptional regulation of gene expression have been developed that use a cis-repressed marker transcript, such as a green fluorescent protein marker, where the ribosomal binding site of the marker is blocked by the cis-repressing sequence, along with a trans-activating RNA transcript. When the trans-activating RNA transcript binds to the cis-repressed marker transcript, the hairpin structure of the cis-repressed marker transcript is altered, and the upstream ribosome binding site of the marker gene is exposed, allowing transcription and expression of the marker gene. However, these methods have not previously been used for the detection of endogenous transcripts, nor successful beyond a basic switching mechanism for controlling expression of genes in cells.

1) Nucleic Acid Molecule Interactions and Mechanisms

The methods of the invention take advantage of the transcript-level regulation mechanisms, including antisense RNA (asRNA) mechanism in cells, to deliver nucleic acid molecules into cells. The antisense mechanism includes all forms of sequence-specific mRNA recognition leading to reduced, eliminated, increased, activated, or otherwise altered expression of a target transcript. See Good, L., *Translation Repression By Antisense Sequences*. Cellular and Molecular Life Sciences, 2003. 60(5): p. 854-861, and Lioliou, E., *RNA-mediated regulation in bacteria: from natural to artificial systems*, New Biotechnology. 2010. 27(3): p. 222-235. Naturally occurring asRNAs are found in all three kingdoms of life, and they affect messenger RNA (mRNA) destruction, repression and activation, as well as RNA processing and transcription. See Sabine, B., *Antisense-RNA regulation and RNA Interference*. Biochimica et Biophysica Acta (BBA)—Gene Structure and Expression, 2001. 1575(1-3): p. 15-25. This mechanism has been exploited in inhibiting protein synthesis for therapeutic applications.

Antisense RNA is a single-stranded RNA that is complementary to a messenger RNA (mRNA) strand transcribed within a cell. asRNA may be introduced into a cell to inhibit translation of a complementary mRNA by base pairing to it and physically obstructing the translation machinery. Antisense RNA anneal to a complementary mRNA target sequence, and translation of the mRNA target sequence is disrupted as a result of steric hindrance of either ribosome access or ribosomal read through.

The antisense RNA mechanism is different from RNA interference (RNAi), a related process in which double-stranded RNA fragments (dsRNA, also called small interfering RNAs (siRNAs)) trigger catalytically mediated gene silencing, most typically by targeting the RNA-induced silencing complex (RISC) to bind to and degrade the mRNA. Annealing of a strand of the dsRNA molecule to mRNA or DNA can result in fast degradation of duplex RNA, hybrid RNA/DNA duplex, or duplex RNA resembling precursor tRNA by ribonucleases in the cell, or by cleavage of the target RNA by the antisense compound itself.

The RNAi pathway is found in many eukaryotes and is initiated by the enzyme Dicer, which cleaves long double-stranded RNA (dsRNA) molecules into short double stranded fragments of ~20 nucleotides that are called siRNAs. Each siRNA is unwound into two single-stranded RNAs (ssRNA), namely the passenger strand and the guide strand. The passenger strand is degraded, and the guide strand is incorporated into the RNA-induced silencing complex (RISC). In post-transcriptional gene silencing, the guide strand base pairs with a complementary sequence in a messenger RNA molecule, and cleavage is induced by a protein called Argonaute, the catalytic component of the RISC complex.

In regards to the nucleic acid interactions of the mechanisms of the invention, interactions between a reporter transcript and a target transcript can rely on base pairings between loops present in both transcripts (e.g., "kissing complexes"), or between a loop and a single-stranded (ss) region. In some cases, the kissing complex formation suffices for mediating the desired effect of the interaction, and in other cases, propagation of the primary contacts will lead to an interaction resulting in the desired effect.

2) Mechanisms for Cis-Repression and Trans-Activation of Translation of a Reporter Construct Via Transcript-Level Regulation The following description illustrates transcript reporter systems based on various repression/activation mechanisms that can be used, according to embodiments of this invention. In each of FIGS. 17-20, a vector includes a reporter construct comprising a reporter sequence, and the regions on the reporter construct are shown in each of the figures, including regions that can be targeted for repression by a cis-repressing sequence. The description below provides non-limiting examples of various inhibition mechanisms, including transcription attenuation, translation attenuation, and destabilization of the transcript, and various activation mechanisms including conformational changes and cleavage.

Figure 17:
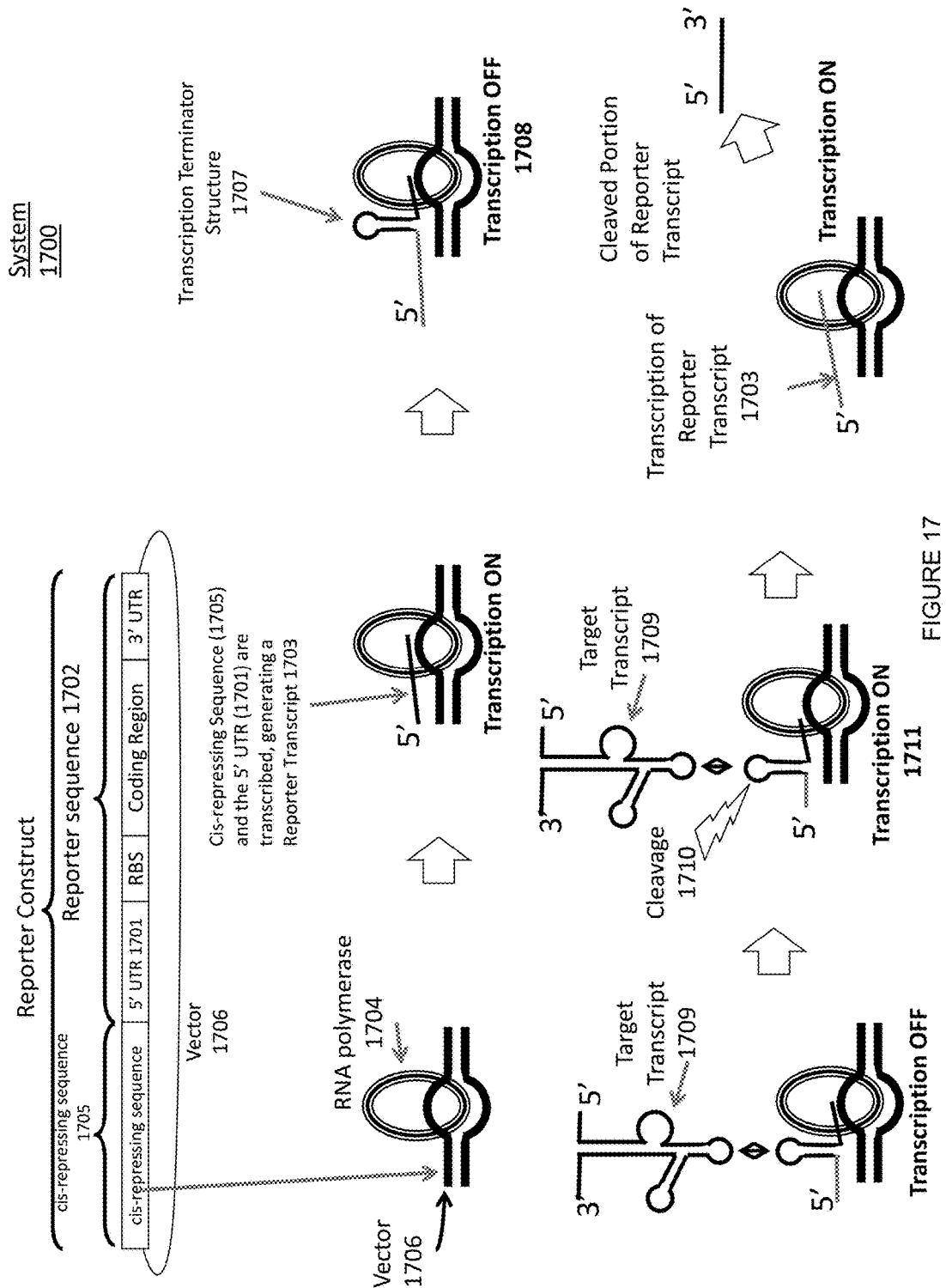
FIG. 17 depicts an example of a system that uses a cis-repression mechanism that can target the 5' UTR (untranslated region) of a reporter sequence on a reporter transcript, according to an embodiment of the invention.

FIG. 17 depicts an example of a system 1700 that uses a cis-repression mechanism that can target the 5' UTR (untranslated region) 1701 of the reporter sequence 1702 on a reporter transcript 1703. The regions within the reporter sequence 1702 (5'UTR (1701), RBS, Coding Region and 3'UTR) are also shown. The cis-repressing sequence 1705 is upstream of the reporter sequence and up to the 5' UTR 1701 of the reporter sequence. An RNA polymerase 1704 transcribes the sequence of the reporter construct 1703 from the vector 1706.

At some point during transcription, the transcription process is stopped by the formation of a transcription termination (TT) stem-loop structure 1707 in the reporter transcript 1703, due to an interaction within the transcribed cis-repressing sequence 1705. The transcription termination 1707 structure stops 1708 the RNA polymerase 1704 from transcribing the vector 1706. In some embodiments, a transcription termination protein (e.g., NusA in *E. coli*) binds to RNA polymerase and/or to the transcription termination 1707 structure to cease transcription of the reporter construct.

When a target transcript 1709 is present in the cell, the target transcript 1709 binds to the reporter transcript 1703. In some embodiments, the binding between the target transcript and the reporter transcript is by base pairing of the nucleotides in each sequence. The interaction between the target transcript 1709 and the reporter transcript 103 causes the transcription termination (TT) stem-loop structure 1707 to be cleaved 1710. Cleavage of the reporter transcript 1703 can occur by a cellular enzyme, such as RNase III, for example. In this case, the secondary structure of a target transcript is analyzed for the presence of an RNAse III consensus sequence among the ssRNA regions of the secondary structure, for example 5'-nnWAWGNNNUUN-3' (SEQ ID NO: 20) or 5'-NAGNNNNCWUWnn-3' (SEQ ID NO: 21) where "N" and "n" are any nucleotide and "W" is A or U and "N" indicates a relatively strict requirement for Watson-Crick base pairing, while "n" indicates a minimal requirement for base pairing. When such a consensus sequence is found on a target transcript, the loop of the transcription termination structure 1707 can be designed to be complementary to said RNAse III consensus sequence such that when the ssRNA in each RNA molecule hybridize, the RNAse III cleavage site is formed allowing for cleavage of the transcription termination structure 1707. In the mecA transcript, loop T23, starting at nucleotide 1,404, has the sequence CAGAUAACAUUUU (SEQ ID NO: 22) that is suitable for such an approach.

In some embodiments, a cleavage site is engineered in the reporter construct, such that the reporter transcript is cleaved after transcription. The cleavage, in the example provided, can occur immediately adjacent to the location of the loop in the transcription terminator structure. Transcription is re-initiated 1711 by the RNA polymerase 104. Cleavage of the transcription termination (TT) stem-loop structure 1707 allows the remainder of the reporter sequence 1702 to be transcribed and subsequently translated. This results in the production of a detectable or selectable marker from the translated reporter molecule.

In prokaryotes, the transcription termination structure 1707 involves a Rho-independent mechanism with a stem-loop structure that is 7-20 base pairs in length, rich in cytosine-guanine base pairs and is followed by a chain of uracil residues. NusA binds to the transcription termination stem-loop structure 1707 causing RNA polymerase to stall during transcription of the poly-uracil sequence. Weak Adenine-Uracil bonds lower the energy of destabilization for the RNA-DNA duplex, allowing it to unwind and dissociate from the RNA polymerase. In eukaryotes, the transcription termination structure 1707 is recognized by protein factors and involves cleavage of the new transcript followed by polyadenylation.

Figure 18:
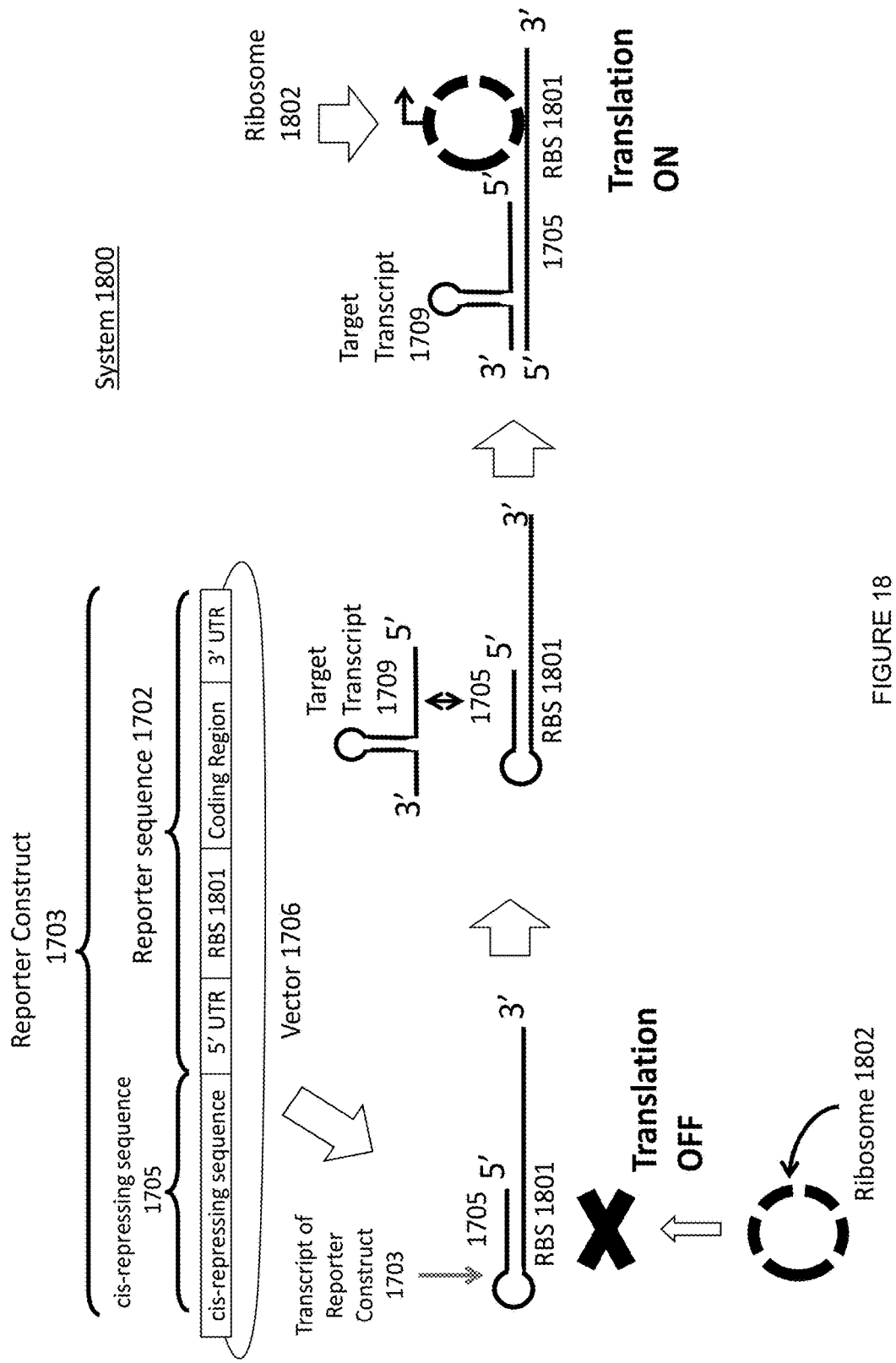
FIG. 18 shows an example of a system for detecting the presence of a target transcript in a cell that is based on a cis-repression mechanism targeting the ribosome binding site (RBS) of a reporter sequence in a reporter transcript, according to an embodiment of the invention.

FIG. 18 shows an example of a system 1800 for detecting the presence of a target transcript in a cell that is based on a cis-repression mechanism targeting the ribosome binding site (RBS) 1801 of the reporter sequence 1702 in the reporter transcript 1703. The RBS 1801 is a sequence of mRNA that is bound by the ribosome 1802 when initiating protein translation. The cis-repressing sequence 1705 is designed to bind to the RBS 1801 (e.g., the cis-repressing sequence 1705 is complementary to the RBS sequence 1801). The RBS 1801 binds to the cis-repressing sequence 1705 and becomes sequestered (inaccessible by a ribosome 1802), preventing the translation of the reporter transcript 1703. When a target transcript 109 from the cell binds to the reporter transcript 1703, the target transcript 1709 has a higher binding affinity for the RBS sequence 1801, and a conformational change occurs in the reporter transcript 1703 in a manner that releases the binding between the cis-repressing 1705 sequence and the RBS sequence 1801. This allows the ribosome 1802 to bind to the RBS 1801, thereby allowing for translation of the reporter transcript 1703.

Figure 19:
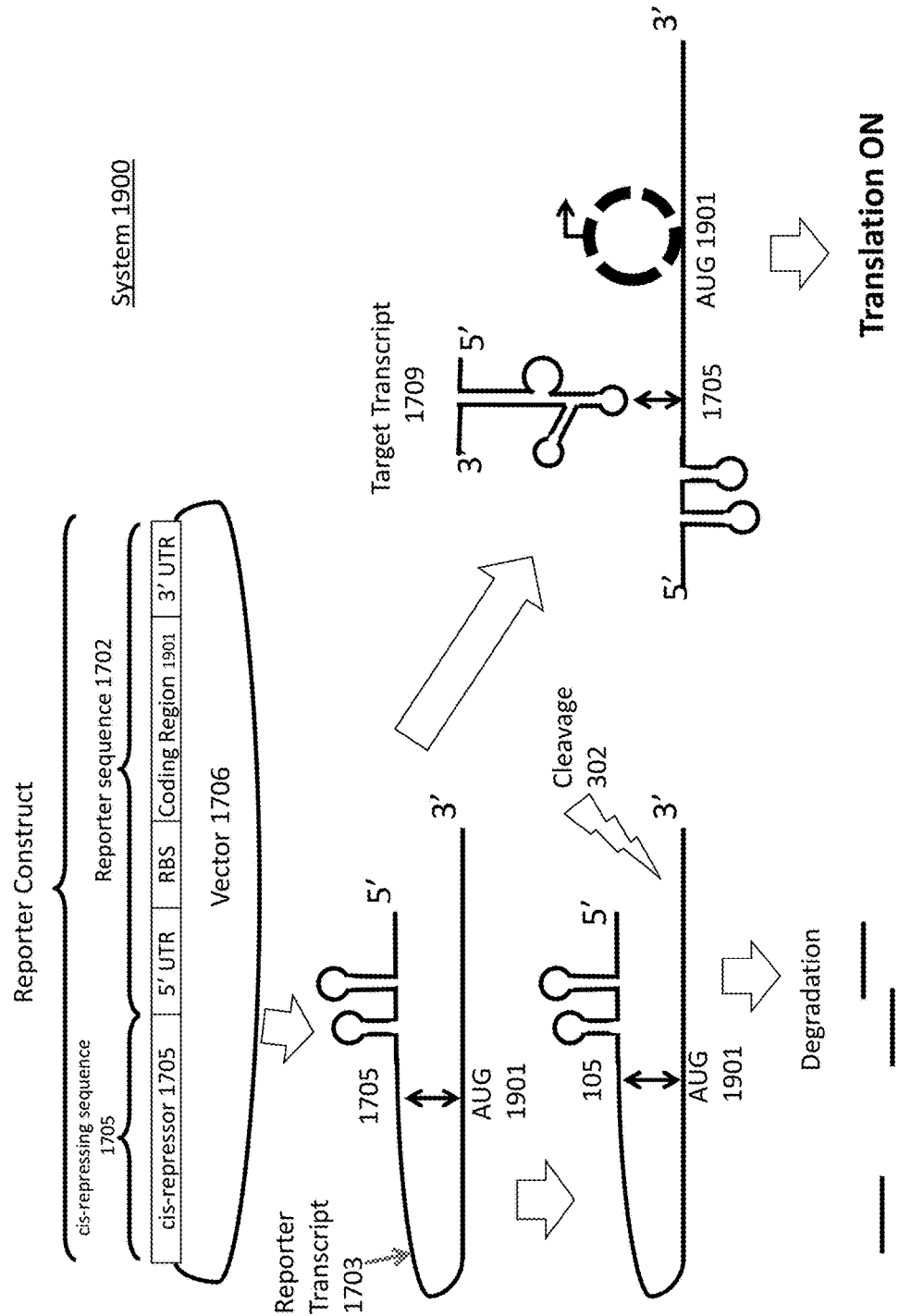
FIG. 19 illustrates an exemplary system for detecting the presence of a target transcript in a cell that is based on a cis-repression mechanism targeting the coding region ("AUG") of a reporter sequence in a reporter transcript, according to an embodiment of the invention.

FIG. 19 illustrates an exemplary system 1900 for detecting the presence of a target transcript in a cell that is based on a cis-repression mechanism targeting the coding region ("AUG") 1901 of the reporter sequence 1702 in the reporter transcript 1703. The cis-repressing sequence 1705 is constructed such that it binds with (e.g., complementary to) the coding region 1901 of the reporter sequence 1702. The "AUG" start codon is shown as part of the coding region 1901. The binding of the cis-repressing sequence 1705 and the coding region 1901 results in a conformation that leads to cleavage 1902 of the reporter construct 1703. Cleavage of the reporter transcript 1703 prevents translation.

When a target transcript 1709 is present in the cell, the target transcript 1709 binds to the cis-repressing sequence 1705 in a manner that causes a conformational change in the reporter transcript 1703. This conformational change prevents or removes the interaction between the cis-repressing sequence 1705 and the coding region 1901 of the reporter sequence 1702, thereby allowing for translation of the reporter sequence 1702.

Figure 20:
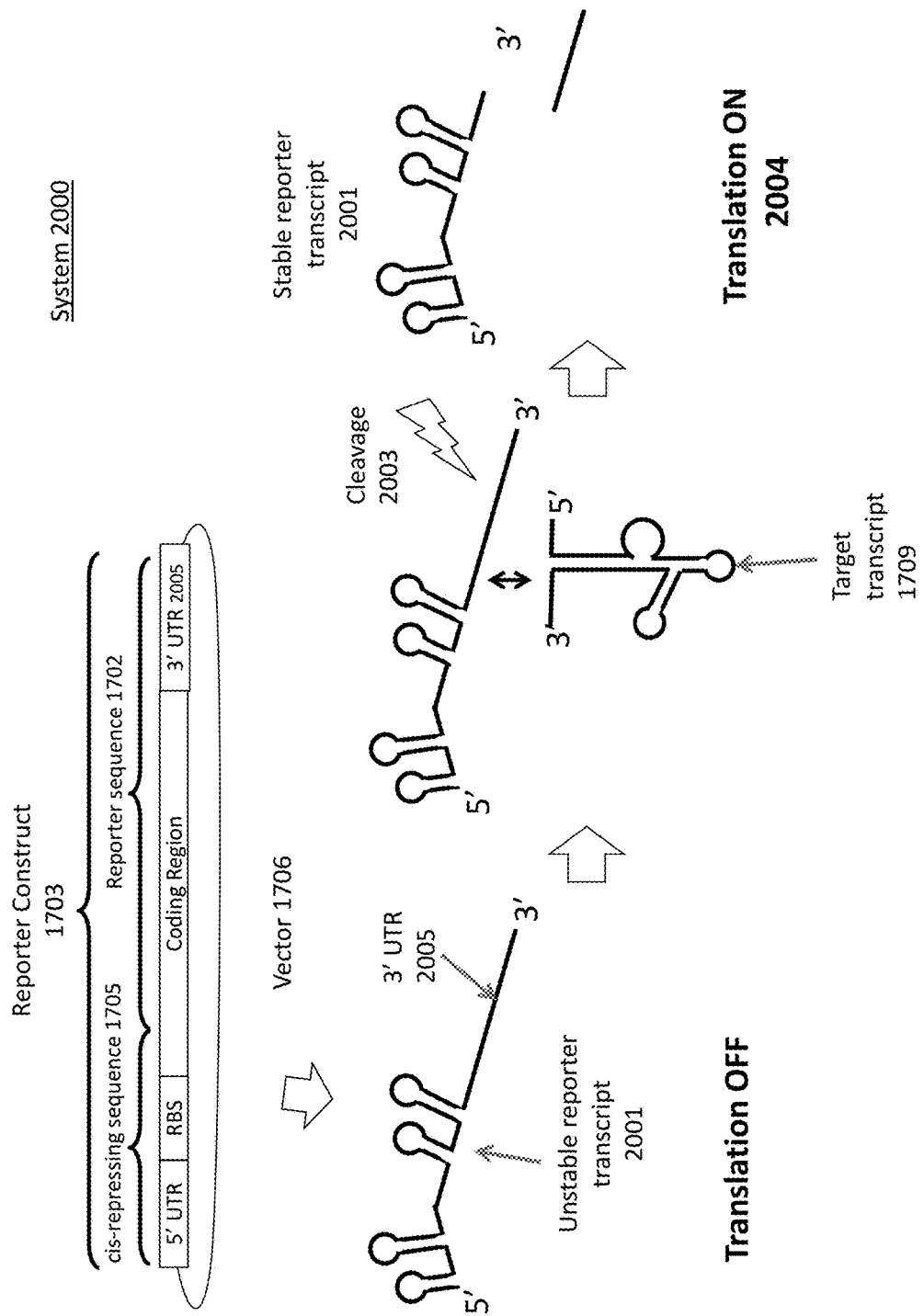
FIG. 20 illustrates an example system for detecting the presence of a target transcript in a cell that is based on a repression mechanism using an unstable reporter transcript, according to an embodiment of the invention.

FIG. 20 illustrates an example system 2000 for detecting the presence of a target transcript in a cell that is based on a repression mechanism using an unstable reporter transcript 2001. The reporter transcript 2001 is designed to be unstable such that it forms an unstable conformation that prevents the translation of the reporter transcript 2001. A reporter transcript 2001 is defined to be unstable if it is prone to rapid degradation due to a variety of factors, such as activity of exosome complexes or a degradosome. A target transcript 1709 in the cell binds to a portion of the unstable reporter transcript 2001. In this example, the portion responsible for destabilizing the transcript is located in the 3' UTR 2005 of the reporter sequence, and the 3' UTR 2005 acts like the cis-repressing sequence of the reporter construct 1703. The binding of the target transcript 1709 with the 3' UTR 2005 of the reporter sequence results in a cleaving event 2003 that stabilizes the reporter transcript 2001 and allows for translation 2004 of the reporter transcript 2001. Cleavage occurs upon binding of the target transcript 1709 and serves to remove the portion of sequence that is responsible for destabilizing the transcript. In this example, the target transcript 1709 binds to the 3' UTR 405 of the reporter sequence, but the system 400 can also be designed such that binding and cleavage occurs in the 5' UTR, upstream of the 5' UTR, or downstream of the 3' UTR. Binding and cleavage can occur anywhere outside of regions necessary for translation of the reporter sequence 1702.

In some embodiments, the cis-repressing sequence itself comprises two sequences that can bind to each other (e.g., complementary to each other), and the conformation of the reporter transcript that results from the binding of the two sequences of the cis-repressing sequence prevents translation of the reporter sequence in the reporter transcript.

3) Naturally Occurring and Synthetic Systems for Repression/Activation Mechanisms Several naturally occurring and synthetically produced transcript-level mechanisms have been described that demonstrate the individual mechanisms (i.e., conformational change and cleavage) employed in each of the examples illustrated in FIGS. 17-20.

Transcription termination has been observed in antisense RNA (asRNA)-mediated transcriptional attenuation. In one example, two loop—loop interactions between RNAIII/repR mRNA are subsequently followed by the formation of a stable duplex. This complex stabilizes a Rho-independent terminator structure to arrest elongation by RNA polymerase (RNAP).

The RBS sequestration mechanism has been described via the development of a synthetic riboswitch system. In this system, a sequence complementary to a RBS is placed upstream of the RBS, allowing the presence of a linker sequence between the two regions. After transcription of the mRNA, the two complementary regions hybridize. creating a hairpin that prevents docking of the ribosome. To activate translation, a synthetic trans-activating RNA carrying the RBS sequence binds to the hybridized RNA, allowing the RBS to be exposed and available for translation.

The prevention of translation due to the cleaving of RNA has also been described in a natural system where the asRNA MicC targets a sequence inside the coding region of ompD mRNA. The interaction, which is promoted by Hfq, causes the cleaving of the mRNA by RNase E.

Yet another natural mechanism demonstrates a cleaving event to activate translation rather than inhibiting it. The *E. coli* GadY asRNA targets the intergenic region between two genes of the gadXW operon. Following the formation of a stable helix between GadY and the 3'UTR of gadX, an RNase cleavage occurs in the transcript and stabilizes gadX transcript allowing for its translation.

4) Mechanism of Conformational Change by Cis-Repression of the Reporter Sequence and by Binding of a Target Transcript The general mechanisms employed in the invention are intermolecular nucleic acid molecule interactions that may result in two subsequent mechanisms: (1) a conformational change in the secondary structure of the nucleic acid molecules, and (2) a cleaving event. Described herein are methods for designing reporter transcripts that can undergo a conformational change between a cis-repressed conformation and a de-repressed conformation, such that the conformational change is induced by binding of a target transcript to the reporter transcript.

As described above, a reporter transcript can comprise a reporter sequence and be designed such that translation of the reporter gene sequence is blocked by cis-repression of the ribosome binding site (RBS) of the reporter gene.

In some embodiments, the following tools can be used for designing the reporter transcripts of the invention.

1) RNA secondary structure is calculated using secondary structure program, such as Mfold available at a server maintained by The RNA Institute College of Arts and Sciences, University at Albany, State University of New York (Mfold web server for nucleic acid folding and hybridization prediction. Nucleic Acids Res. 31 (13), 3406-15, (2003)).

2) Intermolecular RNA interactions are calculated using a software program such as RNA-RNA InterACTion prediction using Integer Programming (RactIP) available at a server maintained by the Graduate School of Information Science, Nara Institute of Science and Technology (NAIST), Department of Biosciences and Informatics, Keio University Japan.

3) RNA secondary structure is visualized using Visualization Applet for RNA (VARNA), which is a Java lightweight Applet dedicated to drawing the secondary structure of RNA.

A secondary structure of the target transcript can be generated based on the lowest energy conformation calculated by MFold and visualized with VARNA.

ssRNA regions or target regions can be identified within the target transcript that can be ideal for binding to a reporter transcript. In some instances, the secondary structure of the target transcript includes a consensus sequence or loop sequence that can bind to a portion of the reporter sequence. For example, in the mecA transcript of methicillin-resistant *S. aureus*, there is a terminal loop that includes a consensus YUNR sequence ("UUGG") that can be used to bind to a cis-repressing sequence of a reporter transcript. Analysis of the secondary structure of the target transcript can reveal these one or more ssRNA regions that can be suitable for binding to a cis-repressing sequence. The cis-repressing sequence of the reporter transcript can then be designed to bind to these one or more ssRNA regions.

In some embodiments, the cis-repressing sequence can be designed to bind to the RBS of the reporter sequence in the reporter transcript and form a stem-loop structure within the reporter transcript, such that the cis-repressing sequence blocks binding of an RNA polymerase to the RBS of the reporter sequence. Upon binding of the cis-repressing sequence to the ssRNA region of the target transcript, the RBS of the reporter sequence can be exposed and translation of the reporter sequence can be initiated.

Figure 28:
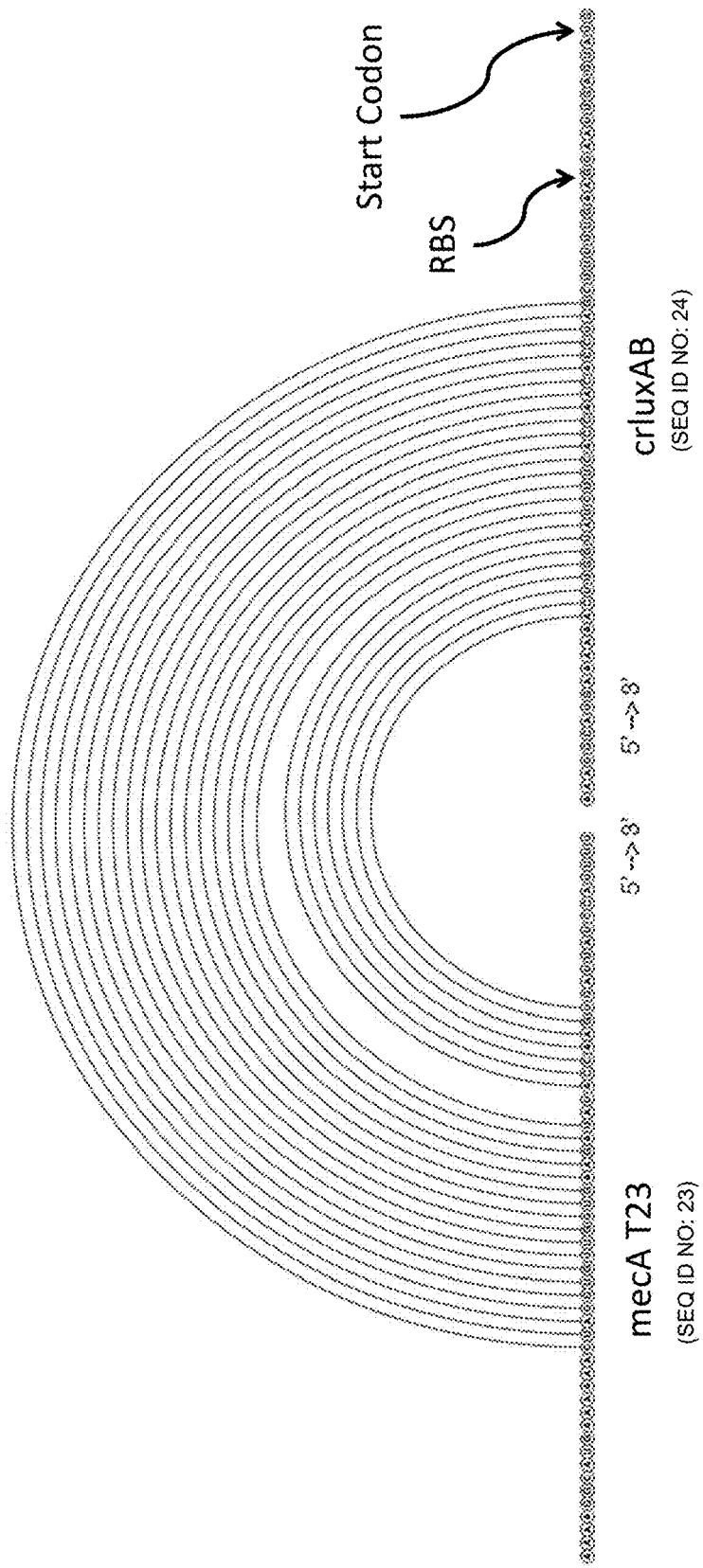
FIG. 28 shows a diagram of base pairing between the target transcript (SEQ ID NO: 23) and the cis-repressing sequence of the reporter transcript (SEQ ID NO: 24).
Figure 29:
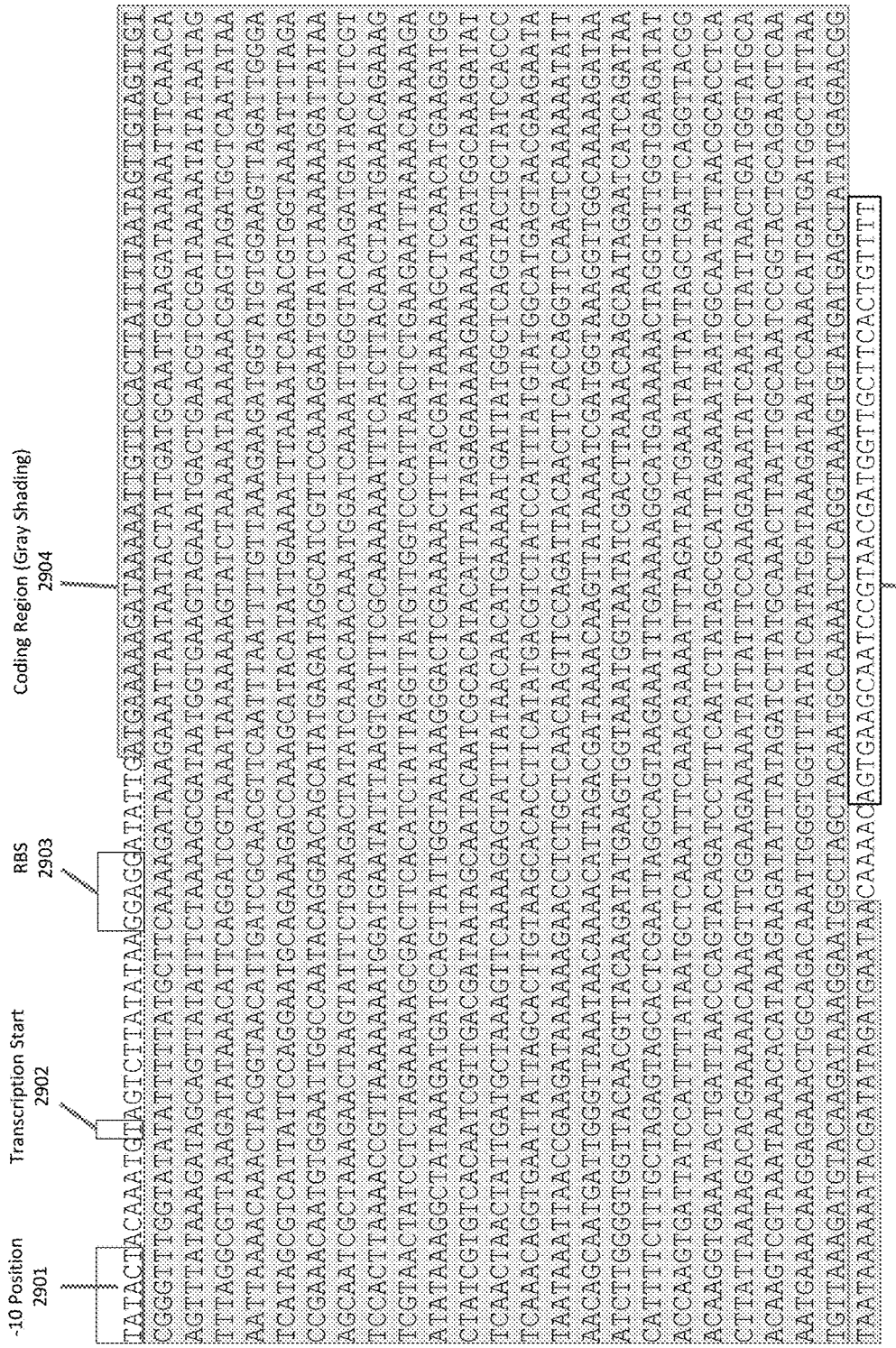
FIG. 29 shows an example of a target mecA gene sequence (SEQ ID NO: 15), according to an embodiment of the invention.
Figure 31:
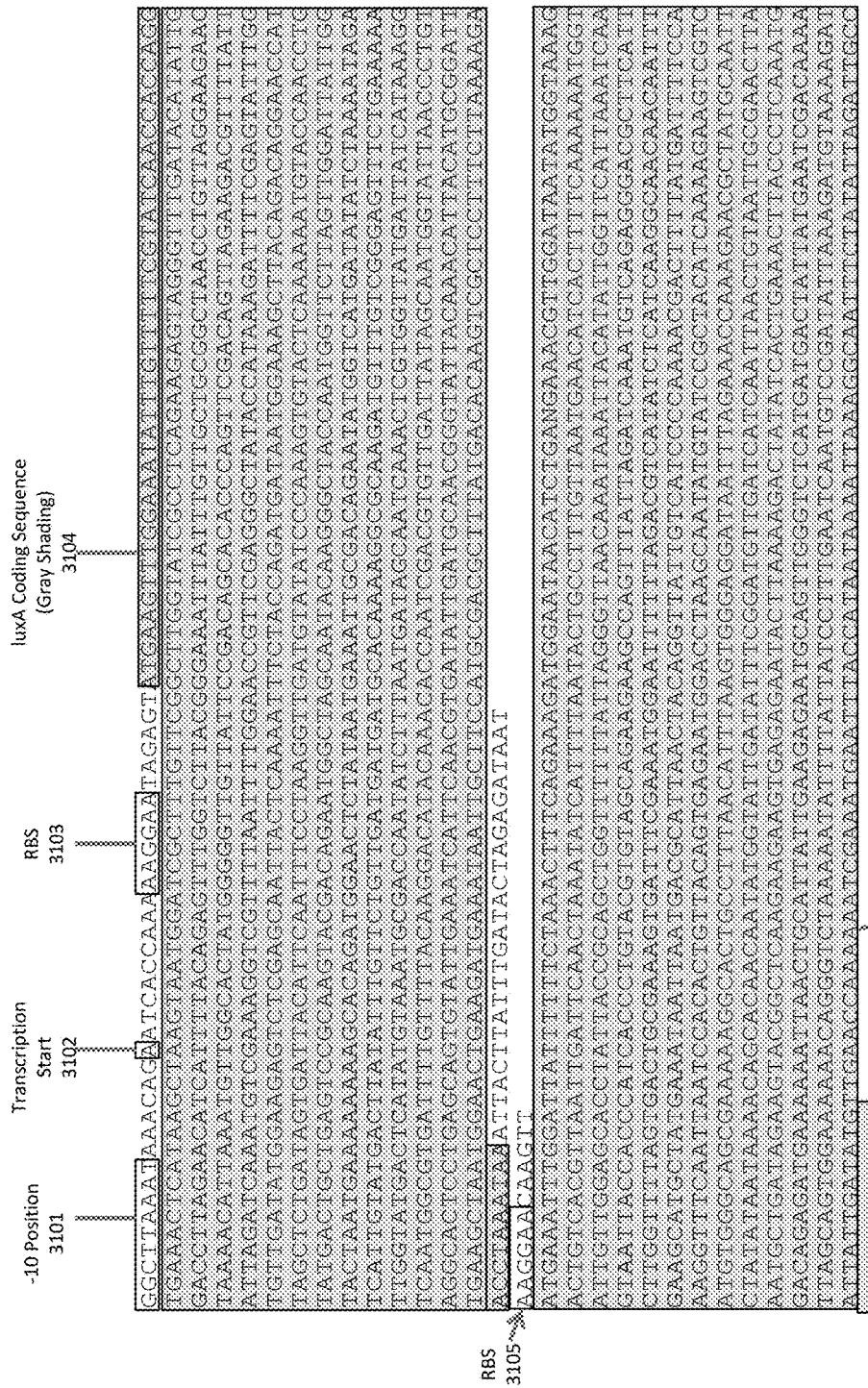
FIG. 31 is an example of a luxAB gene loci DNA sequence that can be used for designing a reporter transcript (SEQ ID NO: 17), according to an embodiment of the invention.
Figure 32:
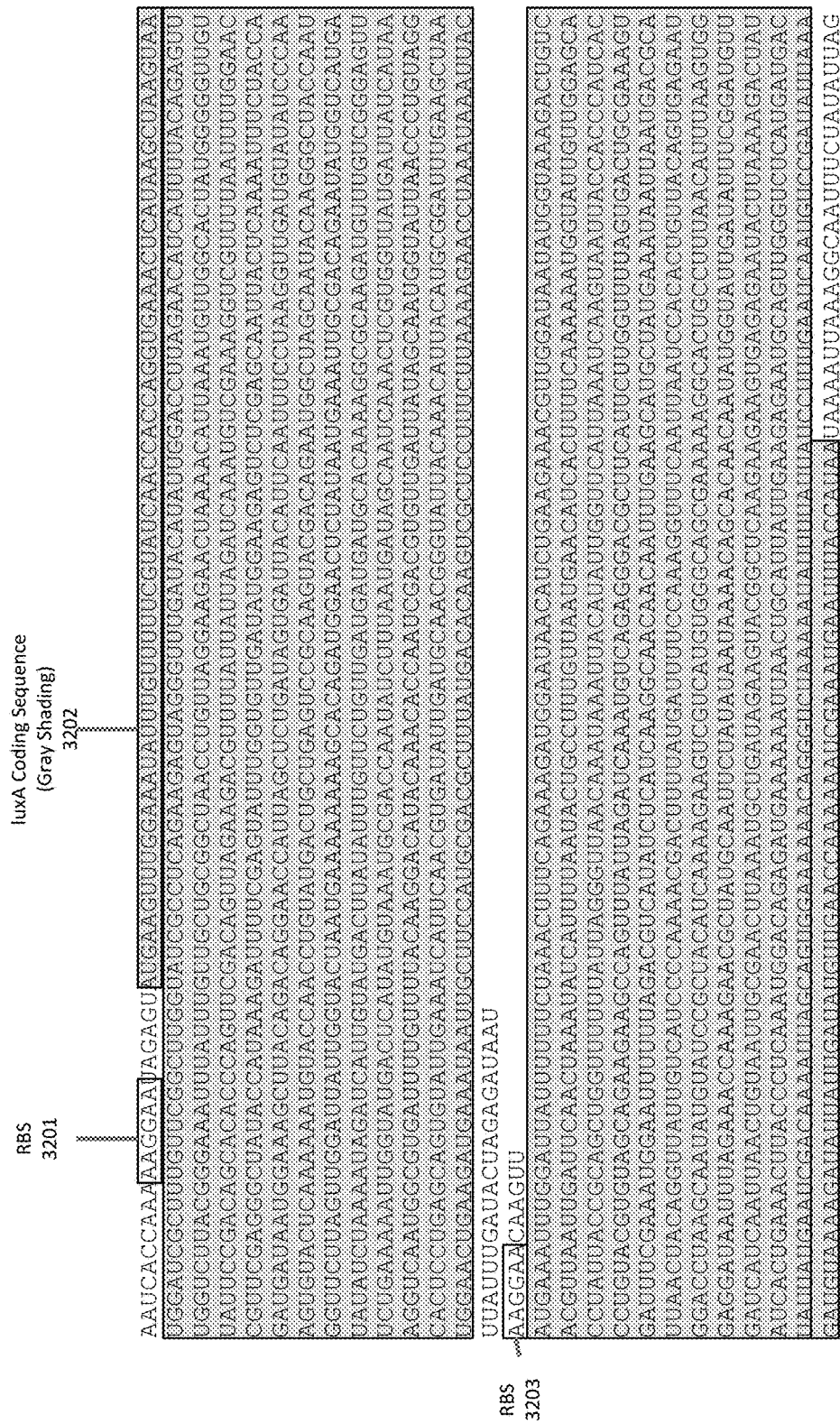
FIG. 32 is an example of a luxAB transcript sequence that can be used for designing a reporter transcript (SEQ ID NO:18), according to an embodiment of the invention.

In some embodiments, the cis-repressing sequence of the reporter transcript can be designed to be positioned at the 5' terminus of the reporter sequence and designed to generate a stem-loop structure in the reporter sequence, such that the RBS sequence of the reporter sequence is blocked. The cis-repressing stem-loop structure can be designed to block the RBS sequence based on the lowest energy conformation of the reporter transcript, as calculated by MFold and visualized with VARNA. The predicted inter-molecular interactions between the target transcript and the cis-repressing sequence of the reporter transcript can be calculated by RactIP and visualized by VARNA. A diagram can be drawn to visualize the base pairing between the target transcript and the cis-repressing sequence of the reporter transcript, as shown in FIG. 28 below.

The interaction can include base pairing between 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 or more nucleotides in the target sequence and cis-repressing sequence. The complementary binding between the two sequences can be fully complementary, substantially complementary or partially complementary. The base pairing can be across contiguous nucleotide sequences or regions within the target and cis-repressing sequences, for example, as shown in FIG. 28.

5) Cleavage Mechanisms for Cis-Repressed Transcripts or Reporter Transcripts

The general mechanisms employed in the invention are intermolecular nucleic acid molecule interactions that may result in two subsequent mechanisms: (1) a conformational change in the secondary structure of the nucleic acid molecules, and (2) a cleaving event. Described herein are methods and systems for designing reporter transcripts that employ a cleaving event.

In some embodiments, a cleaving mechanism can be employed in the system and methods of the invention for cis-repression or for trans-activation. For example, as described above in FIGS. 17, 19 and 20, a system can be designed to take advantage of a cleaving mechanism by exposing a nucleic acid sequence of the reporter transcript to a cleaving enzyme (RNase) or sequestering a single-stranded sequence that is recognized by a sequence specific RNAase.

In one example, an ribonuclease E (RNAse E) site can be designed in the reporter transcript ("*" indicates the cleaving site): (G,A)N(C,A)N(G)(G,U,A)*(A,U)(C,U)N(C,A)(C,A) (SEQ ID NO: 25). See Kaberdin et al., Probing the substrate specificity of *E. coli* RNase E using a novel oligonucleotide-based assay. Nucleic Acids Research, 2003, Vol. 31, No. 16 (doi: 10.1093/nar/gkg690).

In a cis-repression system, a cis-repressing sequence can be incorporated in the design of a reporter transcript, such that when transcribed, the conformation of the reporter transcript exposes a single stranded region containing a sequence RNAse E recognition motif at the desired site to be cleaved. In some embodiments, the cleavage site can be involved in repression of the transcription of the reporter transcript, for example, if the cleavage site is within the coding region of the reporter gene.

For a trans-derepression system, the cis-repressed transcript can be engineered to bind to a target transcript, such that the interaction causes a conformational change in the reporter transcript that sequesters the single-stranded region containing the RNAse E site.

The system can be designed such that the cis-repressing mechanism is due to a specific secondary structure generated by a conformation of the cis-repressing sequence, such as the transcription termination structure described above. In this example, a cleaving event serves to de-repress the reporter sequence. This can be accomplished by designing the cis-repressing sequence to interact with (bind to) a naturally-occurring plasmid or other cellular transcript, such that the interaction results in the generation of a single-stranded region containing the RNAse E site that can be cleaved and thus removes the cis-repressing sequence from the reporter transcript.

In some embodiments, when a cleavage event is employed for expression of the reporter, the RNAse E site is designed to be outside of the coding region of a reporter sequence with enough sequence length in the 5' and 3' UTR in order to allow for a viable reporter transcript. In this case, the RNAse E site is designed to be at least 0, 1, 2, 3, 4, 5, 10, 20, 30, 40, 50, 60, 70, 80, 90, 100, 200, 300, 400, 500, or more base pairs upstream of the start codon in prokaryotic systems and at least 18, 20, 30, 40, 50, 60, 70, 80, 90, 100, 200, 300, 400, 500, or more base pairs upstream of the start codon in eukaryotic systems or at least 10, 20, 30, 40, 50, 60, 70, 80, 90, 100, 200, 300, 400, 500, or more base pairs downstream of the stop codon. In other embodiments, when a cleavage event is employed for repression of the reporter, the RNAse E site is designed to be within the coding region of the reporter sequence or otherwise placed in order to inhibit expression of the reporter.

6) Transcripts

As described above, a transcript is a length of nucleotide sequence (DNA or RNA) transcribed from a DNA or RNA template sequence or gene. The transcript can be a cDNA sequence transcribed from an RNA template or an mRNA sequence transcribed from a DNA template. The transcript can be transcribed from an engineered nucleic acid construct. The transcript can have regions of complementarity within itself, such that the transcript includes two regions that can form an intra-molecular duplex. One region can be referred to as a "cis-repressing sequence" that binds to and blocks translation of a reporter sequence. A second region of the transcript is called a "reporter sequence" that encodes a reporter molecule, such as a detectable or selectable marker.

The transcripts of the invention can be a transcript sequence that can be 5, 6, 7, 8, 9, 10, 11, 12, 13, 14, 15, 16, 17, 18, 19, 20, 21, 22, 23, 24, or 25 nucleotides in length. In other embodiments, the transcript can be at least 25, 30, 40, 50, 60, 70, 80, 90, 100, 500, 1000, 1500, 2000, 3000, 4000, 5000 or more nucleotides in length. The cis-repressing sequence and the reporter sequence can be the same length or of different lengths.

In some embodiments, the cis-repressing sequence is separated from the reporter sequence by 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, or more spacer nucleotides.

7) Vectors

In another aspect, the transcripts (including antisense and sense sequences) of the invention are expressed from transcription units inserted into DNA or RNA vectors (see, e.g., Couture, A, et al., *TIG*. (1996), 12:5-10; Skillern, A., et al., International PCT Publication No. WO 00/22113, Conrad, International PCT Publication No. WO 00/22114, and Conrad, U.S. Pat. No. 6,054,299). These sequences can be introduced as a linear construct, a circular plasmid, or a viral vector, including bacteriophage-based vectors, which can be incorporated and inherited as a transgene integrated into the host genome. The transcript can also be constructed to permit it to be inherited as an extrachromosomal plasmid (Gassmann, et al., *Proc. Natl. Acad. Sci. USA* (1995) 92:1292).

The transcript sequences can be transcribed by a promoter located on the expression plasmid. In one embodiment, the cis-repressing and reporter sequences are expressed as an inverted repeat joined by a linker polynucleotide sequence such that the transcript has a stem and loop structure.

Recombinant expression vectors can be used to express the transcripts of the invention. Recombinant expression vectors are generally DNA plasmids or viral vectors. Viral vectors expressing the transcripts can be constructed based on, but not limited to, adeno-associated virus (for a review, see Muzyczka, et al., *Curr. Topics Micro. Immunol.* (1992) 158:97-129)); adenovirus (see, for example, Berkner, et al., BioTechniques (1998) 6:616), Rosenfeld et al. (1991, Science 252:431-434), and Rosenfeld et al. (1992), *Cell* 68:143-155)); or alphavirus as well as others known in the art. Retroviruses have been used to introduce a variety of genes into many different cell types, including epithelial cells, in vitro and/or in vivo (see, e.g., Eglitis, et al., Science (1985) 230:1395-1398; Danos and Mulligan, Proc. Natl. Acad. Sci. USA (1998) 85:6460-6464; Wilson et al., 1988, Proc. Natl. Acad. Sci. USA 85:3014-3018; Armentano et al., 1990, Proc. Natl. Acad. Sci. USA 87:61416145; Huber et al., 1991, Proc. Natl. Acad. Sci. USA 88:8039-8043; Ferry et al., 1991, Proc. Natl. Acad. Sci. USA 88:8377-8381; Chowdhury et al., 1991, Science 254:1802-1805; van Beusechem. et al., 1992, Proc. Natl. Acad. Sci. USA 89:7640-19; Kay et al., 1992, Human Gene Therapy 3:641-647; Dai et al., 1992, Proc. Natl. Acad. Sci. USA 89:10892-10895; Hwu et al., 1993, J. Immunol. 150:4104-4115; U.S. Pat. Nos. 4,868,116; 4,980,286; PCT Application WO 89/07136; PCT Application WO 89/02468; PCT Application WO 89/05345; and PCT Application WO 92/07573). Recombinant retroviral vectors capable of transducing and expressing genes inserted into the genome of a cell can be produced by transfecting the recombinant retroviral genome into suitable packaging cell lines such as PA317 and Psi-CRIP (Comette et al., 1991, Human Gene Therapy 2:5-10; Cone et al., 1984, Proc. Natl. Acad. Sci. USA 81:6349). Recombinant adenoviral vectors can be used to infect a wide variety of cells and tissues in susceptible hosts (e.g., rat, hamster, dog, and chimpanzee) (Hsu et al., 1992, J. Infectious Disease, 166:769), and also have the advantage of not requiring mitotically active cells for infection.

Any viral vector capable of accepting the coding sequences for the transcript(s) to be expressed can be used, for example, vectors derived from adenovirus (AV); adeno-associated virus (AAV); retroviruses (e.g., lentiviruses (LV), Rhabdoviruses, murine leukemia virus); herpes virus, and the like. The tropism of viral vectors can be modified by pseudotyping the vectors with envelope proteins or other surface antigens from other viruses, or by substituting different viral capsid proteins, as appropriate.

For example, lentiviral vectors featured in the invention can be pseudotyped with surface proteins from vesicular stomatitis virus (VSV), rabies, Ebola, Mokola, and the like. AAV vectors featured in the invention can be made to target different cells by engineering the vectors to express different capsid protein serotypes. Techniques for constructing AAV vectors which express different capsid protein serotypes are within the skill in the art; see, e.g., Rabinowitz J E et al. (2002), J Virol 76:791-801, the entire disclosure of which is herein incorporated by reference.

Selection of recombinant viral vectors suitable for use in the invention, methods for inserting nucleic acid sequences for expressing the transcripts into the vector, and methods of delivering the viral vector to the cells of interest are within the skill in the art. See, for example, Dornburg R (1995), Gene Therap. 2: 301-310; Eglitis M A (1988), Biotechniques 6: 608-614; Miller A D (1990), Hum Gene Therap. 1: 5-14; Anderson W F (1998), Nature 392: 25-30; and Rubinson D A et al., Nat. Genet. 33: 401-406, the entire disclosures of which are herein incorporated by reference.

Viral vectors can be derived from AV and AAV. A suitable AV vector for expressing the transcripts featured in the invention, a method for constructing the recombinant AV vector, and a method for delivering the vector into target cells, are described in Xia H et al. (2002), *Nat. Biotech.* 20: 1006-1010. Suitable AAV vectors for expressing the transcripts featured in the invention, methods for constructing the recombinant AV vector, and methods for delivering the vectors into target cells are described in Samulski R et al. (1987), J. Virol. 61: 3096-3101; Fisher K J et al. (1996), J. Virol, 70: 520-532; Samulski R et al. (1989), J. Virol. 63: 3822-3826; U.S. Pat. Nos. 5,252,479; 5,139,941; International Patent Application No. WO 94/13788; and International Patent Application No. WO 93/24641, the entire disclosures of which are herein incorporated by reference.

The promoter driving transcript expression in either a DNA plasmid or viral vector featured in the invention may be a eukaryotic RNA polymerase I (e.g., ribosomal RNA promoter), RNA polymerase II (e.g., CMV early promoter or actin promoter or U1 snRNA promoter) or generally RNA polymerase III promoter (e.g., U6 snRNA or 7SK RNA promoter) or a prokaryotic promoter, for example the T7 promoter, provided the expression plasmid also encodes T7 RNA polymerase required for transcription from a T7 promoter. The promoter can also direct transgene expression to the pancreas (see, e.g., the insulin regulatory sequence for pancreas (Bucchini et al., 1986, Proc. Natl. Acad. Sci. USA 83:2511-2515)).

In addition, expression of the transcript can be precisely regulated, for example, by using an inducible regulatory sequence and expression systems such as a regulatory sequence that is sensitive to certain physiological regulators, e.g., circulating glucose levels, or hormones (Docherty et al., 1994, FASEB J. 8:20-24). Such inducible expression systems, suitable for the control of transgene expression in cells or in mammals include regulation by ecdysone, by estrogen, progesterone, tetracycline, chemical inducers of dimerization, and isopropyl-beta-D-1-thiogalactopyranoside (IPTG). A person skilled in the art would be able to choose the appropriate regulatory/promoter sequence based on the intended use of the dsRNA transgene.

Generally, recombinant vectors capable of expressing transcript molecules are delivered as described below, and persist in target cells. Alternatively, viral vectors can be used that provide for transient expression of transcript molecules. Such vectors can be repeatedly administered as necessary. Once expressed, the transcript binds to target RNA and modulates its function or expression. Delivery of transcript expressing vectors can be systemic, such as by intravenous or intramuscular administration, by administration to target cells ex-planted from the patient followed by reintroduction into the patient, or by any other means that allows for introduction into a desired target cell.

Transcript expression DNA plasmids are typically transfected into target cells as a complex with cationic lipid carriers (e.g., Oligofectamine) or non-cationic lipid-based carriers (e.g., Transit-TKO™). Multiple lipid transfections for dsRNA-mediated knockdowns targeting different regions of a single PROC gene or multiple PROC genes over a period of a week or more are also contemplated by the invention. Successful introduction of vectors into host cells can be monitored using various known methods. For example, transient transfection can be signaled with a reporter, such as a fluorescent marker, such as Green Fluorescent Protein (GFP). Stable transfection of cells ex vivo can be ensured using markers that provide the transfected cell with resistance to specific environmental factors (e.g., antibiotics and drugs), such as hygromycin B resistance.

The delivery of the vector containing the recombinant DNA can by performed by abiologic or biologic systems. Including but not limited to liposomes, virus-like particles, transduction particles derived from phage or viruses, and conjugation.

8) Reporters for Transcript Assay

In some embodiments, the nucleic acid construct comprises a reporter sequence (e.g., a reporter gene sequence). The reporter gene encodes a reporter molecule that produces a signal when expressed in a cell. In some embodiments, the reporter molecule can be a detectable or selectable marker. In certain embodiments, the reporter molecule can be a fluorescent reporter molecule, such as a green fluorescent protein (GFP), yellow fluorescent protein (YFP), cyan fluorescent protein (CFP), blue fluorescent protein (BFP), or red fluorescent protein (RFP). In other embodiments, the reporter molecule can be a chemiluminescent protein.

Reporter molecules can be a bacterial luciferase, an eukaryotic luciferase, a fluorescent protein, an enzyme suitable for colorimetric detection, a protein suitable for immunodetection, a peptide suitable for immunodetection or a nucleic acid that function as an apatamer or that exhibits enzymatic activity.

Selectable markers can also be used as a reporter. The selectable marker can be an antibiotic resistance gene, for example.

9) Cells and Target Genes for Transcript Reporter Assay

Examples of cells that can be used for detection include Gram-positive and Gram-negative bacteria, such as *S. aureus, E. coli, K pneumoniae*, etc., fungi such as *Streptomyces coelicolor*, and other eukaryotic cells, including cells from humans, other mammals, insects, invertebrates, or plants.

Target transcripts can include any endogenous transcript, whether coding or non-coding. Target transcripts can be derived from eukaryotic and prokaryotic cells, including, for example, mecA transcript in *S. aureus* cells (indicative of MRSA), the tcdB transcript in *C. difficile* (indicative of toxigenic C. diff), and HPV E6/E7 transcripts in cervical epithelial cells (indicative of cervical cancer). Genes associated with infectious agents, such as viruses, can be targets as well, including HIV, HPV, etc. Other examples of target genes include non-coding RNA such as transfer RNA (tRNA) and ribosomal RNA (rRNA), as well as RNAs such as snoRNAs, microRNAs, siRNAs, snRNAs, exRNAs, and piRNAs and ncRNAs.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, Proteins: *Structures and Molecular Properties* (W. H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, 18th Edition (Easton, Pa.: Mack Publishing Company, 1990); Carey and Sundberg *Advanced Organic Chemistry* $3^{rd}$ *Ed.* (Plenum Press) Vols A and B(1992).

Example 1: Silent Mutation/Complementation Packaging System

The following is an example of the design and construction of a silent mutation/complementation-based packaging system for producing non-replicative transduction particles.

The materials used for developing the packaging system are listed below:

Bacterial Strains:
N1706, an *E. coli* K-12 P1 c1-100 Tn9 lysogen
Vectors:
Y14439 (pBHR1 backbone)
The following GenBank accession numbers (N.B., the sequences referred to by accession number are those listed in the database as of the priority date of this application) or SEQ ID NOs. can be used for the vector backbone and cassette sequences:
X06758 (bacterial luciferase genes luxAB)
SEQ ID NO:1 (Native P1 pac-site)
SEQ ID NO:3 (P1 lytic replicon containing the C1 repressor-controlled P53 promoter, the promoter P53 antisense, the repL genes, and an in-frame deletion of the kilA gene)
SEQ ID NO:4 (Pblast promoter driving luxAB expression)
Construction of N1706(Pac): pacA Mutated Strain:
An exemplary sequence of a pacA mutated sequence is shown in SEQ ID NO: 2, shown in the informal sequence listing below. The mutation can be accomplished by constructing the mutated sequence via gene synthesis and then replacing the native sequence in N1706 with the mutated sequence via an allelic exchange approach.

Construction of the GWP10001 Reporter Vector:
The GWP10001 vector contains the pBHR1 origin of replication exhibiting broad Gram-negative activity, two selectable markers for kanamycin and chloramphenicol, the native bacteriophage P1 pac-site sequence, the luxA and luxB genes are from Vibrio harveyi operatively linked to the constitutive blasticillin promoter (Pblast), and the P1 lytic replicon containing the C1 repressor-controlled P53 promoter, the promoter P53 antisense, the repL genes, and an in-frame deletion of the kilA gene.

FIG. 2 shows the resulting vector (GWP10001, SEQ ID NO:11), which can be constructed in a variety of manners that are known to one of skill in the art including obtaining the cassettes via PCR from their native sources or via gene synthesis and assembly of the vector via traditional restriction enzyme-based cloning or alternative techniques such as Gibson assembly.

Silent/Complementation Packaging System:
The packaging system includes the pacA mutant strain N1706(pac) complemented with the vector pGWP10001. As known to one of skill in the art, the manner of constructing this system can be accomplished by transformation N1706 (pac) with vector pGWP10001. The vector pGWP10001 can be maintained in cultures of the transformed N1706(pac) by growing the transformant in the presence of 50 ug/mL of kanamycin.

Production of Transduction Particles Carrying Plasmid DNA:
Non-replicative transduction particles carrying vector pGWP10001 can be produced from N1706(pac) transformants via thermal induction at 42° C. Incubation at 42° C. results in induction of the P1 lytic cycle in which the prophage excises from the N1706 genome, produces phage structural elements, and packages pGWP10001 concatameric DNA formed by the lytic replicon in progeny phage particles, as depicted in FIG. 1. The resulting cell lysate is then collected and contains non-replicative transduction particles, each consisting of bacteriophage P1 particles carrying a linear concatamer of pGWP10001 DNA.

Example 2: Deletion/Complementation Packaging System

The following is an example of the design and construction of a deletion/complementation-based packaging system for producing non-replicative transduction particles.

The materials used for developing the packaging system are listed below:

Bacterial Strains:
RN4220 is a restriction defective *S. aureus* strain that is a non-lysogenic derivative of NCTC 8325 and is an efficient recipient for *E. coli* DNA. It was first described in Kreiswirth, B. N. et al., *The toxic shock syndrome exotoxin structural gene is not detectably transmitted by a prophage.* Nature, 1983. 305(5936): p. 709-712.

RN10616 is derived by lysogenizing RN4220 with bacteriophage φ80α. Ubeda, C. et al., *Specificity of staphylococcal phage and SaPI DNA packaging as revealed by integrase and terminase mutations.* Molecular Microbiology, 2009. 72(1): p. 98-108.

ST24 is derived from deleting the small terminase gene terS from the lysogenized bacteriophage φ80α in RN10616. Ubeda, C. et al., *Specificity of staphylococcal phage and SaPI DNA packaging as revealed by integrase and terminase mutations.* Molecular Microbiology, 2009. 72(1): p. 98-108.

Vectors:
Examples of plasmids that can be used as source plasmids for cassettes, in some embodiments of the invention are described in Charpentier, E., et al., *Novel Cassette-Based Shuttle Vector System for Gram Positive Bacteria.* Appl. Environ. Microbiol., 2004. 70(10): p. 6076-6085.

The following GenBank accession numbers can be used for cassette sequences:

SEQ ID NO:5 (*S. aureus* pT181 plasmid origin or replication copy number variant pT181cop-623 repC)
M21136 (tetA(M))
SEQ ID NO:12 ($P_{clpB}$ promoter sequence)
SEQ ID NO:9 ((φ11 small terminase (terS) gene sequence)
L09137 (amp ColE1 ori)
X06758 (luxAB)
M62650 (Transcription Termination)
terS Deletion:

The construction of the terS knockout strain ST24 can be accomplished via an allelic-exchange-based strategy resulting in an in-frame deletion removing most of the coding sequence of the φ80α small terminase gene. The details of this strategy are described in Ubeda, C. et al., *Specificity of staphylococcal phage and SaPI DNA packaging as revealed by integrase and terminase mutations*. Molecular Microbiology, 2009. 72(1): p. 98-108.

An exemplary sequence of a terS knockout strain is shown in SEQ ID NO:13, (shown in the sequence listing below). SEQ ID NO:13 is a RN10616 genomic sequence loci showing the φ80α terS deletion and complementation.

Vector Construction:

The GW80A0001 vector is an *E. coli/S. aureus* shuttle vector. The vector contains *S. aureus* (pT181cop-623 repC) and *E. coli* (ColE1ori) origins of replication, the selectable markers for ampicillin (amp) and tetracycline (tet(M)) resistance for selection in *E. coli* and *S. aureus*, respectively, the φ11 small terminase (terS) gene sequence that includes its own promoter, the luxA and luxB genes are from *Vibrio harveyi* operatively linked to the constitutive *S. aureus* $P_{clpB}$ promoter, and a transcription termination sequence (TT).

FIG. 4 shows the resulting vector (pGW80A0001, SEQ ID NO:14), which can be constructed in a variety of manners that are known to one of skill in the art. In one example, the tet(M) cassette and luxAB genes can be obtained via PCR amplification from the publically available pCN36 and pCN58 vectors (Charpentier, E., et al.). $P_{clpB}$ can be obtained from PCR amplification from *S. aureus* RN4220 and terS can be obtained via PCR amplification from RN10616. A vector backbone can be obtained by removing the ermC gene from the publically available vector pCN48 (Charpentier, E., et al.), and the various components of the final vector pGW80A0001 can be assembled onto this vector backbone via appropriately designed restriction enzyme-based cloning.

Deletion/Complementation Packaging System:

The packaging system can include the terS knockout strain ST24 complemented with the vector pGW80A0001 to generate strain GW24. As known to one of skill in the art, the manner of constructing this system can be accomplished by transformation ST24 with vector pGW80A0001. The vector pGW80A0001 can be maintained in cultures of the transformed ST24 by growing the transformant in the presence of 5 ug/mL of tetracycline.

Production of Transduction Particles Carrying Plasmid DNA:

Non-replicative transduction particles carrying vector pGW80A0001 can be produced from GW24 via a Mitomycin C-induction method that was first demonstrated in *E. coli* and is now a standard technique for obtaining prophages from lysogenized bacteria. Otsuji, N. et al., *Induction of Phage Formation in the Lysogenic Escherichia coli K-12 by Mitomycin C*. Nature, 1959. 184(4692): p. 1079-1080. This prophage induction method results in induction of the φ80α lytic cycle in which the prophage excises from the GW24 genome, produces phage structural elements, and packages pGW80A0001 concatameric DNA in progeny phage particles, as depicted in FIG. 2. The resulting cell lysate is then collected and contains non-replicative transduction particles, each consisting of bacteriophage φ80α particles carrying a linear concatamer of pGW80A0001 DNA.

Example 3: SaPIbov2-Based Packing System Lacking Integrase

The following is an example of the design and construction of a SaPIbov2-based packaging system for producing non-replicative transduction particles.

The materials used for developing the packaging system are listed below:

The following materials can be used to develop a SaPIbov2-based packaging system lacking integrase.

Bacterial Strains:

RN451 is a *S. aureus* strain lysogenized with bacteriophage φ11.

JP2131 is RN451 that has been lysogenized with SaPIbov2. See Maiques, E. et al., Role of *Staphylococcal* Phage and SaPI Integrase in Intra- and Interspecies SaPI Transfer. J. Bacteriol., 2007. 189(15): p. 5608-5616.

JP2488 is strain JP2131 in which the int gene has been deleted from SapIbov2 (SaPIbov2Δint). Maiques, E. et al., Role of Staphylococcal Phage and SaPI Integrase in Intra- and Interspecies SaPI Transfer. J. Bacteriol., 2007. 189(15): p. 5608-5616.

Bacteriophage:

Bacteriophage φ11 can be obtained from *S. aureus* strain RN0451 via a Mitomycin C-induction method that was first described in *E. coli* and is now a standard technique for obtaining prophages from lysogenized bacteria. Otsuji, N. et al., *Induction of Phage Formation in the Lysogenic Escherichia coliK-12 by Mitomycin C*. Nature, 1959. 184(4692): p. 1079-1080.

Promoters:

$P_{clpB}$ can be used as a promoter in this example. The clpB gene promoter is a constitutive promoter used for controlling the expression of the int gene. The *S. aureus* clpB ($P_{clpB}$) gene promoter sequence was first described in 2004. Frees, D., et al., Clp ATPases are required for stress tolerance, intracellular replication and biofilm formation in *Staphylococcus aureus*. Molecular Microbiology, 2004. 54(5): p. 1445-1462. It was also first employed for controlling the gene expression in a plasmid in 2004. Arnaud, M., A. Chastanet, and M. Debarbouille, *New Vector for Efficient Allelic Replacement in Naturally Nontransformable, Low-GC-Content, Gram-Positive Bacteria*. Appl. Environ. Microbiol., 2004. 70(11): p. 6887-6891. The promoter can be obtained from *S. aureus* RN4220 using primers described in 2004. Id.

Production of φ11 SaPIbov2Δint Co-Lysogen (RN451 (φ11 SaPIbov2Δint)):

The strain JP2488(φ11 SaPIbov2Δint) can be produced by lysogenizing JP2488 with φ11.

Deletion of φ11 terS (RN451(φ11ΔterS SaPIbov2Δint)):

The strain RN451(φ11ΔterS SaPIbov2Δint) can be produced by deleting the φ11 terS gene from RN451 (φ11SaPIbov2Δint), as described in Tormo, M. A. et al., *Staphylococcus aureus Pathogenicity Island DNA Is Packaged in Particles Composed of Phage Proteins*. J. Bacteriol., 2008. 190(7): p. 2434-2440.

Incorporation of $P_{clpB}$-int into *S. aureus* Genome (RN451 (φ11ΔterS SaPIbov2Δint $P_{clpB}$-int)):

RN451(φ11ΔterS SaPIbov2Δint $P_{clpB}$-int) can be produced by first fusing $P_{clpB}$ and int via standard molecular biology techniques then inserting the $P_{clpB}$-int fusion into the genome of RN451(φ11ΔterS SaPIbov2Δint) and then selecting clones that have $P_{clpB}$-int inserted outside of the φ11 and SaPIbov2 regions.

Production of φ11 Particles Carrying Only SaPIbov2Δint $P_{clpB}$-int Concatamers:

φ11 particles carrying only SaPIbov2Δint $P_{clpB}$-int concatamers can be produced via mitomycin-C induction of RN451(∠11ΔterS SaPIbov2Δint $P_{clpB}$-int), as described by Otsuji, N. et al., *Induction of Phage Formation in the Lysogenic Escherichia coli*K-12 *by Mitomycin C*. Nature, 1959. 184(4692): p. 1079-1080. The cell lysate contains non-replicative transduction particles, each consisting of bacteriophage φ11 structural proteins carrying a linear concatamer of GI-derived DNA.

One of skill in the art will understand how to construct the NRTPs of the invention using the above-referenced materials and well-known molecular biology and genetic techniques in the art.

Example 4: terS Deletion/Complementation-Based SarS Reporter Transduction Particles The following is an example of an inducer reporter-based SarS reporter system that employs a terS deletion/complementation-based non-replicative transduction particle.

Reporter Gene:

Bacterial luciferase (luxAB). The luxA and luxB genes are from Vibrio harveyi. They lack a transcriptional promoter and each contains their own ribosomal binding site.

Spa gene promoter ($P_{spa}$): The spa gene promoter will be used for controlling the expression of the luxAB genes.

Construction of $P_{spa}$-luxAB Fusion:

The luxAB genes can be fused to the $P_{spa}$ promoter sequence such that the luxAB genes are operatively linked to the $P_{spa}$ promoter.

Construction of the luxAB-Expressing Reporter Vector

The luxAB-expressing reporter vector can be constructed via standard molecular biological techniques by incorporating the $P_{Spa}$-luxAB fusion product into the MCS of an *E. coli/S aureus* shuttle vector described below.

*E. coli/S. aureus* shuttle vector that carries a *S. aureus* (pT181cop-623 repC) and *E. coli* (ColE1ori) origins of replication, genes for ampicillin (amp) and tetracycline (tet(M)) resistance, the φ11 small terminase (terS) gene under the control of a constitutive promoter ($P_{clpB}$), a multiple cloning site (MCS), and a transcription termination sequence (TT).

GenBank accession numbers for cassette sequences:
J01764 (pT181 replicons)
M21136 (tetA(M))
Accession number not yet available ($P_{clpB}$)
AF424781 REGION: 16526.16966 (terS)
L09137 (amp ColE1 ori)
M62650 (TT)

Propagation of the vector for conducting in vitro manipulations and for verification of manipulations can be accomplished via the *E. coli* Top 10 and the final modified vector can then be introduced into *S. aureus* RN0451ΔterS. Transduction particles carrying shuttle vector can be produced from the RN0451ΔterS transformants via a Mitomycin C-induction method that was first described in *E. coli* 1959 and is now a standard technique for obtaining prophages from lysogenized bacteria. Otsuji, N., et al., Induction of Phage Formation in the Lysogenic *Escherichia coli*K-12 by Mitomycin C. Nature, 1959. 184(4692): p. 1079-1080. The cell lysate is then collected and contains non-replicative transduction particles each consisting of bacteriophage φ11 structural proteins carrying a linear concatamer of plasmid DNA capable of reporting on the presence of SarS in target *S. aureus* cells.

Example 5: terS Deletion/Complementation-Based β-lactamase Reporter Transduction Particles The following is an example of an intracellular enzyme reporter-based β-lactamase reporter system that employs a terS deletion/complementation-based non-replicative transduction particle.

Reporter Gene:

Renilla luciferase (ruc)

Promoter:

The promoter can be $P_{blaZ}$. The constitutive beta-lactamase promoter can be used for driving the expression of the ruc gene.

Caged Substrate:

Caged coelenterazine-phosphate as described in Daniel Sobek, J. R., *Enzyme detection system with caged substrates,* 2007, Zymera, Inc.

Construction of $P_{blaZ}$-Ruc Fusion:

The ruc genes can be fused to the $P_{blaZ}$ promoter sequence such that the ruc genes are operatively linked to the $P_{blaZ}$ promoter.

Construction of the Ruc-Expressing Reporter Vector:

The ruc-expressing reporter vector can be constructed via standard molecular biological techniques by incorporating the $P_{blaz}$-ruc fusion product into the MCS of the shuttle vector depicted in Section V, A, 3), i) above.

Propagation of the vector for conducting in vitro manipulations and for verification of manipulations can be accomplished via the *E. coli* Top 10 and the final modified vector can then be introduced into *S. aureus* RN0451ΔterS. Transduction particles carrying shuttle vector can be produced from the RN0451ΔterS transformants via a Mitomycin C-induction method that was first described in *E. coli* 1959 and is now a standard technique for obtaining prophages from lysogenized bacteria. Otsuji, N., et al., Induction of Phage Formation in the Lysogenic *Escherichia coli*K-12 by Mitomycin C. Nature, 1959. 184(4692): p. 1079-1080. The cell lysate is then collected and contains NRTPs each consisting of bacteriophage φ11 structural proteins carrying a linear concatamer of plasmid DNA capable of expressing Renilla luciferase within viable *S. aureus* cells within the φ11 host range.

Example 6: terS Deletion/Complementation-Based Intracellular Molecule Reporter Transduction Particles The following is an example of an intracellular molecule reporter-based reporter system that employs a terS deletion/complementation-based non-replicative transduction particle.

Promoter:

The promoter can be $P_{blaz}$. The constitutive beta-lactamase promoter can be used for driving the expression of the ruc gene.

Switchable Aptamer:

Switchable aptamers can be designed and constructed as described in Samie Jaffrey, J. P., *Coupled recognition/detection system for in vivo and in vitro use,* 2010, Cornell University.

Fluorophore Substrate:

Corresponding fluorophore substrates in conjunction with the above switchable aptamers can be designed and constructed as described in Samie Jaffrey, J. P., *Coupled recognition/detection system for in vivo and in vitro use*, 2010, Cornell University.

Construction of $P_{blaZ}$-SA Fusion:

The SA gene can be fused to the $P_{blaZ}$ promoter sequence such that the SA gene is operatively linked to the $P_{blaZ}$ promoter.

Construction of the SA-Expressing Reporter Vector:

The SA-expressing reporter vector can be constructed via standard molecular biological techniques by incorporating the $P_{blaZ}$-SA fusion product into the MCS of the shuttle vector depicted in Example 4 above. Propagation of the vector for conducting in vitro manipulations and for verification of manipulations can be accomplished via the *E. coli* Top 10 and the final modified vector can then be introduced into *S. aureus* RN0451ΔterS. Transduction particles carrying shuttle vector can be produced from the RN0451ΔterS transformants via a Mitomycin C-induction method that was first described in *E. coli* 1959 and is now a standard technique for obtaining prophages from lysogenized bacteria. Otsuji, N. et al., *Induction of Phage Formation in the Lysogenic Escherichia coli K-12 by Mitomycin C*. Nature, 1959. 184(4692): p. 1079-1080. The cell lysate is then collected and contains non-replicative transduction particles each consisting of bacteriophage φ11 structural proteins carrying a linear concatamer of plasmid DNA capable of expressing the SA within viable *S. aureus* cells within the φ11 host range.

Example 7: Non-Replicative Transduction Particle-Based Reporter System

The non-replicative transduction particles described above can be used in a reporter system for detecting the presence of viable bacteria via the expression of a reporter molecule (e.g. luxAB). When this transduction particle introduces a reporter vector (e.g. pGW80A0001) into a cell within the host range of the transduction particle, cells in which the promoter (e.g. $P_{clpB}$) is recognized by the cells transcription machinery are able to drive the expression of the reporter molecule within that cell.

To test the functionality of non-replicative transduction particles as reporters for detecting the presence of *S. aureus* cells, various MSSA/MRSA reporter assays were developed. In an embodiment, a non-replicative transduction particle was developed from a *S. aureus*-specific bacteriophage, and the bacterial luciferase genes luxAB under the control of a constitutive promoter were incorporated. When the non-replicative transduction particle delivered the reporter nucleic acid into *S. aureus*, the constitutive promoter expressed luxAB suitable for reporting on the presence of a viable *S. aureus*.

In addition, the antibiotic cefoxitin was added prior to, simultaneously with, or after the addition of the transduction particles to a sample containing *S. aureus* cells. If the cells were not phenotypically resistant to cefoxitin (i.e., were not MRSA), luminescence was decreased or eliminated, indicating that the cells were MSSA. If, however, the cells were phenotypically resistant to cefoxitin (i.e., were MRSA), increased or detectable luminescence was observed, indicating that the cells were MRSA.

Non-Replicative Transduction Particle-Based Viable Cell Reporter Assay Function

The function of the non-replicative transduction particle as a reporter was assayed. The transduction host range of the bacteriophage φ80α-based non-replicative transduction particle was examined in 101 clinical MRSA isolates. The transduction assay was conducted by exposing cultures of each bacterial isolate grown in modified TSB to GW24 cell lysate containing the non-replicative transduction particles and culturing the mixture on solid media containing tetracycline.

In this example, the non-replicative transduction particle carried a tetracycline selectable marker. Cells transduced with the non-replicative transduction particles were expected to be resistant to tetracycline. In addition, transduction was examined via luminescence assay by exposing each bacterial isolate in liquid culture to cell lysate containing the non-replicative transduction particles and evaluating the mixture for bacterial luciferase luminescence activity after an incubation period.

The transduction assay showed that the φ80α-based non-replicative transduction particle was able to transduce all of the 101 clinical isolates of MRSA and none of the non-*S. aureus* Staphylococci.

Figure 21:
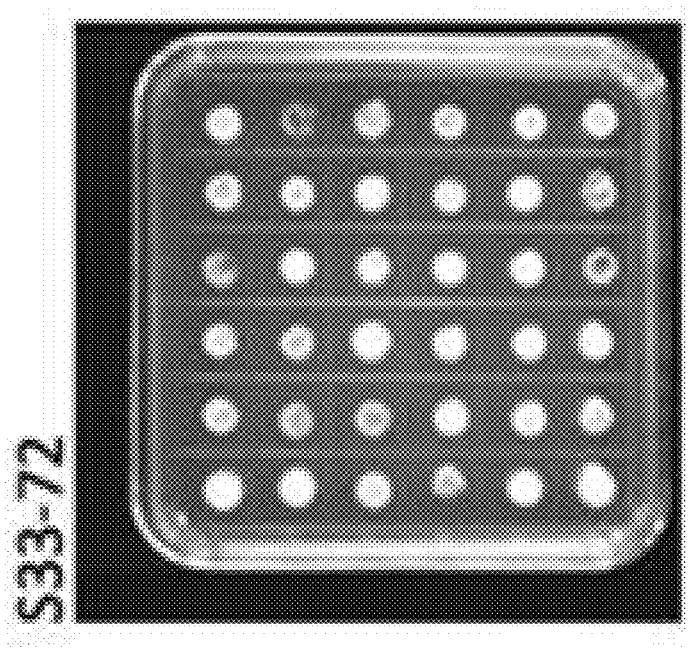
FIG. 21 shows the results of the transduction assay in which 36 tetracycline-sensitive MRSA were exposed to transduction particles carrying pGW80A0001 and then were spotted onto media plates containing 5 ug/mL of tetracycline, according to an embodiment of the invention.

FIG. 21 shows the results of the transduction assay in which 36 tetracycline-sensitive MRSA were exposed to transduction particles carrying pGW80A0001 and then were spotted onto media plates containing 5 ug/mL of tetracycline. The results show that all 36 MRSA strains grew on the media containing tetracycline due to transduction with pGW80A0001. Control experiments in which MRSA isolates were spotted onto tetracycline containing media without exposure to transduction particles showed no growth (not shown). Furthermore, plasmid isolation from transduced MRSA strains demonstrated recovery of the pGW80A0001 plasmid as confirmed via sequencing of the isolated plasmid. The transduction results thus demonstrated that the origin of replication of the reporter plasmid exhibits activity on all of the MRSA isolates tested.

Figure 22:
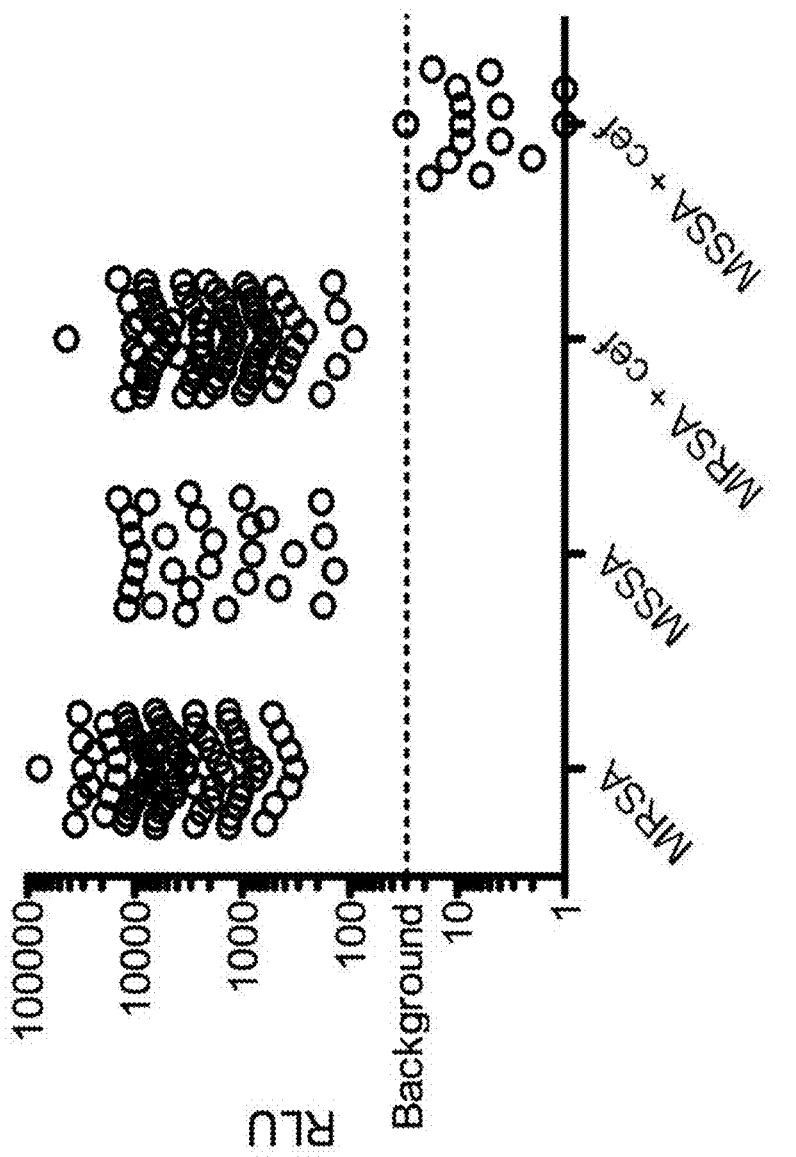
FIG. 22 illustrates the luminescence measured from 80 clinical isolates of MRSA and 28 clinical isolates of methicillin sensitive *S. aureus* (MSSA) transduced with the transduction particle, according to an embodiment of the invention.

FIG. 22 illustrates the luminescence measured from 80 clinical isolates of MRSA and 28 clinical isolates of methicillin sensitive *S. aureus* (MSSA) transduced with the transduction particle. In the experiment, cultures of MRSA and MSSA were grown to an optical density at 600 nm of 0.1 and then 100 uL of the cultures grown in Modified TSB were mixed with 10 uL of GW24 cell lysates containing transduction particles and further incubated at 37° C. for a period of 4 hours prior to assaying for luminescence. Luminescence measurements were conducted by adding 10 uL of a 1 mM solution of Decanal, an aldehyde that triggers a luminescent reaction within cells expressing bacterial luciferase. As expected, luminescence was observed from both MRSA and MSSA transduced with the *S. aureus*-specific non-replicative transduction particle. Furthermore, when cefoxitin was added to the cell cultures at the same time as the addition of transduction particles, luminescence was observed from MRSA but not from MSSA, thus demonstrating the ability for the transduction particles to report on both the presence of MSSA and of MRSA. The luminescence results thus demonstrate that the promoter driving luxAB expression exhibits activity on all of the *S. aureus* isolates tested.

Optimization of Non-Replicative Transduction Particle-Based Viable Cell Reporter MRSA Assay—Transduction Particle Reagent Formulation The production and formulation of the non-replicative transduction particle reagent was optimized to a final formulation. In summary, a 15 L scale fermentation was performed using TSB media including peroxide induction of GW24. The 15 L fermenter batch was inoculated from a 200 mL overnight seed culture (an inoculum ratio of 1.3% (v/v)). The culture was induced at an O.D. of 0.8 with hydrogen peroxide and cooled to 25° C. post induction without pH or DO control. Culture supernatant was harvested by tangential flow filtration (TFF) the following morning for the purpose of clarifying the phage transduction particles from the cell debris. The material was then further concentrated and diafiltered into SM Buffer without gelatin and stored at 2-8° C. prior to final sterile filtration and storage.

A detailed summary of the process is outlined below:

---

Seed flask growth

---

(1) Inoculate 200 mL of TSB containing 5 ug/mL tetracycline with GW24
(2) Incubate at 37° C., 200 RPM for 10-18 hours.
Fermentation Innoculation (15 L TSB with 5 ug/mL tetracycline)

(1) Prepare the fermenter skid with the following fermentation conditions: 37° C., agitation at 250 RPM, airflow at 15 LPM, and backpressure at 3 psig.
(2) Inoculate the fermentor using the 200 mL overnight seed culture.
Induce Culture (1) Once the OD600 nm reaches 0.8 (0.6-0.9), induce the culture with 0.5 mM H2O2
(2) Increase temperature setpoint of fermenter to 42° C.
Post-Induction Conditions and Monitoring (1) Once 30 minute induction is complete, reset temperature target for fermenter to 25° C.
(2) One hour post cooling, turn off air feed to fermenter and set agitation to zero
(3) Monitor the fermentation culture at hour intervals, or more frequently as necessary, until the OD600 nm has decreased to or below 0.40.
Harvest/Clarification (1) After the fermentation culture OD600 has reached a minimum less than or equal to 0.40, take a 20 mL aseptic sample and add 30 µL of Benzonase to the fermentor.
(2) Reset agitation to 250 rpm. Allow 60 minutes with agitation for Benzonase incubation.
(3) Clarify the EOF sample with a 15 minute centrifugation at 3000 g.
(4) Pass the clarified material through a 0.45 uM membrane filter
Concentration and Buffer Exchange (1) Concentrate the clarified culture by TFF using 500 kDa flat sheet membrane 10-fold.
(2) Diafilter the concentrated culture at a constant volume against SM Buffer without gelatin using the 500 kDa TFF membrane used for concentration
Final Filtration (1) Filter the concentrated buffer exchanged material through a 0.2 µm filter.
(2) Store the final filtered phage material at 2-8° C.

---

Various other reagents and formulations can be used as known to those of skill in the art to derive the formulation.

Optimization of Non-Replicative Transduction Particle-Based Viable Cell Reporter MRSA Assay—Growth Media Formulation A growth media formulation was optimized for the NRTP-based viable cell reporter MRSA assay. In order to produce luminescence in the NRTP-based MRSA Assay, the media needs to be balanced for *Staphylococcus aureus* growth and have adequate concentration of cations and additives to favor NRTP transduction. The TSBmod media used in assays prior to this development study was known to have precipitation issues that would affect the stability of the media. Growth media formulation required stability in the final formulation with a goal of 1 year at room temperature.

Methods/Procedures: Cells Preparation for MRSA Assay (1) Ten unique strains of MRSA for the Subset Assay and one unique strains of MSSA were tested in the MRSA Assay.
(2) Overnight cultures were started in a deep 96 well plate at a 1:50 dilution in TSB from a frozen one-time use stock and incubated at 37° C. on an orbital shaker for >15 hours. MRSA/MSSA (8 µl) in TSB (392 µl)
(3) The next day, a day culture at a 1:50 dilution from the overnight culture was started in TSB in 96 well deep well plate (392 µl TSB + 8 µl cells) and incubated at 37° C. on an orbital shaker for 4 hours.
(4) Cells were spun in a centrifuge for 5 minutes at 1800 g force and 10° C., spent media was aspirated without disturbing the pellet.
(5) Spun cells were washed in 50 mM Tris-HCl pH 7.2, centrifuged, buffer aspirated without disturbing pellet and re-suspended in 400 µl RPMI. RPMI is used in order to reduce variability in the metabolic state of cells and to mimic low metabolism as found in clinical samples.
(6) Plate was covered with airpore seal and incubated on bench for 48 hrs.
(7) OD was read by transferring 200 µl of RPMI culture in a shallow well OD plate and blank well with RPMI media alone was used to subtract blank OD.
(8) Cells were normalized to OD 0.1 in 100 µl
(9) Another dilution was made 1:10 in RPMI to yield an OD of 0.005

Assay base media was prepared to be tested as shown in Table 2 and a representative set of media modifications in preparation for MRSA assay are shown in Table 3.

TABLE 2

Base Media for Growth Media Formulation Development

| Components | TSB | B2 | BSS-2 | Notes |
|---|---|---|---|---|
| Enzymatic Digest of Soybean Meal (g) | 3 | 0 | 3 | Adjust pH to 7.2 with 10N NaOH. Autoclave or filter sterilize |
| Enzymatic Digest of Casein (g) | 17 | 10 | 10 | |
| Yeast Extract (g) | N/A | 25 | 25 | |
| Sodium Chloride (g) | 5 | 25 | 25 | |
| Dipotassium Phosphate (g) | 2.5 | 1 | 0 | |
| alpha-D Glucose (g) | 2.5 | 5 | 5 | |
| Volume (litre) | 1 | 1 | 1 | |

TABLE 3

Base Media Modifications for Growth Media Formulation Development
Concentration of salt/additives for modification

| Base media (30 ml) | Mod number | CaCl2 (mM) | MgCl2 (mM) | BGP (mM) | Tris-HCl pH7.0 (mM) | EDTA (mM) | HEPES (mM) |
|---|---|---|---|---|---|---|---|
| B2 | M53 | 5.0 | 2.0 | 0.0 | 50.0 | 10.0 | 0.0 |
| BSS-2 | M50 | 10.0 | 2.0 | 60.0 | 50.0 | 10.0 | 0.0 |
| BSS-2 | M54 | 6.7 | 3.3 | 60.0 | 50.0 | 0.0 | 0.0 |
| BSS-2 | M55 | 5.0 | 5.0 | 60.0 | 50.0 | 0.0 | 0.0 |
| BSS-2 | M56 | 6.7 | 3.3 | 60.0 | 0.0 | 0.0 | 10.0 |
| BSS-2 | M57 | 5.0 | 5.0 | 60.0 | 0.0 | 0.0 | 10.0 |
| TSB | M1 (original) | 5.0 | 10.0 | 60.0 | 0.0 | 0.0 | 0.0 |
| TSB | M58 | 5.0 | 10.0 | 60.0 | 0.0 | 11.1 | 0.0 |

To each media preparation, NRTP and Cefoxitin was added according to Table 4 below to make the NRTP media reagent:

TABLE 4

MRSA Assay Growth Media/Transduction particle reagent combination

| 30 ml media | Final Concentration |
|---|---|
| Cefoxitin | 5 ug/ml |
| GW24 Lysate | 30X |

The MRSA Assay was run with the following steps:

(1) Assay Plate Setup: Add 198 µl of Phage Media Reagent and 2.0 µl of each dilution of bacteria 0.05 OD and 0.005 OD in RPMI (roughly equivalent to 20,000 and 2,000 CFU/mL, respectively) or 2.0 uL of RPMI as a blank.
(2) Incubate Assay Plate: Incubate Assay plate on orbital shaker at ~100 rpm for 4 hours at 37° C.
(3) Prepare Luminometer (Molecular Devices SpectraMax L): Wash reagent line with 70% ethanol followed by DI water then prime with the substrate reagent. Set up software as Fast Kinetic with injection of 50 µL of substrate reagent at 250 µl/sec after 10 baseline points and read at 40 points every 0.25 seconds.
(4) Run Assay: Test each bacterial dilution plate, after letting plate equilibrate to room temperature for 5 minutes.

Analysis (1) Determine cutoff by averaging blank RLU across all replicates and time points and adding three standard deviations.
(2) Determine maximum RLU for each sample using SoftMaxPro.
(3) Determine if the maximum RLU was greater than the cutoff RLU, and if so, then the sample data was used for comparisons of media performance.
(4) Normalize all max RLU values to the Max RLU in TSB M1 (media in use until development started) for the strain being analyzed at the specific dilution.
(5) Average the normalized RLU values across all MRSA strains for a particular media and its modification
(6) Average the averages for the two dilution plates, ultimately leading to a
single numerical value representing the fold increase in performance based on RLU of a particular media across 10 different MRSA strains in 2 cell dilutions tested.

Results of NRTP-Based Viable Cell Reporter MRSA Assay

Determination of Cutoff RLU: The average and standard deviation of the RLU was calculated across all time points (25) for each blank replicate (4). The cutoff was calculated for each plate as the average blank RLU plus three standard deviations.

Determination of Relative Improvements: The maximum RLU was exported for each sample (blanks, MSSA and MRSA at all dilutions) from SoftMaxPro and compared to the cutoff RLU. If the sample had 2 data points greater than the cutoff for phage concentration, then the max RLU value was utilized for analysis.

The values were normalized by dividing a particular max RLU by the max RLU of its control condition (that strain in TSB M1-origianl media, at the dilution being analyzed). The ratios obtained were averaged across 10 MRSA for each media condition and each dilution, as shown in Table 5. The average across the two dilutions is also shown in the table.

TABLE 5

MRSA Assay Results from Various Growth Media Formulations

| Media | | Plate 1 | Plate 2 | Average for both dilutions |
|---|---|---|---|---|
| B2 | M53 | 1.89 | 1.88 | 1.89 |
| BSS-2 | M50 | 1.37 | 1.47 | 1.42 |
| BSS-2 | M54 | 1.50 | 1.76 | 1.63 |
| BSS-2 | M55 | 1.82 | 2.90 | 2.36 |
| BSS-2 | M56 | 2.38 | 6.00 | 4.19 |
| BSS-2 | M57 | 2.00 | 3.92 | 2.96 |
| TSB | M1 | 1.00 | 1.00 | 1.00 |
| TSB | M58 | 1.18 | 0.96 | 1.07 |

Conclusions

BSS2-M56 exhibited the best performance on average across the various media tested. HEPES buffer based media performed better than Tris-HCl buffered media. HEPES is known to be a biologically favorable buffering system as opposed to Tris-HCl. B2 based base/broth had better performance than TSB based broth.

Various other reagents and formulations can be used as known to those of skill in the art to derive the formulation. Other suitable formulations were developed via similar experiments as described above. Examples of other suitable formulations are included below in Tables 6, 7, and 8.

TABLE 6

BSC Media Formulation

| BSC Components | Amount |
|---|---|
| Enzymatic Digest of Casein | 14.5 g |
| Yeast Extract | 35.5 g |
| Sodium Chloride | 35.5 g |
| alpha-D Glucose | 7 g |
| Total Vol | 1 L |

TABLE 7

BSC Media Modification

| BSC-M64 Chemical Name | Final (Assay) Conc |
|---|---|
| BGP (mM) | 60.0 |
| HEPES (mM) | 10.0 |
| LiCl (mM) | 84.0 |
| BSC | To 1 L |

TABLE 8

Transduction Particle Media Modification

| Transduction Particle Formulation (PM4) Chemicals | Final (Assay) conc |
|---|---|
| CaCl2 (M) | 0.00667 |
| MgCl2 (M) | 0.00335 |
| HEPES (M) | 0.01000 |
| GW24 lysate stock | 0.01250 |
| Sodium Azide (%) | 0.0006 |
| Water | To 1 mL |

Optimization of Non-Replicative Transduction Particle-Based Viable Cell Reporter MRSA Assay—Substrate Reagent Formulation In order to produce luminescence in the MRSA Assay, the Substrate Reagent must include an aldehyde as a substrate for luciferase. An initially developed aliphatic aldehyde formulation (4.2 mM Tridecanal in TSB) was not stable and formed a heterogeneous emulsion rather than a solution. This example outlines the development of a Substrate Reagent formulation that addresses these issues with a goal of 6 months at room temperature or 2-8° C. stability.

This example describes the steps that were taken to develop the Substrate Reagent to a final formulation.

Methods/Procedures

All screening and stability experiments were tested using a "Model System" that consists of S. aureus strain RN4220 harboring a LuxAB-expressing plasmid. The typical preparation and testing method was as follows.

(1) Overnight Culture: 2 mL TSB + 1 uL of 10 mg/mL Tetracycline + 1 colony of Model System Bacteria from TSA plate, shaking at 225 rpm overnight at 37° C.
(2) Day Culture: Diluted overnight culture 1:50 or 1:100 into TSB + 5 ug/mL Tetracycline, shaking at 225 rpm for 1.5-2 hours at 37° C.
(3) Normalize Day Culture: Measured 1 mL of day culture on Nanodrop with cuvette at 600 nm, blanking with TSB + 5 ug/mL Tetracycline. Diluted to 0.1 OD with TSB + 5 ug/mL Tetracycline.
(4) Dilute Culture for Testing: Diluted 0.1 OD Culture with TSB + 5 ug/mL Tetracycline to a 1:200, 1:2000 and 1:20000 dilution which was roughly equivalent to 100000, 10000 and 1000 CFU/mL.
(5) Plate Bacteria: Added 200 uL of each dilution and a blank (TSB + 5 ug/mL Tetracycline with no bacteria) in three replicates to a Greiner Bio-one white assay plate for each substrate to be tested.
(6) Prepare Luminometer (SpectraMax L): Wash reagent line with 70% ethanol followed by DI water then prime with the substrate. Set up software as Fast Kinetic with injection of 50 uL substrate at 250 ul/sec after 10 baseline points and read at 40 points every 0.25 seconds.
(7) Run Assay: Test each formulation of Substrate Reagents with washing and priming SpectraMax L between each substrate. Bring all Substrate Reagents to room temperature before testing.

All confirmation experiments were tested using the MRSA Assay in order to ensure similar results on the actual assay as the Model System used to screen new formulations.

(1) Prepare Culture: Ten MRSA low performing strains and one MSSA strain were grown to log-phase in TSB in a 2 mL deep well block. Cells were spun down, washed with 1 × PBS then resuspended in RPMI media.
(2) Normalize Bacteria: Measure 200 uL of RPMI culture and RPMI blank in Greiner Bio-one clear plate on VersaMax at 600 nm. Subtract blank OD from each strain. Normalize each strain to 0.05 OD in RPMI media.
(3) Dilute Bacteria: Dilute 0.05 OD culture 1:10 in RPMI media to 0.005 OD.
(4) Prepare Phage Media Reagent: Add Phage, Cefoxitin and Sodium Pyruvate to BSS-M56 including:
a. Cefoxitin (5 ug/mL)
b. GW24 lysate stock (0.03X)
c. Sodium Pyruvate (0.025M)
(5) Set up Assay Plate = Add 198 uL of Phage Media Reagent and 2 uL of each dilution of bacteria (0.05 OD and 0.005 OD in RPMI, roughly equivalent to 20000 or 2000 CFU/mL) or 2 uL of RPMI as a blank in two replicates.
(6) Incubate Assay Plate = Incubate Assay plate on orbital shaker at ~100 rpm (speed 3) for 4 hours at 37° C.
(7) Prepare Luminometer (SpectraMax L) = Wash reagent line with 70% ethanol followed by DI water then prime with the substrate. Set up software as Fast Kinetic with injection of 50 uL substrate at 250 ul/sec after 10 baseline points and read at 40 points every 0.25 seconds.
(8) Run Assay = Test each formulation of Substrate Reagents with washing and priming SpectraMax L between each substrate.

Experiments for the development of Substrate Reagent formulation were designed to improve the following:

(1) Improve solubility via adding surfactants (Tween 20, Triton X-100, NP-40, Brij-35, SNS, etc.), adding solvents (Ethanol, Methanol, DMSO, etc.), adding non-volatile oils (Castor Oil)
(2) Improve stability via adding stabilizers (Triethanolamine, Cyclodextrin etc.), adding antioxidants (Vitamin E, Vitamin E Acetate, Vitamin E PEG 1000, Oxyrase, etc.), adjust method of Tridecanal addition (with surfactant, with solvent, into final solution, with antioxidant, etc.), storing Tridecanal and Substrate Reagent under nitrogen to reduce oxidation of aldehyde, and reducing possibility of microbial contamination by adding preservatives such as ProClin and by sterile filtration of the Substrate Reagent.
(3) Improve Assay Performance via adjustment of the pH of the formulation and the pH buffer system
(4) Improve overall performance via determining the aldehyde with highest RLU output (tested aldehydes from 6-14 carbons in multiple formulations to determine if an improvement in solubility, stability and assay performance was observed).
(5) Improve overall performance via adding antifoam in order to reduce foaming during preparation of reagent and addition of reagent to sample during the assay.

Analysis and Results

The kinetic reaction was plotted for each sample and a line fit to the average at each read point of three replicates. Typically results showed at 1:2000 dilution of 0.1 OD model system bacteria, roughly equivalent to 10,000 CFU/mL or 2,000 CFU/assay.

The normalized maximum RLU to that of the reference substrate reagent was analyzed for stability experiments. At each stability time point, maximum RLU for each sample was normalized to the reference substrate maximum RLU. Normalized Maximum RLU was plotted over time points and linear regression with 95% CI was plotted.

Conclusions

The key parameters adjusted from the reference formulation for producing a final Substrate Reagent formulation are summarized in Table 9.

TABLE 9

Summary of Reagent Formulation Development Results

| Modification to Substrate Reagent | Reason |
| --- | --- |
| 4.2 mM Tridecanal + TSB | Original Substrate Reagent |
| Remove TSB | Reduce possibility of contamination |
| Add 1% Tween 20 | Improve Solubility |
| Adjust to pH3 with 79.45% 0.1 M Citric Acid-19.55% 0.2 M Sodium Phosphate Dibasic Buffer | Improve Assay Performance |
| Add Tridecanal directly to concentrated surfactant | Improve Stability |
| Add Filtering of Substrate Reagent through 0.2 um PES membrane | Improve Stability |
| Add 0.05% ProClin 300 | Improve Stability |
| Add Triethanolamine | Improve Stability |
| Change 1% Tween 20 to 0.5% Triton X-100 | Improve Stability, Improve Solubility |
| Change from 79.45% 0.1 M Citric Acid-19.55% 0.2 M Sodium Phosphate Dibasic Buffer to 82% 0.1 M Citric Acid-18% 0.1 M Sodium Citrate Buffer, remain at pH 3 | Improve Assay Performance, reduce possibility of precipitation with removal of phosphate buffer |
| Add 100 ppm Antifoam Y30 | Improve Assay Performance |
| Add 0.5% Vitamin E Acetate | Improve Stability, reduce precipitation |
| Change Primary Tridecanal Manufacturer from Alfa Aesar to Sigma/OmegaChem | Improve Assay Performance |
| Change 0.5% Vitamin E Acetate to 1-2% Vitamin E PEG 1000 | Improve Assay Performance, Improve Solubility, Improve Stability |

Two Substrate Reagent Formulations were prepared for two different storage temperatures, one for storage at 2-8° C. and one at 18-24° C.

Final Substrate Reagent Formulations Stored at 2-8° C.

Formulation: 0.5% Triton X–100+4.2 mM Tridecanal+0.5% Vitamin E Acetate+100 ppm Antifoam Y30+0.5% Triethanolamine+82% 0.1 M Citric Acid+18% 0.1 M Sodium Citrate @pH3+0.05% ProClin 300. The formulation did not precipitate after 1 month at 2-8° C. and was able to detect MRSA strains the same as on Day 0.

Final Substrate Reagent Formulations Stored at 18-24° C.

Formulation: 0.5% Triton X–100+6.3 mM Tridecanal+100 ppm Antifoam Y30+0.5% Triethanolamine+82% 0.1 M Citric Acid+18% 0.1 M Sodium Citrate @pH3+2% a-Tocopherol-PEG 1000 Succinate+0.05% ProClin 300. The formulation did not precipitate after 1 month at 18-24° C. and was able to detect MRSA strains the same as on Day 0.

Various other reagents and formulations can be used as known to those of skill in the art to derive the formulation.

Analytical Performance of Non-Replicative Transduction Particle-Based Viable Cell Reporter MRSA Assay The analytical performance of the optimized NRTP MRSA assay was examined, including an analysis of the assay's limit of detection and an analysis of the cross-reactivity and microbial interference of the assay when challenged with non-target organisms.

A) Limit of Detection Assay

The Limit of Detection of the NRTP assay was assessed via determining the lowest amount of MRSA cells representing various strains that could produce a relative light unit (RLU) signal above that of a threshold determined from blank samples. MRSA strains included the SCCmec Types I, II, and IV as well as a MRSA strain carrying the mecA gene variant mecC—a strain of MRSA that conventional FDA-cleared MRSA PCR assays have failed to detect.

The following key materials were used in the clinical performance study:

Growth Media Reagent: BSS-M56

Substrate Reagent: Final Substrate Reagent Formulations to be stored at 18-24° C. as described above.

Transduction Particle Reagent: BSS-M56 base with 10 ug/mL (i.e. 2× concentration) cefoxitin and transduction particle reagent as described above at 2× concentration.

LoD Study Protocol:

Overnight Culture:

For each MRSA strain and a MSSA negative control strain, 2 mL of TSB were inoculated with a colony of the strain previously grown on TSA plates. Overnight MRSA cultures included 5 ug/mL cefoxitin. All samples were incubated overnight at 37° C. in a shaking incubator.

Day Culture:

20 uL of each of the overnight cultures were transferred into a new culture tube containing 2 mL of Growth Media Reagent. The inoculums were then incubated at 37 C with shaking for approximately 1 hr 45 min, until the OD (600 nm) reached 0.1.

Serial Dilutions:

a) 1000 uL of each of the samples were dispensed into row A of 2 mL deep well 96-well plate.
b) The remaining rows (B-H) were then filled with 900 uL of Growth Media Reagent.
c) 10-fold serial dilutions were then prepared taking 100 uL from row A and mixing in row B, etc., such that row H contained samples of row A material at $10^{-7}$ dilution.

Enumeration of Bacterial Load:

5 uL of each well of row E was spotted onto a TSA plate which was then tilted to allow the spot of liquid to spread onto the plate (in order to later facilitate colony counting). (Row E is a $10^{-4}$ dilution of row A). Plates were then incubated overnight at 37° C.

Assay Preparation:

a) Wells of a white 96 well assay plate were filled with 100 uL of 2× Transduction Particle Reagent.
b) Rows F and G (i.e., $10^{-5}$ and $10^{-6}$-fold dilutions of row A, respectively) were then used to fill wells of the 96 well assay plate containing Transduction Particle Reagent such that each sample was added to the plate in four-replicates.
c) The plate was then sealed with a breathable seal and incubated for 4 hours at 37° C. with moderate shaking, 50 rpm.

At the end of 4 hours, the plate was remove from incubator and immediately measured for luminescence on a SpectraMax L that injected 50 µl of the Substrate Reagent and measured luminescence for a period of 1 minute.

Analysis:

The luminescence data from each sample was plotted as RLU vs. time. Blank samples were used to determine a Cutoff calculated from all time points of the blank samples using the following formula: (Mean Blank RLU+3*SD Blank RLU)

The average peak RLU post-substrate injection was then obtained for each sample in order to determine the sample of highest dilution for which an RLU value was generated that was above the blank samples Cutoff. The colony forming unit (CFU) counts at the highest dilution for which an RLU value was generated that was above the blank samples Cutoff was determined from the enumeration study, and this CFU count was reported as the LoD in the study.

Results:

The LoD for all MRSA samples tested was determined to be below 10 CFU. Table 11 summarizes the results of the lowest LoDs obtained in the study.

TABLE 11

Results of the lowest LoDs obtained in the LoD study.

| SCCmec Type | LoD (CFU) |
|---|---|
| I | 3 |
| II | 2 |
| IV | 3 |
| mecC | 1 |

All MRSA strains tested resulted in fewer than 10 CFU detected with the NRTP assay above a Cutoff calculated from blank samples. MSSA did not generate RLU values above the blank samples Cutoff RLU values are shown at the highest dilution for which an RLU value was generated that was above the blank samples Cutoff were plotted as the average RLU value and standard deviation for the four replicates tested for each sample. The horizontal axis is set at the blank samples Cutoff and the CFU counts for the sample that generated each RLU data point is superimposed with the data. All MRSA samples generated RLU values above the Cutoff while MSSA did not.

Cross-Reactivity and Microbial Interference Study

A cross-reactivity and microbial interference study was performed. The purpose of the study was to test a set of bacterial strains commonly encountered in clinical samples and known to potentially be in the host range of the bacteriophage φ80α in the MRSA Assay to see if there was cross reactivity or interference of these strains with phage or substrate used in the test.

Previous experiments with clinical samples had resulted in false positive results with a presence of *Enterococci faecalis* and *Staphylococcus epidermidis* as indicated from the presence of blue and white colonies when plating on BBL™ CHROMagar™ Staph aureus plates. In addition, *Listeria monocytogenes* and *Listeria innocua* may be within the infective or penetrative host range of the phage φ80α which may also contribute to cross-reactivity in the MRSA assay. The study tested *Enterococci faecalis, Staphylococcus epidermidis, Listeria monocytogenes* and *Listeria innocua* for cross reactivity/interference with Viability MRSA assay. Each strain was tested at high cell numbers in the order of $10^6$, $10^7$ or $10^8$ cells in the assay volume. Tests were done without the addition of GW24 lysate to address potential autoluminescence of strains.

Experiment 1 tested various strains (MSSA-S121, NRS# 9-*Staphylococcus haemolyticus*, NRS# 6-*Staphylococcus epidermidis*, ATCC 12228-*Staphylococcus epidermidis*, ATCC 15305-*Staphylococcus saprophyticus*, ATCC 29212-*Enterococcus. faecalis*, ATCC 60193-*Candida albicans*, ATCC 12453-*Proteus mirabilis*) for luminescence at high cell numbers under normal assay conditions.

Experiment 2: A subset of strains that were luminescent from Experiment 1 were re-assayed in the presence of various antibiotics at various concentrations to quench background luminescence.

Experiment 3: *E. faecalis* and S32 (MRSA) were tested with various substrate formulations developed as described above without GW24 lysate and without incubation.

Experiment 4: ATCC 33090-*Listeria innocua* and ATCC 19111-*Listeria monocytogenes* were tested for background signal and non-specific luminescence and retested with various substrate formulations developed as described above along with *E. faecalis* and *S. epidermidis*.

Experiment 5: *E. faecalis* was retested with a final substrate formulation developed as described above.

Substrate Reagent formulations tested in this study are summarized in Table 9.

TABLE 10

Substrate Reagent Formulations

| Experiment | Substrate | Description |
|---|---|---|
| 1 | Original Substrate | 1% Tween20 + 4.2 mM Tridecanal, |
| 2 | Original Substrate | pH 3.0 |
| 3 | Substrate 1 | 6.3 mM Tridecanal + 0.5% Vitamin E Acetate, pH 3.0 |
|  | Substrate 2 | 20 mM Nonanal + 0.5% Vitamin E Acetate, pH 3.0 |
|  | Substrate 3 | 8.4 mM Tridecanal + 0.5% Vitamin E Acetate, pH 3.0 |
|  | Substrate 4 | 6.3 mM Tridecanal + 1% a-Tocopherol-PEG 1000 Succinate, pH 3.0 |
| 4 | Original substrate | 1% Tween20 + 4.2 mM Tridecanal, pH 3.0 |
|  | Substrate 5 | 0.5% Triton + 4.2 mM Tridecanal (Sigma) + 0.5% Vitamin E Acetate, pH 3.0 |
| 5 | Substrate 6 | 6.3 mM Tridecanal + 2% VitE PEG, pH 3.0 |

Methods/Procedures:

The following were steps performed for the MRSA Assay.

A) Strains Grown for Experiments 1-5

On the day before the assay, an overnight culture was started in a deep 96 well plate at a 1:50 dilution in TSB from a frozen one-time use stock and incubated at 37° C. on an orbital shaker for >15 hours. Bacteria (8 uL) in TSB (392 uL).

The absorbance of culture was measured on Versamax. The TSB was set as blank in template on SoftmaxPro. Optical density (OD) was measured at 600 nm.

On the day of the assay, cells were re-suspended to an OD 0.5 to set up the assays. Prepared BSS-M56 for Experiments 1-5.

B) Transduction Particle Media Reagent was Prepared for all Experiments 1, 2, 4 and 5 (No Transduction Particle Reagent Used in Experiment 3): 15 ug/mL Cefoxitin+GW24 Lysate Stock from as Described Above at 30×.

C) Sample Preparation:

Various dilutions were made from overnight cultures of strains. All strains were diluted BSS M56.

D) MRSA Assay was Run for Experiments 1-5

Media was loaded with or without phage and cefoxitin at 5 μg/ml to assay plate. 2.5 ul cells were added. The assay plate was incubated with a plate lid at 37° C. on an orbital shaker with the speed set to approximately 100 rpm for 4 hours.

Next, the assay plates were measured on the SpectraMax L with the following standard assay parameters:

Fast Kinetic Luminescence

Read for 20 time points at 0.5 second intervals. Substrate was injected with M injector with 50 uL/well at 250 ul/sec including 5 baseline reads. No incubation temperature was set and was read at room temperature.

The SpectraMax L was primed with Substrate Reagent before running the assay.

The results were analyzed with the following:

A) Determined cutoff by averaging blank RLU across all replicates and time points and adding three standard deviations.

B) Determined maximum RLU for each sample using SoftMaxPro.

C) Determined if the maximum RLU was greater than the cutoff RLU, and if so, then the sample data was used for analysis.

Results Summary

Experiment 1

Various strains were tested for cross reactivity and interference using the Original Substrate formulation, out of those tested, NRS#9-*S. haemolyticus*, NRS #6-*S. epidermidis* and *E. faecalis* tested false positive in MRSA assay.

Experiment 2

Out of the three strains tested, NRS #9 and *E. faecalis* tested MRSA positive with all Cefoxitin conditions tested. All three strains (NRS #9, *E. faecalis*, NRS #6) tested positive when no transduction particle reagent was used in the assay, indicating that non-specific luminescence was not transduction particle reagent-dependent but rather strain and substrate reagent dependent. Carb (Carbencillin) at all concentrations tested was effective in removing the false positive signal.

Experiment 3

*E. faecalis* gave a positive signal without transduction particle reagent. MRSA strain S32 also gave a positive signal without transduction particle reagent. This result was indicative of the substrate reagent causing background luminescence. Substrate 4 was effective in eliminating background signal in the assay.

Experiment 4

Strains ATCC 33090-*Listeria innocua*, ATCC 19111-*Listeria monocytogenes*, were tested for luminescence with transduction particle reagent and substrate reagent as *Listeria sp.* can be within the host range of the bacteriophage used in the MRSA assay. Luminescence was observed from *L. innocua* with and without transduction particle reagent using Original Substrate formulation indicating that the luminescence was due to non-specific reaction potentially with the substrate. Substrate 5 was effective in eliminating luminescence from Listeria but not E. faecalis.

Experiment 5

Retested E. faecalis with Substrate 6. In two independent runs on two different days with high load of cells at 0.5 OD, the assay yielded negative results.

Conclusions

The cross-reactivity study demonstrated background luminescence from several bacterial species at high loads. The light output did not require transduction particle reagent and certain substrate formulations utilizing phosphate ions contributed to non-specific signal. Because no light output from cross-reactive species was observed from the use of transduction particle reagent, in the case that φ80α penetrates cross-reactive species, light output is prevented from the lack of activity of the S. aureus PclpB promoter that is operatively linked to the bacterial luciferase genes and/or the lack of activity of the S. aureus pT181 origin of replication within these species.

Replacing the buffer from sodium phosphate dibasic in the formulation with sodium citrate and citric acid eliminated background luminescence from all cross-reactive species tested except for E. faecalis. Substrate 6 with the added ingredient of a tocopherol-PEG 1000 Succinate eliminated the remaining non-specific signal from E. faecalis.

Clinical Performance of Non-Replicative Transduction Particle-Based Viable Cell Reporter MRSA Assay—Results with Reference to Direct Plating onto CHROMAgar MRSA II A MRSA screening assay was developed employing φ80α-based luxAB expressing non-replicative transduction particles (NRTP). The assay consisted of adding NRTP to a clinical sample suspected of containing MRSA, incubating the sample for a period of 4 hours at 37° C., and then assaying the incubated sample by injecting an aldehyde into the sample while measuring for luminescence with a photomultiplier tube. The results of the assay were compared to that of commercially available chromogenic media designed for the detection of MRSA as a reference in order to determine the sensitivity and specificity of the assay. The NRTP-based assay was expected to correlate well with the culture-based reference since both require the presence of viable MRSA cells and both rely on the expression of the MRSA phenotype. The results showed excellent correlation with the reference.

The purpose of the study was to determine the performance of the NRTP-based MRSA Assay with reference to CHROMAgar MRSA II from testing remnant nasal swab samples collected for the purpose of MRSA screening.

Scope:

De-identified nasal swab samples collected from patients for the purpose of MRSA surveillance by a clinical institution were tested for the presence of MRSA using the NRTP-based MRSA Assay, CHROMAgar MRSA II, CHROMAgar SA and Blood Agar TSA via direct plating and via enriched culture followed by plating. The results of the NRTP-based MRSA Assay were compared with the results of the CHROMAgar MRSA II assay in order to calculate the sensitivity and specificity of the NRTP-based MRSA Assay with reference to CHROMAgar MRSA II.

The following key materials were used in the clinical performance study:

Growth Media Reagent: BSS-M56
Substrate Reagent: Final Substrate Reagent Formulations to be stored at 18-24° C. as described as described above Transduction Particle Reagent: BSS-M56 base with 10 ug/mL (i.e. 2× concentration) cefoxitin and transduction particle reagent as described above at 2× concentration.

Methods/Procedures

Clinical Sample Description:

Sample transport tubes containing liquid Amies (220093-BD BBL™ CultureSwab™ Liquid Amies) were provided to a clinical institution for collecting de-identified remnant nasal swabs collected by the clinical institution. Prior to placing the nasal swabs into the provided sample transport tube, the clinical institution used the swab for performing their own direct culture MRSA screening by streaking the swab onto a culture plate. More specifically, anterior nares specimens were collected at the clinical institution internal standard procedures and using the clinical institution's standard collection swab. The clinical institution then performed direct culture screening with the swab. The remnant swab was then added to the sample transport tube in which the swab tip was submerged in the Amies buffer in the sample transport tube. Samples were then kept at room temperature for 2-24 hours prior to further processing.

Sample Handling:

Upon receipt, samples were stored overnight at room temperature in a biosafety cabinet upright to ensure swab immersion in the sample transport tube Amies buffer. After overnight storage, samples were further processed as follows.

Clinical Sample Preparation

Using a 1 mL Pipette, 300 µl of Growth Media Reagent was added to 15 mL falcon tubes.

The swabs from remnant nasal swabs were removed from the original transport tube and immersed into the Growth Media Reagent in a corresponding falcon tube. The swab contents were then eluted into the Growth Media Reagent in the falcon tube by rolling it back and forth in the Growth Media Reagent 4-6 times. The swab was then placed back into the original transport tube and stored at 2-8° C. until the end of the study while the eluted clinical samples in the falcon tube were transferred to 1.5 mL tubes and kept at room temperature until further processing.

Running the NRTP MRSA Assay:

The following samples were loaded directly into a white 96 well assay plate.

Clinical Samples: 100 µl of the eluted material of each clinical sample in singlet.

MRSA positive control: 2 µl of a thoroughly mixed 0.1 OD culture of a known MRSA isolate into 98 uL of Growth Media Reagent in triplicate.

MSSA negative control: 2 µl of a thoroughly mixed 0.1 OD culture of a known MSSA isolate into 98 uL of Growth Media Reagent in triplicate.

Blanks: 100 µl of Growth Media Reagent in triplicate.

To each sample, 100 µl of Transduction Particle Reagent was added. The assay plate was then placed in an incubator set at 37° C., shaking on orbital shaker for 4 hours. At the end of 4 hours, the plate was removed from incubator and immediately measured for luminescence on a SpectraMax L that injected 50 µl of the Substrate Reagent and measured luminescence for a period of 1 minute.

Bacteria Plating for Clinical Sample CFU Enumeration:

Each eluted clinical sample was plated in order to determine bacterial colony counts on CHROMAgar MRSA II, CHROMAgar SA and Blood Agar (TSA II) via direct and enriched culture as follows. Organism CFU counts were determined by direct plating. MRSA CFU counts were determined by plating on CHROMAgar MRSA II. S. aureus CFU counts were determined by plating on CHROMAgar SA plate. CFU counts of any organism whose growth is supported by Blood Agar TSA were determined by plating on Blood Agar TSA. In the case that direct plating did not produce colonies due to the load of organisms being below the limit of detection of the plates used, sample enrichment was also performed by incubating a portion of the eluted clinical sample in TSB overnight at 37° C. with shaking and then again plating the enriched culture on CHROMAgar MRSA II. All plates were incubated for 20-24 hours at 37° C. After incubation, the CFU counts of any colonies appearing on each plate were recorded.

Analysis:

The presence and CFU load of MRSA, *S. aureus*, and total organisms per eluted clinical sample were calculated based on the CFU counts obtained on CHROMAgar MRSA II, CHROMAgar SA, and Blood Agar TSA, respectively.

NRTP Assay analysis:

Data from each sample were plotted as RLU vs. time.

Cutoff Determination:

The Assay Cutoff was calculated from all time points of the blank samples using the following formula: (Mean Blank RLU+3*SD Blank RLU).

MRSA Positive Determination:

The RLU of each time point after substrate injection was determined to be above or below the Assay Cutoff. If two or more data points after injection were above the Assay Cutoff then the sample was designated as "MRSA Positive."

Results:

The MRSA positive results of the NRTP Assay were compared to those of the direct and enriched culture plating onto CHROMAgar MRSA II. The following calculations were conducted in order to determine the NTRP Assay Sensitivity and Specificity with reference to CHROMAgar MRSA II.

True Positive (TP)
Sample that produced a MRSA positive result on both the NRTP Assay and CHROMAgar MRSA II
True Negative (TN)
Sample that produced a MRSA negative result on both the NRTP Assay and CHROMAgar MRSA II
False Positive (FP)
Sample that produced a MRSA positive result on the NRTP Assay and a MRSA negative result on CHROMAgar MRSA II
False Negative (FN)
Sample that produced a MRSA negative result on the NRTP Assay and a MRSA positive result on CHROMAgar MRSA II
Sensitivity = TP/(TP + FN)
Specificity = TN/(TN + FP)

Results with Reference to Direct Plating onto CHROMAgar MRSA II

Table 11 shows following results were obtained comparing the NRTP Assay with reference to direct plating on CHROMAgar MRSA II.

Based on the above data, the sensitivity and specificity of the assay with reference to direct plating onto CHROMAgar MRSA II were calculated to be:

Sensitivity=100%
Specificity=92%

Clinical Performance of Non-Replicative Transduction Particle-Based Viable Cell Reporter MRSA Assay—Results with Reference to Enriched Culture, Followed by Plating onto CHROMAgar MRSA II Based on the results with reference to direct plating on CHROMAgar MRSA II, all clinical samples were re-tested with reference to enriched culture, followed by plating on CHROMAgar MRSA II. The rationale for the follow-on testing was based on the possibility that false positive results when compared to direct plating may indeed be true positives that were detected by the NRTP assay but may have been missed by direct plating. A portion of the remaining eluted swab samples were re-tested via the NRTP assay as described above. Another portion of the remaining eluted swab samples were also tested via enriched culture, followed by plating onto CHROMAgar MRSA II. Enriched culture testing consisted of adding 100 uL of the remaining eluted swab material to 2 mL of TSB and incubating at 37 C with shaking for a period of 18-24 hours. The resulting culture was then streaked onto CHROMAgar MRSA II in order to determine the presence of MRSA in the culture. Table 12 summarizes the data from both the direct plating and enrichment followed by plating assays—only the samples that produced a MRSA positive result on either NRTP Assay or CHROMAgar MRSA II are shown.

TABLE 12

NRTP Assay Results vs. Direct Plating and Enriched Culture followed by Plating on CHROMAgar MRSA II

| Sample # | NRTP Assay | Direct CHROMagar MRSA II | Enrichment + NRTP Asssay | Enrichment + CHROMagar MRSA II |
|---|---|---|---|---|
| 1 | + | + | + | + |
| 2 | + | + | + | + |
| 3 | + | + | + | + |
| 4 | + | + | + | + |
| 5 | + | + | + | + |
| 6 | + | + | + | + |
| 7 | + | + | + | + |
| 8 | + | − | + | + |
| 9 | + | − | + | + |
| 10 | + | − | + | + |
| 11 | + | − | + | + |
| 12 | + | − | + | − |

Only the samples that produced a MRSA positive result on either NRTP Assay or CHROMAgar MRSA II are shown.

Table 13 shows following results were obtained comparing the NRTP Assay with reference to enriched culture of clinical samples, followed by plating on CHROMAgar MRSA II.

TABLE 11

NRTP Assay Results vs. Direct Plating on CHROMAgar MRSA II Results

| Total Samples | CHROMAgar MRSA II Positive | CHROMAgar MRSA II Negative | NRTP ASSAY Positive | NRTP ASSAY Negative | True Positive | True Negative | False Positive | False Negative |
|---|---|---|---|---|---|---|---|---|
| 69 | 7 | 62 | 12 | 57 | 7 | 57 | 5 | 0 |

TABLE 13

NRTP Assay Results vs. Enriched Culture Followed By Plating on CHROMAgar MRSA II Results

| Total Samples | CHROMAgar MRSA II Positive | CHROMAgar MRSA II Negative | NRTP ASSAY Positive | NRTP ASSAY Negative | True Positive | True Negative | False Positive | False Negative |
|---|---|---|---|---|---|---|---|---|
| 69 | 11 | 58 | 12 | 57 | 11 | 57 | 1 | 0 |

Based on the above data, the sensitivity and specificity of the assay with reference to enriched culture followed by plating onto CHROMAgar MRSA II was calculated to be:
Sensitivity=100%
Specificity=98.3%

Example 8: NRTP-Based Assay for Antimicrobial Susceptibility Testing—Correlation of Minimum Inhibitory Concentration to Luminescence Output In another example, a S. aureus cefoxitin susceptibility assay was developed to determine the minimum inhibitory concentration of cefoxitin required to inhibit the growth of cefoxitin resistant S. aureus. Unlike a MRSA cefoxitin resistance assay as described above, which differentiates cefoxitin sensitive from cefoxitin resistant S. aureus, the MRSA cefoxitin susceptibility assay in this example describes the development of an assay to determine the minimum amount of cefoxitin needed to inhibit the grown of S. aureus in the presence of cefoxitin.

The following key materials were used in the clinical performance study:
Growth Media Reagent: BSS-M56
Substrate Reagent: Final Substrate Reagent Formulations to be stored at 18-24° C. as described in Example 7.
Transduction Particle Reagent: BSS-M56 base with 10 ug/mL (i.e. 2× concentration) cefoxitin and transduction particle reagent as described in Example 7 at 2× concentration MIC Study Protocol.

Overnight Culture: For each MRSA strain (NRS35 and S7) and a MSSA negative control strain (MSSA121), 2 mL of TSB were inoculated with a colony of the strain previously grown on TSA plates. Overnight MRSA cultures included 5 ug/mL cefoxitin. All samples were incubated overnight at 37° C. in a shaking incubator.

Day Culture: 20 uL of each of the overnight cultures were transferred into a new culture tube containing 2 mL of Growth Media Reagent. The inoculums were then incubated at 37 C with shaking for approximately 1 hr 45 min, until the OD (600 nm) reached 0.1.

MIC Determination Via Plating:
a) Each of the day cultures was streaked onto TSA plates containing cefoxitin at 4, 8, 16, 32, 64, and 128 ug/mL.
b) Plates were incubated for 18 hours at 37 C to determine growth.

NRTP Assay Preparation:
a) Wells of a white 96 well assay plate were filled with 100 uL of 2× Transduction Particle Reagent.
b) For each of the day cultures, five wells were then filled with 100 uL of day culture.
c) For each of the day cultures, cefoxitin was added to one well each such that the cefoxitin concentration in the well was at 4, 8, 16, 32, 64, and 128 ug/mL.
d) The plate was then sealed with a breathable seal and incubated for 4 hours at 37° C. with moderate shaking, 50 rpm.

At the end of 4 hours, the plate was remove from incubator and immediately measured for luminescence on a SpectraMax L that injected 50 µl of the Substrate Reagent and measured luminescence for a period of 1 minute.

Analysis:
The maximum luminescence value after Substrate Reagent addition from each sample was plotted. MSSA sample RLU values were used to determine a Cutoff calculated using the following formula: (Mean MSSA RLU+ 3*SD MSSA RLU).

Figure 23:
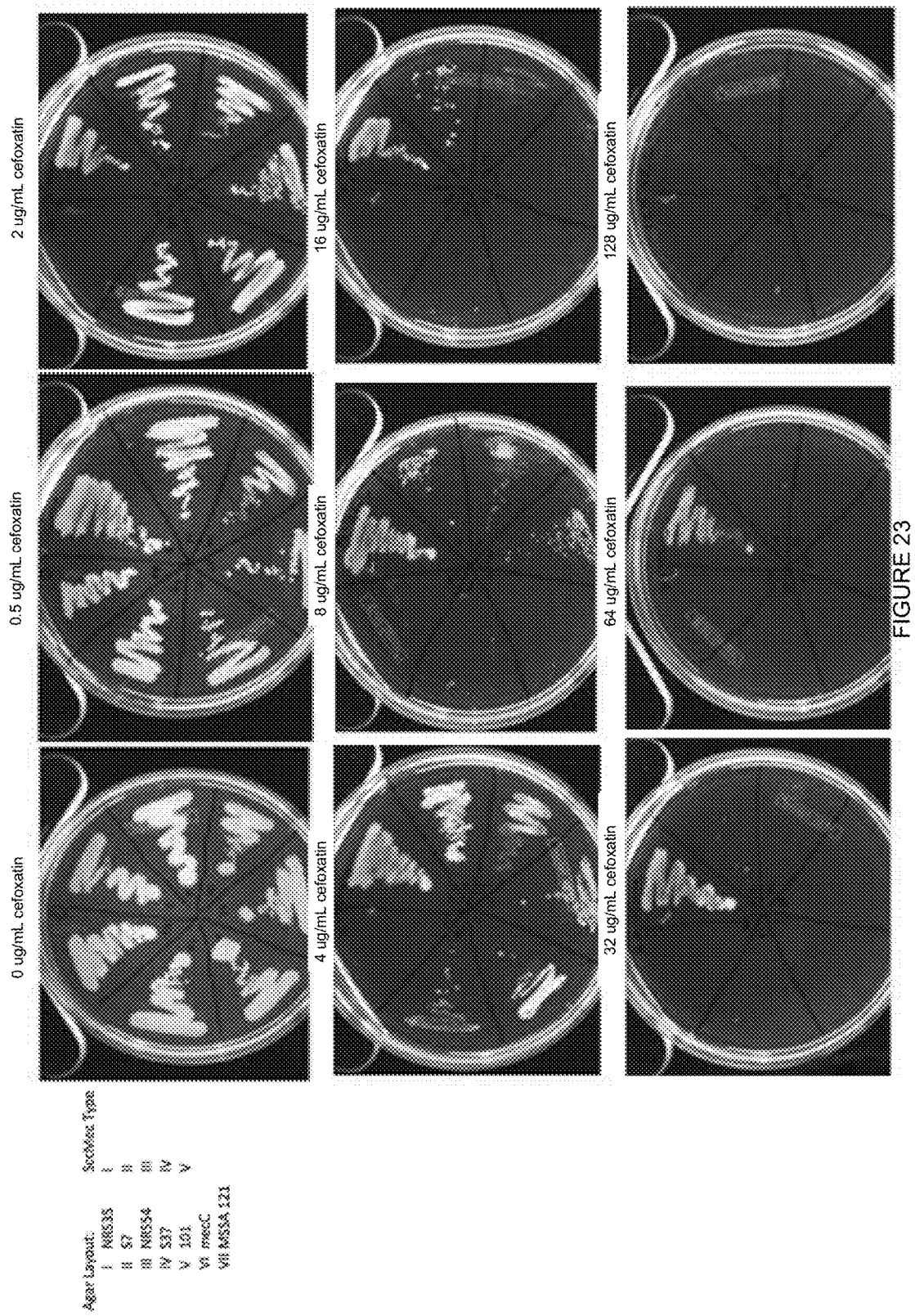
FIG. 23 shows the results of *S. aureus* growth at 4, 8, 16, 32, 64, and 128 ug/mL of cefoxitin.
Figure 24:
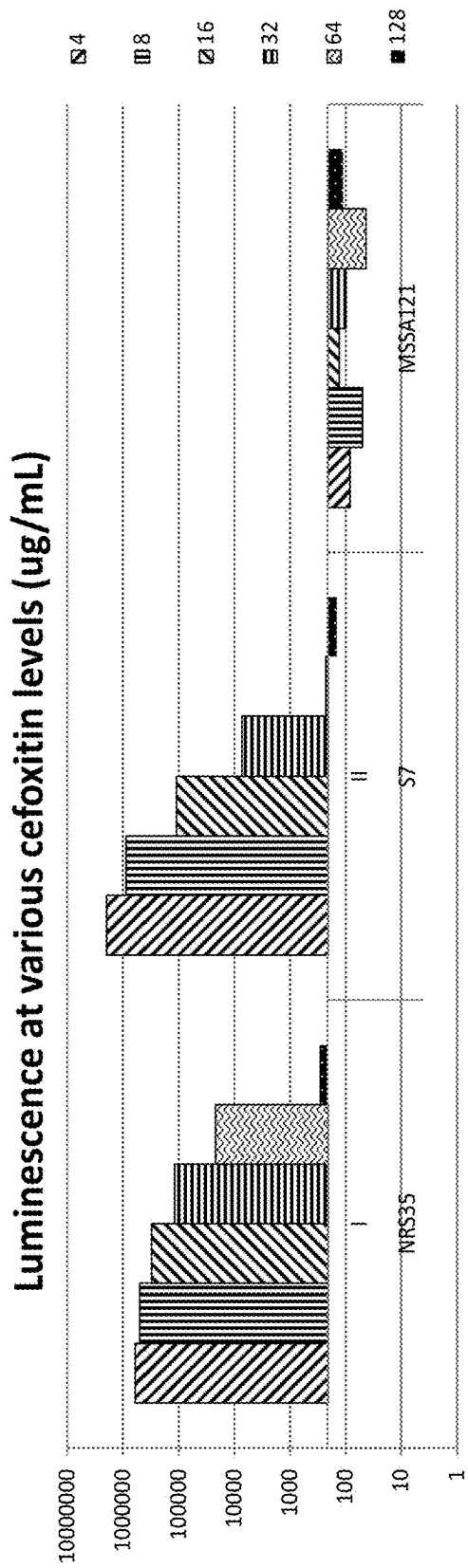
FIG. 24 shows the RLU values obtained by the NRTP assay in the presence of 4, 8, 16, 32, 64, and 128 ug/mL cefoxitin. The x-axis in FIG. 24 is set at the MSSA RLU cutoff value.

Results:
FIG. 23 shows the results of S. aureus growth at 4, 8, 16, 32, 64, and 128 ug/mL of cefoxitin. FIG. 24 shows the RLU values obtained by the NRTP assay in the presence of 4, 8, 16, 32, 64, and 128 ug/mL cefoxitin. The x-axis in FIG. 24 is set at the MSSA RLU cutoff value.

As can be seen in FIG. 23, MRSA NRS25 exhibited a MIC of 128 ug/mL cefoxitin while MRSA S7 exhibited a MIC of 64 ug/mL cefoxitin. Correspondingly, MRSA NRS25 exhibited appreciable luminescence above the MSSA RLU cutoff to a cefoxitin concentration up to 64 ug/mL cefoxitin while MRSA S7 exhibited luminescence above the MSSA RLU cutoff to a cefoxitin concentration up to 32 ug/mL.

Based on the above data, the NRTP assay demonstrates that RLU values obtained from the assay correlate with MIC results and thus the NRTP assay may be used to develop antibiotic susceptibility assays.

Example 9: Transcript Reporter Assay: Mechanism of Conformational Change by RBS-Blocking Cis-Repression of Luxab Translation Activated by the mecA Gene Transcript of Mrsa As described above, a reporter transcript can be designed such that translation of the reporter gene sequence is blocked by cis-repression of the ribosome-binding site (RBS) of the reporter gene.

The following tools were used for designing the reporter transcripts of the invention.
1) RNA secondary structure was calculated using secondary structure program, such as Mfold.
2) Intermolecular RNA interactions were calculated using a software program such as RNA-RNA InterACTion prediction using Integer Programming (RactIP).
3) RNA secondary structure was visualized using Visualization Applet for RNA (VARNA).

Figure 25:
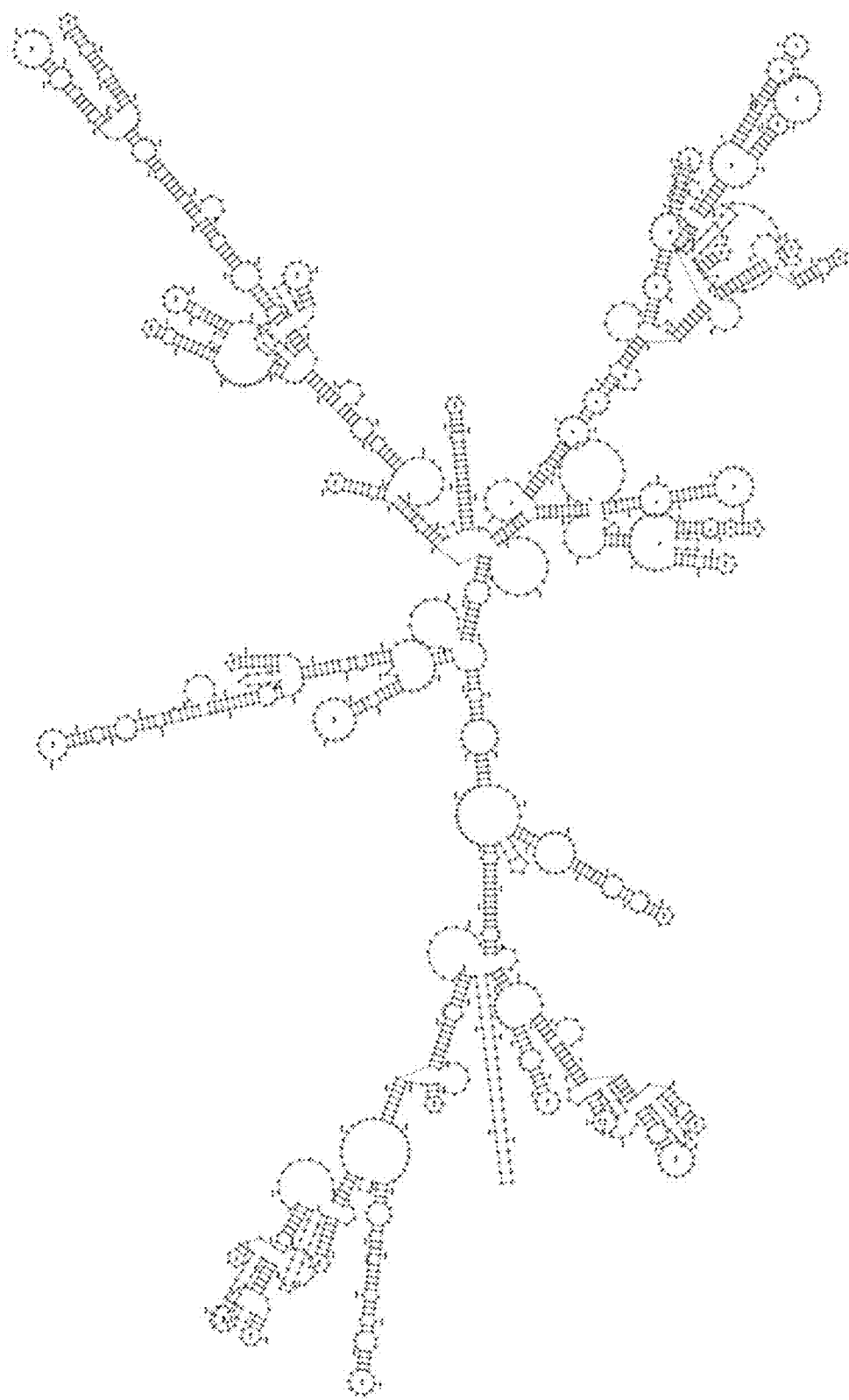
FIG. 25 shows a secondary structure of the mecA transcript (SEQ ID NO:19) generated based on the lowest energy conformation calculated by MFold and visualized with VARNA.

FIG. 25 shows a secondary structure of the mecA transcript generated based on the lowest energy conformation calculated by MFold and visualized with VARNA. The terminal loop 23 (T23) contains a YUNR sequence UUGG consisting of bases 1,487-1,490 of the mecA transcript sequence. Analysis of the secondary structure of the mecA gene transcript revealed several ssRNA regions that were suitable for designing a cis-repressed luxAB reporter that can be de-repressed via interactions between the reporter and an ssRNA region.

Figure 26:
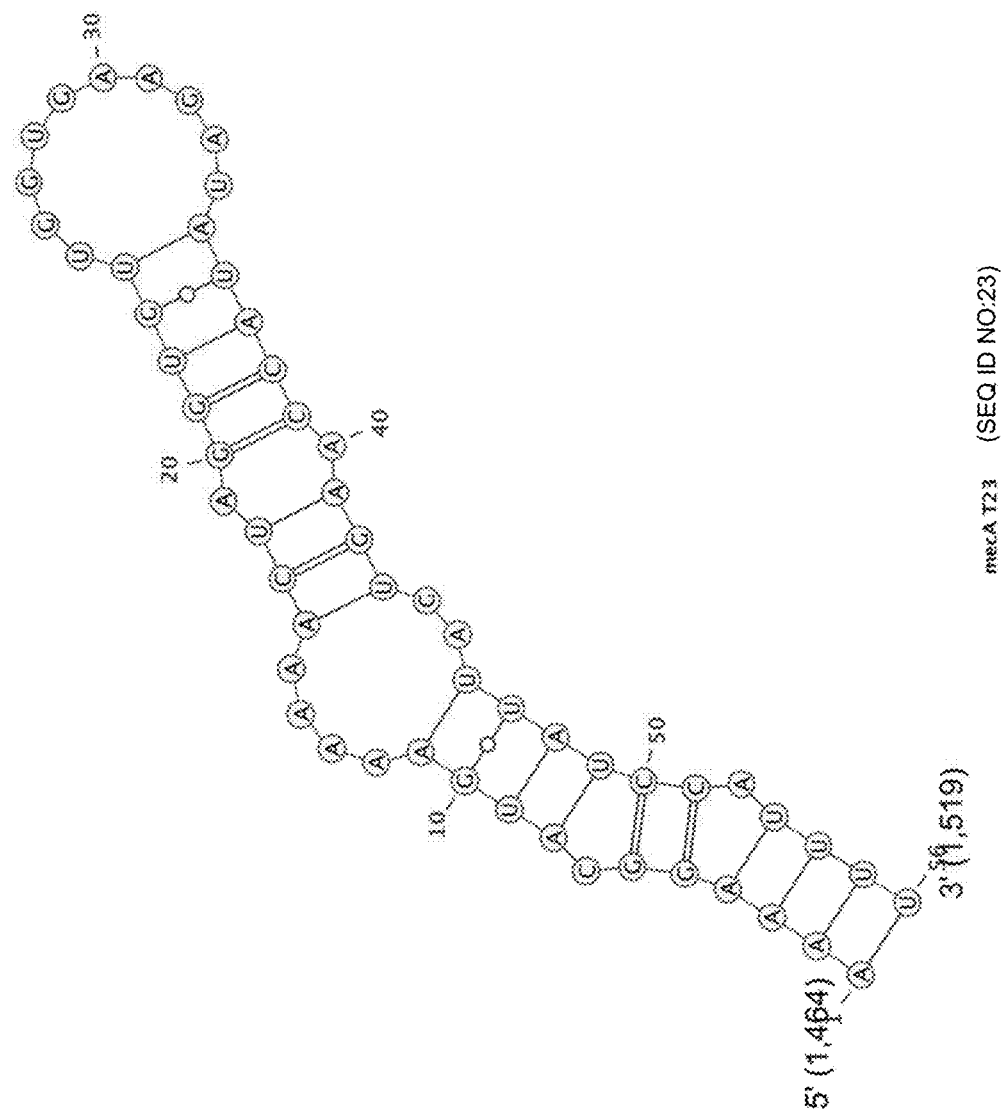
FIG. 26 shows the terminal loop 23 (T23) of the mecA transcript (SEQ ID NO:23) that contains a YUNR consensus sequence.

As shown in detail in FIG. 26, the terminal loop 23 (T23) of the mecA transcript contains a YUNR consensus sequence. A YUNR (pYrimidine-Uracil-Nucleotide-puRine) consensus sequence has been shown to be a critical target for intermolecular RNA complexes in natural systems. A cis-repressing sequence was designed to form a stem-loop structure with the RBS of the reporter sequence, such that the cis-repressing sequence blocks binding of an RNA polymerase to the RBS of the reporter sequence. The reporter sequence was exposed upon binding of the loop of the cis-repressing stem-loop structure with T23 of the mecA transcript.

Figure 27:
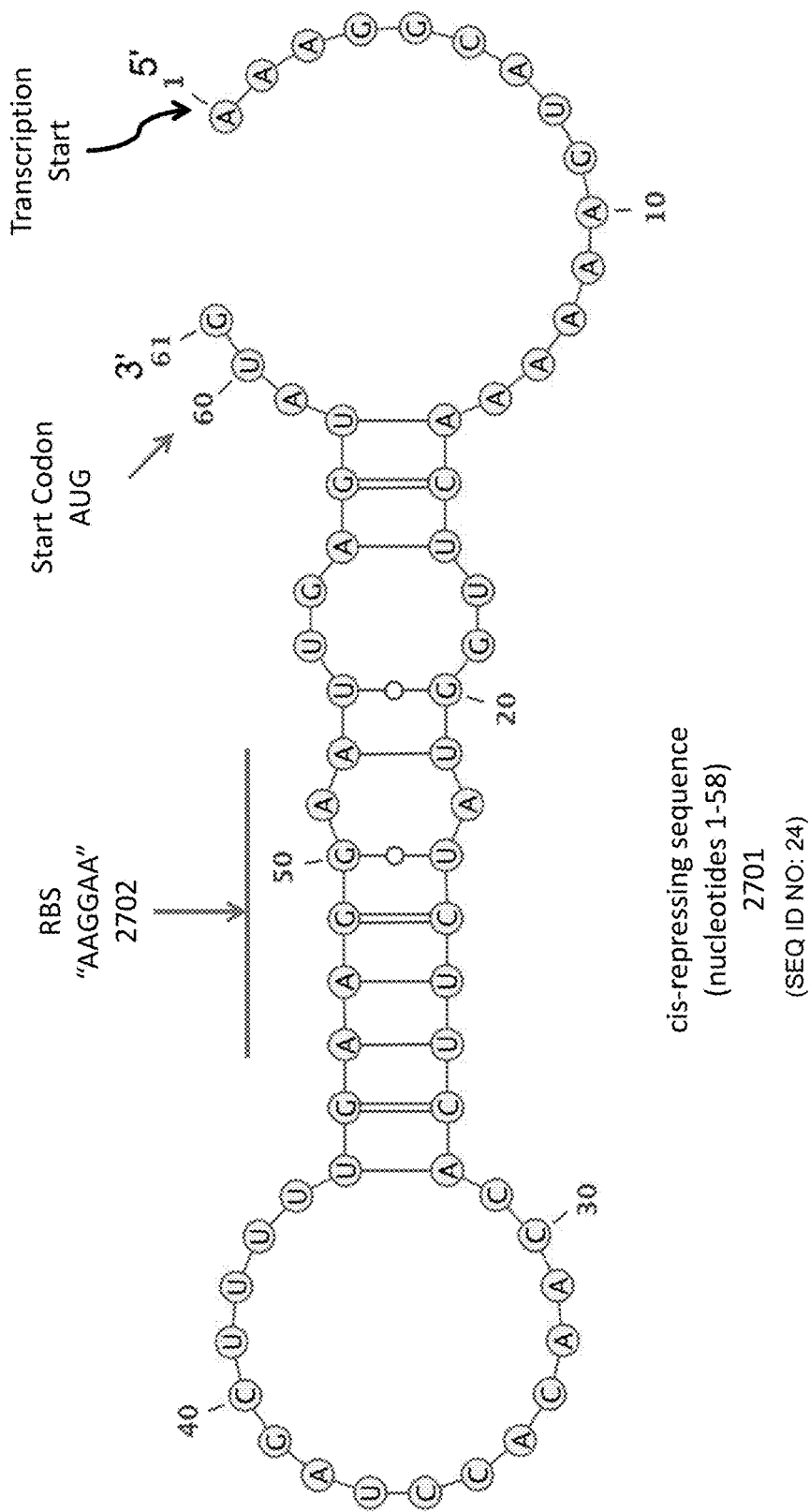
FIG. 27 depicts a cis-repressing sequence (SEQ ID NO: 24) added to the 5' terminus of the luxAB genes and designed to form a stem-loop structure that blocks the RBS sequence ("AAGGAA") of the luxA gene.

As shown in FIG. 27, a cis-repressing sequence 2701 was added to the 5' terminus of the luxAB genes and designed to form a stem-loop structure that blocks the RBS sequence ("AAGGAA") 2702 of the luxA gene. The cis-repressing stem-loop structure was predicted to block the luxA RBS ("AAGGAA") sequence, based on the lowest energy conformation of the luxAB transcript including the cis-repressing sequence at the 5' terminus of the luxAB transcript, as calculated by MFold and visualized with VARNA.

The first 61 nucleotides of the cis-repressed luxAB genes are shown in FIG. 7, up to the start codon AUG of the luxA gene. The RBS sequence "AAGGAA" includes bases 47-52. This terminal loop of the reporter transcript was designed to interact with (bind to) the terminal loop 23 (T23) of the mecA transcript, which contains a YUNR sequence.

The terminal loop of the cis-repressing sequence was designed to interact with T23 of the mecA transcript, such that hybridization of the cis-repressed luxAB transcript and the mecA transcript via the interaction of the loop from the cis-repressing stem-loop structure and T23 of the mecA transcript results in exposure of the RBS of the luxA gene. FIG. 28 shows the predicted inter-molecular interactions between the mecA T23 sequence and the cis-repressing sequence on the luxAB transcript calculated by RactIP and visualized by VARNA. Lines indicate base pairing between the mecA transcript and the cis-repressed luxAB transcript. The interaction between the two sequences results in exposure of the luxA RBS sequence AAGGAA and thus de-repression of the luxAB reporter.

Example 10: Transcript Reporter Assay: Methods of Detecting Target Transcripts or Genes Using a mecA—luxAB Reporter System In another example, a method for detecting a target mecA gene is provided using a mecA-luxAB reporter system. Here, mecA is the target transcript, and luxAB is the reporter molecule.

1. Construction of the Reporter Construct

A vector comprising a reporter construct encoding luxAB can be constructed via standard molecular biological techniques by incorporating the reporter construct into a shuttle vector capable of propagating in both *E. coli* and *S. aureus*. The vector can contain an origin of replication that is functional in *E. coli* and a selectable marker that is expressed in *E. coli* and suitable for allowing the growth of *E. coli* cells transformed with the vector and grown under selective conditions. The vector can also contain an origin of replication that is functional in *S. aureus* and a selectable marker that is expressed in *S. aureus* and suitable for allowing the growth of *E. coli* cells transformed with the vector and grown under selective conditions. Propagation of the vector for conducting in vitro manipulations and for verification of manipulations can be accomplished via a suitable laboratory cloning strain of *E. coli* and the final modified vector can then be introduced into *S. aureus* strains.

The reporter construct can be first introduced into a *S. aureus* cell for transcribing the construct and producing the reporter transcript.

2. Construction of a Cis-Repressed Reporter Transcript

Methods are provided for constructing a cis-repressed reporter transcript that can bind to a mecA-target transcript. The reporter transcript can be constructed via standard molecular biological techniques. The luxA and luxB genes serve as reporter genes and can be derived from Vibrio harveyi. The genes lack a transcriptional promoter, and each contains its own ribosomal binding site (RBS). When both the luxA and luxB genes are translated in a cell, the luxA and luxB proteins complex to form the active luciferase enzyme (LuxAB). See Farinha, M. A. and A. M. Kropinski, Construction of broad-host-range plasmid vectors for easy visible selection and analysis of promoters. J. Bacteriol., 1990. 172(6): p. 3496-3499.

The cis-repressing sequence can be situated upstream of the luxAB genes and downstream of a promoter and includes a sequence that is complementary to the luxA RBS. A linker sequence can separate the complementary regions of the cis-repressing sequence and the luxA sequence. After transcription of the vector, the complementary regions of the cis-repressing sequence and the luxA RBS sequence complex, creating a stem loop that prevents docking of a ribosome and hence translation.

The stem loop of the reporter transcript is designed to destabilize and form an open complex when it interacts with a naturally-occurring mecA transcript sequence (endogenous to the cell). To activate translation of the luxA gene sequence, the natural mecA transcript serves as a trans-activating RNA that binds to the cis-repressed reporter transcript and opens the inhibitory stem loop that sequesters the RBS of the luxA gene. Once the RBS is not sequestered by the cis-repressing sequence, translation of luxA can occur. Transcription of the reporter construct is accomplished via operatively linking the reporter sequence to a constitutive promoter, upstream of the cis-repressing sequence.

An example of a target mecA gene sequence is shown in FIG. 29. The sequence is a mecA gene loci DNA sequence (from *Staphylococcus aureus* subsp. aureus SA40, complete genome GenBank: CP003604.1; SEQ ID NO:15) and can be used for generating a reporter construct comprising a reporter sequence and a cis-repressing sequence. The −10 position 2901, the transcription start position 2902, the RBS 2903, the coding region (in grey 904) and the transcription termination sequence 2905 are shown.

FIG. 30 shows an exemplary mecA transcript sequence that can be used for designing a reporter transcript (SEQ ID NO:16), according to an embodiment of the invention. The RBS 3001 and the coding sequence 3002 are shown for mecA.

FIG. 31 is an example of a luxAB gene loci DNA sequence that can be used for designing a reporter transcript, according to an embodiment of the invention. The luxAB gene loci DNA sequence was obtained from Vibrio fischeri genes luxA and luxB for luciferase alpha and beta subunits (GenBank: X06758.1) (SEQ ID NO: 17). The −10 position 3101, the transcription start position 3102, the RBS for lux A 3103, the luxA coding sequence 3104 (gray shading), the RBS for luxB 3105, and the luxB coding sequence (gray shading) 3106 are shown.

FIG. 32 is an example of a luxAB transcript sequence that can be used for designing a reporter transcript (SEQ ID NO:18). The RBS for lux A 3201, the luxA coding sequence 3202 (gray shading), the RBS for luxB 3203, and the luxB coding sequence (gray shading) 3204 are shown.

Figure 33:
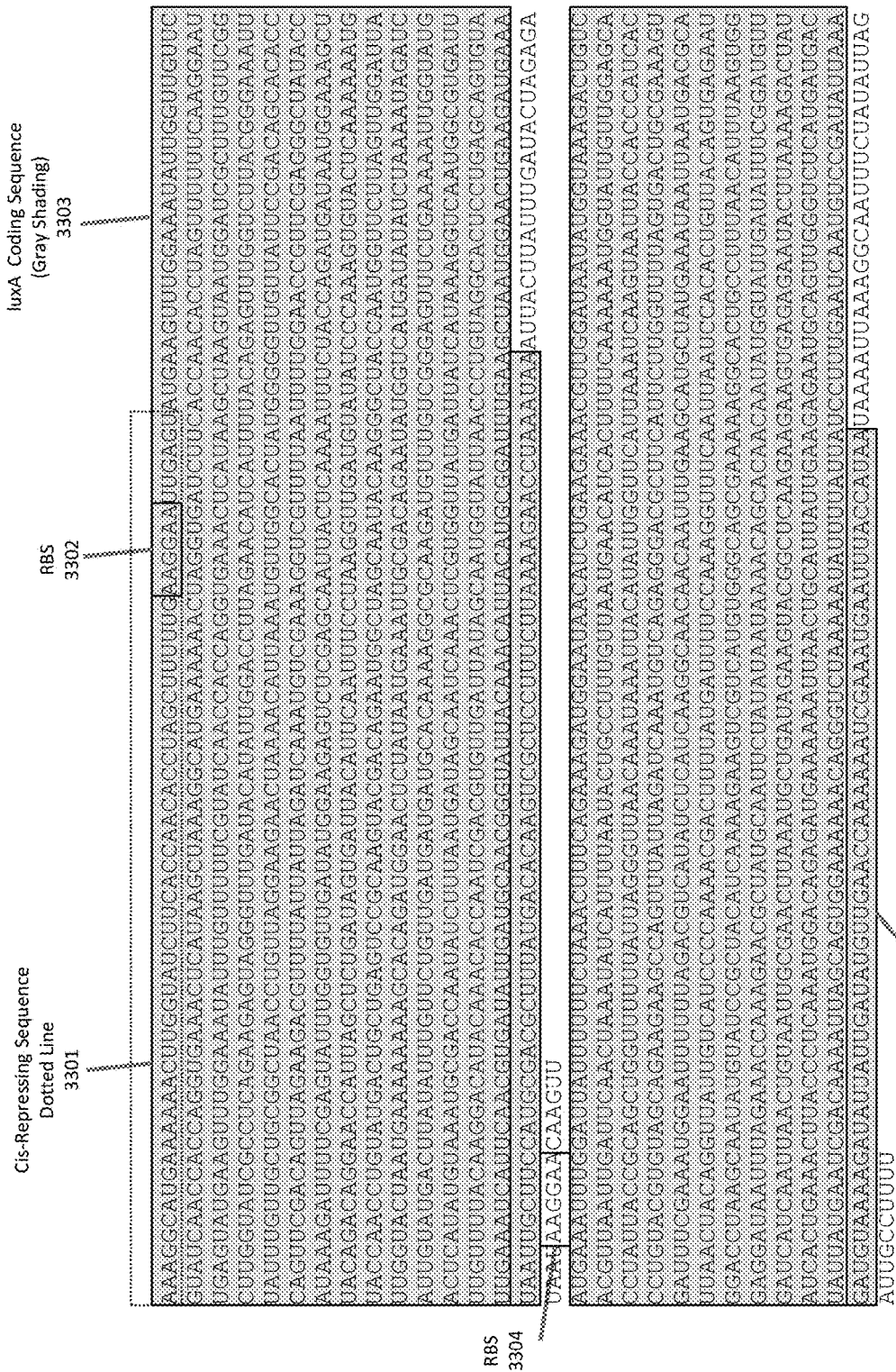
FIG. 33 is an example of a luxAB cis-repressed transcript sequence that can be used in a reporter transcript (SEQ ID NO:19), according to an embodiment of the invention.

FIG. 33 is an example of a luxAB cis-repressed transcript sequence that can be used in a reporter transcript (SEQ ID NO:19). The cis-repressing sequence (dotted line box) 3301, the RBS for lux A 3302, the luxA coding sequence 3303 (gray shading), the RBS for luxB 3304, and the luxB coding sequence (gray shading) 3305 are shown.

Figure 34:
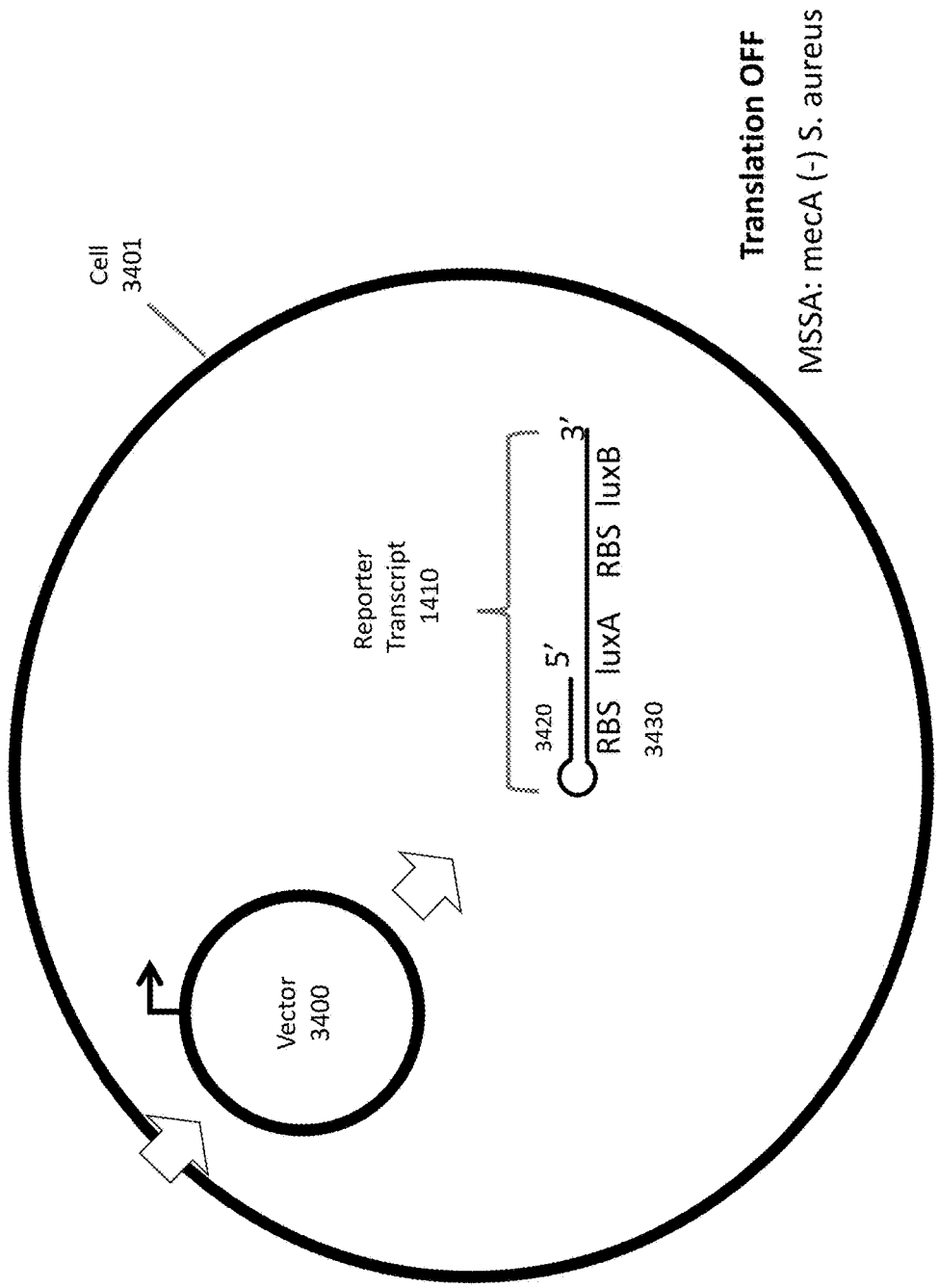
FIG. 34 shows an example of a cell comprising a vector that encodes a reporter transcript, where there is no endogenous mecA transcript in the cell, according to an embodiment of the invention.

3. Methods for Detecting the Presence or Absence of a mecA Target Transcript Using the Reporter Transcript Examples are provided for detecting the presence or absence of a mecA target transcript in a cell using the reporter transcripts of the invention. FIG. 34 shows an example of a cell comprising a vector 3400 that encodes a reporter transcript 1410, where there is no endogenous mecA transcript in the cell 3401 (e.g., the cell's genome does not contain the mecA gene). In this case, the cis-repressing sequence 3420 binds to the RBS 3430 of the luxAB genes. In some embodiments, the cis-repressing sequence 3420 can bind to a portion of or all of the RBS of the luxA gene, the RBS of the luxB gene, or both. This binding event blocks and prevents the translation of the luxAB genes, and the reporter molecule (e.g., luciferase) is not produced in the cell. Thus, no signal is detected, indicating the absence of the mecA gene in the cell.

Figure 35:
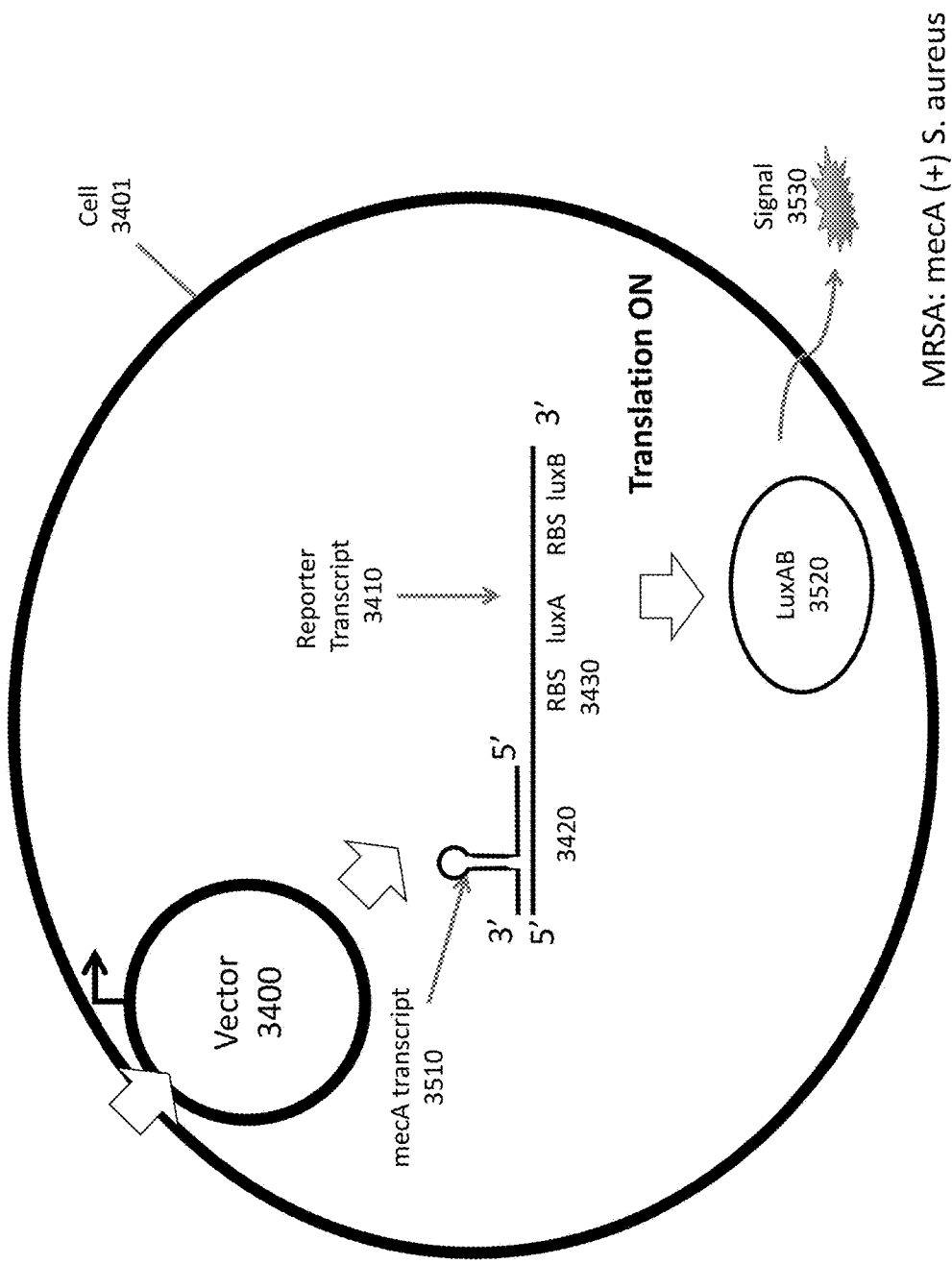
FIG. 35 shows a vector introduced into a cell, where the vector encodes the reporter transcript, which includes a cis-repressing sequence and a reporter sequence (luxA and luxB genes). When the mecA transcript present in the cell binds to the cis-repressing sequence, the inhibitory hairpin loop opens up and the RBS for the luxA gene is exposed. Translation of the reporter sequences (luxA and luxB) can occur, resulting in the formation of a luxAB enzyme. The luxAB enzyme produces a detectable luminescent signal. In this manner, the transcript reporter vector reports the presence of endogenous mecA transcripts within a cell.

In another example, the cell includes an endogenous mecA transcript (e.g., the cell's genome contains the mecA gene). FIG. 35 shows a vector 3400 introduced into a cell 3401. The vector 3400 encodes the reporter transcript 3410, which includes a cis-repressing sequence 3420 and a reporter sequence (luxA and luxB genes). When the mecA transcript 3510 present in the cell binds to the cis-repressing sequence 1420, the inhibitory hairpin loop opens up and the RBS 3430 for the luxA gene is exposed. Translation of the reporter sequences (luxA and luxB) can occur, resulting in the formation of a luxAB enzyme 3520. The luxAB enzyme 3520 produces a detectable luminescent signal 3530. In this manner, the transcript reporter vector 3400 reports the presence of endogenous mecA transcripts 3510 within a cell 3401.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

REFERENCES CITED

1. Michael G. Schmidt, D. A. S., Caroline Westwater, Joseph W. Dolan, Brian D. Hoel, Philip A. Werner, James S. Norris, Laura M. Kasman, Nucleic Acid Delivery and Expression, 2005.
2. Kreiswirth, B. N. et al., The toxic shock syndrome exotoxin structural gene is not detectably transmitted by a prophage. Nature, 1983. 305(5936): p. 709-712.
3. Ubeda, C. et al., Specificity of staphylococcal phage and SaPI DNA packaging as revealed by integrase and terminase mutations. Molecular Microbiology, 2009. 72(1): p. 98-108.
4. Otsuji, N. et al., Induction of Phage Formation in the Lysogenic *Escherichia coli* K-12 by Mitomycin C. Nature, 1959. 184(4692): p. 1079-1080.
5. Brantl, S. (2007) Regulatory mechanisms employed by cis-encoded antisense RNAs. Curr. Opin. Microbiol. 10, 102-109.
6. Isaacs, F. J. et al. (2004) Engineered riboregulators enable post-transcriptional control of gene expression. Nat. Biotechnol. 22, 841-847.
7. Pfeiffer, V. et al. (2009) Coding sequence targeting by MicC RNA reveals bacterial mRNA silencing downstream of translational initiation. Nat. Struct. Mol. Biol. 16, 840-846.
8. Opdyke, J. A. et al. (2004) GadY, a small-RNA regulator of acid response genes in *Escherichia coli*. J. Bacteriol. 186, 6698-6705.
9. Carriere, C., et al., *Conditionally replicating luciferase reporter phages: Improved sensitivity for rapid detection and assessment of drug susceptibility of Mycobacterium tuberculosis*. Journal of Clinical Microbiology, 1997. 35(12): p. 3232-3239.
10. Merten, O.-W. and M. Al-Rubeai, *Viral Vectors for Gene Therapy: Methods and Protocols*. Methods in Molecular Biology. Vol. 737. 2011.
11. Lofdahl, S., J. E. Sjostrom, and L. Philipson, *CLONING OF RESTRICTION FRAGMENTS OF DNA FROM STAPHYLOCOCCAL BACTERIOPHAGE-PHI-*11. Journal of Virology, 1981. 37(2): p. 795-801.
12. Charpentier, E., et al., *Novel Cassette-Based Shuttle Vector System for Gram-Positive Bacteria*. Appl. Environ. Microbiol., 2004. 70(10): p. 6076-6085.
13. Novick, R. P., I. Edelman, and S. Lofdahl, *Small staphylococcus-auerus plasmids are transduced as linear multimers that are formed and resolved by replicative processes*. Journal of Molecular Biology, 1986. 192(2): p. 209-220.
14. Westwater, C., et al., Development of a P1 phagemid system for the delivery of DNA into Gram-negative bacteria. Microbiology, 2002. 148(4): p. 943-950.
15. Norris, J. U., et al., Tissue-Specific and Pathogen-Specific Toxic Agents and Ribozymes. 1999.
16. Maiques, E., et al., Role of Staphylococcal Phage and SaPI Integrase in Intra- and Interspecies SaPI Transfer. J. Bacteriol., 2007. 189(15): p. 5608-5616.
17. Frees, D., et al., Clp ATPases are required for stress tolerance, intracellular replication and biofilm formation in *Staphylococcus aureus*. Molecular Microbiology, 2004. 54(5): p. 1445-1462.
18. Arnaud, M., A. Chastanet, and M. Debarbouille, New Vector for Efficient Allelic Replacement in Naturally Nontransformable, Low-GC-Content, Gram-Positive Bacteria. Appl. Environ. Microbiol., 2004. 70(11): p. 6887-6891.
19. Tormo, M. A., et al., *Staphylococcus aureus* Pathogenicity Island DNA Is Packaged in Particles Composed of Phage Proteins. J. Bacteriol., 2008. 190(7): p. 2434-2440.
20. Arthur, M., et al., The VanS sensor negatively controls VanR-mediated transcriptional activation of glycopeptide resistance genes of Tn1546 and related elements in the absence of induction. J. Bacteriol., 1997. 179(1): p. 97-106.
21. Karlsson, S., et al., Expression of *Clostridium difficile* Toxins A and B and Their Sigma Factor TcdD Is Controlled by Temperature. Infect. Immun., 2003. 71(4): p. 1784-1793.
22. Daniel Sobek, J. R., Enzyme detection system with caged substrates, 2007, Zymera, Inc.
23. Samie Jaffrey, J. P., Coupled recognition/detection system for in vivo and in vitro use, 2010, Cornell University.

24. Good, L., Translation repression by antisense sequences. Cellular and Molecular Life Sciences, 2003. 60(5): p. 854-861.

25. Sabine, B., Antisense-RNA regulation and RNA interference. Biochimica et Biophysica Acta (BBA)—Gene Structure and Expression, 2002. 1575(1-3): p. 15-25.

What is claimed:

1. A bacterial cell packaging system for packaging a reporter nucleic acid molecule into a non-replicative transduction particle (NRTP) for introduction into a cell, the packaging system comprising:
   a host bacteria cell;
   a first nucleic acid construct inside the host bacteria cell, comprising of a bacteriophage genome having a first bacteriophage gene that contains a non-functional packaging initiation site sequence, wherein the non-functional packaging initiation site sequence prevents packaging of the bacteriophage genome into the NRTP; and
   a second nucleic acid construct inside the host bacteria cell and separate from the first nucleic acid construct, comprising of the reporter nucleic acid molecule having a reporter gene and a second bacteriophage gene that contains a functional packaging initiation site sequence for facilitating packaging of a replicon of the reporter nucleic acid molecule into the NRTP, wherein the functional packaging initiation site sequence on the second nucleic acid construct complements the non-functional packaging initiation site sequence in the bacteriophage genome on the first nucleic acid construct.

2. The bacterial cell packaging system of claim 1, wherein the reporter gene is luxAB.

3. The bacterial cell packaging system of claim 1, wherein the reporter gene is operatively linked to a constitutive promoter.

4. The bacterial cell packaging system of claim 3, wherein the constitutive promoter is a *Staphylococcus aureus* (*S. aureus*) clpB promoter.

5. The bacterial cell packaging system of claim 4, wherein the *S. aureus* clpB promoter comprises the sequence of SEQ ID NO: 12.

6. The bacterial cell packaging system of claim 1, wherein the bacteriophage genome is a φ80α genome.

7. The bacterial cell packaging system of claim 1, wherein the first bacteriophage gene and the second bacteriophage gene is a φ80α small terminase (terS) gene.

8. The bacterial cell packaging system of claim 1, wherein the second bacteriophage gene comprises the sequence of SEQ ID NO: 9.

9. The bacterial cell packaging system of claim 1, wherein the bacteriophage genome is an Enterobacteriaceae bacteriophage P1 genome.

10. The bacterial cell packaging system of claim 1, wherein the first bacteriophage gene and the second bacteriophage gene is a pacA terminase gene of Enterobacteriaceae bacteriophage P1.

11. The bacterial cell packaging system of claim 1, wherein the second bacteriophage gene comprises the sequence of SEQ ID NO: 7.

12. The bacterial cell packaging system of claim 1, wherein the reporter nucleic acid molecule is a plasmid comprising at least one origin of replication.

13. The bacterial cell packaging system of claim 12, wherein the at least one origin of replication is a pT181 origin of replication.

14. The bacterial cell packaging system of claim 12, wherein the at least one origin of replication comprises the sequence of SEQ ID NO: 5.

15. The bacterial cell packaging system of claim 1, wherein the reporter nucleic acid molecule is a plasmid comprising the sequence of SEQ ID NO: 14.

16. A bacterial cell packaging system for packaging a reporter plasmid into a non-replicative transduction particle (NRTP) for introduction into a cell, the packaging system comprising:

a host bacteria cell;

a first nucleic acid construct inside the host bacteria cell, comprising of a φ80α bacteriophage genome having a non-functional packaging initiation site sequence within a φ80α small terminase (terS) gene, wherein the non-functional packaging initiation site sequence prevents packaging of the φ80α bacteriophage genome into the NRTP; and a second nucleic acid construct inside the host bacteria cell and separate from the first nucleic acid construct, comprising of the reporter plasmid having a luxAB reporter gene operatively linked to a *S. aureus* clpB promoter comprising the sequence of SEQ ID NO: 12, a pT181 origin of replication comprising the sequence of SEQ ID NO: 5, and a φ80α small terminase (terS) gene comprising the sequence of SEQ ID NO: 9 that contains a functional packaging initiation site sequence that facilitates packaging of a replicon of the reporter plasmid into the NRTP, wherein the functional packaging initiation site sequence in the φ80α small terminase (terS) gene on the second nucleic acid construct complements the non-functional packaging initiation site sequence in the φ80α bacteriophage genome on the first nucleic acid construct.

17. A bacterial cell packaging system for packaging a reporter plasmid into a non-replicative transduction particle (NRTP) for introduction into a cell, the packaging system comprising:

a host bacteria cell;

a first nucleic acid construct inside the host bacteria cell, comprising of an Enterobacteriaceae bacteriophage P1 genome having a non-functional packaging initiation site sequence within a bacteriophage P1 pacA terminase gene, wherein the non-functional packaging initiation site sequence prevents packaging of the bacteriophage P1 genome into the NRTP; and a second nucleic acid construct inside the host bacteria cell and separate from the first nucleic acid construct, comprising of the reporter plasmid having a luxAB reporter gene operatively linked to an Enterobacteriaceae β-lactamase gene bla promoter, a pBBR1-derived origin of replication, and a bacteriophage P1 pacA terminase gene comprising the sequence of SEQ ID NO: 7 that contains a functional packaging initiation site sequence that facilitates packaging of a replicon of the reporter plasmid into the NRTP, wherein the functional packaging initiation site sequence in the bacteriophage P1 pacA terminase gene on the second nucleic acid construct complements the non-functional packaging initiation site sequence in the bacteriophage P1 genome on the first nucleic acid construct.

* * * * *

SEQUENCE LISTING

<160> NUMBER OF SEQ ID NOS: 25

<210> SEQ ID NO 1
<211> LENGTH: 177
<212> TYPE: DNA
<213> ORGANISM: Enterobacteria phage P1

<400> SEQUENCE: 1

```
ccactaaaaa gcatgatcat tgatcactct aatgatcaac atgcaggtga tcacattgcg      60
gctgaaatag cggaaaaaca aagagttaat gccgttgtca gtgccgcagt cgagaatgcg     120
aagcgccaaa ataagcgcat aaatgatcgt tcagatgatc atgacgtgat cacccgc        177
```

<210> SEQ ID NO 2
<211> LENGTH: 177
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 2

```
ccactaaaaa gcatgataat agaccactct aacgaccaac atgcagggga gcacattgcg      60
gctgaaatag cggaaaagca gagggtgaat gccgttgtca gtgccgcagt cgagaatgcg     120
aagcgccaaa ataagcgcat aaacgaccgt tcagacgacc atgacgttat tacccgc        177
```

<210> SEQ ID NO 3
<211> LENGTH: 1727
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 3

```
cactatagggg cgaattggcg gaaggccgtc aaggccgcat ttgggcccgg cgcgccggat      60
ccgctagctc tagactggca ggtttctgag cagatcgtcc aacccgatct ggatcgggtc     120
agaaaaattt gctctaataa atttcgtttt ctaagtgcaa agaatcacca tttcgagctg     180
gtgattgaag gttgatgcaa atttggagaa aaaatgcaac aaacattcaa tgcggatatg     240
aatatatcaa accttcatca aaatgtcgat ccttcaacca ctctgcccgt tatttgtggt     300
gttgaaatta cgaccgaccg cgctggccgt tacaacctta atgctctaca cagagcgagc     360
ggactcggtg cccataaagc gccagctcaa tggctaagaa cgctgtcagc taaacagctc     420
atcgaagagc ttgaaaaaga aactatgcag aattgcatag tttcgttcac aagcaatgga     480
agcaggattt ctttcacgac tcgtataacc ggcaaaggtc agcagtggct gatgaagcga     540
ttgcttgatg ctggtgtgct ggtacctgtc gcggcaacgc gctaacagac gtagtaagaa     600
ccaccagcat tgtaatgctg gctaaagtca ctttcctgag ctgtataacg atgagcgatt     660 ttacttttc tggctatgaa ttggcctgct ttgtaacaca ctccggtcta tcccgtagcg     720
ccgggcatat cctgtcgcaa tgtgcaaatc tcgcggcaac aaccagtgaa tacttcattc     780
acaagcctca ccgcctgatc gcggcagaaa ctggttatag ccaatcaacc gtcgttcgtg     840
cattccgtga agctgtaaac aaaggaattc tgtctgtaga gattgttatc ggcgatcacc     900
```

```
gtgaacgtcg cgctaacctg taccggttta caccatcctt tttggccttc gcacaacaag    960
ccaaaaatgc gctgatagaa agcaaattaa agatctcttc agcggcaacc aaggttaaag   1020
ctgttctcgc taagacattg gctttattta attttttatc cacaccccca tgtcaaaatg   1080 atacccctc ccctgtcag gatgacgtgg caataaagaa taagaagtca caagttaaaa    1140
aaacaaaaag atcagtttcc ggcggtgccg gaacaaccag cctcaaaaaa ttgacttcat   1200
ggatcgctaa ggcaaaagca aaggctgaca atctgcggtt atccaaaaaa cgcactcaaa   1260
aacatgagtt caagcagaaa gtagaggcgg ctgcgcggaa atatgcttac ctgaagaaca   1320
agcgttcgcc tgatattggc gggatatcaa acttcgataa cctaccgcat tgcatgacgg   1380
taaacgaagc tcttaatgcg gttttagcca aaaataaaga taacgaacaa tggggtatac   1440
cggcaggatt cagagggtaa tgaattgctc taattataac catgcatact ttcaacacct   1500
ctagtttgcc atgaggcaaa ctcataggtg tcctggtaag aggacactgt tgccaaaact   1560
ggacgcccca ttattgcaat taataaacaa ctaacggaca attctaccta acaataagtg   1620
gcttaaaaaa acccgccccg gcgggttttt ttatctagag ctagcggatc cggcgcgccg   1680
ggcccttctg ggcctcatgg gccttccgct cactgcccgc tttccag                 1727
```

<210> SEQ ID NO 4
<211> LENGTH: 131
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4

```
cgtcaggtgg cacttttcgg gaaatgtgcg cggaacccct atttgtttat tttctaaata    60
cattcaaata tgtatccgct catgagacaa taaccctgat aaatgcttca ataatattga   120
aaaggaagag t                                                         131
```

<210> SEQ ID NO 5
<211> LENGTH: 4681
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (301)..(301)
<223> OTHER INFORMATION: a, c, t, g, unknown or other
<220> FEATURE:
<221> NAME/KEY: modified_base
<222> LOCATION: (4056)..(4056)
<223> OTHER INFORMATION: a, c, t, g, unknown or other

<400> SEQUENCE: 5

```
tttgcggaaa gagttagtaa gttaacagaa gacgagccaa acctaaatgg tttagcagga    60
aacttagata aaaaaatgaa tccagaatta tattcagaac aggaacagca acaagagcaa   120
caaaagaatc aaaaacgaga tagaggtatg cacttataga acatgcattt atgccgagaa   180
aacttattgg ttggaatggg ctatgtgtta gctaacttgt tagcgagttg gttggacttg   240
aattgggatt aatcccaaga agtaccggc tcaacaaccc ataaagccct gtaggttccg    300
nccaataagg aaattggaat aaagcaataa aaggagttga agaaatgaaa ttcagagaag   360
cctttgagaa tttttataaca agtaagtatg tacttggtgt tttagtagtc ttaactgttt   420
accagataat acaaatgctt aaataaaaaa agacttgatc tgattagacc aaatcttttg   480
```

```
atagtgttat attaataaca aaataaaaag gagtcgctca cgccctacca aagtttgtga    540
acgacatcat tcaagaaaaa aaacactgag ttgtttttat aatcttgtat atttagatat    600
taaacgatat ttaaatatac atcaagatat atatttgggt gagcgattac ttaaacgaaa    660
ttgagattaa ggagtcgatt tttatgtat aaaaacaatc atgcaaatca ttcaaatcat     720
ttggaaaatc acgatttaga caattttttct aaaaccggct actctaatag ccggttggac   780
gcacatactg tgtgcatatc tgatccaaaa ttaagttttg atgcaatgac gatcgttgga    840
aatctcaacc gagacaacgc tcaggccctt tctaaattta tgagtgtaga gccccaaata    900
agactttggg atattcttca aacaaagttt aaagctaaag cacttcaaga aaagtttat     960 attgaatatg acaaagtgaa agcagatagt tgggatagac gtaatatgcg tattgaattt    1020
aatccaaaca aacttacacg agatgaaatg atttggttaa aacaaaatat aataagctac    1080
atggaagatg acggttttac aagattagat ttagcctttg attttgaaga tgatttgagt    1140
gactactatg caatgtctga taaagcagtt aagaaaacta ttttttatgg tcgtaatggt    1200
aagccagaaa caaaatattt tggcgtgaga gatagtaata gatttattag aatttataat    1260
aaaaagcaag aacgtaaaga taatgcagat gctgaagtta tgtctgaaca tttatggcgt    1320
gtagaaatcg aacttaaaag agatatggtg gattactgga atgattgctt tagtgattta    1380
catatcttgc aaccagattg gaaaactatc caacgcactg cggatagagc aatagttttt    1440
atgttattga gtgatgaaga agaatgggga aagcttcaca gaaattctag aacaaaatat    1500
aagaatttga taaagaaat ttcgccagtc gatttaacgg acttaatgaa atcgacttta     1560
aaagcgaacg aaaaacaatt gcaaaaacaa atcgattttt ggcaacatga atttaaattt    1620
tggaaatagt gtacatatta atattactga acaaaaatga tatatttaaa ctattctaat    1680
ttaggaggat ttttttatga agtgtctatt taaaaatttg gggaatttat atgaggtgaa    1740
agaataattt accccctataa actttagcca cctcaagtaa agaggtaaaa ttgtttagtt    1800
tatataaaaa atttaaaggt ttgttttata gcgttttatt ttggctttgt attctttcat    1860
tttttagtgt attaaatgaa atggttttaa atgtttcttt acctgatatt gcaaatcatt    1920
ttaatactac tcctggaatt acaaactggg taaacactgc atatatgtta acttttttcga   1980 taggaacagc agtatatgga aaattatctg attatataaa tataaaaaaa ttgttaatta    2040
ttggtattag tttgagctgt cttggttcat tgattgcttt tattgggccc acctaggcaa    2100
atatgctctt acgtgctatt atttaagtga ctatttaaaa ggagttaata aatatgcggc    2160
aaggtattct taaataaact gtcaatttga tagcgggaac aaataattag atgtccttttt   2220 ttaggagggc ttagttttttt gtacccagtt taagaatacc tttatcatgt gattctaaag   2280
tatccagaga atatctgtat gctttgtata cctatggtta tgcataaaaa tcccagtgat    2340
aaaagtattt atcactggga tttttatgcc cttttgggtt tttgaatgga ggaaaatcac    2400
atgaaaatta ttaatattgg agtttttagct catgttgatg caggaaaaac taccttaaca   2460
gaaagcttat tatataacag tggagcgatt acagaattag gaagcgtgga caaaggtaca    2520
acgaggacgg ataatacgct tttagaacgt cagagaggaa ttacaattca gacaggaata    2580
acctcttttc agtgggaaaa tacgaaggtg aacatcatag acacgccagg acatatggat    2640
ttcttagcag aagtatatcg ttcattatca gttttagatg gggcaattct actgatttct    2700
gcaaaagatg gcgtacaagc acaaactcgt atattatttc atgcacttag gaaaatgggg    2760
attcccacaa tcttttttat caataagatt gaccaaaatg gaattgattt atcaacggtt    2820
```

```
tatcaggata ttaaagagaa actttctgcc gaaattgtaa tcaaacagaa ggtagaactg      2880
tatcctaata tgtgtgtgac gaactttacc gaatctgaac aatgggatac ggtaatagag      2940
ggaaacgata accttttaga gaaatatatg tccggtaaat cattagaagc attggaactc      3000
gaacaagagg aaagcataag atttcagaat tgttctctgt tccctctttta tcatggaagt      3060 gcaaaaagta atatagggat tgataaccct atagaagtta ttactaataa attttattca      3120
tcaacacatc gaggtccgtc tgaactttgc ggaaatgttt tcaaaattga atatacaaaa      3180
aaaagacaac gtcttgcata tatacgcctt tatagtggag tactacattt acgagattcg      3240
gttagagtat cagaaaaaga aaaataaaa gttacagaaa tgtatacttc aataaatggt      3300
gaattatgta agattgatag agcttattct ggagaaattg ttatttttgca aaatgagttt      3360 ttgaagttaa atagtgttct ggagatacaa aactattgc cacagagaaa aaagattgaa      3420
aatccgcacc ctctactaca acaactgtt gaaccgagta aacctgaaca gagagaaatg      3480
ttgcttgatg cccttttgga aatctcagat agtgatccgc ttctacgata ttacgtggat      3540
tctacgacac atgaaattat actttctttc ttagggaaag tacaaatgga agtgattagt      3600
gcactgttgc aagaaaagta tcatgtggag atagaactaa aagagcctac agtcatttat      3660
atggagagac cgttaaaaaa tgcagaatat accattcaca tcgaagtgcc gccaaatcct      3720
ttctgggctt ccattggttt atctgtatca ccgcttccgt gggaagtgg aatgcagtat      3780 gagagctcgg tttctcttgg atacttaaat caatcatttc aaaatgcagt tatggaaggg      3840
gtacgctatg gttgcgaaca aggattatat ggttggaatg tgacggattg taaaatctgt      3900
tttaagtacg gttatacta tagccctgtt agtactccag cagattttcg gatgcttact      3960
cctattgtac tggagcaagc ctttagaaaa gctggaacag aattgttaga gccatatctt      4020
agttttaaag tttatgcacc acaggaatat ctttcncggg catataacga tgctcccaaa      4080
tattgtgcaa atatcgtaaa tactcaactg aaaaataatg aggtcattat tattggagaa      4140
attcctgctc gatgtattca agattatcgc aatgatttaa cttttttttac aaatgggctt      4200 agtgtttgtt tagcagagct aaaaggatat caggttacca ctggcgaacc tgtttgccag      4260
acccgtcgtc taaatagtcg gatagataaa gtaagatata tgttcaataa aataacttag      4320
tgcgttttat gttgttatat aaatatggtt tcttattaaa taagatgaaa tattctttaa      4380 tatagattttg aattaaagtg gaaggagga gattgttatt ataaactaca agtggatatt      4440
gtgtcctatt tgtggaaata aaacaagact acgaatacga gtggatacta tacttaaaaa      4500 tttccctta tacagcccca aatgtaagaa cgaaacttta attaatgttc aaaaaatgaa      4560
tataataaca atcaaagagc cagacgccaa gacgcagagc cgataaatttg agaaatgaaa      4620 ctctcatctt atcggctctt tttgtttatc tgaattttac tgactagcct tcaatatttc      4680
c                                                                      4681

<210> SEQ ID NO 6
<211> LENGTH: 1194
<212> TYPE: DNA
<213> ORGANISM: Enterobacteria phage P1

<400> SEQUENCE: 6
gtgacctggg acgatcacaa gaagaatttt gctcgcctgg cgcgagatgg tggttacacc        60
atcgcacagt atgccgccga gtttaatctt aaccctaata ccgcacgtcg ttatctccgt       120
gccttcaaag aagacaccag gactacggac agccgcaagc caaataagcc agtcaggaag       180
ccactaaaaa gcatgatcat tgatcactct aatgatcaac atgcaggtga tcacattgcg       240
```

```
gctgaaatag cggaaaaaca aagagttaat gccgttgtca gtgccgcagt cgagaatgcg      300
aagcgccaaa ataagcgcat aaatgatcgt tcagatgatc atgacgtgat cacccgcgcc      360
caccggacct tacgtgatcg cctggaacgc gacaccctgg atgatgatgg tgaacgcttt      420
gaattcgaag ttggcgatta cctgatagat aacgttgaag cgcggaaggc cgcgcgcgct      480
atgttgcgtc ggtccggggc cgatgttctg gaaaccactc ttctggaaaa gtctctttct      540
catctcctta tgctggagaa cgccagggat acgtgtattc gcctggtgca ggaaatgcgc      600
gatcagcaaa aagacgatga tgaaggtact ccgcctgaat accgtatcgc gagcatgcta      660
aacagctgtt ccgcgcagat aagcagcctg atcaacacca tttacagcat ccggaataac      720
tatcgaaaag aaagccggga ggcggaaaag cacgctttat ctatggggca agctggcatt      780
gttaagctgg catacgaacg aaagcgtgaa ataactggt cagtgctgga agcggctgaa        840
ttcatcgagg cgcatggagg aaaagtgccg cccctgatgc tggagcaaat caaagccgat      900
ctgcgtgctc ctaagaccaa taccgatgat gaggaaaacc aaacagcatc tggcgctcca      960
tcacttgaag atctggataa atcgcgcga gaacgggccg ccagccgccg cgctgatgcc      1020
gcattgtgga ttgagcatcg tagagaagaa attgccgata tcgtcgatac aggtggttat      1080
ggtgatgtcg atgcggaagg catatcaaac gaagcatggc ttgaacagga tctggacgaa      1140
gacgaggagg aagacgaaga agttacccgc aaactgtacg ggatgatga ttaa             1194

<210> SEQ ID NO 7
<211> LENGTH: 1194
<212> TYPE: DNA
<213> ORGANISM: Enterobacteria phage P1

<400> SEQUENCE: 7
gtgacctggg acgatcacaa gaagaattt gctcgcctgg cgcgagatgg tggttacacc        60
atcgcacagt atgccgccga gtttaatctt aaccctaata ccgcacgtcg ttatctccgt      120
gccttcaaag aagacaccag gactacggac agccgcaagc caaataagcc agtcaggaag      180
ccactaaaaa gcatgatcat tgatcactct aatgatcaac atgcaggtga tcacattgcg      240
gctgaaatag cggaaaaaca aagagttaat gccgttgtca gtgccgcagt cgagaatgcg      300
aagcgccaaa ataagcgcat aaatgatcgt tcagatgatc atgacgtgat cacccgcgcc      360
caccggacct tacgtgatcg cctggaacgc gacaccctgg atgatgatgg tgaacgcttt      420
gaattcgaag ttggcgatta cctgatagat aacgttgaag cgcggaaggc cgcgcgcgct      480
atgttgcgtc ggtccggggc cgatgttctg gaaaccactc ttctggaaaa gtctctttct      540
catctcctta tgctggagaa cgccagggat acgtgtattc gcctggtgca ggaaatgcgc      600
gatcagcaaa aagacgatga tgaaggtact ccgcctgaat accgtatcgc gagcatgcta      660
aacagctgtt ccgcgcagat aagcagcctg atcaacacca tttacagcat ccggaataac      720
tatcgaaaag aaagccggga ggcggaaaag cacgctttat ctatggggca agctggcatt      780
gttaagctgg catacgaacg aaagcgtgaa ataactggt cagtgctgga agcggctgaa        840
ttcatcgagg cgcatggagg aaaagtgccg cccctgatgc tggagcaaat caaagccgat      900
ctgcgtgctc ctaagaccaa taccgatgat gaggaaaacc aaacagcatc tggcgctcca      960
tcacttgaag atctggataa atcgcgcga gaacgggccg ccagccgccg cgctgatgcc      1020
gcattgtgga ttgagcatcg tagagaagaa attgccgata tcgtcgatac aggtggttat      1080
ggtgatgtcg atgcggaagg catatcaaac gaagcatggc ttgaacagga tctggacgaa      1140
```

```
gacgaggagg aagacgaaga agttacccgc aaactgtacg gggatgatga ttaa          1194
```

<210> SEQ ID NO 8
<211> LENGTH: 525
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8

```
atgaacgaaa acaaaagag attcgcagat gaatatataa tgaatggatg taatggtaaa     60
aaagcagcaa tttcagcagg ttatagtaag aaaacagcag agtctttagc aagtcgattg   120
ttaagaaatg ttaatgtttc ggaatatatt aagaacgat tagaacagat acaagaagag   180
cgtttaatga gcattacaga agctttagcg ttatctgctt ctattgctag aggagaacct   240
caagaggctt acagtaagaa atatgaccat ttaaacgatg aagtggaaaa agaggttact   300
tacacaatca caccaacttt tgaagagcgt cagagatcta ttgaccacat actaaaagtt   360
catggtgcgt atatcgacaa aaaagaaatt actcagaaga atattgagat taatattaga   420
tctattgacc acatactaaa agttcatggt gcgtatatcg acaaaaaaga aattactcag   480
aagaatattg agattaatat tggtgagtac gatgacgaaa gttaa                  525
```

<210> SEQ ID NO 9
<211> LENGTH: 663
<212> TYPE: DNA
<213> ORGANISM: Staphylococcus phage 80alpha

<400> SEQUENCE: 9

```
aattggcagt aaagtggcag tttttgatac ctaaaatgag atattatgat agtgtaggat     60
attgactatc ttactgcgtt tcccttatcg caattaggaa taaggatct atgtgggttg    120
gctgattata gccaatcctt ttttaatttt aaaaagcgta tagcgcgaga gttggtggta   180
aatgaaatga acgaaaaaca aaagagattc gcagatgaat atataatgaa tggatgtaat   240
ggtaaaaaag cagcaatttc agcaggttat agtaagaaaa cagcagagtc tttagcaagt   300
cgattgttaa gaaatgttaa tgtttcggaa tatattaaag aacgattaga acagatacaa   360
gaagagcgtt taatgagcat tacagaagct ttagcgttat ctgcttctat tgctagagga   420
gaacctcaag aggcttacag taagaaatat gaccatttaa acgatgaagt ggaaaaagag   480
gttacttaca caatcacacc aacttttgaa gagcgtcaga gatctattga ccacatacta   540
aaagttcatg gtgcgtatat cgacaaaaaa gaaattactc agaagaatat tgagattaat   600
attggtgagt acgatgacga agttaaatt aaactttaac aaaccatcta atgttttcaa   660
cag                                                                663
```

<210> SEQ ID NO 10
<211> LENGTH: 1116
<212> TYPE: DNA
<213> ORGANISM: Staphylococcus aureus

<400> SEQUENCE: 10

```
tcataaatat ttaactattt ctttctgtgt actagggtac aaatgaccgt atcggttata     60
tacttcatta ctatcagcat ggcctaaacg ctgtgctatt accatgatac ttgcgccatg   120
attgactagc atagacgcat ggctatgtct taactcatga attacaattc tagggaatgt   180
ctgaccgtct ggtagttgtt catctaatac ttttaatgca gcggtaaacc aacgatctat   240
```

| | |
|---|---|
| agttgattca ctataagctt tgaagaatgt accgaataat acataatcat ctttatatac | 300 |
| attgttttct ttgtaccatt ttaaatattc tttgatatca ttcatcatgt gaacaggtaa | 360 |
| gtatatatca cgtattgctg cttttgtttt aggggctgtc acttcaccgt gatagtctgt | 420 |
| tttgttaata tgtatgaaat catcatcata gttaatatca cgccatgtga gggctctaat | 480 |
| ttcgccctta cgtgcaccag agtaaaacag tagcttaaag aataacttt gttgttgtgt | 540 |
| agctaaagcc tcatagaatt gattgaattg ttctaatgtc caatagttca aacgcttatt | 600 |
| tgattctatt tcaaagttac ctactagaga ggctacattt tgctttagat catgaaactt | 660 |
| catagcatgg ttaagtaacg atactaagaa cacgtgcatt ttctttaggt actctccaga | 720 |
| gtgtccctct tttaacttcg tattctgaaa cttcataata tcttgtgtag tcatattaaa | 780 |
| cacgtccata gacttaaaat agggtagcaa atggttgttt gtatgtgtct ttaatgcttt | 840 |
| cacactagat gacttacgac gtgcagaata ccactctata tactcatcta cgagcttatc | 900 |
| aaagggcagt ttgtttatct gtcctacacc ctctaactcg tccataattt cattacattt | 960 |
| cttcaatgcc tctttacgct gtttaaagcc actcttttt atttctttac gttgattaaa | 1020 |
| tttatcatag tattttatac gaaaatagta tgtaccacgt ttagcgtctt tatatatgtt | 1080 |
| gtgggatagg tttaagttgt gttctatggg aatcac | 1116 |

```
<210> SEQ ID NO 11
<211> LENGTH: 10844
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (8807)..(8807)
<223> OTHER INFORMATION: a, c, t, g, unknown or other

<400> SEQUENCE: 11
```

| | |
|---|---|
| ctcgggccgt ctcttgggct tgatcggcct tcttgcgcat ctcacgcgct cctgcggcgg | 60 |
| cctgtagggc aggctcatac ccctgccgaa ccgcttttgt cagccggtcg gccacggctt | 120 |
| ccggcgtctc aacgcgcttt gagattccca gcttttcggc caatccctgc ggtgcatagg | 180 |
| cgcgtggctc gaccgcttgc gggctgatgg tgacgtggcc cactggtggc cgctccaggg | 240 |
| cctcgtagaa cgcctgaatg cgcgtgtgac gtgccttgct gccctcgatg ccccgttgca | 300 |
| gccctagatc ggccacagcg gccgcaaacg tggtctggtc gcgggtcatc tgcgctttgt | 360 |
| tgccgatgaa ctccttggcc gacagcctgc cgtcctgcgt cagcggcacc acgaacgcgg | 420 |
| tcatgtgcgg gctggtttcg tcacggtgga tgctggccgt cacgatgcga tccgccccgt | 480 |
| acttgtccgc cagccacttg tgcgccttct cgaagaacgc cgcctgctgt tcttggctgg | 540 |
| ccgacttcca ccattccggg ctggccgtca tgacgtactc gaccgccaac acagcgtcct | 600 |
| tgcgccgctt ctctggcagc aactcgcgca gtcggcccat cgcttcatcg gtgctgctgg | 660 |
| ccgcccagtg ctcgttctct ggcgtcctgc tggcgtcagc gttgggcgtc tcgcgctcgc | 720 |
| ggtaggcgtg cttgagactg gccgccacgt tgcccatttt cgccagcttc ttgcatcgca | 780 |
| tgatcgcgta tgccgccatg cctgccccct ccttttggtg tccaaccggc tcgacggggg | 840 |
| cagcgcaagg cggtgcctcc ggcgggccac tcaatgcttg agtatactca ctagactttg | 900 |
| cttcgcaaag tcgtgaccgc ctacggcggc tgcggcgccc tacggcttg ctctccgggc | 960 |
| ttcgccctgc gcggtcgctg cgctcccttg ccagcccgtg gatatgtgga cgatggccgc | 1020 |

```
gagcggccac cggctggctc gcttcgctcg gcccgtggac aaccctgctg acaagctga    1080 tggacaggct gcgcctgccc acgagcttga ccacagggat tgcccaccgg ctaccactat    1140
agggcgaatt ggcggaaggc cgtcaaggcc gcatttgggc ccggcgcgcc ggatccgcta    1200
gctctagacc tctagaccag ccaggacaga aatgcctcga cttcgctgct gcccaaggtt    1260
gccgggtgac gcacaccgtg gaaacggatg aaggcacgaa cccagtggac ataagcctgt    1320
tcggttcgta agctgtaatg caagtagcgt gcccgttccg ggccttttga catgtgactt    1380
tcgttaccct cgcgtcaaaa agagttttta cgaaggaag cataagtgac ctgggacgat    1440
cacaagaaga attttgctcg cctggcgcga gatggtggtt acaccatcgc acagtatgcc    1500
gccgagttta atcttaaccc taataccgca cgtcgttatc tccgtgcctt caaagaagac    1560
accaggacta cggacagccg caagccaaat aagccagtca ggaagccact aaaaagcatg    1620
atcattgatc actctaatga tcaacatgca ggtgatcaca ttgcggctga aatagcggaa    1680
aaacaaagag ttaatgccgt tgtcagtgcc gcagtcgaga atgcgaagcg ccaaaataag    1740
cgcataaatg atcgttcaga tgatcatgac gtgatcaccc gcgcccaccg gaccttacgt    1800
gatcgcctgg aacgcgacac cctggatgat gatggtgaac gctttgaatt cgaagttggc    1860
gattacctga tagataacgt tgaagcgcgg aaggccgcgc gcgctatgtt gcgtcggtcc    1920
ggggccgatg ttctggaaac cactcttctg gaaaagtctc tttctcatct ccttatgctg    1980
gagaacgcca gggatacgtg tattcgcctg gtgcaggaaa tgcgcgatca gcaaaaagac    2040
gatgatgaag gtactccgcc tgaataccgt atcgcgagca tgctaaacag ctgttccgcg    2100
cagataagca gcctgatcaa caccatttac agcatccgga ataactatcg aaaagaaagc    2160
cgggaggcgg aaaagcacgc tttatctatg gggcaagctg gcattgttaa gctggcatac    2220
gaacgaaagc gtgaaaataa ctggtcagtg ctggaagcgg ctgaattcat cgaggcgcat    2280
ggaggaaaag tgccgcccct gatgctggag caaatcaaag ccgatctgcg tgctcctaag    2340
accaataccg atgatgagga aaaccaaaca gcatctggcg ctccatcact tgaagatctg    2400
gataaaatcg cgcgagaacg ggccgccagc cgccgcgctg atgccgcatt gtggattgag    2460
catcgtagag aagaaattgc cgatatcgtc gatacaggtg gttatggtga tgtcgatgcg    2520
gaaggcatat caaacgaagc atggcttgaa caggatctgg acgaagacga ggaggaagac    2580
gaagaagtta cccgcaaact gtacggggat gatgattaat aaaaaaaacc cgccccggcg    2640
ggttttttta tctagagcta gcggatccgg cgcgccgggc ccttctgggc ctcatgggcc    2700
ttccgctcac tgcccgcttt ccagcactat agggcgaatt ggcggaaggc cgtcaaggcc    2760
gcatttgggc ccggcgcgcc ggatccgcta gctctagact ggcaggtttc tgagcagatc    2820
gtccaacccg atctggatcg ggtcagaaaa atttgctcta ataaatttcg ttttctaagt    2880
gcaaagaatc accatttcga gctggtgatt gaaggttgat gcaaatttgg agaaaaaatg    2940
caacaaacat tcaatgcgga tatgaatata tcaaaccttc atcaaaatgt cgatccttca    3000
accactctgc ccgttatttg tggtgttgaa attacgaccg accgcgctgg ccgttacaac    3060
cttaatgctc tacacagagc gagcggactc ggtgcccata agcgccagc tcaatggcta    3120 agaacgctgt cagctaaaca gctcatcgaa gagcttgaaa agaaactat gcagaattgc    3180 atagtttcgt tcacaagcaa tggaagcagg atttctttca cgactcgtat aaccggcaaa    3240
ggtcagcagt ggctgatgaa gcgattgctt gatgctggtg tgctggtacc tgtcgcggca    3300
acgcgctaac agacgtagta agaaccacca gcattgtaat gctggctaaa gtcactttcc    3360
tgagctgtat aacgatgagc gattttactt tttctggcta tgaattggcc tgctttgtaa    3420
```

```
cacactccgg tctatcccgt agcgccgggc atatcctgtc gcaatgtgca aatctcgcgg    3480
caacaaccag tgaatacttc attcacaagc ctcaccgcct gatcgcggca gaaactggtt    3540
atagccaatc aaccgtcgtt cgtgcattcc gtgaagctgt aaacaaagga attctgtctg    3600
tagagattgt tatcggcgat caccgtgaac gtcgcgctaa cctgtaccgg tttacaccat    3660 ccttttggc cttcgcacaa caagccaaaa atgcgctgat agaaagcaaa ttaaagatct    3720
cttcagcggc aaccaaggtt aaagctgttc tcgctaagac attggcttta tttaattttt    3780
tatccacacc cccatgtcaa aatgataccc cctcccctg tcaggatgac gtggcaataa    3840
agaataagaa gtcacaagtt aaaaaaacaa aaagatcagt ttccggcggt gccggaacaa    3900
ccagcctcaa aaaattgact tcatggatcg ctaaggcaaa agcaaaggct gacaatctgc    3960
ggttatccaa aaaacgcact caaaaacatg agttcaagca gaaagtagag gcggctgcgc    4020
ggaaatatgc ttacctgaag aacaagcgtt cgcctgatat tggcgggata tcaaacttcg    4080
ataacctacc gcattgcatg acggtaaacg aagctcttaa tgcggtttta gccaaaaata    4140
aagataacga acaatggggt ataccggcag gattcagagg gtaatgaatt gctctaatta    4200
taaccatgca tactttcaac acctctagtt tgccatgagg caaactcata ggtgtcctgg    4260
taagaggaca ctgttgccaa aactggacgc cccattattg caattaataa acaactaacg    4320
gacaattcta cctaacaata agtggcttaa aaaaacccgc cccggcgggt tttttatct    4380 agagctagcg gatccggcgc gccgggccct tctgggcctc atgggccttc cgctcactgc    4440 ccgcttttcca gccagccttc gaccacatac ccaccggctc caactgcgcg gcctgcggcc    4500
ttgccccatc aatttttta attttctctg gggaaaagcc tccggcctgc ggcctgcgcg    4560
cttcgcttgc cggttggaca ccaagtggaa ggcgggtcaa ggctcgcgca gcgaccgcgc    4620
agcggcttgg ccttgacgcg cctggaacga cccaagccta tgcgagtggg ggcagtcgaa    4680
ggcgaagccc gccgcctgc ccccgagac ctgcaggggg gggggggcgc tgaggtctgc    4740
ctcgtgaaga aggtgttgct gactcatacc aggcctgaat cgccccatca tccagccaga    4800
aagtgaggga gccacggttg atgagagctt tgttgtaggt ggaccagttg gtgattttga    4860
acttttgctt tgccacggaa cggtctgcgt tgtcgggaag atgcgtgatc tgatccttca    4920
actcagcaaa agttcgattt attcaacaaa gccgccgtcc cgtcaagtca gcgtaatgct    4980
ctgccagtgt tacaaccaat taaccaattc tgattagaaa aactcatcga gcatcaaatg    5040
aaactgcaat ttattcatat caggattatc aataccatat ttttgaaaaa gccgtttctg    5100
taatgaagga gaaaactcac cgaggcagtt ccataggatg gcaagatcct ggtatcggtc    5160
tgcgattccg actcgtccaa catcaataca acctattaat ttcccctcgt caaaaataag    5220
gttatcaagt gagaaatcac catgagtgac gactgaatcc ggtgagaatg gcaaaagctt    5280
atgcatttct ttccagactt gttcaacagg ccagccatta cgctcgtcat caaaatcact    5340
cgcatcaacc aaaccgttat tcattcgtga ttgcgcctga gcgagacgaa atacgcgatc    5400
gctgttaaaa ggacaattac aaacaggaat cgaatgcaac cggcgcagga acactgccag    5460
cgcatcaaca atattttcac ctgaatcagg atattcttct aatacctgga atgctgtttt    5520
cccggggatc gcagtggtga gtaaccatgc atcatcagga gtacggataa aatgcttgat    5580
ggtcggaaga ggcataaatt ccgtcagcca gtttagtctg accatctcat ctgtaacatc    5640
attggcaacg ctacctttgc catgtttcag aaacaactct ggcgcatcgg gcttcccata    5700
caatcgatag attgtcgcac ctgattgccc gacattatcg cgagcccatt tatacccata    5760
```

```
taaatcagca tccatgttgg aatttaatcg cggcctcgag caagacgttt cccgttgaat    5820
atggctcata acaccccttg tattactgtt tatgtaagca gacagtttta ttgttcatga    5880
tgatatattt ttatcttgtg caatgtaaca tcagagattt tgagacacaa cgtggctttc    5940
cccccccccc ctgcaggtcc cgagcctcac ggcggcgagt gcgggggttc caagggggca    6000
gcgccacctt gggcaaggcc gaaggccgcg cagtcgatca acaagccccg gagggccac    6060 tttttgccgg aggggagcc gcgccgaagg cgtgggggaa ccccgcaggg gtgcccttct    6120
ttgggcacca agaactaga tatagggcga aatgcgaaag acttaaaaat caacaactta    6180 aaaaagggggg gtacgcaaca gctcattgcg gcaccccccg caatagctca ttgcgtaggt    6240
taaagaaaat ctgtaattga ctgccacttt tacgcaacgc ataattgttg tcgcgctgcc    6300
gaaaagttgc agctgattgc gcatggtgcc gcaaccgtgc ggcaccccta ccgcatggag    6360
ataagcatgg ccacgcagtc cagagaaatc ggcattcaag ccaagaacaa gcccggtcac    6420
tgggtgcaaa cggaacgcaa agcgcatgag gcgtgggccg ggcttattgc gaggaaaccc    6480
acggcggcaa tgctgctgca tcacctcgtg gcgcagatgg gccaccagaa cgccgtggtg    6540
gtcagccaga agacactttc caagctcatc ggacgttctt tgcggacggt ccaatacgca    6600
gtcaaggact tggtggccga gcgctggatc tccgtcgtga agctcaacgg ccccggcacc    6660
gtgtcggcct acgtggtcaa tgaccgcgtg gcgtggggcc agcccgcgca ccagttgcgc    6720
ctgtcggtgt tcagtgccgc cgtggtggtt gatcacgacg accaggacga atcgctgttg    6780
gggcatggcg acctgcgccg catcccgacc ctgtatccgg gcgagcagca actaccgacc    6840
ggccccggcg aggagccgcc cagccagccc ggcattccgg gcatggaacc agacctgcca    6900
gccttgaccg aaacggagga atgggaacgg cgcgggcagc agcgcctgcc gatgcccgat    6960
gagccgtgtt ttctggacga tggcgagccg ttggagccgc cgacacgggt cacgctgccg    7020
cgccggtagc acttgggttg cgcagcaacc cgtaagtgcg ctgttccaga ctatcggctg    7080
tagccgcctc gccgcccсtat accttgtctg cctccccgcg ttgcgtcgcg gtgcatggag    7140
ccgggccacc tcgacctgaa tggaagccgg cggcacctcg ctaacggatt caccgttttt    7200
atcaggctct gggaggcaga ataaatgatc atatcgtcaa ttattacctc cacggggaga    7260
gcctgagcaa actggcctca ggcatttgag aagcacacgg tcacactgct tccggtagtc    7320
aataaaccgg taaccagca atagacataa gcggctattt aacgaccctg ccctgaaccg    7380
acgaccgggt cgaatttgct ttcgaatttc tgccattcat ccgcttatta tacttattca    7440
ggcgtagcac caggcgttta agggcaccaa taactgcctt aaaaaaatta cgccccgccc    7500
tgccactcat cgcactcgtc aggtggcact tttcgggaa atgtgcgcgg aacccctatt    7560
tgtttatttt tctaaataca ttcaaatatg tatccgctca tgagcaata accctgataa    7620 atgcttcaat aatattgaaa aggaagagt atgaagtttg gaaatatttg ttttгcgtat    7680 caaccaccag gtgaaactca taagctaagt aatggatcgc tttgttcggc ttggtatcgc    7740
ctcagaagag tagggtttga tacatattgg accttagaac atcattttac agagtttggt    7800
cttacgggaa atttatttgt tgctgcggct aacctgttag gaagaactaa acattaaat    7860 gttggcacta tgggggttgt tattccgaca gcacacccag ttcgacagtt agaagacgtt    7920
ttattattag atcaaatgtc gaaaggtcgt tttaattttg gaaccgttcg agggctatac    7980
cataaagatt ttcgagtatt tggtgttgat atggaagagt ctcgagcaat tactcaaaat    8040
ttctaccaga tgataatgga aagcttacag acaggaacca ttagctctga tagtgattac    8100
attcaatttc ctaaggttga tgtatatccc aaagtgtact caaaaaatgt accaacctgt    8160
```

```
atgactgctg agtccgcaag tacgacagaa tggctagcaa tacaagggct accaatggtt    8220
cttagttgga ttattggtac taatgaaaaa aaagcacaga tggaactcta taatgaaatt    8280
gcgacagaat atggtcatga tatatctaaa atagatcatt gtatgactta tatttgttct    8340
gttgatgatg atgcacaaaa ggcgcaagat gtttgtcggg agtttctgaa aaattggtat    8400
gactcatatg taaatgcgac caatatcttt aatgatagca atcaaactcg tggttatgat    8460
tatcataaag gtcaatggcg tgattttgtt ttacaaggac atacaaacac caatcgacgt    8520
gttgattata gcaatggtat taaccctgta ggcactcctg agcagtgtat tgaaatcatt    8580
caacgtgata ttgatgcaac gggtattaca aacattacat gcggatttga agctaatgga    8640
actgaagatg aaataattgc ttccatgcga cgctttatga cacaagtcgc tccttttctta   8700 aaagaaccta ataaaattac ttatttgata ctagagataa taaggaacaa gttatgaaat    8760
ttggattatt ttttctaaac tttcagaaag atggaataac atctgangaa acgttggata    8820
atatggtaaa gactgtcacg ttaattgatt caactaaata tcattttaat actgcctttg    8880
ttaatgaaca tcacttttca aaaaatggta ttgttggagc acctattacc gcagctggtt    8940
ttttattagg gttaacaaat aaattacata ttggttcatt aaatcaagta attaccaccc    9000
atcaccctgt acgtgtagca gaagaagcca gtttattaga tcaaatgtca gagggacgct    9060
tcattcttgg ttttagtgac tgcgaaagtg atttcgaaat ggaattttttt agacgtcata   9120 tctcatcaag gcaacaacaa tttgaagcat gctatgaaat aattaatgac gcattaacta    9180
caggttattg tcatccccaa aacgactttt atgattttcc aaaggtttca attaatccac    9240
actgttacag tgagaatgga cctaagcaat atgtatccgc tacatcaaaa gaagtcgtca    9300
tgtgggcagc gaaaaaggca ctgcctttaa catttaagtg ggaggataat ttagaaacca    9360
aagaacgcta tgcaattcta tataataaaa cagcacaaca atatggtatt gatatttcgg    9420
atgttgatca tcaattaact gtaattgcga acttaaatgc tgatagaagt acggctcaag    9480
aagaagtgag agaatactta aaagactata tcactgaaac ttaccctcaa atggacagag    9540
atgaaaaaat taactgcatt attgaagaga atgcagttgg gtctcatgat gactattatg    9600
aatcgacaaa attagcagtg gaaaaaacag ggtctaaaaa tattttatta tcctttgaat    9660
caatgtccga tattaaagat gtaaaagata ttattgatat gttgaaccaa aaaatcgaaa    9720
tgaatttacc ataaagtagt actgttgtaa ttcattaagc attctgccga catggaagcc    9780
atcacagacg gcatgatgaa cctgaatcgc cagcggcatc agcaccttgt cgccttgcgt    9840
ataatatttg cccatggtga aaacgggggc gaagaagttg tccatattgg ccacgtttaa    9900
atcaaaactg gtgaaactca cccagggatt ggctgagacg aaaaacatat tctcaataaa    9960 cccctttaggg aaataggcca ggttttcacc gtaacacgcc acatcttgcg aatatatgtg   10020
tagaaactgc cggaaatcgt cgtggtattc actccagagc gatgaaaacg tttcagtttg   10080
ctcatggaaa acggtgtaac aagggtgaac actatcccat atcaccagct caccgtcttt   10140
cattgccata cggaattccg gatgagcatt catcaggcgg gcaagaatgt gaataaaggc   10200
cggataaaac ttgtgcttat ttttctttac ggtctttaaa aaggccgtaa tatccagctg   10260
aacggtctgg ttataggtac attgagcaac tgactgaaat gcctcaaaat gttctttacg   10320
atgccattgg gatatatcaa cggtggtata tccagtgatt ttttttctcca ttttagcttc   10380 cttagctcct gaaaatctcg ataactcaaa aaatacgccc ggtagtgatc ttatttcatt   10440
atggtgaaag ttggaacctc ttacgtgccg atcaacgtct catttttcgcc aaaagttggc   10500
```

| | |
|---|---:|
| ccagggcttc ccggtatcaa cagggacacc aggatttatt tattctgcga agtgatcttc | 10560 |
| cgtcacaggt atttattcga agacgaaagg gcctcgtgat acgcctattt ttataggtta | 10620 |
| atgtcatgat aataatggtt tcttagacgt caggtggcac ttttcgggga aatgtgcgcg | 10680 |
| cccgcgttcc tgctggcgct gggcctgttt ctggcgctgg acttcccgct gttccgtcag | 10740 |
| cagcttttcg cccacggcct tgatgatcgc ggcggccttg gcctgcatat cccgattcaa | 10800 |
| cggccccagg gcgtccagaa cgggcttcag gcgctcccga aggt | 10844 |

<210> SEQ ID NO 12
<211> LENGTH: 128
<212> TYPE: DNA
<213> ORGANISM: Staphylococcus aureus

<400> SEQUENCE: 12

| | |
|---|---:|
| gtctagttaa tgtgtaacgt aacattagct agatttttt attcaaaaaa atatttacaa | 60 |
| atattaggaa atttaagtgt aaaagagttg ataaatgatt atattgggac tataatataa | 120 |
| ttaaggtc | 128 |

<210> SEQ ID NO 13
<211> LENGTH: 2769
<212> TYPE: DNA
<213> ORGANISM: Staphylococcus phage 80alpha

<400> SEQUENCE: 13

| | |
|---|---:|
| attagacaac aaacaagtca ttgaaaattc cgacttatta ttcaaaaaga aatttgatag | 60 |
| cgcagatata caagctaggt taaaagtagg cgataaggta gaagttaaaa caatcggtta | 120 |
| tagaatacac tttttaaatt tatatccggt cttatacgaa gtaaagaagg tagataaaca | 180 |
| atgattaaac aaatactaag actattattc ttactagcaa tgtatgagtt aggtaagtat | 240 |
| gtaactgagc aagtatatat tatgatgacg gctaatgatg atgtagaggt gccgagtgac | 300 |
| ttcgcgaagt tgagcgatca gtcagatttg atgagggcgg aggtgacgga gtagatgatg | 360 |
| tggttagtca tagcaattat attactagtc atcttattgt ttggtgtgat gttgcaagct | 420 |
| gaacagttaa aaggcgatgt gaaagttaaa gagcgggaga tagagatatt aagaagtaga | 480 |
| ttgagacatt ttgaagatta aaaatatttg tatggagggt attcatgact aaaaagaaat | 540 |
| atggattaaa attatcaaca gttcgaaagt tagaagatga gttgtgtgat tatcctaatt | 600 |
| atcataagca actcgaagat ttaagaagtg aaataatgac accatggatt ccaacagata | 660 |
| caaatatagg cggggagttt gtaccgtcta atacatcgaa aacagaaatg gcagtaacta | 720 |
| attatctttg tagtatacga agaggtaaaa tccttgagtt taagagcgct attgaacgta | 780 |
| taatcaacac atcaagtagg aaagaacgcg aattcattca agagtattat tttaataaaa | 840 |
| aggaattagt gaaagtttgt gatgacatac acatttctga tagaactgct catagaatca | 900 |
| aaaggaaaat catatctaga ttggcggaag agttagggga agagtgaaat tggcagtaaa | 960 |
| gtggcagttt ttgataccta aaatgagata ttatgatagt gtaggatatt gactatctta | 1020 |
| ctgcgtttcc cttatcgcaa ttaggaataa aggatctatg tgggttggct gattatagcc | 1080 |
| aatccttttt taattttaaa aagcgtatag cgcgagagtt ggtggtaaat gaaatgaacg | 1140 |
| aaaaacaaaa gagattcgca gatgaatata taatgaatgg atgtaatggt aaaaagcag | 1200 |
| caatttcagc aggttatagt aagaaaacag cagagtcttt agcaagtcga ttgttaagaa | 1260 |
| atgttaatgt ttcggaatat attaagaaac gattagaaca gatacaagaa gagcgtttaa | 1320 |
| tgagcattac agaagcttta gcgttatctg cttctattgc tagaggagaa cctcaagagg | 1380 |

```
cttacagtaa gaaatatgac catttaaacg atgaagtgga aaaagaggtt acttacacaa    1440
tcacaccaac ttttgaagag cgtcagagat ctattgacca catactaaaa gttcatggtg    1500
cgtatatcga caaaaaagaa attactcaga agaatattga gattaatatt ggtgagtacg    1560
atgacgaaag ttaaattaaa ctttaacaaa ccatctaatg ttttcaacag aaacatattc    1620
gaaatactaa ccaattacga taacttcact gaagtacatt acggtggagg ttcgagtggt    1680
aagtctcacg gcgttataca aaaagttgta cttaaagcat tgcaagactg gaaatatcct    1740
aggcgtatac tatggcttag aaaagtccaa tcaacaatta agatagtttt attcgaagat    1800
gtcaaagatt gtttgataaa cttcggtatt tgggacatgt gcctttggaa taagactgat    1860
aacaaagttg aattgccaaa cggcgcagtt ttttttgttta aaggattaga tacccagag    1920 aaaataaagt cgataaaagg catatcagac atagtcatgg aagaagcgtc tgaattcaca    1980
ctaaatgatt acacgcaatt aacgttgcgt ttgagggagc gtaaacacgt gaataagcaa    2040 atattttttga tgtttaaccc agtatctaaa ctgaattggg tttataagta tttctttgaa    2100
catggtgaac caatggaaaa tgtcatgatt agacaatcta gttatcgaga ataagtttt    2160 cttgatgaaa tgcacgacga aaacttagag ttgttagcaa atcgtaatcc agcatattac    2220
aaaatttatg cgttaggtga attttctaca ctagacaaat tggttttccc taagtatgaa    2280
aaacgtttaa taaataaaga tgagttaaga catttacctt cttatttgg attggacttt    2340 ggctacgtta atgatcctag tgcttttata cattctaaaa tagatgtaaa gaaaagaag    2400 ttatacatca ttgaagagta tgttaaacaa ggtatgctga atgatgaaat agctaatgtc    2460
ataaagcaac ttggttatgc taagaagaa attacagcag atagtgcaga acaaaaagt    2520 atagctgaat taaggaatct agggcttaaa aggattttac caaccaaaaa agggaagggc    2580
tcggttgtac aagggttaca attcttaatg caatttgaaa tcattgttga tgaacgttgt    2640
ttcaagacta ttgaagagtt tgacaactac acatggcaaa aggacaaaga tacaggtgaa    2700
tataccaatg aaccagtaga tacatacaat cattgtatcg attcgttgcg ttattcagtg    2760
gaacgattc                                                          2769

<210> SEQ ID NO 14
<211> LENGTH: 10319
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
ggcgccatgg ttaagggccc tttgcggaaa gagttagtaa gttaacagaa gacgaaccaa      60
aactaaatgg tttagcagga aacttagata aaaaaatgaa tccagaatta tattcagaac     120
aggaacagca acaagaacaa caaaagaatc aaaaacgaga tagaggtatg cacttataga     180
acatgcattt atgccgagaa aacttattgg ttggaatggg ctatgtgtta gctaacttgt     240
tagcgagttg gttggacttg aattgggatt aatcccaaga aagtaccaac tcaacaacac     300
ataaagccct gtaggttccg accaataagg aaattggaat aaagcaataa aaggagttga     360
agaaatgaaa ttcagagaag cctttgagaa ttttataaca agtaagtatg tacttggtgt     420
tttagtagtc ttaactgttt accagataat acaaatgctt aaataaaaaa agacttgatc     480
tgattagacc aaatctttg atagtgttat attaataaca aaataaaaag gagtcgctca     540
cgccctacca agtttgtga acgacatcat tcaaagaaaa aaacactgag ttgttttat      600
```

```
aatcttgtat atttagatat taaacgatat ttaaatatac atcaagatat atatttgggt    660
gagcgattac ttaaacgaaa ttgagattaa ggagtcgatt ttttatgtat aaaaacaatc    720
atgcaaatca ttcaaatcat ttggaaaatc acgatttaga caattttcct aaaaccggct    780
actctaatag ccggttggac gcacatactg tgtgcatatc tgatccaaaa ttaagttttg    840
atgcaatgac gatcgttgga aatctcaacc gagacaacgc tcaggcccct tctaaattta    900
tgagtgtaga gccccaaata agactttggg atattcttca aacaaagttt aaagctaaag    960
cacttcaaga aaaagtttat attgaatatg acaaagtgaa agcagatagt tgggatagac   1020
gtaatatgcg tattgaattt aatccaaaca aacttacacg agatgaaatg atttggttaa   1080
aacaaaatat aataagctac atggaagatg acggttttac aagattagat ttagcctttg   1140
attttgaaga tgatttgagt gactactatg caatgtctga taaagcagtt aagaaaacta   1200 tttttttatgg tcgtaatggt aagccagaaa caaaatattt tggcgtgaga gatagtaata   1260
gatttattag aatttataat aaaaagcaag aacgtaaaga taatgcagat gctgaagtta   1320
tgtctgaaca tttatggcgt gtagaaatcg aacttaaaag agatatggtg gattactgga   1380
atgattgctt tagtgattta catatcttgc aaccagattg gaaaactatc caacgcactg   1440
cggatagagc aatagttttt atgttattga gtgatgaaga agaatgggga aagcttcaca   1500
gaaattctag aacaaaatat aagaatttga taaaagaaat ttcgccagtc gatttaacgg   1560
acttaatgaa atcgacttta aaagcgaacg aaaaacaatt gcaaaacaa atcgattttt    1620 ggcaacatga atttaaattt tggaaatagt gtacatatta atattactga acaaaaatga   1680
tatatttaaa ctattctaat ttaggaggat ttttttatga agtgtctatt taaaaatttg   1740 gggaattttat atgaggtgaa agaataattt acccctataa actttagcca cctcaagtaa   1800
agaggtaaaa ttgtttagtt tatataaaaa atttaaaggt ttgttttata gcgttttatt   1860
ttggctttgt attctttcat ttttagtgt attaaatgaa atggttttaa atgtttcttt    1920
acctgatatt gcaaatcatt ttaatactac tcctggaatt acaaactggg taaacactgc   1980
atatatgtta acttttttcga taggaacagc agtatatgga aaattatctg attatataaa   2040
tataaaaaaa ttgttaatta ttggtattag tttgagctgt cttggttcat tgattgcttt   2100
tattgggccc acctaggcaa atatgctctt acgtgctatt atttaagtga ctatttaaaa   2160
ggagttaata aatatgcggc aaggtattct taaataaact gtcaatttga tagcgggaac   2220
aaataattag atgtcctttt ttaggagggc ttagtttttt gtacccagtt taagaatacc   2280
tttatcatgt gattctaaag tatccagaga atatctgtat gctttgtata cctatggtta   2340
tgcataaaaa tcccagtgat aaaagtattt atcactggga ttttatgcc cttttgggtt    2400 tttgaatgga ggaaaatcac atgaaaatta ttaatattgg agttttagct catgttgatg   2460
caggaaaaac taccttaaca gaaagcttat tatataacag tggagcgatt acagaattag   2520
gaagcgtgga caaaggtaca acgaggacgg ataatacgct tttagaacgt cagagaggaa   2580
ttacaattca gacaggaata acctcttttc agtgggaaaa tacgaaggtg aacatcatag   2640
acacgccagg acatatggat ttcttagcag aagtatatcg ttcattatca gttttagatg   2700
gggcaattct actgatttct gcaaaagatg gcgtacaagc acaaactcgt atattatttc   2760
atgcacttag gaaaatgggg attcccacaa tcttttttat caataagatt gaccaaaatg   2820
gaattgattt atcaacggtt tatcaggata ttaaagagaa actttctgcc gaaattgtaa   2880
tcaaacagaa ggtagaactg tatcctaata tgtgtgtgac gaactttacc gaatctgaac   2940
```

```
aatgggatac ggtaatagag ggaaacgata acctttaga gaaatatatg tccggtaaat    3000
cattagaagc attggaactc gaacaagagg aaagcataag atttcagaat tgttctctgt    3060
tccctcttta tcatggaagt gcaaaagta atataggat tgataacctt atagaagtta    3120
ttactaataa attttattca tcaacacatc gaggtccgtc tgaactttgc ggaaatgttt    3180
tcaaaattga atatacaaaa aaaagacaac gtcttgcata tatacgcctt tatagtggag    3240
tactacattt acgagattcg gttagagtat cagaaaaaga aaaataaaa gttacagaaa    3300 tgtatacttc aataaatggt gaattatgta agattgatag agcttattct ggagaaattg    3360
ttattttgca aaatgagttt ttgaagttaa atagtgttct tggagataca aaactattgc    3420
cacagagaaa aaagattgaa aatccgcacc ctctactaca aacaactgtt gaaccgagta    3480
aacctgaaca gagagaaatg ttgcttgatg ccctttgga aatctcagat agtgatccgc    3540
ttctacgata ttacgtggat tctacgacac atgaaattat actttctttc ttagggaaag    3600
tacaaatgga agtgattagt gcactgttgc aagaaaagta tcatgtggag atagaactaa    3660
aagagcctac agtcatttat atggagagac cgttaaaaaa tgcagaatat accattcaca    3720
tcgaagtgcc gccaaatcct ttctgggctt ccattggttt atctgtatcg ccgcttccgt    3780
tgggaagtgg aatgcagtat gagagctcgg tttctcttgg atacttaaat caatcatttc    3840
aaaatgcagt tatggaaggg gtacgctatg gttgcgaaca aggattatat ggttggaatg    3900
tgacggattg taaaatctgt tttaagtacg gtttatacta tagccctgtt agtactccag    3960
cagattttcg gatgcttact cctattgtac tggagcaagc ctttagaaaa gctggaacag    4020
aattgttaga gccatatctt agttttaaag tttatgcacc acaggaatat ctttcacggg    4080
catataacga tgctcccaaa tattgtgcaa atatcgtaaa tactcaactg aaaaataatg    4140
aggtcattat tattggagaa attcctgctc gatgtattca agattatcgc aatgatttaa    4200 cttttttac aaatgggctt agtgtttgtt tagcagagct aaaaggatat caggttacca    4260
ctggcgaacc tgtttgccag acccgtcgtc taaatagtcg gatagataaa gtaagatata    4320
tgttcaataa aataacttag tgcgttttat gttgttatat aaatatggtt tcttattaaa    4380
taagatgaaa tattctttaa tatagatttg aattaaagtg gaaaggagga gattgttatt    4440
ataaactaca agtggatatt gtgtcctagt tgtggaaata aaacaagact acgaatacga    4500
gtggatacta tacttaaaaa tttccctta tacagcccca aatgtaagaa cgaaacttta    4560
attaatgttc aaaaaatgaa tataataaca atcaaagagc cagacgccaa gacgcagagc    4620
cgataatttg agaaatgaaa ctctcatctt atcggctctt tttgtttatc tgaattttac    4680
tgactagcct tcaatatttc cgcggccagc ttactatgcc attattaagc ttgtaatatc    4740
ggagggttta ttaattggca gtaaagtggc agtttttgat accttaaatg agatattatg    4800
atagtgtagg atattgacta tcgtactgcg tttccctacc gcaaattagg aataaaggat    4860
ctatgtgggt tggctgatta tagccaatcc tttttaatt ttaaaaagcg tatagcgcga    4920
gagttggtgg taaatgaaat gaacgaaaaa caaaagagat tcgcagatga atatataatg    4980
aatggatgta atggtaaaaa agcagcaatt acagtaggtt atagtaagaa aacagcagag    5040 tcttagcaa gtcgattgtt aagaaatgtt aatgtttcgg aatatattaa agaacgatta    5100
gaacaggtac aagaagagcg tttaatgagt attacagaag ctttagcgtt atctgcttct    5160
attgctagag gagaacctca agaggcttac agtaagaaat atgaccattt aaacgatgaa    5220
gtggaaaaag aggttactta cacaatcaca ccaacttttg aagagcgtca gagatctatt    5280
gaccacatac taaaagtaca tggtgcgtat atcgataaaa aagaaattac tcagaagaat    5340
```

```
attgagatta atattggtga gtacgatgac gaaagttaaa ttgaacttta acaaaccgtc    5400
taatgttttc aatagccgcg ggggcccaac acaccaactt ttgaagagcg tcagagatct    5460
attgaccaca tactaaaagt acatggtgcg tatatcgata aaaaagaaat tactcagaag    5520
aatattgaga ttaatattgg tgagtacgat gacgaaagtt aaattaaact ttaacaaacc    5580
gtctaatgtt ttcaatagcc gcggggggccc aacgagcggc cgcatagtta agccagcccc   5640
gacacccgcc aacacccgct gacgcgccct gacgggcttg tctgctcccg gcatccgctt    5700
acagacaagc tgtgaccgtc tccgggagct gcatgtgtca gaggttttca ccgtcatcac    5760
cgaaacgcgc gagacgaaag ggcctcgtga tacgcctatt tttataggtt aatgtcatga    5820
taataatggt ttcttagacg tcaggtggca cttttcgggg aaatgtgcgc ggaacccta    5880 tttgtttatt tttctaaata cattcaaata tgtatccgct catgagacaa taaccctgat    5940
aaatgcttca ataatattga aaaggaaga gtatgagtat tcaacatttc cgtgtcgccc    6000
ttattccctt ttttgcggca ttttgccttc ctgttttgc tcacccagaa acgctggtga    6060
aagtaaaaga tgctgaagat cagttgggtg cacgagtggg ttacatcgaa ctggatctca    6120
acagcggtaa gatccttgag agtttttcgcc ccgaagaacg ttttccaatg atgagcactt    6180
ttaaagttct gctatgtggc gcggtattat cccgtattga cgccgggcaa gagcaactcg    6240
gtcgccgcat acactattct cagaatgact tggttgagta ctcaccggtc acagaaaagc    6300
atcttacgga tggcatgaca gtaagagaat tatgcagtgc tgccataacc atgagtgata    6360
acactgcggc caacttactt ctgacaacga tcggaggacc gaaggagcta accgcttttt    6420
tgcacaacat gggggatcat gtaactcgcc ttgatcgttg ggaaccggag ctgaatgaag    6480
ccataccaaa cgacgagcgt gacaccacga tgcctgtagc aatggcaaca acgttgcgca    6540
aactattaac tggcgaacta cttactctag cttcccggca acaattaata gactggatgg    6600
aggcggataa agttgcagga ccacttctgc gctcggccct tccggctggc tggtttattg    6660
ctgataaatc tggagccggt gagcgtgggt ctcgcggtat cattgcagca ctggggccag    6720
atggtaagcc ctcccgtatc gtagttatct acacgacggg gagtcaggca actatggatg    6780
aacgaaatag acagatcgct gagataggtg cctcactgat taagcattgg taactgtcag    6840
accaagttta ctcatatata ctttagattg atttaaaact tcatttttaa tttaaaagga    6900
tctaggtgaa gatcctttt gataatctca tgaccaaaat cccttaacgt gagttttcgt    6960
tccactgagc gtcagacccc gtagaaaaga tcaaaggatc ttcttgagat ccttttttc    7020 tgcgcgtaat ctgctgcttg caaacaaaaa aaccaccgct accagcggtg ttttttttgc    7080
cggatcaaga gctaccaact ctttttccga aggtaactgg cttcagcaga gcgcagatac    7140
caaatactgt tcttctagtg tagccgtagt taggccacca cttcaagaac tctgtagcac    7200
cgcctacata cctcgctctg ctaatcctgt taccagtggc tgctgccagt ggcgataagt    7260
cgtgtcttac cgggttggac tcaagacgat agttaccgga taaggcgcag cggtcgggct    7320
gaacgggggg ttcgtgcaca cagcccagct tggagcgaac gacctacacc gaacctgaga    7380
tacctacagc gtgagctatg agaaagcgcc acgcttcccg aagggagaaa ggcggacagg    7440
tatccggtaa gcggcagggt cggaacagga gagcgcacga gggagcttcc agggggaaac    7500
gcctggtatc tttatagtcc tgtcgggttt cgccacctct gacttgagcg tcgatttttg    7560
tgatgctcgt caggggggcg gagcctatgg aaaaacgcca gcaacgcggc cttttttacgg    7620 ttcctggcct tttgctggcc ttttgctcac atgttctttc ctgcgttatc ccctgattct    7680
```

```
gtggataacc gtattaccgc ctttgagtga gctggcgggt ctagttaatg tgtaacgtaa    7740
cattagctag attttttat tcaaaaaaat atttacaaat attaggaaat ttaagtgtaa     7800
aagagttgat aaatgattat attgggacta taatataatt aaggtcgatt gaattcgtta    7860
actaattaat caccaaaaag gaatagagta tgaagtttgg aaatatttgt ttttcgtatc    7920
aaccaccagg tgaaactcat aagcaagtaa tggatcgctt tgttcggctt ggtatcgcct    7980
cagaagaggt agggtttgat acatattgga ccttagaaca tcattttaca gagtttggtc    8040
ttacgggaaa tttatttgtt gctgcggcta acctgttagg aagaactaaa acattaaatg    8100
ttggcactat gggggttgtt attccgacag cacacccagt tcgacagtta gaagacgttt    8160
tattattaga tcaaatgtcg aaaggtcgtt ttaattttgg aaccgttcga gggctatacc    8220
ataaagattt tcgagtattt ggtgttgata tggaagagtc tcgagcaatt actcaaaatt    8280
tctaccagat gataatggaa agcttacaga caggaaccat tagctctgat agtgattaca    8340
ttcaatttcc taaggttgat gtatatccca aagtgtactc aaaaaatgta ccaacctgta    8400
tgactgctga gtccgcaagt acgacagaat ggctagcaat acaagggcta ccaatggttc    8460
ttagttggat tattggtact aatgaaaaaa aagcacagat ggaactctat aatgaaattg    8520
cgacagaata tggtcatgat atatctaaaa tagatcattg tatgacttat atttgttctg    8580
ttgatgatga tgcacaaaag gcgcaagatg tttgtcggga gtttctgaaa aattggtatg    8640
actcatatgt aaatgcgacc aatatcttta atgatagcaa tcaaactcgt ggttatgatt    8700
atcataaagg tcaatggcgt gattttgttt tacaaggaca tacaaacacc aatcgacgtg    8760
ttgattatag caatggtatt aacccgtag gcactcctga gcagtgtatt gaaatcattc      8820
aacgtgatat tgatgcaacg ggtattacaa acattacatg cggatttgaa gctaatggaa    8880
ctgaagatga aataattgct tccatgcgac gctttatgac acaagtcgct cctttcttaa    8940
aagaacctaa ataaattact tatttgatac tagagataat aaggaacaag ttatgaaatt    9000
tggattattt tttctaaact ttcagaaaga tggaataaca tctgaagaaa cgttggataa    9060
tatggtaaag actgtcacgt taattgattc aactaaatat catttttaata ctgcctttgt    9120
taatgaacat cacttttcaa aaaatggtat tgttggagca cctattaccg cagctggttt     9180
tttattaggg ttaacaaata aattacatat tggttcatta aatcaagtaa ttaccaccca    9240
tcaccctgta cgtgtagcag aagaagccag tttattagat caaatgtcag agggacgctt    9300
cattcttggt tttagtgact gcgaaagtga tttcgaaatg gaattttta gacgtcatat     9360
ctcatcaagg caacaacaat ttgaagcatg ctatgaaata attaatgacg cattaactac    9420
aggttattgc catccccaaa acgacttta tgattttcca aaggtttcaa ttaatccaca    9480
ctgttacagt gagaatggac ctaagcaata tgtatccgct acatcaaaag aagtcgtcat    9540
gtgggcagcg aaaaaggcac tgcctttaac gtttaagtgg gaggataatt tagaaaccaa    9600
agaacgctat gcaattctat ataataaaac agcacaacaa tatggtattg atatttcgga    9660
tgttgatcat caattaactg taattgcgaa cttaaatgct gatagaagta cggctcaaga    9720
agaagtgaga gaatacttaa aagactatat cactgaaact taccctcaaa tggacagaga    9780
tgaaaaaatt aactgcatta ttgaagagaa tgcagttggg tctcatgatg actattatga    9840
atcgacaaaa ttagcagtgg aaaaaacagg gtctaaaaat atttattat cctttgaatc      9900
aatgtccgat attaaagatg taaagatat tattgatatg ttgaaccaaa aaatcgaaat     9960
gaatttacca taataaaatt aaaggcaatt tctatattag attgccttt tggcgcgcct     10020
attctaatgc ataataaata ctgataacat cttatatttt gtattatatt ttgtattatc    10080
```

```
gttgacatgt ataattttga tatcaaaaac tgattttccc tctattattt tcgagattta    10140
ttttcttaat tctctttaac aaactagaaa tattgtatat acaaaaaatt ataaataata    10200
gatgaatagt ttaattatag gtgttcatca atcgaaaaag caacgtatct tatttaaagt    10260
gcgttgcttt tttctcattt ataaggttaa ataattctca tatatcaagc aaagtgaca    10319

<210> SEQ ID NO 15
<211> LENGTH: 2088
<212> TYPE: DNA
<213> ORGANISM: Staphylococcus aureus

<400> SEQUENCE: 15
tatactacaa atgtagtctt atataaggag gatattgatg aaaagataa aaattgttcc      60 acttatttta atagttgtag ttgtcgggtt tggtatatat ttttatgctt caaaagataa     120
agaaattaat aatactattg atgcaattga agataaaaat ttcaaacaag tttataaaga     180
tagcagttat atttctaaaa gcgataatgg tgaagtagaa atgactgaac gtccgataaa     240
aatatataat agtttaggcg ttaaagatat aaacattcag gatcgtaaaa taaaaaaagt     300
atctaaaaat aaaaaacgag tagatgctca atataaaatt aaaacaaact acggtaacat     360
tgatcgcaac gttcaattta attttgttaa agaagatggt atgtggaagt tagattggga     420
tcatagcgtc attattccag gaatgcagaa agaccaaagc atacatattg aaaatttaaa     480
atcagaacgt ggtaaaattt tagaccgaaa caatgtggaa ttggccaata caggaacagc     540
atatgagata ggcatcgttc caaagaatgt atctaaaaaa gattataaag caatcgctaa     600
agaactaagt atttctgaag actatatcaa acaacaaatg gatcaaaatt gggtacaaga     660
tgataccttc gttccactta aaccgttaaa aaaaatggat gaatatttaa gtgatttcgc     720
aaaaaaattt catcttacaa ctaatgaaac agaaagtcgt aactatcctc tagaaaaagc     780
gacttcacat ctattaggtt atgttggtcc cattaactct gaagaattaa aacaaaaaga     840
atataaaggc tataaagatg atgcagttat tggtaaaaag ggactcgaaa aactttacga     900
taaaaagctc caacatgaag atggctatcg tgtcacaatc gttgacgata atagcaatac     960
aatcgcacat acattaatag agaaaaagaa aaaagatggc aaagatattc aactaactat    1020
tgatgctaaa gttcaaaaga gtatttataa caacatgaaa aatgattatg gctcaggtac    1080
tgctatccac cctcaaacag gtgaattatt agcacttgta agcacacctt catatgacgt    1140
ctatccattt atgtatggca tgagtaacga agaatataat aaattaaccg aagataaaaa    1200
agaacctctg ctcaacaagt tccagattac aacttcacca ggttcaactc aaaaaatatt    1260
aacagcaatg attgggttaa ataacaaaac attagacgat aaaacaagtt ataaaatcga    1320
tggtaaaggt tggcaaaaag ataaatcttg gggtggttac aacgttacaa gatatgaagt    1380
ggtaaatggt aatatcgact taaaacaagc aatagaatca tcagataaca ttttctttgc    1440
tagagtagca ctcgaattag gcagtaagaa atttgaaaaa ggcatgaaaa aactaggtgt    1500
tggtgaagat ataccaagtg attatccatt ttataatgct caaatttcaa acaaaaattt    1560
agataatgaa atattattag ctgattcagg ttacggacaa ggtgaaatac tgattaaccc    1620
agtacagatc ctttcaatct atagcgcatt agaaaataat ggcaatatta acgcacctca    1680
cttattaaaa gacacgaaaa acaaagtttg gaagaaaaat attatttcca agaaaatat    1740 caatctatta actgatggta tgcaacaagt cgtaaataaa acacataaag aagatattta    1800
tagatcttat gcaaacttaa ttggcaaatc cggtactgca gaactcaaaa tgaaacaagg    1860
```

-continued

| | |
|---|---|
| agaaactggc agacaaattg ggtggtttat atcatatgat aaagataatc caaacatgat | 1920 |
| gatggctatt aatgttaaag atgtacaaga taaaggaatg gctagctaca atgccaaaat | 1980 |
| ctcaggtaaa gtgtatgatg agctatatga gaacggtaat aaaaaatacg atatagatga | 2040 |
| ataacaaaac agtgaagcaa tccgtaacga tggttgcttc actgtttt | 2088 |

<210> SEQ ID NO 16
<211> LENGTH: 2075
<212> TYPE: RNA
<213> ORGANISM: Staphylococcus aureus

<400> SEQUENCE: 16

| | |
|---|---|
| uagucuuaua uaaggaggau auugaugaaa agauaaaaa uuguuccacu uauuuaaua | 60 |
| guuguaguug ucggguuugg uauauauuuu uaugcuucaa aagauaaaga aauuaauaau | 120 |
| acuauugaug caauugaaga uaaaaauuuc aaacaaguuu auaagauag caguuauauu | 180 |
| ucuaaaagcg auaaugguga aguagaaaug acugaacguc cgauaaaaau auauaauagu | 240 |
| uuaggcguua aagauauaaa cauucaggau cguaaaauaa aaaaaguauc uaaaaauaaa | 300 |
| aaacgaguag augcucaaua uaaaauuaaa acaaacuacg guaacauuga ucgcaacguu | 360 |
| caauuuaauu uuguuaaaga agaugguaug uggaaguuga auugggauca uagcgucauu | 420 |
| auuccaggaa ugcagaaaga ccaaagcaua cauauugaaa auuuaaaauc agaacguggu | 480 |
| aaaauuuuag accgaaacaa uguggaauug gccauacag gaacagcaua ugagauaggc | 540 |
| aucguuccaa agaauguauc uaaaaagau auaaagcaa ucgcuaaaga acuaaguauu | 600 |
| ucugaagacu auaucaaaca acaauggau caaaauuggg uacaagauga uaccuucguu | 660 |
| ccacuuaaaa ccguuaaaaa auggaugaa uauuuaagug auucgcaaa aaaauuucau | 720 |
| cuuacaacua augaaacaga aagucgaaac uauccucuag aaaaagcgac uucacaucua | 780 |
| uuagguuaug uugguccau uaacucugaa gaauuaaaac aaaagaauaa uaaaggcuau | 840 |
| aaagaugaug caguuauugg uaaaaaggga cucgaaaaac uuuacgauaa aaagcuccaa | 900 |
| caugaagaug gcuaucgugu cacaaucguu gacgauaaua gcaauacaau cgcacauaca | 960 |
| uuaauagaga aaagaaaaa agauggcaaa gauauucaac uaacuauuga ugcuaaaguu | 1020 |
| caaaagagua uuuauaacaa caugaaaaau gauuauggcu cagguacugc uauccacccu | 1080 |
| caaacaggug aauuauuagc acuuguaagc acaccuucau augcgucua uccauuuaug | 1140 |
| uauggcauga guaacgaaga auauaauaaa uuaaccgaag auaaaaaaga accucugcuc | 1200 |
| aacaaguucc agauuacaac uucaccaggu ucaacucaaa aauauuuaac agcaaugauu | 1260 |
| gggguuaaaua acaaaacauu agacgauaaa acaaguuaua aaaucgaugg uaaagguugg | 1320 |
| caaaaagaua aaucuuggg ugguuacaac guuacaagau augaaguggu aaauggauau | 1380 |
| aucgacuuaa aacaagcaau agaaucauca gauaacauuu ucuuugcuag aguagcacuc | 1440 |
| gaauuaggca guaagaaauu ugaaaaaggc augaaaaaac uagguguugg ugaagauaua | 1500 |
| ccaagugauu auccauuuua uaaugcucaa auuucaaaca aaaauuuaga uaaugaaaua | 1560 |
| uuauuagcug auucagguua cggacaaggu gaaauacuga uuaacccagu acagauccuu | 1620 |
| ucaaucuaua gcgcauuaga aaauaauggc aauauuaacg caccucacuu auuaaaagac | 1680 |
| acgaaaaaca aaguuuggaa gaaaauauu auuuccaaag aaaauaucaa ucuauuaacu | 1740 |
| gaugguaugc aacaagucgu aaauaaaaca cauaagaaag auauuauag aucuauugca | 1800 |
| aacuuaauug gcaaauccgg uacugcagaa cucaaaauga acaaggaga aacuggcaga | 1860 |
| caaauuggu gguuuauauc auaugauaaa gauaauccaa acaugaugau ggcuauuaau | 1920 | guuaaagaug uacaagauaa aggaauggcu agcuacaaug ccaaaaucuc agguaaagug   1980 uaugaugagc uauaugagaa cgguaauaaa aaauacgaua uagaugaaua acaaaacagu   2040 gaagcaaucc guaacgaugg uugcuucacu guuuu                              2075

<210> SEQ ID NO 17
<211> LENGTH: 2166
<212> TYPE: DNA
<213> ORGANISM: Vibrio fischeri
<220> FEATURE:
<221> NAME/KEY: modified_base
<222> LOCATION: (1194)..(1194)
<223> OTHER INFORMATION: a, c, t, g, unknown or other

<400> SEQUENCE: 17
ggcttaaata aacagaatca ccaaaaagga atagagtatg aagtttggaa atatttgttt     60
ttcgtatcaa ccaccaggtg aaactcataa gctaagtaat ggatcgcttt gttcggcttg    120
gtatcgcctc agaagagtag ggtttgatac atattggacc ttagaacatc attttacaga   180
gtttggtctt acgggaaatt tatttgttgc tgcggctaac ctgttaggaa gaactaaaac    240
attaaatgtt ggcactatgg gggttgttat tccgacagca cacccagttc gacagttaga    300
agacgtttta ttattagatc aaatgtcgaa aggtcgtttt aattttggaa ccgttcgagg    360
gctataccat aaagattttc gagtatttgg tgttgatatg gaagagtctc gagcaattac    420
tcaaaatttc taccagatga taatggaaag cttacagaca ggaaccatta gctctgatag    480
tgattacatt caatttccta aggttgatgt atatcccaaa gtgtactcaa aaaatgtacc    540
aacctgtatg actgctgagt ccgcaagtac gacagaatgg ctagcaatac aagggctacc    600
aatggttctt agttggatta ttggtactaa tgaaaaaaaa gcacagatgg aactctataa    660
tgaaattgcg acagaatatg gtcatgatat atctaaaata gatcattgta tgacttatat    720
ttgttctgtt gatgatgatg cacaaaaggc gcaagatgtt tgtcgggagt ttctgaaaaa    780
ttggtatgac tcatatgtaa atgcgaccaa tatctttaat gatagcaatc aaactcgtgg    840
ttatgattat cataaaggtc aatggcgtga ttttgtttta caaggacata caaacaccaa    900
tcgacgtgtt gattatagca atggtattaa ccctgtaggc actcctgagc agtgtattga    960
aatcattcaa cgtgatattg atgcaacggg tattacaaac attacatgcg gatttgaagc   1020
taatggaact gaagatgaaa taattgcttc catgcgacgc tttatgacac aagtcgctcc   1080
tttcttaaaa gaacctaaat aaattactta tttgatacta gagataataa ggaacaagtt   1140
atgaaatttg gattattttt tctaaacttt cagaaagatg gaataacatc tgangaaacg   1200
ttggataata tggtaaagac tgtcacgtta attgattcaa ctaaatatca ttttaatact   1260
gcctttgtta atgaacatca cttttcaaaa aatggtattg ttggagcacc tattaccgca   1320
gctggttttt tattagggtt aacaaataaa ttacatattg gttcattaaa tcaagtaatt   1380
accacccatc accctgtacg tgtagcagaa gaagccagtt tattagatca aatgtcagag   1440
ggacgcttca ttcttggttt tagtgactgc gaaagtgatt tcgaaatgga atttttttaga   1500 cgtcatatct catcaaggca acaacaattt gaagcatgct atgaaataat taatgacgca   1560
ttaactacag gttattgtca tccccaaaac gactttatg attttccaaa ggtttcaatt   1620
aatccacact gttacagtga gaatggacct aagcaatatg tatccgctac atcaaaagaa   1680
gtcgtcatgt gggcagcgaa aaaggcactg cctttaacat ttaagtggga ggataattta   1740
gaaaccaaag aacgctatgc aattctatat aataaaacag cacaacaata tggtattgat   1800

| atttcggatg ttgatcatca attaactgta attgcgaact taaatgctga tagaagtacg | 1860 |
| gctcaagaag aagtgagaga atacttaaaa gactatatca ctgaaactta ccctcaaatg | 1920 |
| gacagagatg aaaaaattaa ctgcattatt gaagagaatg cagttgggtc tcatgatgac | 1980 |
| tattatgaat cgacaaaatt agcagtggaa aaaacagggt ctaaaaatat tttattatcc | 2040 |
| tttgaatcaa tgtccgatat taagatgta aaagatatta ttgatatgtt gaaccaaaaa | 2100 |
| atcgaaatga atttaccata ataaaattaa aggcaatttc tatattagat tgccttttta | 2160 |
| aatttc | 2166 |

<210> SEQ ID NO 18
<211> LENGTH: 2143
<212> TYPE: RNA
<213> ORGANISM: Vibrio fischeri

<400> SEQUENCE: 18

| aaucaccaaa aaggaauaga guaugaaguu uggaaauauu uguuuuucgu aucaaccacc | 60 |
| aggugaaacu cauaagcuaa guaauggauc gcuuuguucg gcuugguauc gccucagaag | 120 |
| aguagggsuuu gauacauauu ggaccuuaga acaucauuuu acagaguuug gucuuacggg | 180 |
| aaauuuauuu guugcugcgg cuaaccuguu aggaagaacu aaaacauuaa auguuggcac | 240 |
| uauggggguu guuauuccga cagcacaccc aguucgacag uuagaagacg uuuuauuauu | 300 |
| agaucaaaug ucgaaagguc guuuuaauuu uggaaccguu cgagggcuau accauaaaga | 360 |
| uuuucgagua uuuggugsuug auauggaaga gucucgagca auuacucaaa auuucuacca | 420 |
| gaugauaaug gaaagcuuac agacaggaac cauuagcucu gauagugauu acauucaauu | 480 |
| uccuaagguu gauguauauc ccaaagugua cucaaaaaau guaccaaccu guaugacugc | 540 |
| ugaguccgca aguacgacag aauggcuagc aauacaaggg cuaccaaugg uucuuagauu | 600 |
| gauuauuggu acuaaugaaa aaaagcaca gauggaacuc uauaaugaaa uugcgacaga | 660 |
| auauggucau gauauaucua aaauagauca uguauagacu uauauuguu cuguugauga | 720 |
| ugaugcacaa aaggcgcaag auguuugucg ggaguuucug aaaaauuggu augacucaua | 780 |
| uguaaaaugcg accauauucu uuaaugauag caaucaaacu cgugguuaug auuaucauaa | 840 |
| aggucaaugg cgugauuuug uuuuacaagg acauacaaac accaaucgac guguugauua | 900 |
| uagcaauggu auuaacccug uaggcacucc ugagcagugu auugaaauca uucaacguga | 960 |
| uauugaugca acgggsuauua caaacauuac augcggauuu gaagcuaaug gaacugaaga | 1020 |
| ugaaauaauu gcuuccaugc gacgcuuuau gacacaaguc gcuccuuucu aaaagaacc | 1080 |
| uaaauaaauu acuuauuuga acuagagaau aauaaggaac aaguuaugaa auuuggauua | 1140 |
| uuuuuucuaa acuuucagaa agauggaaua acaucgaag aaacguugga uaauauggua | 1200 |
| aagacuguca cguuaauuga uucaacuaaa uaucauuuua auacugccuu uguuaaugaa | 1260 |
| caucacuuuu caaaaaaugg uauuguugga gcaccauauua ccgcagcugg uuuuuauua | 1320 |
| ggguuaacaa auaaauuaca uauugguuca uuaaaucaag uaauuaccac ccaucacccu | 1380 |
| guacguguag cagaagaagc caguuuauua gaucaaaugu cagagggacg cuucauucuu | 1440 |
| gguuuagsug acugcgaaag ugauuucgaa auggaauuu uuagacguca uaucucauca | 1500 |
| aggcaacaac aauuugaagc augcuaugaa auaauuaaug acgcauuaac uacagguuau | 1560 |
| ugucauccc aaaacgacuu uuaugauuuu ccaaaggvuu caauuaauc acacuguuac | 1620 |
| agugagaaug gaccuaagca auauguaucc gcuacaucaa aagaagucgu caugugggca | 1680 |
| gcgaaaaagg cacugccuuu aacauuuaag ugggaggaua auuuagaaac caaagaacgc | 1740 |

| uaugcaauuc uauauaauaa aacagcacaa caauaugqua uuqauauuuc qqauquuqau | 1800 |
| caucaauuaa cuquaauuqc qaacuuaaau qcuqauaqaa qucqqcuca aqaaqaaquq | 1860 |
| aqaqaauacu uaaaqacuua uaucacuqaa acuuacccuc aaauqqacaq aauqaaaaa | 1920 |
| auuaacuqca uuauuqaaqa qaauqcaquu qqqucaauq auqacuauua uqaaucqaca | 1980 |
| aaauuaqcaq uqqaaaaaac aqqqucuaaa aauauuuuau uaccuuuqa aucaauqucc | 2040 |
| qauauuaaaq auquaaaaqa uauuauuqau auquuqaacc aaaaaaucqa aauqaauuua | 2100 |
| ccauaauaaa auuaaaqqca auuucuauau uaqauuqccu uuu | 2143 |

<210> SEQ ID NO 19
<211> LENGTH: 2294
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 19

| aaaqqcauqa aaaacuuqq uaucuucacc aacaccuaqc uuuuqaaqq aauuqaquau | 60 |
| qaaquuuqqa aauauuqquu quucquauca accaccaqqu qaaacucaua aqcuaaaqqc | 120 |
| auqaaaaaac uaqquqaucu ucaccaacac cuaquuuuuu caaqqaauuq aquauqaaqu | 180 |
| uuqqaaauau uuquuuucq uaucaaccac caqqqaaac ucauaaqcua aquaauqqau | 240 |
| cqcuuuquuc qqcuuqquau cqccucaqaa qaquaqqquu uqauacauau uqqaccuuaq | 300 |
| aacaucauuu uacaqaquuu qqucuuacqq qaaauuuauu uquuqcuqcq qcuaaccuqu | 360 |
| uaqqaaqaac uaaaacauua aauquuqqca cuaqqqqqu uquuauuccq acaqcacacc | 420 |
| caquccqaca quuaqaaqac quuuuauuau uaqaucaaau qucqaaaqqu cquuuuaauu | 480 |
| uuqqaaccqu ucqaqqqcua uaccauaaaq auuuucqaqu auuqququu qauauqqaaq | 540 |
| aqucucqaqc aauuacucaa aauuucuacc aqauqauaau qqaaaqcuua caqacaqqaa | 600 |
| ccauuaqcuc uqauaquqau uacauucaau uuccaaqqu uqauquauau cccaaaququ | 660 |
| acucaaaaaa uquaccaacc uquauqacuq cuqaquccqc aaqucqaca qaauqqcuaq | 720 |
| caauacaaqq qcuaccaauq quucuuaquu qqauuauuqq uacuauqaa aaaaaaqcac | 780 |
| aqauqqaacu cuauauqaa auuqcqacaq aauauqquca uqauauaucu aaaauaqauc | 840 |
| auuquauqac uuauauuuqu ucuquuqauq auqauqcaca aaaqqcqcaa qauquuuquc | 900 |
| qqqaquuucu qaaaaauuqq uauqacucau auquaauqc qaccaauauc uuuaauqaua | 960 |
| qcaaucaaac ucquqquau qauuaucaua aaqqucaauq qcquqauuuu quuuacaaq | 1020 |
| qacauacaaa caccaaucqa cququuqauu auaqcaauqq uauuaacccu quaqqcacuc | 1080 |
| cuqaqcaquq uauuqaaauc auucaacquq auauuqauqc aacqquauu acaaacauua | 1140 |
| cauqcqqauu uqaaqcuaau qqaacuqaaq auqaaauaau uqcuuccauq cqacqcuuua | 1200 |
| uqacacaaqu cqcuccuuuc uuaaaaqaac cuaaauaaau uacuuauuuq auacuaqaqa | 1260 |
| uaauaaqqaa caaquuauqa auuuqqauu auuuuucua aacuuucaqa aqauqqaau | 1320 |
| aacaucuqaa qaaacquuqq auaauauqqu aaaqacuquc acquuaauuq auucaacuaa | 1380 |
| auaucauuuu aauacuqccu uuquuaauqa acaucacuuu ucaaaaaauq quauuquuqq | 1440 |
| aqcaccuauu accqcaqcuq quuuuuauau aqqquuaaca aauaaauuac auauuqquuc | 1500 |
| auuaaaucaa quaauuacca cccaucaccc uqucqcqua qcaqaaqaaq ccaquuuauu | 1560 |
| aqaucaaauq ucaqaqqqac qcuucauucu uqquuuuaqu qacuqcqaaa quqauuucqa | 1620 |

```
aauggaauuu uuuagacguc auaucucauc aaggcaacaa caauuugaag caugcuauga    1680
aauaauuaau gacgcauuaa cuacagguua uugucauccc caaaacgacu uuuaugauuu    1740
uccaaagguu ucaauuaauc cacacuguua cagugagaau ggaccuaagc aauauguauc    1800
cgcuacauca aaagaagucg ucaugugggc agcgaaaaag gcacugccuu uaacauuuaa    1860
gugggaggau aauuuagaaa ccaaagaacg cuaugcaauu cuauauaaua aaacagcaca    1920
acaauauggu auugauauuu cggauguuga ucaucaauua acugaaauug cgaacuuaaa    1980
ugcugauaga aguacggcuc aagaagaagu gagagaauac uuaaaagacu auaucacuga    2040
aacuuacccu caaauggaca gagaugaaaa aauuaacgc auuauugaag agaaugcagu     2100
ugggucucau gaugacuauu augaaucgac aaaauuagca guggaaaaaa cagggucuaa    2160
aaauauuuua uuauccuuug aaucaauguc cgauauaaaa gaugaaaag auauuauuga    2220 uauguugaac caaaaaaucg aaaugaauuu accauaauaa aauuaaaggc aauuucuaua    2280
uuagauugcc uuuu                                                     2294
```

<210> SEQ ID NO 20
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, u, g, unknown or other
<220> FEATURE:
<221> NAME/KEY: modified_base
<222> LOCATION: (7)..(9)
<223> OTHER INFORMATION: a, c, u, g, unknown or other
<220> FEATURE:
<221> NAME/KEY: modified_base
<222> LOCATION: (12)..(12)
<223> OTHER INFORMATION: a, c, u, g, unknown or other
<220> FEATURE:
<223> OTHER INFORMATION: See specification as filed for detailed
      description of substitutions and preferred embodiments

<400> SEQUENCE: 20
nnwawgnnnu un                                                       12

<210> SEQ ID NO 21
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, u, g, unknown or other
<220> FEATURE:
<221> NAME/KEY: modified_base
<222> LOCATION: (4)..(7)
<223> OTHER INFORMATION: a, c, u, g, unknown or other
<220> FEATURE:
<221> NAME/KEY: modified_base
<222> LOCATION: (12)..(13)
<223> OTHER INFORMATION: a, c, u, g, unknown or other
<220> FEATURE:
<223> OTHER INFORMATION: See specification as filed for detailed
      description of substitutions and preferred embodiments

<400> SEQUENCE: 21

-continued

```
nagnnnncwu wnn                                                          13

<210> SEQ ID NO 22
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
cagauaacau uuu                                                          13

<210> SEQ ID NO 23
<211> LENGTH: 56
<212> TYPE: RNA
<213> ORGANISM: Staphylococcus aureus

<400> SEQUENCE: 23
aaaaggcaug aaaaacuag guguuggguga agauauacca agugauuauc cauuuu           56

<210> SEQ ID NO 24
<211> LENGTH: 61
<212> TYPE: RNA
<213> ORGANISM: Artificial Sequence
<220> FEATURE:
<223> OTHER INFORMATION: Description of Artificial Sequence: cis-
      repressor

<400> SEQUENCE: 24
aaaggcauga aaaacuugg uaucuucacc aacaccuagc uuuuugaagg aauugaguau        60
g                                                                       61

<210> SEQ ID NO 25
<211> LENGTH: 11
<212> TYPE: RNA
<213> ORGANISM: Artificial Sequence
<220> FEATURE:
<223> OTHER INFORMATION: Description of Artificial Sequence:
      ribonuclease E site
<220> FEATURE:
<221> NAME/KEY: modified_base
<222> LOCATION: (2)..(2)
<223> OTHER INFORMATION: a, c, u, g, unknown or other
<220> FEATURE:
<221> NAME/KEY: modified_base
<222> LOCATION: (4)..(4)
<223> OTHER INFORMATION: a, c, u, g, unknown or other
<220> FEATURE:
<221> NAME/KEY: modified_base
<222> LOCATION: (9)..(9)
<223> OTHER INFORMATION: a, c, u, g, unknown or other
<220> FEATURE:
<223> OTHER INFORMATION: See specification as filed for detailed
      description of substitutions and preferred embodiments

<400> SEQUENCE: 25
rnmngdwynm m                                                            11
```